US009459261B2

(12) United States Patent
Anderberg et al.

(10) Patent No.: US 9,459,261 B2
(45) Date of Patent: Oct. 4, 2016

(54) METHODS AND COMPOSITIONS FOR DIAGNOSIS AND PROGNOSIS OF RENAL INJURY AND RENAL FAILURE

(75) Inventors: Joseph Anderberg, Encinitas, CA (US); Jeff Gray, Solana Beach, CA (US); Paul McPherson, Encinitas, CA (US); Kevin Nakamura, Cardiff by the Sea, CA (US); James Patrick Kampf, San Diego, CA (US)

(73) Assignee: ASTUTE MEDICAL, INC., San Diego, CA (US)

( * ) Notice: Subject to any disclaimer, the term of this patent is extended or adjusted under 35 U.S.C. 154(b) by 103 days.

(21) Appl. No.: 14/241,005

(22) PCT Filed: Aug. 24, 2012

(86) PCT No.: PCT/US2012/052298
§ 371 (c)(1),
(2), (4) Date: Mar. 4, 2014

(87) PCT Pub. No.: WO2013/043310
PCT Pub. Date: Mar. 28, 2013

(65) Prior Publication Data
US 2014/0213477 A1    Jul. 31, 2014

Related U.S. Application Data

(60) Provisional application No. 61/528,000, filed on Aug. 26, 2011, provisional application No. 61/528,003, filed on Aug. 26, 2011.

(51) Int. Cl.
*G01N 31/00*    (2006.01)
*G01N 33/53*    (2006.01)
*G01N 33/68*    (2006.01)

(52) U.S. Cl.
CPC ..... *G01N 33/6893* (2013.01); *G01N 2800/347* (2013.01); *G01N 2800/60* (2013.01)

(58) Field of Classification Search
CPC .................. G01N 33/6893; G01N 2800/347
See application file for complete search history.

(56) References Cited

U.S. PATENT DOCUMENTS

| 5,480,792 | A | 1/1996 | Buechler |
| 5,525,524 | A | 6/1996 | Buechler et al. |
| 5,571,698 | A | 11/1996 | Ladner et al. |
| 5,631,171 | A | 5/1997 | Sandstrom et al. |
| 5,679,526 | A | 10/1997 | Buechler et al. |
| 5,824,799 | A | 10/1998 | Buechler et al. |
| 5,851,776 | A | 12/1998 | Valkirs |
| 5,885,527 | A | 3/1999 | Buechler |
| 5,922,615 | A | 7/1999 | Nowakowski et al. |
| 5,939,272 | A | 8/1999 | Buechler et al. |
| 5,947,124 | A | 9/1999 | Buechler et al. |
| 5,955,377 | A | 9/1999 | Maul et al. |
| 5,985,579 | A | 11/1999 | Buechler et al. |
| 6,019,944 | A | 2/2000 | Buechler |
| 6,057,098 | A | 5/2000 | Buechler et al. |
| 6,113,855 | A | 9/2000 | Buechler et al. |
| 6,143,576 | A | 11/2000 | Buechler |
| 8,993,250 | B2 * | 3/2015 | Anderberg ......... G01N 33/6893 422/430 |
| 9,229,010 | B2 * | 1/2016 | Anderberg ......... G01N 33/6893 |
| 2011/0195429 | A1 * | 8/2011 | Anderberg ......... G01N 33/6893 435/7.1 |

FOREIGN PATENT DOCUMENTS

| CA | 2781754 | 5/2011 |
| CA | 2781754 A1 | 5/2011 |
| CN | 101027556 A | 8/2007 |
| WO | 2004088276 A2 | 10/2004 |
| WO | 2009062520 | 5/2009 |
| WO | 2009107384 | 9/2009 |
| WO | 2011106746 | 9/2011 |

OTHER PUBLICATIONS

International Search Report and Written Opinion issued in PCT/US2012/052298 on Jan. 8, 2013.
Wang et al., "Induction of heat shock protein 70 inhibits ischemic renal injury", International Society of Nephrology, 2011, 79:861-870.
Office Action and Search Report issued by SIPO in PRC application No. 201280049909.5 dated Dec. 24, 2014—incl Engl lang transl.
Partial European Search Report issued in EP 12832845 dated Jul. 2, 2015.
Atkins et al., Heat shock proteins in renal cell carcinomas. Contrib Nephrol. 2005;148:35-56.
Eissa et al., Noninvasive Diagnosis of Bladder Cancer by Detection of Matrix Metalloproteinases (MMP-2 and MMP-9) and Their Inhibitor (TIMP-2) in Urine.Eur Urol. Nov. 2007;52(5):1388-1397.
Kolkenbrock et al., Biochemical Characterization of the Catalytic Domain of Membrane-Type 4 Matrix Metalloproteinase. Biol Chem. Sep. 1999;380(9):1103-1108.
Lenz et al., Matrix Metalloproteinases in Renal Development and Disease. J Amer Soc Nephrol. 2000;11(3):574-581.

(Continued)

*Primary Examiner* — Lisa Cook
(74) *Attorney, Agent, or Firm* — Michael A. Whittaker

(57) ABSTRACT

The present invention relates to methods and compositions for monitoring, diagnosis, prognosis, and determination of treatment regimens in subjects suffering from or suspected of having a renal injury. In particular, the invention relates to using a one or more assays configured to detect a kidney injury marker selected from the group consisting of Heat shock 70 kDa protein 1, Alpha-1-antitrypsin Neutrophil elastase complex, Stromelysin-1:Metalloproteinase inhibitor 2 complex, 72 kDa type IV collagenase:Metalloproteinase inhibitor 2 complex, Insulin-like growth factor 1 receptor, Myeloid differentiation primary response protein MyD88, Neuronal cell adhesion molecule, and Tumor necrosis factor ligand superfamily member 10 as diagnostic and prognostic biomarkers in renal injuries.

10 Claims, No Drawings

(56) References Cited

OTHER PUBLICATIONS

Lichte et al., The recombinant catalytic domain of membrane-type matrix metalloproteinase—1 (MT1-MMP) induces activation of progelatinase A and progelatinase A complexed with TIMP-2. FEBS Lett. Nov. 18, 1996;397(2-3):277-282.
Obata et al., A one-step sandwich enzyme immunoassay for human matrix metalloproteinase 3 (stromelysin-1) using monoclonal antibodies. Clin Chim Acta. Oct. 15, 1992;211(1-2):59-72.
Ramp et al., Expression of heat shock protein 70 in renal cell carcinoma and its relation to tumor progression and prognosis. Histol Histopathol. Oct. 2007;22(10):1099-1107.
Seo et al., TIMP-2 Mediated Inhibition of Angiogenesis: An MMP-Independent Mechanism. Cell. Jul. 25, 2003;114 (2):171-180.
Asanuma et al., Selective modulation of the secretion of proteinases and their inhibitors by growth factors in cultured differentiated podocytes. Kidney Int. Sep. 2002;62(3):822-831.
Bagshaw et al., A multi-centre evaluation of the RIFLE criteria for early acute kidney injury in critically ill patients. Nephrol Dial Transplant. Apr. 2008;23(4):1203-1210.
Bellomo et al., Acute renal failure—definition, outcome measures, animal models, fluid therapy and information technology needs: the Second International Consensus Conference of the Acute Dialysis Quality Initiative (ADQI) Group. Crit Care. Aug. 2004;8(4):R204-212.
Berthier and Marti, Metzincins, including matrix metalloproteinases and meprin, in kidney transplantation. Swiss Med Wkly. Dec. 23, 2006;136(49-50):789-794.
Brook et al., Fibrosis-associated gene expression in renal transplant glomeruli after acute renal allograft rejection. Br J Surg. Aug. 2003;90(8):1009-1014.
Caron et al., Ischemia injury alters endothelial cell properties of kidney cortex: Stimulation of MMP-9. Exp Cell Res. Oct. 15, 2005;310(1):105-116.
Caron et al., Ischemia-reperfusion injury stimulates gelatinase expression and activity in kidney glomeruli. Can J Physiol Pharmacol. Mar. 2005;83(3):287-300.
Catania et al., Role of matrix metalloproteinases in renal pathophysiologies. Am J Physiol Renal Physiol. Mar. 2007;292(3):F905-F911.
Chawla et al., Identifying critically ill patients at high risk for developing acute renal failure: a pilot study. Kidney Int. Nov. 2005;68(5):2274-2280.
Chertow et al., Acute kidney injury, mortality, length of stay, and costs in hospitalized patients. J Am Soc Nephrol. Nov. 2005;16(11):3365-3370.
Extended European Search Report issued in EP 12832845 dated Oct. 29, 2015.
Office action and search report issued by SIPO in Chinese application No. 201280049909.5 dated Sep. 28, 2015—incl Engl tang transl.
Cwirla et al., Peptides on phage: a vast library of peptides for identifying ligands. Proc Natl Acad Sci U S A. Aug. 1990;87(16):6378-6382.
Devlin et al., Random peptide libraries: a source of specific protein binding molecules Science. Jul. 27, 1990;249 (4967):404-406.
Fischer et al., A readers' guide to the interpretation of diagnostic test properties: clinical example of sepsis. Intensive Care Med. Jul. 2003;29(7):1043-1051.
Gharagozlian et al., Matrix metalloproteinases in subjects with type 1 diabetes. BMC Clin Pathol. Sep. 16, 2009;9:7.
Goldstein and Chawla., Renal angina. Clin J Am Soc Nephrol. May 2010;5(5):943-949.
Hanley and McNeil, The meaning and use of the area under a receiver operating characteristic (ROC) curve. Radiology. Apr. 1982;143(1):29-36.
Hayashi et al., Enhanced Expression of Membrane Type-1 Matrix Metalloproteinase in Mesangial Proliferative Glomerulonephritis. J Am Soc Nephrol. Dec. 1998;9(12):2262-2271.
Kamata et al., Up-regulation of glomerular extracellular matrix and transforming growth factor-beta expression in RF/J mice. Kidney Int. Mar. 1999;55(3):864-876.
Kellum., Acute kidney injury, Crit Care Med, 2008;36(4):S141-S145.
Khanna et al., Expression of TGF-beta and fibrogenic genes in transplant recipients with tacrolimus and cyclosporine nephrotoxicity. Kidney Int. Dec. 2002;62(6):2257-2263.
Laplante et al., Modulation of matrix gelatinases and metalloproteinase-activating process in acute kidney rejection. Transpl Int. Apr. 2003;16(4):262-269.
Lassnigg et al., Minimal changes of serum creatinine predict prognosis in patients after cardiothoracic surgery: a prospective cohort study. J Am Soc Nephrol. Jun. 2004;15(6):1597-1605.
McCullough et al., Contrast-Induced Nephropathy (CIN) Consensus Working Panel: executive summary. Rev. Cardiovasc Med. 2006 Fall;7(4):177-197.
Mehran et al., A simple risk score for prediction of contrast-induced nephropathy after percutaneous coronary intervention: development and initial validation. J Am Coll Cardiol. Oct. 6, 2004;44(7):1393-1399.
Mehta et al., Acute Kidney Injury Network: report of an initiative to improve outcomes in acute kidney injury. Crit Care. 2007;11(2):R31.
Nelson and Griswold, A computer program for calculating antibody affinity constants. Comput Methods Programs Biomed. Jul.-Aug. 1988;27(1):65-68.
Praught and Shlipak, Are small changes in serum creatinine an important risk factor? Curr Opin Nephrol Hypertens. May 2005;14(3):265-270.
Ricci et al., The RIFLE criteria and mortality in acute kidney injury: A systematic review. Kidney Int Mar. 2008;73 (5):538-546.
Rysz et al., Serum matrix metalloproteinases MMP-2 and MMP-9 and metalloproteinase tissue inhibitors TIMP-1 and TIMP-2 in diabetic nephropathy. J Nephrol. Jul.-Aug. 2007;20(4):444-452.
Schaefer et al., Tubular gelatinase A (MMP-2) and its tissue inhibitors in polycystic kidney disease in the Han: SPRD rat. Kidney Int. Jan. 1996;49(1):75-81.
Scott and Smith, Searching for peptide ligands with an epitope library. Science. Jul. 27, 1990;249(4967):386-390.
Thakar et al., A clinical score to predict acute renal failure after cardiac surgery. J Am Soc Nephrol. Jan. 2005;16 (1):162-168.
Thrailkill et al., Matrix Metalloproteinase-2 Dysregulation in Type 1 Diabetes. Diabetes Care. Sep. 2007;30 (9):2321-2326.
Uchio-Yamada et al., Decreased Expression of Matrix Metalloproteinases and Tissue Inhibitors of Metalloproteinase in the Kidneys of Hereditary Nephrotic (ICGN) Mice. J Vet Med Sci. Jan. 2005;67(1):35-41.
Van Erp et al., Application of a sol particle immunoassay to the determination of affinity constants of monoclonal antibodies. J Immunoassay. 1991;12(3):425-443.
Vasala and Turpeenniemi-Hujanen, Serum tissue inhibitor of metalloproteinase-2 (TIMP-2) and matrix metalloproteinase-2 in complex with the inhibitor (MMP-2:TIMP-2) as prognostic markers in bladder cancer. Clin Biochem. Jun. 2007;40(9-10):640-644.
Wagrowska-Danilewicz and Danilewicz, Aberrant Tubulointerstitial Immunoexpression of Matrix Metalloproteinases MMP-2, MMP-9 and Tissue Inhibitor of Matrix Proteinase-2 (TIMP-2) in Acute Cellular Rejection of Human Renal Allograft. Pol J Pathol. 2008;59(4):189-194.
Ward et al., Binding activities of a repertoire of single immunoglobulin variable domains secreted from *Escherichia coli*. Nature. Oct. 12, 1989;341(6242):544-546.
Wasilewska and Zoch-Zwier, Urinary levels of matrix metalloproteinases and their tissue inhibitors in nephrotic children. Pediatr Nephrol. Oct. 2008;23(10):1795-1802.
Wijeysundera et al., Derivation and validation of a simplified predictive index for renal replacement therapy after aardiac surgery. JAMA. Apr. 25, 2007;297(16):1801-1809.
Wilson et al., Simplified conjugation chemistry for coupling peptides to F(ab') fragments: autologous red cell agglutination assay for HIV-1 antibodies. J Immunol Methods. Oct. 14, 1994;175(2):267-273.
Yarmush et al., Coupling of antibody-binding fragments to solid-phase supports: site-directed binding of F(ab')2 fragments. J Biochem Biophys Methods. Dec. 1992;25(4):285-297.
Zhang et al., Significance of MMP=2 and TIMP-2 mRNA Expressions on Glomerular Cells in the Development of L-Glomerulosclerosis. Chin Med Sci J. Jun. 2004;19(2):84-88.

* cited by examiner

SEQUENCE LISTING

<160> NUMBER OF SEQ ID NOS: 10

<210> SEQ ID NO 1
<211> LENGTH: 641
<212> TYPE: PRT
<213> ORGANISM: Homo sapiens

<400> SEQUENCE: 1

| Met<br>1 | Ala | Lys | Ala | Ala<br>5 | Ile | Gly | Ile | Asp | Leu<br>10 | Gly | Thr | Thr | Tyr | Ser<br>15 |
|---|---|---|---|---|---|---|---|---|---|---|---|---|---|---|
| Cys | Val | Gly<br>20 | Val | Phe | Gln | His | Gly<br>25 | Lys | Val | Glu | Ile | Ile<br>30 | Ala | Asn | Asp |
| Gln | Gly | Asn<br>35 | Arg | Thr | Thr | Pro | Ser<br>40 | Tyr | Val | Ala | Phe | Thr<br>45 | Asp | Thr | Glu |
| Arg<br>50 | Leu | Ile | Gly | Asp | Ala<br>55 | Ala | Lys | Asn | Gln | Val<br>60 | Ala | Leu | Asn | Pro | Gln |
| Asn<br>65 | Thr | Val | Phe | Asp | Ala<br>70 | Lys | Arg | Leu | Ile | Gly<br>75 | Arg | Lys | Phe | Gly | Asp<br>80 |
| Pro | Val | Val | Gln | Ser<br>85 | Asp | Met | Lys | His | Trp<br>90 | Pro | Phe | Gln | Val | Ile<br>95 | Asn |
| Asp | Gly | Asp | Lys<br>100 | Pro | Lys | Val | Gln | Val<br>105 | Ser | Tyr | Lys | Gly | Glu<br>110 | Thr | Lys |
| Ala | Phe | Tyr<br>115 | Pro | Glu | Glu | Ile | Ser<br>120 | Ser | Met | Val | Leu | Thr<br>125 | Lys | Met | Lys |
| Glu<br>130 | Ile | Ala | Glu | Ala | Tyr<br>135 | Leu | Gly | Tyr | Pro | Val<br>140 | Thr | Asn | Ala | Val | Ile |
| Thr<br>145 | Val | Pro | Ala | Tyr | Phe<br>150 | Asn | Asp | Ser | Gln | Arg<br>155 | Gln | Ala | Thr | Lys | Asp<br>160 |
| Ala | Gly | Val | Ile | Ala<br>165 | Gly | Leu | Asn | Val | Leu<br>170 | Arg | Ile | Ile | Asn | Glu<br>175 | Pro |
| Thr | Ala | Ala | Ala | Ile<br>180 | Ala | Tyr | Gly | Leu | Asp<br>185 | Arg | Thr | Gly | Lys | Gly<br>190 | Glu |
| Arg | Asn | Val<br>195 | Leu | Ile | Phe | Asp | Leu<br>200 | Gly | Gly | Gly | Thr | Phe<br>205 | Asp | Val | Ser |
| Ile<br>210 | Leu | Thr | Ile | Asp | Asp<br>215 | Gly | Ile | Phe | Glu | Val<br>220 | Lys | Ala | Thr | Ala | Gly |
| Asp<br>225 | Thr | His | Leu | Gly | Gly<br>230 | Glu | Asp | Phe | Asp | Asn<br>235 | Arg | Leu | Val | Asn | His<br>240 |
| Phe | Val | Glu | Glu | Phe<br>245 | Lys | Arg | Lys | His | Lys<br>250 | Lys | Asp | Ile | Ser | Gln<br>255 | Asn |
| Lys | Arg | Ala | Val<br>260 | Arg | Arg | Leu | Arg | Thr<br>265 | Ala | Cys | Glu | Arg | Ala<br>270 | Lys | Arg |
| Thr | Leu | Ser<br>275 | Ser | Ser | Thr | Gln | Ala<br>280 | Ser | Leu | Glu | Ile | Asp<br>285 | Ser | Leu | Phe |
| Glu<br>290 | Gly | Ile | Asp | Phe | Tyr<br>295 | Thr | Ser | Ile | Thr | Arg<br>300 | Ala | Arg | Phe | Glu | Glu |
| Leu<br>305 | Cys | Ser | Asp | Leu | Phe<br>310 | Arg | Ser | Thr | Leu | Glu<br>315 | Pro | Val | Glu | Lys | Ala<br>320 |
| Leu | Arg | Asp | Ala | Lys<br>325 | Leu | Asp | Lys | Ala | Gln<br>330 | Ile | His | Asp | Leu | Val<br>335 | Leu |
| Val | Gly | Gly | Ser<br>340 | Thr | Arg | Ile | Pro | Lys<br>345 | Val | Gln | Lys | Leu | Leu<br>350 | Gln | Asp |
| Phe | Phe | Asn<br>355 | Gly | Arg | Asp | Leu | Asn<br>360 | Lys | Ser | Ile | Asn | Pro<br>365 | Asp | Glu | Ala |

Val Ala Tyr Gly Ala Ala Val Gln Ala Ile Leu Met Gly Asp Lys
    370                 375                 380

Ser Glu Asn Val Gln Asp Leu Leu Leu Asp Val Ala Pro Leu Ser
385                 390                 395                 400

Leu Gly Leu Glu Thr Ala Gly Gly Val Met Thr Ala Leu Ile Lys Arg
                405                 410                 415

Asn Ser Thr Ile Pro Thr Lys Gln Thr Gln Ile Phe Thr Thr Tyr Ser
                420                 425                 430

Asp Asn Gln Pro Gly Val Leu Ile Gln Val Tyr Glu Gly Glu Arg Ala
                435                 440                 445

Met Thr Lys Asp Asn Asn Leu Leu Gly Arg Phe Glu Leu Ser Gly Ile
450                 455                 460

Pro Pro Ala Pro Arg Gly Val Pro Gln Ile Glu Val Thr Phe Asp Ile
465                 470                 475                 480

Asp Ala Asn Gly Ile Leu Asn Val Thr Ala Thr Asp Lys Ser Thr Gly
                485                 490                 495

Lys Ala Asn Lys Ile Thr Ile Thr Asn Asp Lys Gly Arg Leu Ser Lys
                500                 505                 510

Glu Glu Ile Glu Arg Met Val Gln Glu Ala Glu Lys Tyr Lys Ala Glu
                515                 520                 525

Asp Glu Val Gln Arg Glu Arg Val Ser Ala Lys Asn Ala Leu Glu Ser
                530                 535                 540

Tyr Ala Phe Asn Met Lys Ser Ala Val Glu Asp Glu Gly Leu Lys Gly
545                 550                 555                 560

Lys Ile Ser Glu Ala Asp Lys Lys Val Leu Asp Lys Cys Gln Glu
                565                 570                 575

Val Ile Ser Trp Leu Asp Ala Asn Thr Leu Ala Glu Lys Asp Glu Phe
                580                 585                 590

Glu His Lys Arg Lys Glu Leu Glu Gln Val Cys Asn Pro Ile Ile Ser
                595                 600                 605

Gly Leu Tyr Gln Gly Ala Gly Gly Pro Gly Pro Gly Gly Phe Gly Ala
                610                 615                 620

Gln Gly Pro Lys Gly Gly Ser Gly Ser Gly Pro Thr Ile Glu Glu Val
625                 630                 635                 640

Asp

<210> SEQ ID NO 2
<211> LENGTH: 477
<212> TYPE: PRT
<213> ORGANISM: Homo sapiens

<400> SEQUENCE: 2

Met Lys Ser Leu Pro Ile Leu Leu Leu Leu Cys Val Ala Val Cys Ser
1               5                   10                  15

Ala Tyr Pro Leu Asp Gly Ala Ala Arg Gly Glu Asp Thr Ser Met Asn
                20                  25                  30

Leu Val Gln Lys Tyr Leu Glu Asn Tyr Tyr Asp Leu Lys Lys Asp Val
                35                  40                  45

Lys Gln Phe Val Arg Arg Lys Asp Ser Gly Pro Val Val Lys Lys Ile
                50                  55                  60

Arg Glu Met Gln Lys Phe Leu Gly Leu Glu Val Thr Gly Lys Leu Asp
65                  70                  75                  80

Ser Asp Thr Leu Glu Val Met Arg Lys Pro Arg Cys Gly Val Pro Asp
                85                  90                  95

Val Gly His Phe Arg Thr Phe Pro Gly Ile Pro Lys Trp Arg Lys Thr
            100                 105                 110

His Leu Thr Tyr Arg Ile Val Asn Tyr Thr Pro Asp Leu Pro Lys Asp
            115                 120                 125

Ala Val Asp Ser Ala Val Glu Lys Ala Leu Lys Val Trp Glu Glu Val
130                 135                 140

Thr Pro Leu Thr Phe Ser Arg Leu Tyr Glu Gly Glu Ala Asp Ile Met
145                 150                 155                 160

Ile Ser Phe Ala Val Arg Glu His Gly Asp Phe Tyr Pro Phe Asp Gly
            165                 170                 175

Pro Gly Asn Val Leu Ala His Ala Tyr Ala Pro Gly Pro Gly Ile Asn
            180                 185                 190

Gly Asp Ala His Phe Asp Asp Asp Glu Gln Trp Thr Lys Asp Thr Thr
            195                 200                 205

Gly Thr Asn Leu Phe Leu Val Ala Ala His Glu Ile Gly His Ser Leu
            210                 215                 220

Gly Leu Phe His Ser Ala Asn Thr Glu Ala Leu Met Tyr Pro Leu Tyr
225                 230                 235                 240

His Ser Leu Thr Asp Leu Thr Arg Phe Arg Leu Ser Gln Asp Asp Ile
            245                 250                 255

Asn Gly Ile Gln Ser Leu Tyr Gly Pro Pro Asp Ser Pro Glu Thr
            260                 265                 270

Pro Leu Val Pro Thr Glu Pro Val Pro Pro Glu Pro Gly Thr Pro Ala
            275                 280                 285

Asn Cys Asp Pro Ala Leu Ser Phe Asp Ala Val Ser Thr Leu Arg Gly
            290                 295                 300

Glu Ile Leu Ile Phe Lys Asp Arg His Phe Trp Arg Lys Ser Leu Arg
305                 310                 315                 320

Lys Leu Glu Pro Glu Leu His Leu Ile Ser Ser Phe Trp Pro Ser Leu
            325                 330                 335

Pro Ser Gly Val Asp Ala Ala Tyr Glu Val Thr Ser Lys Asp Leu Val
            340                 345                 350

Phe Ile Phe Lys Gly Asn Gln Phe Trp Ala Ile Arg Gly Asn Glu Val
            355                 360                 365

Arg Ala Gly Tyr Pro Arg Gly Ile His Thr Leu Gly Phe Pro Pro Thr
370                 375                 380

Val Arg Lys Ile Asp Ala Ala Ile Ser Asp Lys Glu Lys Asn Lys Thr
385                 390                 395                 400

Tyr Phe Phe Val Glu Asp Lys Tyr Trp Arg Phe Asp Glu Lys Arg Asn
            405                 410                 415

Ser Met Glu Pro Gly Phe Pro Lys Gln Ile Ala Glu Asp Phe Pro Gly
            420                 425                 430

Ile Asp Ser Lys Ile Asp Ala Val Phe Glu Glu Phe Gly Phe Phe Tyr
            435                 440                 445

Phe Phe Thr Gly Ser Ser Gln Leu Glu Phe Asp Pro Asn Ala Lys Lys
450                 455                 460

Val Thr His Thr Leu Lys Ser Asn Ser Trp Leu Asn Cys
465                 470                 475

<210> SEQ ID NO 3
<211> LENGTH: 660
<212> TYPE: PRT
<213> ORGANISM: Homo sapiens

```
<400> SEQUENCE: 3

Met Glu Ala Leu Met Ala Arg Gly Ala Leu Thr Gly Pro Leu Arg Ala
1               5                   10                  15

Leu Cys Leu Leu Gly Cys Leu Leu Ser His Ala Ala Ala Ala Pro Ser
            20                  25                  30

Pro Ile Ile Lys Phe Pro Gly Asp Val Ala Pro Lys Thr Asp Lys Glu
        35                  40                  45

Leu Ala Val Gln Tyr Leu Asn Thr Phe Tyr Gly Cys Pro Lys Glu Ser
    50                  55                  60

Cys Asn Leu Phe Val Leu Lys Asp Thr Leu Lys Lys Met Gln Lys Phe
65                  70                  75                  80

Phe Gly Leu Pro Gln Thr Gly Asp Leu Asp Gln Asn Thr Ile Glu Thr
                85                  90                  95

Met Arg Lys Pro Arg Cys Gly Asn Pro Asp Val Ala Asn Tyr Asn Phe
            100                 105                 110

Phe Pro Arg Lys Pro Lys Trp Asp Lys Asn Gln Ile Thr Tyr Arg Ile
        115                 120                 125

Ile Gly Tyr Thr Pro Asp Leu Asp Pro Glu Thr Val Asp Asp Ala Phe
    130                 135                 140

Ala Arg Ala Phe Gln Val Trp Ser Asp Val Thr Pro Leu Arg Phe Ser
145                 150                 155                 160

Arg Ile His Asp Gly Glu Ala Asp Ile Met Ile Asn Phe Gly Arg Trp
                165                 170                 175

Glu His Gly Asp Gly Tyr Pro Phe Asp Gly Lys Asp Gly Leu Leu Ala
            180                 185                 190

His Ala Phe Ala Pro Gly Thr Gly Val Gly Gly Asp Ser His Phe Asp
        195                 200                 205

Asp Asp Glu Leu Trp Thr Leu Gly Glu Gly Gln Val Val Arg Val Lys
    210                 215                 220

Tyr Gly Asn Ala Asp Gly Glu Tyr Cys Lys Phe Pro Phe Leu Phe Asn
225                 230                 235                 240

Gly Lys Glu Tyr Asn Ser Cys Thr Asp Thr Gly Arg Ser Asp Gly Phe
                245                 250                 255

Leu Trp Cys Ser Thr Thr Tyr Asn Phe Glu Lys Asp Gly Lys Tyr Gly
            260                 265                 270

Phe Cys Pro His Glu Ala Leu Phe Thr Met Gly Gly Asn Ala Glu Gly
        275                 280                 285

Gln Pro Cys Lys Phe Pro Phe Arg Phe Gln Gly Thr Ser Tyr Asp Ser
    290                 295                 300

Cys Thr Thr Glu Gly Arg Thr Asp Gly Tyr Arg Trp Cys Gly Thr Thr
305                 310                 315                 320

Glu Asp Tyr Asp Arg Asp Lys Lys Tyr Gly Phe Cys Pro Glu Thr Ala
                325                 330                 335

Met Ser Thr Val Gly Gly Asn Ser Glu Gly Ala Pro Cys Val Phe Pro
            340                 345                 350

Phe Thr Phe Leu Gly Asn Lys Tyr Glu Ser Cys Thr Ser Ala Gly Arg
        355                 360                 365

Ser Asp Gly Lys Met Trp Cys Ala Thr Thr Ala Asn Tyr Asp Asp Asp
    370                 375                 380

Arg Lys Trp Gly Phe Cys Pro Asp Gln Gly Tyr Ser Leu Phe Leu Val
385                 390                 395                 400

Ala Ala His Glu Phe Gly His Ala Met Gly Leu Glu His Ser Gln Asp
                405                 410                 415
```

```
Pro Gly Ala Leu Met Ala Pro Ile Tyr Thr Tyr Lys Asn Phe Arg
            420                 425                 430

Leu Ser Gln Asp Asp Ile Lys Gly Ile Gln Glu Leu Tyr Gly Ala Ser
        435                 440                 445

Pro Asp Ile Asp Leu Gly Thr Gly Pro Thr Pro Thr Leu Gly Pro Val
        450                 455                 460

Thr Pro Glu Ile Cys Lys Gln Asp Ile Val Phe Asp Gly Ile Ala Gln
465                 470                 475                 480

Ile Arg Gly Glu Ile Phe Phe Lys Asp Arg Phe Ile Trp Arg Thr
                485                 490                 495

Val Thr Pro Arg Asp Lys Pro Met Gly Pro Leu Leu Val Ala Thr Phe
            500                 505                 510

Trp Pro Glu Leu Pro Glu Lys Ile Asp Ala Val Tyr Glu Ala Pro Gln
        515                 520                 525

Glu Glu Lys Ala Val Phe Phe Ala Gly Asn Glu Tyr Trp Ile Tyr Ser
        530                 535                 540

Ala Ser Thr Leu Glu Arg Gly Tyr Pro Lys Pro Leu Thr Ser Leu Gly
545                 550                 555                 560

Leu Pro Pro Asp Val Gln Arg Val Asp Ala Ala Phe Asn Trp Ser Lys
                565                 570                 575

Asn Lys Lys Thr Tyr Ile Phe Ala Gly Asp Lys Phe Trp Arg Tyr Asn
                580                 585                 590

Glu Val Lys Lys Lys Met Asp Pro Gly Phe Pro Lys Leu Ile Ala Asp
            595                 600                 605

Ala Trp Asn Ala Ile Pro Asp Asn Leu Asp Ala Val Val Asp Leu Gln
            610                 615                 620

Gly Gly His Ser Tyr Phe Phe Lys Gly Ala Tyr Tyr Leu Lys Leu
625                 630                 635                 640

Glu Asn Gln Ser Leu Lys Ser Val Lys Phe Gly Ser Ile Lys Ser Asp
                645                 650                 655

Trp Leu Gly Cys
            660

<210> SEQ ID NO 4
<211> LENGTH: 220
<212> TYPE: PRT
<213> ORGANISM: Homo sapiens

<400> SEQUENCE: 4

Met Gly Ala Ala Ala Arg Thr Leu Arg Leu Ala Leu Gly Leu Leu Leu
1               5                   10                  15

Leu Ala Thr Leu Leu Arg Pro Ala Asp Ala Cys Ser Cys Ser Pro Val
                20                  25                  30

His Pro Gln Gln Ala Phe Cys Asn Ala Asp Val Val Ile Arg Ala Lys
            35                  40                  45

Ala Val Ser Glu Lys Glu Val Asp Ser Gly Asn Asp Ile Tyr Gly Asn
        50                  55                  60

Pro Ile Lys Arg Ile Gln Tyr Glu Ile Lys Gln Ile Lys Met Phe Lys
65                  70                  75                  80

Gly Pro Glu Lys Asp Ile Glu Phe Ile Tyr Thr Ala Pro Ser Ser Ala
                85                  90                  95

Val Cys Gly Val Ser Leu Asp Val Gly Gly Lys Lys Glu Tyr Leu Ile
            100                 105                 110

Ala Gly Lys Ala Glu Gly Asp Gly Lys Met His Ile Thr Leu Cys Asp
        115                 120                 125
```

-continued

Phe Ile Val Pro Trp Asp Thr Leu Ser Thr Thr Gln Lys Lys Ser Leu
130                 135                 140

Asn His Arg Tyr Gln Met Gly Cys Glu Cys Lys Ile Thr Arg Cys Pro
145                 150                 155                 160

Met Ile Pro Cys Tyr Ile Ser Ser Pro Asp Glu Cys Leu Trp Met Asp
                165                 170                 175

Trp Val Thr Glu Lys Asn Ile Asn Gly His Gln Ala Lys Phe Phe Ala
                180                 185                 190

Cys Ile Lys Arg Ser Asp Gly Ser Cys Ala Trp Tyr Arg Gly Ala Ala
            195                 200                 205

Pro Pro Lys Gln Glu Phe Leu Asp Ile Glu Asp Pro
210                 215                 220

<210> SEQ ID NO 5
<211> LENGTH: 1367
<212> TYPE: PRT
<213> ORGANISM: Homo sapiens

<400> SEQUENCE: 5

Met Lys Ser Gly Ser Gly Gly Ser Pro Thr Ser Leu Trp Gly Leu
1               5                   10                  15

Leu Phe Leu Ser Ala Ala Leu Ser Leu Trp Pro Thr Ser Gly Glu Ile
                20                  25                  30

Cys Gly Pro Gly Ile Asp Ile Arg Asn Asp Tyr Gln Gln Leu Lys Arg
            35                  40                  45

Leu Glu Asn Cys Thr Val Ile Glu Gly Tyr Leu His Ile Leu Leu Ile
50                  55                  60

Ser Lys Ala Glu Asp Tyr Arg Ser Tyr Arg Phe Pro Lys Leu Thr Val
65                  70                  75                  80

Ile Thr Glu Tyr Leu Leu Leu Phe Arg Val Ala Gly Leu Glu Ser Leu
                85                  90                  95

Gly Asp Leu Phe Pro Asn Leu Thr Val Ile Arg Gly Trp Lys Leu Phe
            100                 105                 110

Tyr Asn Tyr Ala Leu Val Ile Phe Glu Met Thr Asn Leu Lys Asp Ile
        115                 120                 125

Gly Leu Tyr Asn Leu Arg Asn Ile Thr Arg Gly Ala Ile Arg Ile Glu
130                 135                 140

Lys Asn Ala Asp Leu Cys Tyr Leu Ser Thr Val Asp Trp Ser Leu Ile
145                 150                 155                 160

Leu Asp Ala Val Ser Asn Asn Tyr Ile Val Gly Asn Lys Pro Pro Lys
                165                 170                 175

Glu Cys Gly Asp Leu Cys Pro Gly Thr Met Glu Glu Lys Pro Met Cys
            180                 185                 190

Glu Lys Thr Thr Ile Asn Asn Glu Tyr Asn Tyr Arg Cys Trp Thr Thr
        195                 200                 205

Asn Arg Cys Gln Lys Met Cys Pro Ser Thr Cys Gly Lys Arg Ala Cys
210                 215                 220

Thr Glu Asn Asn Glu Cys Cys His Pro Glu Cys Leu Gly Ser Cys Ser
225                 230                 235                 240

Ala Pro Asp Asn Asp Thr Ala Cys Val Ala Cys Arg His Tyr Tyr Tyr
                245                 250                 255

Ala Gly Val Cys Val Pro Ala Cys Pro Pro Asn Thr Tyr Arg Phe Glu
            260                 265                 270

Gly Trp Arg Cys Val Asp Arg Asp Phe Cys Ala Asn Ile Leu Ser Ala
        275                 280                 285

```
Glu Ser Ser Asp Ser Glu Gly Phe Val Ile His Asp Gly Glu Cys Met
290                 295                 300
Gln Glu Cys Pro Ser Gly Phe Ile Arg Asn Gly Ser Gln Ser Met Tyr
305                 310                 315                 320
Cys Ile Pro Cys Glu Gly Pro Cys Pro Lys Val Cys Glu Glu Glu Lys
                325                 330                 335
Lys Thr Lys Thr Ile Asp Ser Val Thr Ser Ala Gln Met Leu Gln Gly
            340                 345                 350
Cys Thr Ile Phe Lys Gly Asn Leu Leu Ile Asn Ile Arg Arg Gly Asn
        355                 360                 365
Asn Ile Ala Ser Glu Leu Glu Asn Phe Met Gly Leu Ile Glu Val Val
370                 375                 380
Thr Gly Tyr Val Lys Ile Arg His Ser His Ala Leu Val Ser Leu Ser
385                 390                 395                 400
Phe Leu Lys Asn Leu Arg Leu Ile Leu Gly Glu Glu Gln Leu Glu Gly
                405                 410                 415
Asn Tyr Ser Phe Tyr Val Leu Asp Asn Gln Asn Leu Gln Gln Leu Trp
            420                 425                 430
Asp Trp Asp His Arg Asn Leu Thr Ile Lys Ala Gly Lys Met Tyr Phe
        435                 440                 445
Ala Phe Asn Pro Lys Leu Cys Val Ser Glu Ile Tyr Arg Met Glu Glu
450                 455                 460
Val Thr Gly Thr Lys Gly Arg Gln Ser Lys Gly Asp Ile Asn Thr Arg
465                 470                 475                 480
Asn Asn Gly Glu Arg Ala Ser Cys Glu Ser Asp Val Leu His Phe Thr
                485                 490                 495
Ser Thr Thr Thr Ser Lys Asn Arg Ile Ile Ile Thr Trp His Arg Tyr
            500                 505                 510
Arg Pro Pro Asp Tyr Arg Asp Leu Ile Ser Phe Thr Val Tyr Tyr Lys
        515                 520                 525
Glu Ala Pro Phe Lys Asn Val Thr Glu Tyr Asp Gly Gln Asp Ala Cys
530                 535                 540
Gly Ser Asn Ser Trp Asn Met Val Asp Val Asp Leu Pro Pro Asn Lys
545                 550                 555                 560
Asp Val Glu Pro Gly Ile Leu Leu His Gly Leu Lys Pro Trp Thr Gln
                565                 570                 575
Tyr Ala Val Tyr Val Lys Ala Val Thr Leu Thr Met Val Glu Asn Asp
            580                 585                 590
His Ile Arg Gly Ala Lys Ser Glu Ile Leu Tyr Ile Arg Thr Asn Ala
        595                 600                 605
Ser Val Pro Ser Ile Pro Leu Asp Val Leu Ser Ala Ser Asn Ser Ser
610                 615                 620
Ser Gln Leu Ile Val Lys Trp Asn Pro Pro Ser Leu Pro Asn Gly Asn
625                 630                 635                 640
Leu Ser Tyr Tyr Ile Val Arg Trp Gln Arg Gln Pro Gln Asp Gly Tyr
                645                 650                 655
Leu Tyr Arg His Asn Tyr Cys Ser Lys Asp Lys Ile Pro Ile Arg Lys
            660                 665                 670
Tyr Ala Asp Gly Thr Ile Asp Ile Glu Glu Val Thr Glu Asn Pro Lys
        675                 680                 685
Thr Glu Val Cys Gly Gly Glu Lys Gly Pro Cys Cys Ala Cys Pro Lys
690                 695                 700
```

-continued

Thr Glu Ala Glu Lys Gln Ala Glu Lys Glu Ala Glu Tyr Arg Lys
705                 710                 715                 720

Val Phe Glu Asn Phe Leu His Asn Ser Ile Phe Val Pro Arg Pro Glu
            725                 730                 735

Arg Lys Arg Arg Asp Val Met Gln Val Ala Asn Thr Thr Met Ser Ser
        740                 745                 750

Arg Ser Arg Asn Thr Thr Ala Ala Asp Thr Tyr Asn Ile Thr Asp Pro
    755                 760                 765

Glu Glu Leu Glu Thr Glu Tyr Pro Phe Glu Ser Arg Val Asp Asn
770                 775                 780

Lys Glu Arg Thr Val Ile Ser Asn Leu Arg Pro Phe Thr Leu Tyr Arg
785                 790                 795                 800

Ile Asp Ile His Ser Cys Asn His Glu Ala Glu Lys Leu Gly Cys Ser
                805                 810                 815

Ala Ser Asn Phe Val Phe Ala Arg Thr Met Pro Ala Glu Gly Ala Asp
            820                 825                 830

Asp Ile Pro Gly Pro Val Thr Trp Glu Pro Arg Pro Glu Asn Ser Ile
        835                 840                 845

Phe Leu Lys Trp Pro Glu Pro Glu Asn Pro Asn Gly Leu Ile Leu Met
    850                 855                 860

Tyr Glu Ile Lys Tyr Gly Ser Gln Val Glu Asp Gln Arg Glu Cys Val
865                 870                 875                 880

Ser Arg Gln Glu Tyr Arg Lys Tyr Gly Gly Ala Lys Leu Asn Arg Leu
                885                 890                 895

Asn Pro Gly Asn Tyr Thr Ala Arg Ile Gln Ala Thr Ser Leu Ser Gly
            900                 905                 910

Asn Gly Ser Trp Thr Asp Pro Val Phe Phe Tyr Val Gln Ala Lys Thr
        915                 920                 925

Gly Tyr Glu Asn Phe Ile His Leu Ile Ile Ala Leu Pro Val Ala Val
    930                 935                 940

Leu Leu Ile Val Gly Gly Leu Val Ile Met Leu Tyr Val Phe His Arg
945                 950                 955                 960

Lys Arg Asn Asn Ser Arg Leu Gly Asn Gly Val Leu Tyr Ala Ser Val
                965                 970                 975

Asn Pro Glu Tyr Phe Ser Ala Ala Asp Val Tyr Val Pro Asp Glu Trp
            980                 985                 990

Glu Val Ala Arg Glu Lys Ile Thr Met Ser Arg Glu Leu Gly Gln Gly
        995                 1000                1005

Ser Phe Gly Met Val Tyr Glu Gly Val Ala Lys Gly Val Val Lys
    1010                1015                1020

Asp Glu Pro Glu Thr Arg Val Ala Ile Lys Thr Val Asn Glu Ala
    1025                1030                1035

Ala Ser Met Arg Glu Arg Ile Glu Phe Leu Asn Glu Ala Ser Val
    1040                1045                1050

Met Lys Glu Phe Asn Cys His His Val Val Arg Leu Leu Gly Val
    1055                1060                1065

Val Ser Gln Gly Gln Pro Thr Leu Val Ile Met Glu Leu Met Thr
    1070                1075                1080

Arg Gly Asp Leu Lys Ser Tyr Leu Arg Ser Leu Arg Pro Glu Met
    1085                1090                1095

Glu Asn Asn Pro Val Leu Ala Pro Pro Ser Leu Ser Lys Met Ile
    1100                1105                1110

-continued

Gln Met Ala Gly Glu Ile Ala Asp Gly Met Ala Tyr Leu Asn Ala
1115                1120                1125

Asn Lys Phe Val His Arg Asp Leu Ala Ala Arg Asn Cys Met Val
1130                1135                1140

Ala Glu Asp Phe Thr Val Lys Ile Gly Asp Phe Gly Met Thr Arg
1145                1150                1155

Asp Ile Tyr Glu Thr Asp Tyr Tyr Arg Lys Gly Gly Lys Gly Leu
1160                1165                1170

Leu Pro Val Arg Trp Met Ser Pro Glu Ser Leu Lys Asp Gly Val
1175                1180                1185

Phe Thr Thr Tyr Ser Asp Val Trp Ser Phe Gly Val Val Leu Trp
1190                1195                1200

Glu Ile Ala Thr Leu Ala Glu Gln Pro Tyr Gln Gly Leu Ser Asn
1205                1210                1215

Glu Gln Val Leu Arg Phe Val Met Glu Gly Gly Leu Leu Asp Lys
1220                1225                1230

Pro Asp Asn Cys Pro Asp Met Leu Phe Glu Leu Met Arg Met Cys
1235                1240                1245

Trp Gln Tyr Asn Pro Lys Met Arg Pro Ser Phe Leu Glu Ile Ile
1250                1255                1260

Ser Ser Ile Lys Glu Glu Met Glu Pro Gly Phe Arg Glu Val Ser
1265                1270                1275

Phe Tyr Tyr Ser Glu Glu Asn Lys Leu Pro Glu Pro Glu Glu Leu
1280                1285                1290

Asp Leu Glu Pro Glu Asn Met Glu Ser Val Pro Leu Asp Pro Ser
1295                1300                1305

Ala Ser Ser Ser Ser Leu Pro Leu Pro Asp Arg His Ser Gly His
1310                1315                1320

Lys Ala Glu Asn Gly Pro Gly Pro Gly Val Leu Val Leu Arg Ala
1325                1330                1335

Ser Phe Asp Glu Arg Gln Pro Tyr Ala His Met Asn Gly Gly Arg
1340                1345                1350

Lys Asn Glu Arg Ala Leu Pro Leu Pro Gln Ser Ser Thr Cys
1355                1360                1365

<210> SEQ ID NO 6
<211> LENGTH: 296
<212> TYPE: PRT
<213> ORGANISM: Homo sapiens

<400> SEQUENCE: 6

Met Ala Ala Gly Gly Pro Gly Ala Gly Ser Ala Ala Pro Val Ser Ser
1               5                   10                  15

Thr Ser Ser Leu Pro Leu Ala Ala Leu Asn Met Arg Val Arg Arg Arg
                20                  25                  30

Leu Ser Leu Phe Leu Asn Val Arg Thr Gln Val Ala Ala Asp Trp Thr
            35                  40                  45

Ala Leu Ala Glu Glu Met Asp Phe Glu Tyr Leu Glu Ile Arg Gln Leu
        50                  55                  60

Glu Thr Gln Ala Asp Pro Thr Gly Arg Leu Leu Asp Ala Trp Gln Gly
65                  70                  75                  80

Arg Pro Gly Ala Ser Val Gly Arg Leu Leu Glu Leu Leu Thr Lys Leu
                85                  90                  95

Gly Arg Asp Asp Val Leu Leu Glu Leu Gly Pro Ser Ile Glu Glu Asp
                100                 105                 110

```
Cys Gln Lys Tyr Ile Leu Lys Gln Gln Glu Glu Ala Glu Lys Pro
            115                 120                 125
Leu Gln Val Ala Ala Val Asp Ser Ser Val Pro Arg Thr Ala Glu Leu
    130                 135                 140
Ala Gly Ile Thr Thr Leu Asp Asp Pro Leu Gly His Met Pro Glu Arg
145                 150                 155                 160
Phe Asp Ala Phe Ile Cys Tyr Cys Pro Ser Asp Ile Gln Phe Val Gln
                165                 170                 175
Glu Met Ile Arg Gln Leu Glu Gln Thr Asn Tyr Arg Leu Lys Leu Cys
            180                 185                 190
Val Ser Asp Arg Asp Val Leu Pro Gly Thr Cys Val Trp Ser Ile Ala
        195                 200                 205
Ser Glu Leu Ile Glu Lys Arg Cys Arg Arg Met Val Val Val Val Ser
    210                 215                 220
Asp Asp Tyr Leu Gln Ser Lys Glu Cys Asp Phe Gln Thr Lys Phe Ala
225                 230                 235                 240
Leu Ser Leu Ser Pro Gly Ala His Gln Lys Arg Leu Ile Pro Ile Lys
                245                 250                 255
Tyr Lys Ala Met Lys Lys Glu Phe Pro Ser Ile Leu Arg Phe Ile Thr
            260                 265                 270
Val Cys Asp Tyr Thr Asn Pro Cys Thr Lys Ser Trp Phe Trp Thr Arg
        275                 280                 285
Leu Ala Lys Ala Leu Ser Leu Pro
    290                 295

<210> SEQ ID NO 7
<211> LENGTH: 1304
<212> TYPE: PRT
<213> ORGANISM: Homo sapiens

<400> SEQUENCE: 7

Met Gln Leu Lys Ile Met Pro Lys Lys Arg Leu Ser Ala Gly Arg
1               5                   10                  15
Val Pro Leu Ile Leu Phe Leu Cys Gln Met Ile Ser Ala Leu Glu Val
            20                  25                  30
Pro Leu Asp Pro Lys Leu Leu Glu Asp Leu Val Gln Pro Thr Ile
        35                  40                  45
Thr Gln Gln Ser Pro Lys Asp Tyr Ile Ile Asp Pro Arg Glu Asn Ile
    50                  55                  60
Val Ile Gln Cys Glu Ala Lys Gly Lys Pro Pro Pro Ser Phe Ser Trp
65                  70                  75                  80
Thr Arg Asn Gly Thr His Phe Asp Ile Asp Lys Asp Pro Leu Val Thr
                85                  90                  95
Met Lys Pro Gly Thr Gly Thr Leu Ile Ile Asn Ile Met Ser Glu Gly
            100                 105                 110
Lys Ala Glu Thr Tyr Glu Gly Val Tyr Gln Cys Thr Ala Arg Asn Glu
        115                 120                 125
Arg Gly Ala Ala Val Ser Asn Asn Ile Val Val Arg Pro Ser Arg Ser
    130                 135                 140
Pro Leu Trp Thr Lys Glu Lys Leu Glu Pro Ile Thr Leu Gln Ser Gly
145                 150                 155                 160
Gln Ser Leu Val Leu Pro Cys Arg Pro Pro Ile Gly Leu Pro Pro Pro
                165                 170                 175
Ile Ile Phe Trp Met Asp Asn Ser Phe Gln Arg Leu Pro Gln Ser Glu
            180                 185                 190
```

```
Arg Val Ser Gln Gly Leu Asn Gly Asp Leu Tyr Phe Ser Asn Val Leu
        195                 200                 205

Pro Glu Asp Thr Arg Glu Asp Tyr Ile Cys Tyr Ala Arg Phe Asn His
    210                 215                 220

Thr Gln Thr Ile Gln Gln Lys Gln Pro Ile Ser Val Lys Val Ile Ser
225                 230                 235                 240

Val Asp Glu Leu Asn Asp Thr Ile Ala Ala Asn Leu Ser Asp Thr Glu
                245                 250                 255

Phe Tyr Gly Ala Lys Ser Ser Arg Glu Arg Pro Pro Thr Phe Leu Thr
            260                 265                 270

Pro Glu Gly Asn Ala Ser Asn Lys Glu Glu Leu Arg Gly Asn Val Leu
        275                 280                 285

Ser Leu Glu Cys Ile Ala Glu Gly Leu Pro Thr Pro Ile Ile Tyr Trp
    290                 295                 300

Ala Lys Glu Asp Gly Met Leu Pro Lys Asn Arg Thr Val Tyr Lys Asn
305                 310                 315                 320

Phe Glu Lys Thr Leu Gln Ile Ile His Val Ser Glu Ala Asp Ser Gly
                325                 330                 335

Asn Tyr Gln Cys Ile Ala Lys Asn Ala Leu Gly Ala Ile His His Thr
            340                 345                 350

Ile Ser Val Arg Val Lys Ala Ala Pro Tyr Trp Ile Thr Ala Pro Gln
        355                 360                 365

Asn Leu Val Leu Ser Pro Gly Glu Asp Gly Thr Leu Ile Cys Arg Ala
    370                 375                 380

Asn Gly Asn Pro Lys Pro Arg Ile Ser Trp Leu Thr Asn Gly Val Pro
385                 390                 395                 400

Ile Glu Ile Ala Pro Asp Asp Pro Ser Arg Lys Ile Asp Gly Asp Thr
                405                 410                 415

Ile Ile Phe Ser Asn Val Gln Glu Arg Ser Ala Val Tyr Gln Cys
            420                 425                 430

Asn Ala Ser Asn Glu Tyr Gly Tyr Leu Leu Ala Asn Ala Phe Val Asn
        435                 440                 445

Val Leu Ala Glu Pro Pro Arg Ile Leu Thr Pro Ala Asn Thr Leu Tyr
    450                 455                 460

Gln Val Ile Ala Asn Arg Pro Ala Leu Leu Asp Cys Ala Phe Phe Gly
465                 470                 475                 480

Ser Pro Leu Pro Thr Ile Glu Trp Phe Lys Gly Ala Lys Gly Ser Ala
                485                 490                 495

Leu His Glu Asp Ile Tyr Val Leu His Glu Asn Gly Thr Leu Glu Ile
            500                 505                 510

Pro Val Ala Gln Lys Asp Ser Thr Gly Thr Tyr Thr Cys Val Ala Arg
        515                 520                 525

Asn Lys Leu Gly Met Ala Lys Asn Glu Val His Leu Glu Ile Lys Asp
    530                 535                 540

Pro Thr Trp Ile Val Lys Gln Pro Glu Tyr Ala Val Val Gln Arg Gly
545                 550                 555                 560

Ser Met Val Ser Phe Glu Cys Lys Val Lys His Asp His Thr Leu Ser
                565                 570                 575

Leu Thr Val Leu Trp Leu Lys Asp Asn Arg Glu Leu Pro Ser Asp Glu
            580                 585                 590

Arg Phe Thr Val Asp Lys Asp His Leu Val Val Ala Asp Val Ser Asp
        595                 600                 605
```

-continued

Asp Asp Ser Gly Thr Tyr Thr Cys Val Ala Asn Thr Thr Leu Asp Ser
610                 615                 620

Val Ser Ala Ser Ala Val Leu Ser Val Val Ala Pro Thr Pro Thr Pro
625                 630                 635                 640

Ala Pro Val Tyr Asp Val Pro Asn Pro Pro Phe Asp Leu Glu Leu Thr
            645                 650                 655

Asp Gln Leu Asp Lys Ser Val Gln Leu Ser Trp Thr Pro Gly Asp Asp
            660                 665                 670

Asn Asn Ser Pro Ile Thr Lys Phe Ile Ile Glu Tyr Glu Asp Ala Met
        675                 680                 685

His Lys Pro Gly Leu Trp His His Gln Thr Glu Val Ser Gly Thr Gln
690                 695                 700

Thr Thr Ala Gln Leu Lys Leu Ser Pro Tyr Val Asn Tyr Ser Phe Arg
705                 710                 715                 720

Val Met Ala Val Asn Ser Ile Gly Lys Ser Leu Pro Ser Glu Ala Ser
                725                 730                 735

Glu Gln Tyr Leu Thr Lys Ala Ser Glu Pro Asp Lys Asn Pro Thr Ala
            740                 745                 750

Val Glu Gly Leu Gly Ser Glu Pro Asp Asn Leu Val Ile Thr Trp Lys
            755                 760                 765

Pro Leu Asn Gly Phe Glu Ser Asn Gly Pro Gly Leu Gln Tyr Lys Val
770                 775                 780

Ser Trp Arg Gln Lys Asp Gly Asp Glu Trp Thr Ser Val Val Val
785                 790                 795                 800

Ala Asn Val Ser Lys Tyr Ile Val Ser Gly Thr Pro Thr Phe Val Pro
                805                 810                 815

Tyr Leu Ile Lys Val Gln Ala Leu Asn Asp Met Gly Phe Ala Pro Glu
            820                 825                 830

Pro Ala Val Val Met Gly His Ser Gly Glu Asp Leu Pro Met Val Ala
            835                 840                 845

Pro Gly Asn Val Arg Val Asn Val Val Asn Ser Thr Leu Ala Glu Val
850                 855                 860

His Trp Asp Pro Val Pro Leu Lys Ser Ile Arg Gly His Leu Gln Gly
865                 870                 875                 880

Tyr Arg Ile Tyr Tyr Trp Lys Thr Gln Ser Ser Ser Lys Arg Asn Arg
                885                 890                 895

Arg His Ile Glu Lys Lys Ile Leu Thr Phe Gln Gly Ser Lys Thr His
            900                 905                 910

Gly Met Leu Pro Gly Leu Glu Pro Phe Ser His Tyr Thr Leu Asn Val
            915                 920                 925

Arg Val Val Asn Gly Lys Gly Glu Gly Pro Ala Ser Pro Asp Arg Val
930                 935                 940

Phe Asn Thr Pro Glu Gly Val Pro Ser Ala Pro Ser Ser Leu Lys Ile
945                 950                 955                 960

Val Asn Pro Thr Leu Asp Ser Leu Thr Leu Glu Trp Asp Pro Pro Ser
                965                 970                 975

His Pro Asn Gly Ile Leu Thr Glu Tyr Thr Leu Lys Tyr Gln Pro Ile
            980                 985                 990

Asn Ser Thr His Glu Leu Gly Pro  Leu Val Asp Leu Lys  Ile Pro Ala
            995                 1000                1005

Asn Lys  Thr Arg Trp Thr Leu  Lys Asn Leu Asn Phe  Ser Thr Arg
    1010                1015                1020

-continued

```
Tyr Lys Phe Tyr Phe Tyr Ala Gln Thr Ser Ala Gly Ser Gly Ser
    1025                1030                1035

Gln Ile Thr Glu Glu Ala Val Thr Thr Val Asp Glu Ala Gly Ile
    1040                1045                1050

Leu Pro Pro Asp Val Gly Ala Gly Lys Val Gln Ala Val Asn Thr
    1055                1060                1065

Arg Ile Ser Asn Leu Thr Ala Ala Ala Ala Glu Thr Tyr Ala Asn
    1070                1075                1080

Ile Ser Trp Glu Tyr Glu Gly Pro Glu His Val Asn Phe Tyr Val
    1085                1090                1095

Glu Tyr Gly Val Ala Gly Ser Lys Glu Glu Trp Arg Lys Glu Ile
    1100                1105                1110

Val Asn Gly Ser Arg Ser Phe Phe Gly Leu Lys Gly Leu Met Pro
    1115                1120                1125

Gly Thr Ala Tyr Lys Val Arg Val Gly Ala Val Gly Asp Ser Gly
    1130                1135                1140

Phe Val Ser Ser Glu Asp Val Phe Glu Thr Gly Pro Ala Met Ala
    1145                1150                1155

Ser Arg Gln Val Asp Ile Ala Thr Gln Gly Trp Phe Ile Gly Leu
    1160                1165                1170

Met Cys Ala Val Ala Leu Leu Ile Leu Ile Leu Leu Ile Val Cys
    1175                1180                1185

Phe Ile Arg Arg Asn Lys Gly Gly Lys Tyr Pro Val Lys Glu Lys
    1190                1195                1200

Glu Asp Ala His Ala Asp Pro Glu Ile Gln Pro Met Lys Glu Asp
    1205                1210                1215

Asp Gly Thr Phe Gly Glu Tyr Ser Asp Ala Glu Asp His Lys Pro
    1220                1225                1230

Leu Lys Lys Gly Ser Arg Thr Pro Ser Asp Arg Thr Val Lys Lys
    1235                1240                1245

Glu Asp Ser Asp Asp Ser Leu Val Asp Tyr Gly Glu Gly Val Asn
    1250                1255                1260

Gly Gln Phe Asn Glu Asp Gly Ser Phe Ile Gly Gln Tyr Ser Gly
    1265                1270                1275

Lys Lys Glu Lys Glu Pro Ala Glu Gly Asn Glu Ser Ser Glu Ala
    1280                1285                1290

Pro Ser Pro Val Asn Ala Met Asn Ser Phe Val
    1295                1300

<210> SEQ ID NO 8
<211> LENGTH: 281
<212> TYPE: PRT
<213> ORGANISM: Homo sapiens

<400> SEQUENCE: 8

Met Ala Met Met Glu Val Gln Gly Gly Pro Ser Leu Gly Gln Thr Cys
1               5                   10                  15

Val Leu Ile Val Ile Phe Thr Val Leu Leu Gln Ser Leu Cys Val Ala
                20                  25                  30

Val Thr Tyr Val Tyr Phe Thr Asn Glu Leu Lys Gln Met Gln Asp Lys
            35                  40                  45

Tyr Ser Lys Ser Gly Ile Ala Cys Phe Leu Lys Glu Asp Asp Ser Tyr
        50                  55                  60

Trp Asp Pro Asn Asp Glu Glu Ser Met Asn Ser Pro Cys Trp Gln Val
65                  70                  75                  80
```

```
Lys Trp Gln Leu Arg Gln Leu Val Arg Lys Met Ile Leu Arg Thr Ser
                85                  90                  95

Glu Glu Thr Ile Ser Thr Val Gln Glu Lys Gln Gln Asn Ile Ser Pro
            100                 105                 110

Leu Val Arg Glu Arg Gly Pro Gln Arg Val Ala Ala His Ile Thr Gly
            115                 120                 125

Thr Arg Gly Arg Ser Asn Thr Leu Ser Ser Pro Asn Ser Lys Asn Glu
        130                 135                 140

Lys Ala Leu Gly Arg Lys Ile Asn Ser Trp Glu Ser Ser Arg Ser Gly
145                 150                 155                 160

His Ser Phe Leu Ser Asn Leu His Leu Arg Asn Gly Glu Leu Val Ile
                165                 170                 175

His Glu Lys Gly Phe Tyr Tyr Ile Tyr Ser Gln Thr Tyr Phe Arg Phe
            180                 185                 190

Gln Glu Glu Ile Lys Glu Asn Thr Lys Asn Asp Lys Gln Met Val Gln
            195                 200                 205

Tyr Ile Tyr Lys Tyr Thr Ser Tyr Pro Asp Pro Ile Leu Leu Met Lys
        210                 215                 220

Ser Ala Arg Asn Ser Cys Trp Ser Lys Asp Ala Glu Tyr Gly Leu Tyr
225                 230                 235                 240

Ser Ile Tyr Gln Gly Gly Ile Phe Glu Leu Lys Glu Asn Asp Arg Ile
                245                 250                 255

Phe Val Ser Val Thr Asn Glu His Leu Ile Asp Met Asp His Glu Ala
            260                 265                 270

Ser Phe Phe Gly Ala Phe Leu Val Gly
        275                 280

<210> SEQ ID NO 9
<211> LENGTH: 418
<212> TYPE: PRT
<213> ORGANISM: Homo sapiens

<400> SEQUENCE: 9

Met Pro Ser Ser Val Ser Trp Gly Ile Leu Leu Leu Ala Gly Leu Cys
1               5                   10                  15

Cys Leu Val Pro Val Ser Leu Ala Glu Asp Pro Gln Gly Asp Ala Ala
                20                  25                  30

Gln Lys Thr Asp Thr Ser His His Asp Gln Asp His Pro Thr Phe Asn
            35                  40                  45

Lys Ile Thr Pro Asn Leu Ala Glu Phe Ala Phe Ser Leu Tyr Arg Gln
        50                  55                  60

Leu Ala His Gln Ser Asn Ser Thr Asn Ile Phe Phe Ser Pro Val Ser
65                  70                  75                  80

Ile Ala Thr Ala Phe Ala Met Leu Ser Leu Gly Thr Lys Ala Asp Thr
                85                  90                  95

His Asp Glu Ile Leu Glu Gly Leu Asn Phe Asn Leu Thr Glu Ile Pro
            100                 105                 110

Glu Ala Gln Ile His Glu Gly Phe Gln Glu Leu Leu Arg Thr Leu Asn
            115                 120                 125

Gln Pro Asp Ser Gln Leu Gln Leu Thr Thr Gly Asn Gly Leu Phe Leu
        130                 135                 140

Ser Glu Gly Leu Lys Leu Val Asp Lys Phe Leu Glu Asp Val Lys Lys
145                 150                 155                 160

Leu Tyr His Ser Glu Ala Phe Thr Val Asn Phe Gly Asp Thr Glu Glu
                165                 170                 175
```

Ala Lys Lys Gln Ile Asn Asp Tyr Val Glu Lys Gly Thr Gln Gly Lys
            180                 185                 190

Ile Val Asp Leu Val Lys Glu Leu Asp Arg Asp Thr Val Phe Ala Leu
            195                 200                 205

Val Asn Tyr Ile Phe Phe Lys Gly Lys Trp Glu Arg Pro Phe Glu Val
            210                 215                 220

Lys Asp Thr Glu Glu Asp Phe His Val Asp Gln Val Thr Thr Val
225                 230                 235                 240

Lys Val Pro Met Met Lys Arg Leu Gly Met Phe Asn Ile Gln His Cys
            245                 250                 255

Lys Lys Leu Ser Ser Trp Val Leu Leu Met Lys Tyr Leu Gly Asn Ala
            260                 265                 270

Thr Ala Ile Phe Phe Leu Pro Asp Glu Gly Lys Leu Gln His Leu Glu
            275                 280                 285

Asn Glu Leu Thr His Asp Ile Ile Thr Lys Phe Leu Glu Asn Glu Asp
            290                 295                 300

Arg Arg Ser Ala Ser Leu His Leu Pro Lys Leu Ser Ile Thr Gly Thr
305                 310                 315                 320

Tyr Asp Leu Lys Ser Val Leu Gly Gln Leu Gly Ile Thr Lys Val Phe
            325                 330                 335

Ser Asn Gly Ala Asp Leu Ser Gly Val Thr Glu Glu Ala Pro Leu Lys
            340                 345                 350

Leu Ser Lys Ala Val His Lys Ala Val Leu Thr Ile Asp Glu Lys Gly
            355                 360                 365

Thr Glu Ala Ala Gly Ala Met Phe Leu Glu Ala Ile Pro Met Ser Ile
            370                 375                 380

Pro Pro Glu Val Lys Phe Asn Lys Pro Phe Val Phe Leu Met Ile Glu
385                 390                 395                 400

Gln Asn Thr Lys Ser Pro Leu Phe Met Gly Lys Val Val Asn Pro Thr
            405                 410                 415

Gln Lys

<210> SEQ ID NO 10
<211> LENGTH: 267
<212> TYPE: PRT
<213> ORGANISM: Homo sapiens

<400> SEQUENCE: 10

Met Thr Leu Gly Arg Arg Leu Ala Cys Leu Phe Leu Ala Cys Val Leu
1               5                   10                  15

Pro Ala Leu Leu Leu Gly Gly Thr Ala Leu Ala Ser Glu Ile Val Gly
            20                  25                  30

Gly Arg Arg Ala Arg Pro His Ala Trp Pro Phe Met Val Ser Leu Gln
            35                  40                  45

Leu Arg Gly Gly His Phe Cys Gly Ala Thr Leu Ile Ala Pro Asn Phe
            50                  55                  60

Val Met Ser Ala Ala His Cys Val Ala Asn Val Asn Val Arg Ala Val
65                  70                  75                  80

Arg Val Val Leu Gly Ala His Asn Leu Ser Arg Arg Glu Pro Thr Arg
            85                  90                  95

Gln Val Phe Ala Val Gln Arg Ile Phe Glu Asn Gly Tyr Asp Pro Val
            100                 105                 110

Asn Leu Leu Asn Asp Ile Val Ile Leu Gln Leu Asn Gly Ser Ala Thr
            115                 120                 125

```
Ile Asn Ala Asn Val Gln Val Ala Gln Leu Pro Ala Gln Gly Arg Arg
    130             135             140

Leu Gly Asn Gly Val Gln Cys Leu Ala Met Gly Trp Gly Leu Leu Gly
145             150             155             160

Arg Asn Arg Gly Ile Ala Ser Val Leu Gln Glu Leu Asn Val Thr Val
                165             170             175

Val Thr Ser Leu Cys Arg Arg Ser Asn Val Cys Thr Leu Val Arg Gly
            180             185             190

Arg Gln Ala Gly Val Cys Phe Gly Asp Ser Gly Ser Pro Leu Val Cys
        195             200             205

Asn Gly Leu Ile His Gly Ile Ala Ser Phe Val Arg Gly Gly Cys Ala
    210             215             220

Ser Gly Leu Tyr Pro Asp Ala Phe Ala Pro Val Ala Gln Phe Val Asn
225             230             235             240

Trp Ile Asp Ser Ile Ile Gln Arg Ser Glu Asp Asn Pro Cys Pro His
            245             250             255

Pro Arg Asp Pro Asp Pro Ala Ser Arg Thr His
            260             265
```

METHODS AND COMPOSITIONS FOR DIAGNOSIS AND PROGNOSIS OF RENAL INJURY AND RENAL FAILURE

The present invention is filed under 35 U.S.C. §371 as the U.S. national phase of International Application No. PCT/US2012/052298, filed Aug. 24, 2012, which designated the U.S. and claims priority to provisional U.S. patent application 61/528,000 filed Aug. 26, 2011, and to provisional U.S. patent application 61/528,003 filed Aug. 26, 2011, which is hereby incorporated in its entirety including all tables, figures, and claims.

SEQUENCE LISTING

The instant application contains a Sequence Listing which has been submitted in ASCII format via EFS-Web and is hereby incorporated by reference in its entirety. Said ASCII copy, created on Feb. 25, 2014, is named AST8104US_SeqListing.txt and is 51 kilobytes in size.

BACKGROUND OF THE INVENTION

The following discussion of the background of the invention is merely provided to aid the reader in understanding the invention and is not admitted to describe or constitute prior art to the present invention.

The kidney is responsible for water and solute excretion from the body. Its functions include maintenance of acid-base balance, regulation of electrolyte concentrations, control of blood volume, and regulation of blood pressure. As such, loss of kidney function through injury and/or disease results in substantial morbidity and mortality. A detailed discussion of renal injuries is provided in Harrison's Principles of Internal Medicine, 17$^{th}$ Ed., McGraw Hill, New York, pages 1741-1830, which are hereby incorporated by reference in their entirety. Renal disease and/or injury may be acute or chronic. Acute and chronic kidney disease are described as follows (from Current Medical Diagnosis & Treatment 2008, 47$^{th}$ Ed, McGraw Hill, New York, pages 785-815, which are hereby incorporated by reference in their entirety): "Acute renal failure is worsening of renal function over hours to days, resulting in the retention of nitrogenous wastes (such as urea nitrogen) and creatinine in the blood. Retention of these substances is called azotemia. Chronic renal failure (chronic kidney disease) results from an abnormal loss of renal function over months to years".

Acute renal failure (ARF, also known as acute kidney injury, or AKI) is an abrupt (typically detected within about 48 hours to 1 week) reduction in glomerular filtration. This loss of filtration capacity results in retention of nitrogenous (urea and creatinine) and non-nitrogenous waste products that are normally excreted by the kidney, a reduction in urine output, or both. It is reported that ARF complicates about 5% of hospital admissions, 4-15% of cardiopulmonary bypass surgeries, and up to 30% of intensive care admissions. ARF may be categorized as prerenal, intrinsic renal, or postrenal in causation. Intrinsic renal disease can be further divided into glomerular, tubular, interstitial, and vascular abnormalities. Major causes of ARF are described in the following table, which is adapted from the Merck Manual, 17$^{th}$ ed., Chapter 222, and which is hereby incorporated by reference in their entirety:

| Type<br>Prerenal | Risk Factors |
| --- | --- |
| ECF volume depletion | Excessive diuresis, hemorrhage, GI losses, loss of intravascular fluid into the extravascular space (due to ascites, peritonitis, pancreatitis, or burns), loss of skin and mucus membranes, renal salt- and water-wasting states |
| Low cardiac output | Cardiomyopathy, MI, cardiac tamponade, pulmonary embolism, pulmonary hypertension, positive-pressure mechanical ventilation |
| Low systemic vascular resistance | Septic shock, liver failure, antihypertensive drugs |
| Increased renal vascular resistance | NSAIDs, cyclosporines, tacrolimus, hypercalcemia, anaphylaxis, anesthetics, renal artery obstruction, renal vein thrombosis, sepsis, hepatorenal syndrome |
| Decreased efferent arteriolar tone (leading to decreased GFR from reduced glomerular transcapillary pressure, especially in patients with bilateral renal artery stenosis)<br>Intrinsic Renal | ACE inhibitors or angiotensin II receptor blockers |
| Acute tubular injury | Ischemia (prolonged or severe prerenal state): surgery, hemorrhage, arterial or venous obstruction; Toxins: NSAIDs, cyclosporines, tacrolimus, aminoglycosides, foscarnet, ethylene glycol, hemoglobin, myoglobin, ifosfamide, heavy metals, methotrexate, radiopaque contrast agents, streptozotocin |
| Acute glomerulonephritis | ANCA-associated: Crescentic glomerulonephritis, polyarteritis nodosa, Wegener's granulomatosis; Anti-GBM glomerulonephritis: Goodpasture's syndrome; Immune-complex: Lupus glomerulonephritis, postinfectious glomerulonephritis, cryoglobulinemic glomerulonephritis |
| Acute tubulointerstitial nephritis | Drug reaction (eg, β-lactams, NSAIDs, sulfonamides, ciprofloxacin, thiazide diuretics, furosemide, phenytoin, allopurinol, pyelonephritis, papillary necrosis |

-continued

| Type<br>Prerenal | Risk Factors |
|---|---|
| Acute vascular nephropathy | Vasculitis, malignant hypertension, thrombotic microangiopathies, scleroderma, atheroembolism |
| Infiltrative diseases | Lymphoma, sarcoidosis, leukemia |
| Postrenal | |
| Tubular precipitation | Uric acid (tumor lysis), sulfonamides, triamterene, acyclovir, indinavir, methotrexate, ethylene glycol ingestion, myeloma protein, myoglobin |
| Ureteral obstruction | Intrinsic: Calculi, clots, sloughed renal tissue, fungus ball, edema, malignancy, congenital defects; Extrinsic: Malignancy, retroperitoneal fibrosis, ureteral trauma during surgery or high impact injury |
| Bladder obstruction | Mechanical: Benign prostatic hyperplasia, prostate cancer, bladder cancer, urethral strictures, phimosis, paraphimosis, urethral valves, obstructed indwelling urinary catheter; Neurogenic: Anticholinergic drugs, upper or lower motor neuron lesion |

In the case of ischemic ARF, the course of the disease may be divided into four phases. During an initiation phase, which lasts hours to days, reduced perfusion of the kidney is evolving into injury. Glomerular ultrafiltration reduces, the flow of filtrate is reduced due to debris within the tubules, and back leakage of filtrate through injured epithelium occurs. Renal injury can be mediated during this phase by reperfusion of the kidney. Initiation is followed by an extension phase which is characterized by continued ischemic injury and inflammation and may involve endothelial damage and vascular congestion. During the maintenance phase, lasting from 1 to 2 weeks, renal cell injury occurs, and glomerular filtration and urine output reaches a minimum. A recovery phase can follow in which the renal epithelium is repaired and GFR gradually recovers. Despite this, the survival rate of subjects with ARF may be as low as about 60%.

Acute kidney injury caused by radiocontrast agents (also called contrast media) and other nephrotoxins such as cyclosporine, antibiotics including aminoglycosides and anticancer drugs such as cisplatin manifests over a period of days to about a week. Contrast induced nephropathy (CIN, which is AKI caused by radiocontrast agents) is thought to be caused by intrarenal vasoconstriction (leading to ischemic injury) and from the generation of reactive oxygen species that are directly toxic to renal tubular epithelial cells. CIN classically presents as an acute (onset within 24-48 h) but reversible (peak 3-5 days, resolution within 1 week) rise in blood urea nitrogen and serum creatinine.

A commonly reported criteria for defining and detecting AKI is an abrupt (typically within about 2-7 days or within a period of hospitalization) elevation of serum creatinine. Although the use of serum creatinine elevation to define and detect AKI is well established, the magnitude of the serum creatinine elevation and the time over which it is measured to define AKI varies considerably among publications. Traditionally, relatively large increases in serum creatinine such as 100%, 200%, an increase of at least 100% to a value over 2 mg/dL and other definitions were used to define AKI. However, the recent trend has been towards using smaller serum creatinine rises to define AKI. The relationship between serum creatinine rise, AKI and the associated health risks are reviewed in Praught and Shlipak, *Curr Opin Nephrol Hypertens* 14:265-270, 2005 and Chertow et al, *J Am Soc Nephrol* 16: 3365-3370, 2005, which, with the references listed therein, are hereby incorporated by reference in their entirety. As described in these publications, acute worsening renal function (AKI) and increased risk of death and other detrimental outcomes are now known to be associated with very small increases in serum creatinine. These increases may be determined as a relative (percent) value or a nominal value. Relative increases in serum creatinine as small as 20% from the pre-injury value have been reported to indicate acutely worsening renal function (AKI) and increased health risk, but the more commonly reported value to define AKI and increased health risk is a relative increase of at least 25%. Nominal increases as small as 0.3 mg/dL, 0.2 mg/dL or even 0.1 mg/dL have been reported to indicate worsening renal function and increased risk of death. Various time periods for the serum creatinine to rise to these threshold values have been used to define AKI, for example, ranging from 2 days, 3 days, 7 days, or a variable period defined as the time the patient is in the hospital or intensive care unit. These studies indicate there is not a particular threshold serum creatinine rise (or time period for the rise) for worsening renal function or AKI, but rather a continuous increase in risk with increasing magnitude of serum creatinine rise.

One study (Lassnigg et all, J Am Soc Nephrol 15:1597-1605, 2004, hereby incorporated by reference in its entirety) investigated both increases and decreases in serum creatinine. Patients with a mild fall in serum creatinine of −0.1 to −0.3 mg/dL following heart surgery had the lowest mortality rate. Patients with a larger fall in serum creatinine (more than or equal to −0.4 mg/dL) or any increase in serum creatinine had a larger mortality rate. These findings caused the authors to conclude that even very subtle changes in renal function (as detected by small creatinine changes within 48 hours of surgery) seriously effect patient's outcomes. In an effort to reach consensus on a unified classification system for using serum creatinine to define AKI in clinical trials and in clinical practice, Bellomo et al., *Crit Care.* 8(4):R204-12, 2004, which is hereby incorporated by reference in its entirety, proposes the following classifications for stratifying AKI patients:

"Risk": serum creatinine increased 1.5 fold from baseline OR urine production of <0.5 ml/kg body weight/hr for 6 hours;

"Injury": serum creatinine increased 2.0 fold from baseline OR urine production <0.5 ml/kg/hr for 12 h;

"Failure": serum creatinine increased 3.0 fold from baseline OR creatinine >355 μmol/l (with a rise of >44) or urine output below 0.3 ml/kg/hr for 24 h or anuria for at least 12 hours;

And included two clinical outcomes:

"Loss": persistent need for renal replacement therapy for more than four weeks.

"ESRD": end stage renal disease—the need for dialysis for more than 3 months.

These criteria are called the RIFLE criteria, which provide a useful clinical tool to classify renal status. As discussed in Kellum, *Crit. Care Med.* 36: S141-45, 2008 and Ricci et al., *Kidney Int.* 73, 538-546, 2008, each hereby incorporated by reference in its entirety, the RIFLE criteria provide a uniform definition of AKI which has been validated in numerous studies.

More recently, Mehta et al., *Crit. Care* 11:R31 (doi: 10.1186.cc5713), 2007, hereby incorporated by reference in its entirety, proposes the following similar classifications for stratifying AKI patients, which have been modified from RIFLE:

"Stage I": increase in serum creatinine of more than or equal to 0.3 mg/dL (≥26.4 µmol/L) or increase to more than or equal to 150% (1.5-fold) from baseline OR urine output less than 0.5 mL/kg per hour for more than 6 hours;

"Stage II": increase in serum creatinine to more than 200% (>2-fold) from baseline OR urine output less than 0.5 mL/kg per hour for more than 12 hours;

"Stage III": increase in serum creatinine to more than 300% (>3-fold) from baseline OR serum creatinine ≥354 µmol/L accompanied by an acute increase of at least 44 µmol/L OR urine output less than 0.3 mL/kg per hour for 24 hours or anuria for 12 hours.

The CIN Consensus Working Panel (McCollough et al, Rev Cardiovasc Med. 2006; 7(4):177-197, hereby incorporated by reference in its entirety) uses a serum creatinine rise of 25% to define Contrast induced nephropathy (which is a type of AKI). Although various groups propose slightly different criteria for using serum creatinine to detect AKI, the consensus is that small changes in serum creatinine, such as 0.3 mg/dL or 25%, are sufficient to detect AKI (worsening renal function) and that the magnitude of the serum creatinine change is an indicator of the severity of the AKI and mortality risk.

Although serial measurement of serum creatinine over a period of days is an accepted method of detecting and diagnosing AKI and is considered one of the most important tools to evaluate AKI patients, serum creatinine is generally regarded to have several limitations in the diagnosis, assessment and monitoring of AKI patients. The time period for serum creatinine to rise to values (e.g., a 0.3 mg/dL or 25% rise) considered diagnostic for AKI can be 48 hours or longer depending on the definition used. Since cellular injury in AKI can occur over a period of hours, serum creatinine elevations detected at 48 hours or longer can be a late indicator of injury, and relying on serum creatinine can thus delay diagnosis of AKI. Furthermore, serum creatinine is not a good indicator of the exact kidney status and treatment needs during the most acute phases of AKI when kidney function is changing rapidly. Some patients with AKI will recover fully, some will need dialysis (either short term or long term) and some will have other detrimental outcomes including death, major adverse cardiac events and chronic kidney disease. Because serum creatinine is a marker of filtration rate, it does not differentiate between the causes of AKI (pre-renal, intrinsic renal, post-renal obstruction, atheroembolic, etc) or the category or location of injury in intrinsic renal disease (for example, tubular, glomerular or interstitial in origin). Urine output is similarly limited, Knowing these things can be of vital importance in managing and treating patients with AKI.

These limitations underscore the need for better methods to detect and assess AKI, particularly in the early and subclinical stages, but also in later stages when recovery and repair of the kidney can occur. Furthermore, there is a need to better identify patients who are at risk of having an AKI.

BRIEF SUMMARY OF THE INVENTION

It is an object of the invention to provide methods and compositions for evaluating renal function in a subject. As described herein, measurement of one or more biomarkers selected from the group consisting of Heat shock 70 kDa protein 1, Alpha-1-antitrypsin Neutrophil elastase complex, Stromelysin-1:Metalloproteinase inhibitor 2 complex, 72 kDa type IV collagenase:Metalloproteinase inhibitor 2 complex, Insulin-like growth factor 1 receptor, Myeloid differentiation primary response protein MyD88, Neuronal cell adhesion molecule, and Tumor necrosis factor ligand superfamily member 10 (each referred to herein as a "kidney injury marker") can be used for diagnosis, prognosis, risk stratification, staging, monitoring, categorizing and determination of further diagnosis and treatment regimens in subjects suffering or at risk of suffering from an injury to renal function, reduced renal function, and/or acute renal failure (also called acute kidney injury).

The kidney injury markers of the present invention may be used, individually or in panels comprising a plurality of kidney injury markers, for risk stratification (that is, to identify subjects at risk for a future injury to renal function, for future progression to reduced renal function, for future progression to ARF, for future improvement in renal function, etc.); for diagnosis of existing disease (that is, to identify subjects who have suffered an injury to renal function, who have progressed to reduced renal function, who have progressed to ARF, etc.); for monitoring for deterioration or improvement of renal function; and for predicting a future medical outcome, such as improved or worsening renal function, a decreased or increased mortality risk, a decreased or increased risk that a subject will require renal replacement therapy (i.e., hemodialysis, peritoneal dialysis, hemofiltration, and/or renal transplantation, a decreased or increased risk that a subject will recover from an injury to renal function, a decreased or increased risk that a subject will recover from ARF, a decreased or increased risk that a subject will progress to end stage renal disease, a decreased or increased risk that a subject will progress to chronic renal failure, a decreased or increased risk that a subject will suffer rejection of a transplanted kidney, etc.

In a first aspect, the present invention relates to methods for evaluating renal status in a subject. These methods comprise performing an assay method that is configured to detect one or more biomarkers selected from the group consisting of Heat shock 70 kDa protein 1, Alpha-1-antitrypsin Neutrophil elastase complex, Stromelysin-1:Metalloproteinase inhibitor 2 complex, 72 kDa type IV collagenase: Metalloproteinase inhibitor 2 complex, Insulin-like growth factor 1 receptor, Myeloid differentiation primary response protein MyD88, Neuronal cell adhesion molecule, and Tumor necrosis factor ligand superfamily member 10 is/are then correlated to the renal status of the subject. This correlation to renal status may include correlating the assay result(s) to one or more of risk stratification, diagnosis, prognosis, staging, classifying and monitoring of the subject as described herein. Thus, the present invention utilizes one or more kidney injury markers of the present invention for the evaluation of renal injury.

In certain embodiments, the methods for evaluating renal status described herein are methods for risk stratification of the subject; that is, assigning a likelihood of one or more future changes in renal status to the subject. In these embodiments, the assay result(s) is/are correlated to one or more such future changes. The following are preferred risk stratification embodiments.

In preferred risk stratification embodiments, these methods comprise determining a subject's risk for a future injury to renal function, and the assay result(s) is/are correlated to a likelihood of such a future injury to renal function. For example, the measured concentration(s) may each be compared to a threshold value. For a "positive going" kidney injury marker, an increased likelihood of suffering a future injury to renal function is assigned to the subject when the measured concentration is above the threshold, relative to a likelihood assigned when the measured concentration is below the threshold. For a "negative going" kidney injury marker, an increased likelihood of suffering a future injury to renal function is assigned to the subject when the measured concentration is below the threshold, relative to a likelihood assigned when the measured concentration is above the threshold.

In other preferred risk stratification embodiments, these methods comprise determining a subject's risk for future reduced renal function, and the assay result(s) is/are correlated to a likelihood of such reduced renal function. For example, the measured concentrations may each be compared to a threshold value. For a "positive going" kidney injury marker, an increased likelihood of suffering a future reduced renal function is assigned to the subject when the measured concentration is above the threshold, relative to a likelihood assigned when the measured concentration is below the threshold. For a "negative going" kidney injury marker, an increased likelihood of future reduced renal function is assigned to the subject when the measured concentration is below the threshold, relative to a likelihood assigned when the measured concentration is above the threshold.

In still other preferred risk stratification embodiments, these methods comprise determining a subject's likelihood for a future improvement in renal function, and the assay result(s) is/are correlated to a likelihood of such a future improvement in renal function. For example, the measured concentration(s) may each be compared to a threshold value. For a "positive going" kidney injury marker, an increased likelihood of a future improvement in renal function is assigned to the subject when the measured concentration is below the threshold, relative to a likelihood assigned when the measured concentration is above the threshold. For a "negative going" kidney injury marker, an increased likelihood of a future improvement in renal function is assigned to the subject when the measured concentration is above the threshold, relative to a likelihood assigned when the measured concentration is below the threshold.

In yet other preferred risk stratification embodiments, these methods comprise determining a subject's risk for progression to ARF, and the result(s) is/are correlated to a likelihood of such progression to ARF. For example, the measured concentration(s) may each be compared to a threshold value. For a "positive going" kidney injury marker, an increased likelihood of progression to ARF is assigned to the subject when the measured concentration is above the threshold, relative to a likelihood assigned when the measured concentration is below the threshold. For a "negative going" kidney injury marker, an increased likelihood of progression to ARF is assigned to the subject when the measured concentration is below the threshold, relative to a likelihood assigned when the measured concentration is above the threshold.

And in other preferred risk stratification embodiments, these methods comprise determining a subject's outcome risk, and the assay result(s) is/are correlated to a likelihood of the occurrence of a clinical outcome related to a renal injury suffered by the subject. For example, the measured concentration(s) may each be compared to a threshold value. For a "positive going" kidney injury marker, an increased likelihood of one or more of: acute kidney injury, progression to a worsening stage of AKI, mortality, a requirement for renal replacement therapy, a requirement for withdrawal of renal toxins, end stage renal disease, heart failure, stroke, myocardial infarction, progression to chronic kidney disease, etc., is assigned to the subject when the measured concentration is above the threshold, relative to a likelihood assigned when the measured concentration is below the threshold. For a "negative going" kidney injury marker, an increased likelihood of one or more of: acute kidney injury, progression to a worsening stage of AKI, mortality, a requirement for renal replacement therapy, a requirement for withdrawal of renal toxins, end stage renal disease, heart failure, stroke, myocardial infarction, progression to chronic kidney disease, etc., is assigned to the subject when the measured concentration is below the threshold, relative to a likelihood assigned when the measured concentration is above the threshold.

In such risk stratification embodiments, preferably the likelihood or risk assigned is that an event of interest is more or less likely to occur within 180 days of the time at which the body fluid sample is obtained from the subject. In particularly preferred embodiments, the likelihood or risk assigned relates to an event of interest occurring within a shorter time period such as 18 months, 120 days, 90 days, 60 days, 45 days, 30 days, 21 days, 14 days, 7 days, 5 days, 96 hours, 72 hours, 48 hours, 36 hours, 24 hours, 12 hours, or less. A risk at 0 hours of the time at which the body fluid sample is obtained from the subject is equivalent to diagnosis of a current condition.

In preferred risk stratification embodiments, the subject is selected for risk stratification based on the pre-existence in the subject of one or more known risk factors for prerenal, intrinsic renal, or postrenal ARF. For example, a subject undergoing or having undergone major vascular surgery, coronary artery bypass, or other cardiac surgery; a subject having pre-existing congestive heart failure, preeclampsia, eclampsia, diabetes mellitus, hypertension, coronary artery disease, proteinuria, renal insufficiency, glomerular filtration below the normal range, cirrhosis, serum creatinine above the normal range, or sepsis; or a subject exposed to NSAIDs, cyclosporines, tacrolimus, aminoglycosides, foscarnet, ethylene glycol, hemoglobin, myoglobin, ifosfamide, heavy metals, methotrexate, radiopaque contrast agents, or streptozotocin are all preferred subjects for monitoring risks according to the methods described herein. This list is not meant to be limiting. By "pre-existence" in this context is meant that the risk factor exists at the time the body fluid sample is obtained from the subject. In particularly preferred embodiments, a subject is chosen for risk stratification based on an existing diagnosis of injury to renal function, reduced renal function, or ARF.

In other embodiments, the methods for evaluating renal status described herein are methods for diagnosing a renal injury in the subject; that is, assessing whether or not a subject has suffered from an injury to renal function, reduced renal function, or ARF. In these embodiments, the assay result(s), for example measured concentration(s) of one or more biomarkers selected from the group consisting of Heat shock 70 kDa protein 1, Alpha-1-antitrypsin Neutrophil elastase complex, Stromelysin-1:Metalloproteinase inhibitor 2 complex, 72 kDa type IV collagenase:Metalloproteinase inhibitor 2 complex, Insulin-like growth factor 1 receptor, Myeloid differentiation primary response protein MyD88, Neuronal cell adhesion molecule, and Tumor necrosis factor ligand superfamily member 10 is/are correlated to the occurrence or nonoccurrence of a change in renal status. The following are preferred diagnostic embodiments.

In preferred diagnostic embodiments, these methods comprise diagnosing the occurrence or nonoccurrence of an injury to renal function, and the assay result(s) is/are correlated to the occurrence or nonoccurrence of such an injury. For example, each of the measured concentration(s) may be compared to a threshold value. For a positive going marker, an increased likelihood of the occurrence of an injury to renal function is assigned to the subject when the measured concentration is above the threshold (relative to the likelihood assigned when the measured concentration is below the threshold); alternatively, when the measured concentration is below the threshold, an increased likelihood of the nonoccurrence of an injury to renal function may be assigned to the subject (relative to the likelihood assigned when the measured concentration is above the threshold). For a negative going marker, an increased likelihood of the occurrence of an injury to renal function is assigned to the subject when the measured concentration is below the threshold (relative to the likelihood assigned when the measured concentration is above the threshold); alternatively, when the measured concentration is above the threshold, an increased likelihood of the nonoccurrence of an injury to renal function may be assigned to the subject (relative to the likelihood assigned when the measured concentration is below the threshold).

In other preferred diagnostic embodiments, these methods comprise diagnosing the occurrence or nonoccurrence of reduced renal function, and the assay result(s) is/are correlated to the occurrence or nonoccurrence of an injury causing reduced renal function. For example, each of the measured concentration(s) may be compared to a threshold value. For a positive going marker, an increased likelihood of the occurrence of an injury causing reduced renal function is assigned to the subject when the measured concentration is above the threshold (relative to the likelihood assigned when the measured concentration is below the threshold); alternatively, when the measured concentration is below the threshold, an increased likelihood of the nonoccurrence of an injury causing reduced renal function may be assigned to the subject (relative to the likelihood assigned when the measured concentration is above the threshold). For a negative going marker, an increased likelihood of the occurrence of an injury causing reduced renal function is assigned to the subject when the measured concentration is below the threshold (relative to the likelihood assigned when the measured concentration is above the threshold); alternatively, when the measured concentration is above the threshold, an increased likelihood of the nonoccurrence of an injury causing reduced renal function may be assigned to the subject (relative to the likelihood assigned when the measured concentration is below the threshold).

In yet other preferred diagnostic embodiments, these methods comprise diagnosing the occurrence or nonoccurrence of ARF, and the assay result(s) is/are correlated to the occurrence or nonoccurrence of an injury causing ARF. For example, each of the measured concentration(s) may be compared to a threshold value. For a positive going marker, an increased likelihood of the occurrence of ARF is assigned to the subject when the measured concentration is above the threshold (relative to the likelihood assigned when the measured concentration is below the threshold); alternatively, when the measured concentration is below the threshold, an increased likelihood of the nonoccurrence of ARF may be assigned to the subject (relative to the likelihood assigned when the measured concentration is above the threshold). For a negative going marker, an increased likelihood of the occurrence of ARF is assigned to the subject when the measured concentration is below the threshold (relative to the likelihood assigned when the measured concentration is above the threshold); alternatively, when the measured concentration is above the threshold, an increased likelihood of the nonoccurrence of ARF may be assigned to the subject (relative to the likelihood assigned when the measured concentration is below the threshold).

In still other preferred diagnostic embodiments, these methods comprise diagnosing a subject as being in need of renal replacement therapy, and the assay result(s) is/are correlated to a need for renal replacement therapy. For example, each of the measured concentration(s) may be compared to a threshold value. For a positive going marker, an increased likelihood of the occurrence of an injury creating a need for renal replacement therapy is assigned to the subject when the measured concentration is above the threshold (relative to the likelihood assigned when the measured concentration is below the threshold); alternatively, when the measured concentration is below the threshold, an increased likelihood of the nonoccurrence of an injury creating a need for renal replacement therapy may be assigned to the subject (relative to the likelihood assigned when the measured concentration is above the threshold). For a negative going marker, an increased likelihood of the occurrence of an injury creating a need for renal replacement therapy is assigned to the subject when the measured concentration is below the threshold (relative to the likelihood assigned when the measured concentration is above the threshold); alternatively, when the measured concentration is above the threshold, an increased likelihood of the nonoccurrence of an injury creating a need for renal replacement therapy may be assigned to the subject (relative to the likelihood assigned when the measured concentration is below the threshold).

In still other preferred diagnostic embodiments, these methods comprise diagnosing a subject as being in need of renal transplantation, and the assay result (s0 is/are correlated to a need for renal transplantation. For example, each of the measured concentration(s) may be compared to a threshold value. For a positive going marker, an increased likelihood of the occurrence of an injury creating a need for renal transplantation is assigned to the subject when the measured concentration is above the threshold (relative to the likelihood assigned when the measured concentration is below the threshold); alternatively, when the measured concentration is below the threshold, an increased likelihood of the nonoccurrence of an injury creating a need for renal transplantation may be assigned to the subject (relative to the likelihood assigned when the measured concentration is above the threshold). For a negative going marker, an increased likelihood of the occurrence of an injury creating a need for renal transplantation is assigned to the subject when the measured concentration is below the threshold (relative to the likelihood assigned when the measured concentration is above the threshold); alternatively, when the measured concentration is above the threshold, an increased likelihood of the nonoccurrence of an injury creating a need for renal transplantation may be assigned to the subject (relative to the likelihood assigned when the measured concentration is below the threshold).

In still other embodiments, the methods for evaluating renal status described herein are methods for monitoring a renal injury in the subject; that is, assessing whether or not renal function is improving or worsening in a subject who has suffered from an injury to renal function, reduced renal function, or ARF. In these embodiments, the assay result(s), for example measured concentration(s) of one or more biomarkers selected from the group consisting of Heat shock 70 kDa protein 1, Alpha-1-antitrypsin Neutrophil elastase complex, Stromelysin-1:Metalloproteinase inhibitor 2 complex, 72 kDa type IV collagenase:Metalloproteinase inhibitor 2 complex, Insulin-like growth factor 1 receptor, Myeloid differentiation primary response protein MyD88, Neuronal cell adhesion molecule, and Tumor necrosis factor ligand superfamily member 10 receptor is/are correlated to the occurrence or nonoccurrence of a change in renal status. The following are preferred monitoring embodiments.

In preferred monitoring embodiments, these methods comprise monitoring renal status in a subject suffering from an injury to renal function, and the assay result(s) is/are correlated to the occurrence or nonoccurrence of a change in renal status in the subject. For example, the measured concentration(s) may be compared to a threshold value. For a positive going marker, when the measured concentration is above the threshold, a worsening of renal function may be assigned to the subject; alternatively, when the measured concentration is below the threshold, an improvement of renal function may be assigned to the subject. For a negative going marker, when the measured concentration is below the threshold, a worsening of renal function may be assigned to the subject; alternatively, when the measured concentration is above the threshold, an improvement of renal function may be assigned to the subject.

In other preferred monitoring embodiments, these methods comprise monitoring renal status in a subject suffering from reduced renal function, and the assay result(s) is/are correlated to the occurrence or nonoccurrence of a change in renal status in the subject. For example, the measured concentration(s) may be compared to a threshold value. For a positive going marker, when the measured concentration is above the threshold, a worsening of renal function may be assigned to the subject; alternatively, when the measured concentration is below the threshold, an improvement of renal function may be assigned to the subject. For a negative going marker, when the measured concentration is below the threshold, a worsening of renal function may be assigned to the subject; alternatively, when the measured concentration is above the threshold, an improvement of renal function may be assigned to the subject.

In yet other preferred monitoring embodiments, these methods comprise monitoring renal status in a subject suffering from acute renal failure, and the assay result(s) is/are correlated to the occurrence or nonoccurrence of a change in renal status in the subject. For example, the measured concentration(s) may be compared to a threshold value. For a positive going marker, when the measured concentration is above the threshold, a worsening of renal function may be assigned to the subject; alternatively, when the measured concentration is below the threshold, an improvement of renal function may be assigned to the subject. For a negative going marker, when the measured concentration is below the threshold, a worsening of renal function may be assigned to the subject; alternatively, when the measured concentration is above the threshold, an improvement of renal function may be assigned to the subject.

In other additional preferred monitoring embodiments, these methods comprise monitoring renal status in a subject at risk of an injury to renal function due to the pre-existence of one or more known risk factors for prerenal, intrinsic renal, or postrenal ARF, and the assay result(s) is/are correlated to the occurrence or nonoccurrence of a change in renal status in the subject. For example, the measured concentration(s) may be compared to a threshold value. For a positive going marker, when the measured concentration is above the threshold, a worsening of renal function may be assigned to the subject; alternatively, when the measured concentration is below the threshold, an improvement of renal function may be assigned to the subject. For a negative going marker, when the measured concentration is below the threshold, a worsening of renal function may be assigned to the subject; alternatively, when the measured concentration is above the threshold, an improvement of renal function may be assigned to the subject.

In still other embodiments, the methods for evaluating renal status described herein are methods for classifying a renal injury in the subject; that is, determining whether a renal injury in a subject is prerenal, intrinsic renal, or postrenal; and/or further subdividing these classes into subclasses such as acute tubular injury, acute glomerulonephritis acute tubulointerstitial nephritis, acute vascular nephropathy, or infiltrative disease; and/or assigning a likelihood that a subject will progress to a particular RIFLE stage. In these embodiments, the assay result(s), for example measured concentration(s) of one or more biomarkers selected from the group consisting of Heat shock 70 kDa protein 1, Alpha-1-antitrypsin Neutrophil elastase complex, Stromelysin-1:Metalloproteinase inhibitor 2 complex, 72 kDa type IV collagenase:Metalloproteinase inhibitor 2 complex, Insulin-like growth factor 1 receptor, Myeloid differentiation primary response protein MyD88, Neuronal cell adhesion molecule, and Tumor necrosis factor ligand superfamily member 10 is/are correlated to a particular class and/or subclass. The following are preferred classification embodiments.

In preferred classification embodiments, these methods comprise determining whether a renal injury in a subject is prerenal, intrinsic renal, or postrenal; and/or further subdividing these classes into subclasses such as acute tubular injury, acute glomerulonephritis acute tubulointerstitial nephritis, acute vascular nephropathy, or infiltrative disease; and/or assigning a likelihood that a subject will progress to a particular RIFLE stage, and the assay result(s) is/are correlated to the injury classification for the subject. For example, the measured concentration may be compared to a threshold value, and when the measured concentration is above the threshold, a particular classification is assigned; alternatively, when the measured concentration is below the threshold, a different classification may be assigned to the subject.

A variety of methods may be used by the skilled artisan to arrive at a desired threshold value for use in these methods. For example, the threshold value may be determined from a population of normal subjects by selecting a concentration representing the 75th, 85th, 90th, 95th, or 99th percentile of a kidney injury marker measured in such normal subjects. Alternatively, the threshold value may be determined from a "diseased" population of subjects, e.g., those suffering from an injury or having a predisposition for an injury (e.g., progression to ARF or some other clinical outcome such as death, dialysis, renal transplantation, etc.), by selecting a concentration representing the 75th, 85th, 90th, 95th, or 99th percentile of a kidney injury marker measured in such subjects. In another alternative, the threshold value may be determined from a prior measurement of a kidney injury marker in the same subject; that is, a temporal change in the level of a kidney injury marker in the subject may be used to assign risk to the subject.

The foregoing discussion is not meant to imply, however, that the kidney injury markers of the present invention must be compared to corresponding individual thresholds. Methods for combining assay results can comprise the use of multivariate logistical regression, log linear modeling, neural network analysis, n-of-m analysis, decision tree analysis, calculating ratios of markers, etc. This list is not meant to be limiting. In these methods, a composite result which is determined by combining individual markers may be treated as if it is itself a marker; that is, a threshold may be determined for the composite result as described herein for individual markers, and the composite result for an individual patient compared to this threshold.

The ability of a particular test to distinguish two populations can be established using ROC analysis. For example, ROC curves established from a "first" subpopulation which is predisposed to one or more future changes in renal status, and a "second" subpopulation which is not so predisposed can be used to calculate a ROC curve, and the area under the curve provides a measure of the quality of the test. Preferably, the tests described herein provide a ROC curve area greater than 0.5, preferably at least 0.6, more preferably 0.7, still more preferably at least 0.8, even more preferably at least 0.9, and most preferably at least 0.95.

In certain aspects, the measured concentration of one or more kidney injury markers, or a composite of such markers, may be treated as continuous variables. For example, any particular concentration can be converted into a corresponding probability of a future reduction in renal function for the subject, the occurrence of an injury, a classification, etc. In yet another alternative, a threshold that can provide an acceptable level of specificity and sensitivity in separating a population of subjects into "bins" such as a "first" subpopulation (e.g., which is predisposed to one or more future changes in renal status, the occurrence of an injury, a classification, etc.) and a "second" subpopulation which is not so predisposed. A threshold value is selected to separate this first and second population by one or more of the following measures of test accuracy:

an odds ratio greater than 1, preferably at least about 2 or more or about 0.5 or less, more preferably at least about 3 or more or about 0.33 or less, still more preferably at least about 4 or more or about 0.25 or less, even more preferably at least about 5 or more or about 0.2 or less, and most preferably at least about 10 or more or about 0.1 or less;
a specificity of greater than 0.5, preferably at least about 0.6, more preferably at least about 0.7, still more preferably at least about 0.8, even more preferably at least about 0.9 and most preferably at least about 0.95, with a corresponding sensitivity greater than 0.2, preferably greater than about 0.3, more preferably greater than about 0.4, still more preferably at least about 0.5, even more preferably about 0.6, yet more preferably greater than about 0.7, still more preferably greater than about 0.8, more preferably greater than about 0.9, and most preferably greater than about 0.95;
a sensitivity of greater than 0.5, preferably at least about 0.6, more preferably at least about 0.7, still more preferably at least about 0.8, even more preferably at least about 0.9 and most preferably at least about 0.95, with a corresponding specificity greater than 0.2, preferably greater than about 0.3, more preferably greater than about 0.4, still more preferably at least about 0.5, even more preferably about 0.6, yet more preferably greater than about 0.7, still more preferably greater than about 0.8, more preferably greater than about 0.9, and most preferably greater than about 0.95;
at least about 75% sensitivity, combined with at least about 75% specificity;
a positive likelihood ratio (calculated as sensitivity/(1-specificity)) of greater than 1, at least about 2, more preferably at least about 3, still more preferably at least about 5, and most preferably at least about 10; or
a negative likelihood ratio (calculated as (1-sensitivity)/specificity) of less than 1, less than or equal to about 0.5, more preferably less than or equal to about 0.3, and most preferably less than or equal to about 0.1.

The term "about" in the context of any of the above measurements refers to +/−5% of a given measurement.

Multiple thresholds may also be used to assess renal status in a subject. For example, a "first" subpopulation which is predisposed to one or more future changes in renal status, the occurrence of an injury, a classification, etc., and a "second" subpopulation which is not so predisposed can be combined into a single group. This group is then subdivided into three or more equal parts (known as tertiles, quartiles, quintiles, etc., depending on the number of subdivisions). An odds ratio is assigned to subjects based on which subdivision they fall into. If one considers a tertile, the lowest or highest tertile can be used as a reference for comparison of the other subdivisions. This reference subdivision is assigned an odds ratio of 1. The second tertile is assigned an odds ratio that is relative to that first tertile. That is, someone in the second tertile might be 3 times more likely to suffer one or more future changes in renal status in comparison to someone in the first tertile. The third tertile is also assigned an odds ratio that is relative to that first tertile.

In certain embodiments, the assay method is an immunoassay. Antibodies for use in such assays will specifically bind a full length kidney injury marker of interest, and may also bind one or more polypeptides that are "related" thereto, as that term is defined hereinafter. Numerous immunoassay formats are known to those of skill in the art. Preferred body fluid samples are selected from the group consisting of urine, blood, serum, saliva, tears, and plasma. In the case of those kidney injury markers which are membrane proteins as described hereinafter, preferred assays detect soluble forms thereof.

The foregoing method steps should not be interpreted to mean that the kidney injury marker assay result(s) is/are used in isolation in the methods described herein. Rather, additional variables or other clinical indicia may be included in the methods described herein. For example, a risk stratification, diagnostic, classification, monitoring, etc. method may combine the assay result(s) with one or more variables measured for the subject selected from the group consisting of demographic information (e.g., weight, sex, age, race), medical history (e.g., family history, type of surgery, pre-existing disease such as aneurism, congestive heart failure, preeclampsia, eclampsia, diabetes mellitus, hypertension, coronary artery disease, proteinuria, renal insufficiency, or sepsis, type of toxin exposure such as NSAIDs, cyclosporines, tacrolimus, aminoglycosides, foscarnet, ethylene glycol, hemoglobin, myoglobin, ifosfamide, heavy metals, methotrexate, radiopaque contrast agents, or streptozotocin), clinical variables (e.g., blood pressure, temperature, respiration rate), risk scores (APACHE score, PREDICT score, TIMI Risk Score for UA/NSTEMI, Framingham Risk Score, risk scores of Thakar et al. (J. Am. Soc. Nephrol. 16: 162-68, 2005), Mehran et al. (J. Am. Coll. Cardiol. 44: 1393-99, 2004), Wijeysundera et al. (JAMA 297: 1801-9, 2007), Goldstein and Chawla (Clin. J. Am. Soc. Nephrol. 5: 943-49, 2010), or Chawla et al. (Kidney Intl. 68: 2274-80, 2005)), a glomerular filtration rate, an estimated glomerular filtration rate, a urine production rate, a serum or plasma creatinine concentration, a urine creatinine concentration, a fractional excretion of sodium, a urine sodium concentration, a urine creatinine to serum or plasma creatinine ratio, a urine specific gravity, a urine osmolality, a urine urea nitrogen to plasma urea nitrogen ratio, a plasma BUN to creatinine ratio, a renal failure index calculated as urine sodium/(urine creatinine/plasma creatinine), a serum or plasma neutrophil gelatinase (NGAL) concentration, a urine NGAL concentration, a serum or plasma cystatin C concentration, a serum or plasma cardiac troponin concentration, a serum or plasma BNP concentration, a serum or plasma NTproBNP concentration, and a serum or plasma proBNP concentration. Other measures of renal function which may be combined with one or more kidney injury marker assay result(s) are described hereinafter and in Harrison's Principles of Internal Medicine, 17$^{th}$ Ed., McGraw Hill, New York, pages 1741-1830, and Current Medical Diagnosis & Treatment 2008, 47$^{th}$ Ed, McGraw Hill, New York, pages 785-815, each of which are hereby incorporated by reference in their entirety.

When more than one marker is measured, the individual markers may be measured in samples obtained at the same time, or may be determined from samples obtained at different (e.g., an earlier or later) times. The individual markers may also be measured on the same or different body fluid samples. For example, one kidney injury marker may be measured in a serum or plasma sample and another kidney injury marker may be measured in a urine sample. In addition, assignment of a likelihood may combine an individual kidney injury marker assay result with temporal changes in one or more additional variables.

In various related aspects, the present invention also relates to devices and kits for performing the methods described herein. Suitable kits comprise reagents sufficient for performing an assay for at least one of the described kidney injury markers, together with instructions for performing the described threshold comparisons.

In certain embodiments, reagents for performing such assays are provided in an assay device, and such assay devices may be included in such a kit. Preferred reagents can comprise one or more solid phase antibodies, the solid phase antibody comprising antibody that detects the intended biomarker target(s) bound to a solid support. In the case of sandwich immunoassays, such reagents can also include one or more detectably labeled antibodies, the detectably labeled antibody comprising antibody that detects the intended biomarker target(s) bound to a detectable label. Additional optional elements that may be provided as part of an assay device are described hereinafter.

Detectable labels may include molecules that are themselves detectable (e.g., fluorescent moieties, electrochemical labels, ecl (electrochemical luminescence) labels, metal chelates, colloidal metal particles, etc.) as well as molecules that may be indirectly detected by production of a detectable reaction product (e.g., enzymes such as horseradish peroxidase, alkaline phosphatase, etc.) or through the use of a specific binding molecule which itself may be detectable (e.g., a labeled antibody that binds to the second antibody, biotin, digoxigenin, maltose, oligohistidine, 2,4-dintrobenzene, phenylarsenate, ssDNA, dsDNA, etc.).

Generation of a signal from the signal development element can be performed using various optical, acoustical, and electrochemical methods well known in the art. Examples of detection modes include fluorescence, radiochemical detection, reflectance, absorbance, amperometry, conductance, impedance, interferometry, ellipsometry, etc. In certain of these methods, the solid phase antibody is coupled to a transducer (e.g., a diffraction grating, electrochemical sensor, etc) for generation of a signal, while in others, a signal is generated by a transducer that is spatially separate from the solid phase antibody (e.g., a fluorometer that employs an excitation light source and an optical detector). This list is not meant to be limiting. Antibody-based biosensors may also be employed to determine the presence or amount of analytes that optionally eliminate the need for a labeled molecule.

DETAILED DESCRIPTION OF THE INVENTION

The present invention relates to methods and compositions for diagnosis, differential diagnosis, risk stratification, monitoring, classifying and determination of treatment regimens in subjects suffering or at risk of suffering from injury to renal function, reduced renal function and/or acute renal failure through measurement of one or more kidney injury markers. In various embodiments, a measured concentration of one or more biomarkers selected from the group consisting of Heat shock 70 kDa protein 1, Alpha-1-antitrypsin Neutrophil elastase complex, Stromelysin-1:Metalloproteinase inhibitor 2 complex, 72 kDa type IV collagenase:Metalloproteinase inhibitor 2 complex, Insulin-like growth factor 1 receptor, Myeloid differentiation primary response protein MyD88, Neuronal cell adhesion molecule, and Tumor necrosis factor ligand superfamily member 10 or one or more markers related thereto, are correlated to the renal status of the subject.

For purposes of this document, the following definitions apply:

As used herein, an "injury to renal function" is an abrupt (within 14 days, preferably within 7 days, more preferably within 72 hours, and still more preferably within 48 hours) measurable reduction in a measure of renal function. Such an injury may be identified, for example, by a decrease in glomerular filtration rate or estimated GFR, a reduction in urine output, an increase in serum creatinine, an increase in serum cystatin C, a requirement for renal replacement therapy, etc "Improvement in Renal Function" is an abrupt (within 14 days, preferably within 7 days, more preferably within 72 hours, and still more preferably within 48 hours) measurable increase in a measure of renal function. Preferred methods for measuring and/or estimating GFR are described hereinafter.

As used herein, "reduced renal function" is an abrupt (within 14 days, preferably within 7 days, more preferably within 72 hours, and still more preferably within 48 hours) reduction in kidney function identified by an absolute increase in serum creatinine of greater than or equal to 0.1 mg/dL (≥8.8 µmol/L), a percentage increase in serum creatinine of greater than or equal to 20% (1.2-fold from baseline), or a reduction in urine output (documented oliguria of less than 0.5 ml/kg per hour).

As used herein, "acute renal failure" or "ARF" is an abrupt (within 14 days, preferably within 7 days, more preferably within 72 hours, and still more preferably within 48 hours) reduction in kidney function identified by an absolute increase in serum creatinine of greater than or equal to 0.3 mg/dl (≥26.4 µmol/l), a percentage increase in serum creatinine of greater than or equal to 50% (1.5-fold from baseline), or a reduction in urine output (documented oliguria of less than 0.5 ml/kg per hour for at least 6 hours). This term is synonymous with "acute kidney injury" or "AKI."

As used herein, the term "Heat shock 70 kDa protein 1" refers to one or more polypeptides present in a biological sample that are derived from the Heat shock 70 kDa protein 1 precursor (human precursor Swiss-Prot P08107 (SEQ ID NO: 1)).

```
         10         20         30         40         50         60
MAKAAAIGID LGTTYSCVGV FQHGKVEIIA NDQGNRTTPS YVAFTDTERL IGDAAKNQVA 70         80         90        100        110        120
LNPQNTVFDA KRLIGRKFGD PVVQSDMKHW PFQVINDGDK PKVQVSYKGE TKAFYPEEIS 130        140        150        160        170        180
SMVLTKMKEI AEAYLGYPVT NAVITVPAYF NDSQRQATKD AGVIAGLNVL RIINEPTAAA 190        200        210        220        230        240
IAYGLDRTGK GERNVLIFDL GGGTFDVSIL TIDDGIFEVK ATAGDTHLGG EDFDNRLVNH 250        260        270        280        290        300
FVEEFKRKHK KDISQNKRAV RRLRTACERA KRTLSSSTQA SLEIDSLFEG IDFYTSITRA 310        320        330        340        350        360
RFEELCSDLF RSTLEPVEKA LRDAKLDKAQ IHDLVLVGGS TRIPKVQKLL QDFFNGRDLN 370        380        390        400        410        420
KSINPDEAVA YGAAVQAAIL MGDKSENVQD LLLLDVAPLS LGLETAGGVM TALIKRNSTI 430        440        450        460        470        480
PTKQTQIFTT YSDNQPGVLI QVYEGERAMT KDNNLLGRFE LSGIPPAPRG VPQIEVTFDI 490        500        510        520        530        540
DANGILNVTA TDKSTGKANK ITITNDKGRL SKEEIERMVQ EAEKYKAEDE VQRERVSAKN 550        560        570        580        590        600
ALESYAFNMK SAVEDEGLKG KISEADKKKV LDKCQEVISW LDANTLAEKD EFEHKRKELE 610        620        630        640
QVCNPIISGL YQGAGGPGPG GFGAQGPKGG SGSGPTIEEV D
```

The following domains have been identified in Heat shock 70 kDa protein 1:

| Residues | Length | Domain ID |
| --- | --- | --- |
| 1 | 1 | Initiator methionine |
| 2-641 | 640 | Heat shock 70 kDa protein 1 |

As used herein, the term "Stromelysin-1:Metalloproteinase inhibitor 2 complex" refers to a polypeptide complex present in a biological sample that comprises one or more polypeptides that are derived from the Stromelysin-1 precursor and one or more polypeptides that are derived from the Metalloproteinase inhibitor 2 precursor.

used herein, the term "72 kDa type IV collagenase: Metalloproteinase inhibitor 2 complex" refers to a polypeptide complex present in a biological sample that comprises one or more polypeptides that are derived from the 72 kDa type IV collagenase precursor and one or more polypeptides that are derived from the Metalloproteinase inhibitor 2 precursor.

The human Stromelysin-1 precursor has the following sequence (Swiss-Prot P08254 (SEQ ID NO: 2)):

```
         10         20         30         40         50         60
MKSLPILLLL CVAVCSAYPL DGAARGEDTS MNLVQKYLEN YYDLKKDVKQ FVRRKDSGPV 70         80         90        100        110        120
VKKIREMQKF LGLEVTGKLD SDTLEVMRKP RCGVPDVGHF RTFPGIPKWR KTHLTYRIVN 130        140        150        160        170        180
YTPDLPKDAV DSAVEKALKV WEEVTPLTFS RLYEGEADIM ISFAVREHGD FYPFDGPGNV 190        200        210        220        230        240
LAHAYAPGPG INGDAHFDDD EQWTKDTTGT NLFLVAAHEI GHSLGLFHSA NTEALMYPLY 250        260        270        280        290        300
HSLTDLTRFR LSQDDINGIQ SLYGPPPDSP ETPLVPTEPV PPEPGTPANC DPALSFDAVS 310        320        330        340        350        360
TLRGEILIFK DRHFWRKSLR KLEPELHLIS SFWPSLPSGV DAAYEVTSKD LVFIFKGNQF 370        380        390        400        410        420
WAIRGNEVRA GYPRGIHTLG FPPTVRKIDA AISDKEKNKT YFFVEDKYWR FDEKRNSMEP 430        440        450        460        470
GFPKQIAEDF PGIDSKIDAV FEEFGFFYFF TGSSQLEFDP NAKKVTHTLK SNSWLNC
```

The following domains have been identified in Stromelysin-1:

| Residues | Length | Domain ID |
|---|---|---|
| 1-17 | 17 | signal sequence |
| 18-99 | 82 | propeptide |
| 100-477 | 378 | Stromelysin-1 |

The human 72 kDa type IV collagenase precursor (Swiss-Prot P08253 (SEQ ID NO: 3)) has the following sequence:

```
         10         20         30         40         50         60
 MEALMARGAL TGPLRALCLL GCLLSHAAAA PSPIIKFPGD VAPKTDKELA VQYLNTFYGC 70         80         90        100        110        120
 PKESCNLFVL KDTLKKMQKF FGLPQTGDLD QNTIETMRKP RCGNPDVANY NFFPRKPKWD 130        140        150        160        170        180
 KNQITYRIIG YTPDLDPETV DDAFARAFQV WSDVTPLRFS RIHDGEADIM INFGRWEHGD 190        200        210        220        230        240
 GYPFDGKDGL LAHAFAPGTG VGGDSHFDDD ELWTLGEGQV VRVKYGNADG EYCKFPFLFN 250        260        270        280        290        300
 GKEYNSCTDT GRSDGFLWCS TTYNFEKDGK YGFCPHEALF TMGGNAEGQP CKFPFRFQGT 310        320        330        340        350        360
 SYDSCTTEGR TDGYRWCGTT EDYDRDKKYG FCPETAMSTV GGNSEGAPCV FPFTFLGNKY 370        380        390        400        410        420
 ESCTSAGRSD GKMWCATTAN YDDDRKWGFC PDQGYSLFLV AAHEFGHAMG LEHSQDPGAL 430        440        450        460        470        480
 MAPIYTYTKN FRLSQDDIKG IQELYGASPD IDLGTGPTPT LGPVTPEICK QDIVFDGIAQ 490        500        510        520        530        540
 IRGEIFFFKD RFIWRTVTPR DKPMGPLLVA TFWPELPEKI DAVYEAPQEE KAVFFAGNEY 550        560        570        580        590        600
 WIYSASTLER GYPKPLTSLG LPPDVQRVDA AFNWSKNKKT YIFAGDKFWR YNEVKKKMDP 610        620        630        640        650        660
 GFPKLIADAW NAIPDNLDAV VDLQGGGHSY FFKGAYYLKL ENQSLKSVKF GSIKSDWLGC
```

The following domains have been identified in 72 kDa type IV collagenase:

| Residues | Length | Domain ID |
|---|---|---|
| 1-29 | 29 | Signal peptide |
| 30-109 | 90 | Activation peptide |
| 110-660 | 551 | 72 kDa type IV collagenase (4-73) |

The human Metalloproteinase inhibitor 2 precursor (Swiss-Prot P16035 (SEQ ID NO: 4)) has the following sequence:

```
         10         20         30         40         50         60
 MGAAARTLRL ALGLLLLATL LRPADACSCS PVHPQQAFCN ADVVIRAKAV SEKEVDSGND 70         80         90        100        110        120
 IYGNPIKRIQ YEIKQIKMFK GPEKDIEFIY TAPSSAVCGV SLDVGGKKEY LIAGKAEGDG 130        140        150        160        170        180
 KMHITLCDFI VPWDTLSTTQ KKSLNHRYQM GCECKITRCP MIPCYISSPD ECLWMDWVTE 190        200        210        220
 KNINGHQAKF FACIKRSDGS CAWYRGAAPP KQEFLDIEDP
```

The following domains have been identified in Metalloproteinase inhibitor 2:

| Residues | Length | Domain ID |
|---|---|---|
| 1-26 | 26 | Signal peptide |
| 27-220 | 194 | Metalloproteinase inhibitor 2 |

As used herein, the term "Insulin-like growth factor 1 receptor" refers to one or more polypeptides present in a biological sample that are derived from the Insulin-like growth factor 1 receptor precursor (Swiss-Prot P08069 (SEQ ID NO: 5)).

```
            10         20         30         40         50         60
    MKSGSGGGSP TSLWGLLFLS AALSLWPTSG EICGPGIDIR NDYQQLKRLE NCTVIEGYLH 70         80         90        100        110        120
    ILLISKAEDY RSYRFPKLTV ITEYLLLFRV AGLESLGDLF PNLTVIRGWK LFYNYALVIF 130        140        150        160        170        180
    EMTNLKDIGL YNLRNITRGA IRIEKNADLC YLSTVDWSLI LDAVSNNYIV GNKPPKECGD 190        200        210        220        230        240
    LCPGTMEEKP MCEKTTINNE YNYRCWTTNR CQKMCPSTCG KRACTENNEC CHPECLGSCS 250        260        270        280        290        300
    APDNDTACVA CRHYYYAGVC VPACPPNTYR FEGWRCVDRD FCANILSAES SDSEGFVIHD 310        320        330        340        350        360
    GECMQECPSG FIRNGSQSMY CIPCEGPCPK VCEEEKKTKT IDSVTSAQML QGCTIFKGNL 370        380        390        400        410        420
    LINIRRGNNI ASELENFMGL IEVVTGYVKI RHSHALVSLS FLKNLRLILG EEQLEGNYSF 430        440        450        460        470        480
    YVLDNQNLQQ LWDWDHRNLT IKAGKMYFAF NPKLCVSEIY RMEEVTGTKG RQSKGDINTR 490        500        510        520        530        540
    NNGERASCES DVLHFTSTTT SKNRIIITWH RYRPPDYRDL ISFTVYYKEA PFKNVTEYDG 550        560        570        580        590        600
    QDACGSNSWN MVDVDLPPNK DVEPGILLHG LKPWTQYAVY VKAVTLTMVE NDHIRGAKSE 610        620        630        640        650        660
    ILYIRTNASV PSIPLDVLSA SNSSSQLIVK WNPPSLPNGN LSYYIVRWQR QPQDGYLYRH 670        680        690        700        710        720
    NYCSKDKIPI RKYADGTIDI EEVTENPKTE VCGGEKGPCC ACPKTEAEKQ AEKEEAEYRK 730        740        750        760        770        780
    VFENFLHNSI FVPRPERKRR DVMQVANTTM SSRSRNTTAA DTYNITDPEE LETEYPFFES 790        800        810        820        830        840
    RVDNKERTVI SNLRPFTLYR IDIHSCNHEA EKLGCSASNF VFARTMPAEG ADDIPGPVTW 850        860        870        880        890        900
    EPRPENSIFL KWPEPENPNG LILMYEIKYG SQVEDQRECV SRQEYRKYGG AKLNRLNPGN 910        920        930        940        950        960
    YTARIQATSL SGNGSWTDPV FFYVQAKTGY ENFIHLIIAL PVAVLLIVGG LVIMLYVFHR 970        980        990       1000       1010       1020
    KRNNSRLGNG VLYASVNPEY FSAADVYVPD EWEVAREKIT MSRELGQGSF GMVYEGVAKG 1030       1040       1050       1060       1070       1080
    VVKDEPETRV AIKTVNEAAS MRERIEFLNE ASVMKEFNCH HVVRLLGVVS QGQPTLVIME 1090       1100       1110       1120       1130       1140
    LMTRGDLKSY LRSLRPEMEN NPVLAPPSLS KMIQMAGEIA DGMAYLNANK FVHRDLAARN 1150       1160       1170       1180       1190       1200
    CMVAEDFTVK IGDFGMTRDI YETDYYRKGG KGLLPVRWMS PESLKDGVFT TYSDVWSFGV 1210       1220       1230       1240       1250       1260
    VLWEIATLAE QPYQGLSNEQ VLRFVMEGGL LDKPDNCPDM LFELMRMCWQ YNPKMRPSFL 1270       1280       1290       1300       1310       1320
    EIISSIKEEM EPGFREVSFY YSEENKLPEP EELDLEPENM ESVPLDPSAS SSSLPLPDRH 1330       1340       1350       1360
    SGHKAENGPG PGVLVLRASF DERQPYAHMN GGRKNERALP LPQSSTC
```

Most preferably, the Insulin-like growth factor 1 receptor assay detects one or more soluble forms of Insulin-like growth factor 1 receptor. Insulin-like growth factor 1 receptor is a single-pass type I membrane protein having a large extracellular domain, most or all of which is present in soluble forms of Insulin-like growth factor 1 receptor generated either through alternative splicing event which deletes all or a portion of the transmembrane domain, or by proteolysis of the membrane-bound form. In the case of an immunoassay, one or more antibodies that bind to epitopes within this extracellular domain may be used to detect these soluble form(s). The following domains have been identified in Insulin-like growth factor 1 receptor:

| Residues | Length | Domain ID |
|---|---|---|
| 1-30 | 30 | signal sequence |
| 31-736 | 706 | Insulin-like growth factor 1 receptor alpha chain (extracellular) |
| 741-1367 | 627 | Insulin-like growth factor 1 receptor beta chain |
| 741-935 | 195 | extracellular |
| 936-959 | 24 | transmembrane |
| 960-1367 | 408 | cytoplasmic |

As used herein, the term "myeloid differentiation primary response protein MyD88" refers to one or more polypeptides present in a biological sample that are derived from the myeloid differentiation primary response protein MyD88 precursor (Swiss-Prot Q99836 (SEQ ID NO: 6)).

```
            10         20         30         40         50         60
    MAAGGPGAGS AAPVSSTSSL PLAALNMRVR RRLSLFLNVR TQVAADWTAL AEEMDFEYLE 70         80         90        100        110        120
    IRQLETQADP TGRLLDAWQG RPGASVGRLL ELLTKLGRDD VLLELGPSIE EDCQKYILKQ 130        140        150        160        170        180
    QQEEAEKPLQ VAAVDSSVPR TAELAGITTL DDPLGHMPER FDAFICYCPS DIQFVQEMIR 190        200        210        220        230        240
    QLEQTNYRLK LCVSDRDVLP GTCVWSIASE LIEKRCRRMV VVVSDDYLQS KECDFQTKFA 250        260        270        280        290
    LSLSPGAHQK RLIPIKYKAM KKEFPSILRF ITVCDYTNPC TKSWFWTRLA KALSLP
```

As used herein, the term "neuronal cell adhesion molecule" refers to one or more polypeptides present in a biological sample that are derived from the neuronal cell adhesion molecule precursor (Swiss-Prot Q92823 (SEQ ID NO: 7)).

```
            10         20         30         40         50         60
    MQLKIMPKKK RLSAGRVPLI LFLCQMISAL EVPLDPKLLE DLVQPPTITQ QSPKDYIIDP 70         80         90        100        110        120
    RENIVIQCEA KGKPPPSFSW TRNGTHFDID KDPLVTMKPG TGTLIINIMS EGKAETYEGV 130        140        150        160        170        180
    YQCTARNERG AAVSNNIVVR PSRSPLWTKE KLEPITLQSG QSLVLPCRPP IGLPPPIIFW 190        200        210        220        230        240
    MDNSFQRLPQ SERVSQGLNG DLYFSNVLPE DTREDYICYA RFNHTQTIQQ KQPISVKVIS 250        260        270        280        290        300
    VDELNDTIAA NLSDTEFYGA KSSRERPPTF LTPEGNASNK EELRGNVLSL ECIAEGLPTP 310        320        330        340        350        360
    IIYWAKEDGM LPKNRTVYKN FEKTLQIIHV SEADSGNYQC IAKNALGAIH HTISVRVKAA 370        380        390        400        410        420
    PYWITAPQNL VLSPGEDGTL ICRANGNPKP RISWLTNGVP IEIAPDDPSR KIDGDTIIFS 430        440        450        460        470        480
    NVQERSSAVY QCNASNEYGY LLANAFVNVL AEPPRILTPA NTLYQVIANR PALLDCAFFG 490        500        510        520        530        540
    SPLPTIEWFK GAKGSALHED IYVLHENGTL EIPVAQKDST GTYTCVARNK LGMAKNEVHL 550        560        570        580        590        600
    EIKDPTWIVK QPEYAVVQRG SMVSFECKVK HDHTLSLTVL WLKDNRELPS DERFTVDKDH 610        620        630        640        650        660
    LVVADVSDDD SGTYTCVANT TLDSVSASAV LSVVAPTPTP APVYDVPNPP FDLELTDQLD
```

```
       670        680        690        700        710        720
KSVQLSWTPG DDNNSPITKF IIEYEDAMHK PGLWHHQTEV SGTQTTAQLK LSPYVNYSFR 730        740        750        760        770        780
VMAVNSIGKS LPSEASEQYL TKASEPDKNP TAVEGLGSEP DNLVITWKPL NGFESNGPGL 790        800        810        820        830        840
QYKVSWRQKD GDDEWTSVVV ANVSKYIVSG TPTFVPYLIK VQALNDMGFA PEPAVVMGHS 850        860        870        880        890        900
GEDLPMVAPG NVRVNVVNST LAEVHWDPVP LKSIRGHLQG YRIYYWKTQS SSKRNRRHIE 910        920        930        940        950        960
KKILTFQGSK THGMLPGLEP FSHYTLNVRV VNGKGEGPAS PDRVFNTPEG VPSAPSSLKI 970        980        990       1000       1010       1020
VNPTLDSLTL EWDPPSHPNG ILTEYTLKYQ PINSTHELGP LVDLKIPANK TRWTLKNLNF 1030       1040       1050       1060       1070       1080
STRYKFYFYA QTSAGSGSQI TEEAVTTVDE AGILPPDVGA GKVQAVNTRI SNLTAAAAET 1090       1100       1110       1120       1130       1140
YANISWEYEG PEHVNFYVEY GVAGSKEEWR KEIVNGSRSF FGLKGLMPGT AYKVRVGAVG 1150       1160       1170       1180       1190       1200
DSGFVSSEDV FETGPAMASR QVDIATQGWF IGLMCAVALL ILILLIVCFI RRNKGGKYPV 1210       1220       1230       1240       1250       1260
KEKEDAHADP EIQPMKEDDG TFGEYSDAED HKPLKKGSRT PSDRTVKKED SDDSLVDYGE 1270       1280       1290       1300
GVNGQFNEDG SFIGQYSGKK EKEPAEGNES SEAPSPVNAM NSFV
```

Most preferably, the neuronal cell adhesion molecule assay detects one or more soluble forms of neuronal cell adhesion molecule. The Neuronal cell adhesion molecule precursor encodes a single-pass type I membrane protein having a large extracellular domain, most or all of which is present in soluble forms of neuronal cell adhesion molecule generated either through alternative splicing event which deletes all or a portion of the transmembrane domain, or by proteolysis of the membrane-bound form. In the case of an immunoassay, one or more antibodies that bind to epitopes within this extracellular domain may be used to detect these soluble form(s). The following domains have been identified in neuronal cell adhesion molecule:

| Residues  | Length | Domain ID                        |
|-----------|--------|----------------------------------|
| 1-24      | 24     | signal sequence                  |
| 25-1304   | 1280   | neuronal cell adhesion molecule  |
| 25-1167   | 1143   | extracellular                    |
| 1168-1190 | 23     | transmembrane                    |
| 1191-1304 | 114    | cytoplasmic                      |

As used herein, the term "Tumor necrosis factor ligand superfamily member 10" refers to one or more polypeptides present in a biological sample that are derived from the Tumor necrosis factor ligand superfamily member 10 precursor (Swiss-Prot P50591 (SEQ ID NO: 8))

```
               10         20         30         40         50         60
        MAMMEVQGGP SLGQTCVLIV IFTVLLQSLC VAVTYVYFTN ELKQMQDKYS KSGIACFLKE 70         80         90        100        110        120
        DDSYWDPNDE ESMNSPCWQV KWQLRQLVRK MILRTSEETI STVQEKQQNI SPLVRERGPQ 130        140        150        160        170        180
        RVAAHITGTR GRSNTLSSPN SKNEKALGRK INSWESSRSG HSFLSNLHLR NGELVIHEKG 190        200        210        220        230        240
        FYYIYSQTYF RFQEEIKENT KNDKQMVQYI YKYTSYPDPI LLMKSARNSC WSKDAEYGLY 250        260        270        280
        SIYQGGIFEL KENDRIFVSV TNEHLIDMDH EASFFGAFLV G
```

This protein is also known as TRAIL and APO2L. Most preferably, the Tumor necrosis factor ligand superfamily member 10 precursor assay detects one or more soluble forms of Tumor necrosis factor ligand superfamily member 10 precursor. The Tumor necrosis factor ligand superfamily member 10 precursor encodes a single-pass type II membrane protein having a large extracellular domain, most or all of which is present in soluble forms of Tumor necrosis factor ligand superfamily member 10 precursor generated either through alternative splicing event which deletes all or a portion of the transmembrane domain, or by proteolysis of the membrane-bound form. In the case of an immunoassay, one or more antibodies that bind to epitopes within this extracellular domain may be used to detect these soluble form(s). The following domains have been identified in Tumor necrosis factor ligand superfamily member 10 precursor:

| Residues | Length | Domain ID |
|---|---|---|
| 1-281 | 281 | Tumor necrosis factor ligand superfamily member 10 |
| 1-17 | 17 | cytoplasmic domain |
| 18-38 | 21 | Signal-anchor for type II membrane protein |
| 39-281 | 243 | extracellular domain |

As used herein, the term "alpha-1-antitrypsin:leukocyte elastase complex" refers to a polypeptide complex present in a biological sample that comprises one or more polypeptides that are derived from the alpha-1-antitrypsin precursor and one or more polypeptides that are derived from the leukocyte elastase precursor.

The human alpha-1-antitrypsin precursor has the following sequence (Swiss-Prot P01009 (SEQ ID NO: 9)):

```
            10         20         30         40         50         60
    MPSSVSWGIL LLAGLCCLVP VSLAEDPQGD AAQKTDTSHH DQDHPTFNKI TPNLAEFAFS 70         80         90        100        110        120
    LYRQLAHQSN STNIFFSPVS IATAFAMLSL GTKADTHDEI LEGLNFNLTE IPEAQIHEGF 130        140        150        160        170        180
    QELLRTLNQP DSQLQLTTGN GLFLSEGLKL VDKFLEDVKK LYHSEAFTVN FGDTEEAKKQ 190        200        210        220        230        240
    INDYVEKGTQ GKIVDLVKEL DRDTVFALVN YIFFKGKWER PFEVKDTEEE DFHVDQVTTV 250        260        270        280        290        300
    KVPMMKRLGM FNIQHCKKLS SWVLLMKYLG NATAIFFLPD EGKLQHLENE LTHDIITKFL 310        320        330        340        350        360
    ENEDRRSASL HLPKLSITGT YDLKSVLGQL GITKVFSNGA DLSGVTEEAP LKLSKAVHKA 370        380        390        400        410
    VLTIDEKGTE AAGAMFLEAI PMSIPPEVKF NKPFVFLMIE QNTKSPLFMG KVVNPTQK
```

The following domains have been identified in alpha-1-antitrypsin:

| Residues | Length | Domain ID |
|---|---|---|
| 1-24 | 24 | signal sequence |
| 25-418 | 394 | alpha-1-antitrypsin |

The human leukocyte elastase precursor (Swiss-Prot P08246 (SEQ ID NO: 10)) has the following sequence:

```
            10         20         30         40         50         60
    MTLGRRLACL FLACVLPALL LGGTALASEI VGGRRARPHA WPFMVSLQLR GGHFCGATLI 70         80         90        100        110        120
    APNFVMSAAH CVANVNVRAV RVVLGAHNLS RREPTRQVFA VQRIFENGYD PVNLLNDIVI 130        140        150        160        170        180
    LQLNGSATIN ANVQVAQLPA QGRRLGNGVQ CLAMGWGLLG RNRGIASVLQ ELNVTVVTSL 190        200        210        220        230        240
    CRRSNVCTLV RGRQAGVCFG DSGSPLVCNG LIHGIASFVR GGCASGLYPD AFAPVAQFVN 250        260
    WIDSIIQRSE DNPCPHPRDP DPASRTH
```

The following domains have been identified in leukocyte elastase:

| Residues | Length | Domain ID |
|---|---|---|
| 1-27 | 315 | signal sequence |
| 28-29 | 2 | pro-peptide |
| 30-267 | 238 | leukocyte elastase |

As used herein, the term "relating a signal to the presence or amount" of an analyte reflects the following understanding. Assay signals are typically related to the presence or amount of an analyte through the use of a standard curve calculated using known concentrations of the analyte of interest. As the term is used herein, an assay is "configured to detect" an analyte if an assay can generate a detectable signal indicative of the presence or amount of a physiologically relevant concentration of the analyte. Because an antibody epitope is on the order of 8 amino acids, an immunoassay configured to detect a marker of interest will also detect polypeptides related to the marker sequence, so long as those polypeptides contain the epitope(s) necessary to bind to the antibody or antibodies used in the assay. The term "related marker" as used herein with regard to a biomarker such as one of the kidney injury markers described herein refers to one or more fragments, variants, etc., of a particular marker or its biosynthetic parent that may be detected as a surrogate for the marker itself or as independent biomarkers. The term also refers to one or more polypeptides present in a biological sample that are derived from the biomarker precursor complexed to additional species, such as binding proteins, receptors, heparin, lipids, sugars, etc.

In this regard, the skilled artisan will understand that the signals obtained from an immunoassay are a direct result of complexes formed between one or more antibodies and the target biomolecule (i.e., the analyte) and polypeptides containing the necessary epitope(s) to which the antibodies bind. While such assays may detect the full length biomarker and the assay result be expressed as a concentration of a biomarker of interest, the signal from the assay is actually a result of all such "immunoreactive" polypeptides present in the sample. Expression of biomarkers may also be determined by means other than immunoassays, including protein measurements (such as dot blots, western blots, chromatographic methods, mass spectrometry, etc.) and nucleic acid measurements (mRNA quantitation). This list is not meant to be limiting.

The term "positive going" marker as that term is used herein refer to a marker that is determined to be elevated in subjects suffering from a disease or condition, relative to subjects not suffering from that disease or condition. The term "negative going" marker as that term is used herein refer to a marker that is determined to be reduced in subjects suffering from a disease or condition, relative to subjects not suffering from that disease or condition.

The term "subject" as used herein refers to a human or non-human organism. Thus, the methods and compositions described herein are applicable to both human and veterinary disease. Further, while a subject is preferably a living organism, the invention described herein may be used in post-mortem analysis as well. Preferred subjects are humans, and most preferably "patients," which as used herein refers to living humans that are receiving medical care for a disease or condition. This includes persons with no defined illness who are being investigated for signs of pathology.

Preferably, an analyte is measured in a sample. Such a sample may be obtained from a subject, or may be obtained from biological materials intended to be provided to the subject. For example, a sample may be obtained from a kidney being evaluated for possible transplantation into a subject, and an analyte measurement used to evaluate the kidney for preexisting damage. Preferred samples are body fluid samples.

The term "body fluid sample" as used herein refers to a sample of bodily fluid obtained for the purpose of diagnosis, prognosis, classification or evaluation of a subject of interest, such as a patient or transplant donor. In certain embodiments, such a sample may be obtained for the purpose of determining the outcome of an ongoing condition or the effect of a treatment regimen on a condition. Preferred body fluid samples include blood, serum, plasma, cerebrospinal fluid, urine, saliva, sputum, and pleural effusions. In addition, one of skill in the art would realize that certain body fluid samples would be more readily analyzed following a fractionation or purification procedure, for example, separation of whole blood into serum or plasma components.

The term "diagnosis" as used herein refers to methods by which the skilled artisan can estimate and/or determine the probability ("a likelihood") of whether or not a patient is suffering from a given disease or condition. In the case of the present invention, "diagnosis" includes using the results of an assay, most preferably an immunoassay, for a kidney injury marker of the present invention, optionally together with other clinical characteristics, to arrive at a diagnosis (that is, the occurrence or nonoccurrence) of an acute renal injury or ARF for the subject from which a sample was obtained and assayed. That such a diagnosis is "determined" is not meant to imply that the diagnosis is 100% accurate. Many biomarkers are indicative of multiple conditions. The skilled clinician does not use biomarker results in an informational vacuum, but rather test results are used together with other clinical indicia to arrive at a diagnosis. Thus, a measured biomarker level on one side of a predetermined diagnostic threshold indicates a greater likelihood of the occurrence of disease in the subject relative to a measured level on the other side of the predetermined diagnostic threshold.

Similarly, a prognostic risk signals a probability ("a likelihood") that a given course or outcome will occur. A level or a change in level of a prognostic indicator, which in turn is associated with an increased probability of morbidity (e.g., worsening renal function, future ARF, or death) is referred to as being "indicative of an increased likelihood" of an adverse outcome in a patient.

Marker Assays

In general, immunoassays involve contacting a sample containing or suspected of containing a biomarker of interest with at least one antibody that specifically binds to the biomarker. A signal is then generated indicative of the presence or amount of complexes formed by the binding of polypeptides in the sample to the antibody. The signal is then related to the presence or amount of the biomarker in the sample. Numerous methods and devices are well known to the skilled artisan for the detection and analysis of biomarkers. See, e.g., U.S. Pat. Nos. 6,143,576; 6,113,855; 6,019,944; 5,985,579; 5,947,124; 5,939,272; 5,922,615; 5,885,527; 5,851,776; 5,824,799; 5,679,526; 5,525,524; and 5,480,792, and The Immunoassay Handbook, David Wild, ed. Stockton Press, New York, 1994, each of which is hereby incorporated by reference in its entirety, including all tables, figures and claims.

The assay devices and methods known in the art can utilize labeled molecules in various sandwich, competitive, or non-competitive assay formats, to generate a signal that is related to the presence or amount of the biomarker of interest. Suitable assay formats also include chromatographic, mass spectrographic, and protein "blotting" methods. Additionally, certain methods and devices, such as biosensors and optical immunoassays, may be employed to determine the presence or amount of analytes without the need for a labeled molecule. See, e.g., U.S. Pat. Nos. 5,631,171; and 5,955,377, each of which is hereby incorporated by reference in its entirety, including all tables, figures and claims. One skilled in the art also recognizes that robotic instrumentation including but not limited to Beckman ACCESS®, Abbott AXSYM®, Roche ELECSYS®, Dade Behring STRATUS® systems are among the immunoassay analyzers that are capable of performing immunoassays. But any suitable immunoassay may be utilized, for example, enzyme-linked immunoassays (ELISA), radioimmunoassays (RIAs), competitive binding assays, and the like.

Antibodies or other polypeptides may be immobilized onto a variety of solid supports for use in assays. Solid phases that may be used to immobilize specific binding members include those developed and/or used as solid phases in solid phase binding assays. Examples of suitable solid phases include membrane filters, cellulose-based papers, beads (including polymeric, latex and paramagnetic particles), glass, silicon wafers, microparticles, nanoparticles, TentaGels, AgroGels, PEGA gels, SPOCC gels, and multiple-well plates. An assay strip could be prepared by coating the antibody or a plurality of antibodies in an array on solid support. This strip could then be dipped into the test sample and then processed quickly through washes and detection steps to generate a measurable signal, such as a colored spot. Antibodies or other polypeptides may be bound to specific zones of assay devices either by conjugating directly to an assay device surface, or by indirect binding. In an example of the later case, antibodies or other polypeptides may be immobilized on particles or other solid supports, and that solid support immobilized to the device surface.

Biological assays require methods for detection, and one of the most common methods for quantitation of results is to conjugate a detectable label to a protein or nucleic acid that has affinity for one of the components in the biological system being studied. Detectable labels may include molecules that are themselves detectable (e.g., fluorescent moieties, electrochemical labels, metal chelates, etc.) as well as molecules that may be indirectly detected by production of a detectable reaction product (e.g., enzymes such as horseradish peroxidase, alkaline phosphatase, etc.) or by a specific binding molecule which itself may be detectable (e.g., biotin, digoxigenin, maltose, oligohistidine, 2,4-dintrobenzene, phenylarsenate, ssDNA, dsDNA, etc.).

Preparation of solid phases and detectable label conjugates often comprise the use of chemical cross-linkers. Cross-linking reagents contain at least two reactive groups, and are divided generally into homofunctional cross-linkers (containing identical reactive groups) and heterofunctional cross-linkers (containing non-identical reactive groups). Homobifunctional cross-linkers that couple through amines, sulfhydryls or react non-specifically are available from many commercial sources. Maleimides, alkyl and aryl halides, alpha-haloacyls and pyridyl disulfides are thiol reactive groups. Maleimides, alkyl and aryl halides, and alpha-haloacyls react with sulfhydryls to form thiol ether bonds, while pyridyl disulfides react with sulfhydryls to produce mixed disulfides. The pyridyl disulfide product is cleavable. Imidoesters are also very useful for protein-protein cross-links. A variety of heterobifunctional cross-linkers, each combining different attributes for successful conjugation, are commercially available.

In certain aspects, the present invention provides kits for the analysis of the described kidney injury markers. The kit comprises reagents for the analysis of at least one test sample which comprise at least one antibody that a kidney injury marker. The kit can also include devices and instructions for performing one or more of the diagnostic and/or prognostic correlations described herein. Preferred kits will comprise an antibody pair for performing a sandwich assay, or a labeled species for performing a competitive assay, for the analyte. Preferably, an antibody pair comprises a first antibody conjugated to a solid phase and a second antibody conjugated to a detectable label, wherein each of the first and second antibodies that bind a kidney injury marker. Most preferably each of the antibodies are monoclonal antibodies. The instructions for use of the kit and performing the correlations can be in the form of labeling, which refers to any written or recorded material that is attached to, or otherwise accompanies a kit at any time during its manufacture, transport, sale or use. For example, the term labeling encompasses advertising leaflets and brochures, packaging materials, instructions, audio or video cassettes, computer discs, as well as writing imprinted directly on kits.

Antibodies

The term "antibody" as used herein refers to a peptide or polypeptide derived from, modeled after or substantially encoded by an immunoglobulin gene or immunoglobulin genes, or fragments thereof, capable of specifically binding an antigen or epitope. See, e.g. Fundamental Immunology, 3rd Edition, W. E. Paul, ed., Raven Press, N.Y. (1993); Wilson (1994; J. Immunol. Methods 175:267-273; Yarmush (1992) J. Biochem. Biophys. Methods 25:85-97. The term antibody includes antigen-binding portions, i.e., "antigen binding sites," (e.g., fragments, subsequences, complementarity determining regions (CDRs)) that retain capacity to bind antigen, including (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR). Single chain antibodies are also included by reference in the term "antibody."

Antibodies used in the immunoassays described herein preferably specifically bind to a kidney injury marker of the present invention. The term "specifically binds" is not intended to indicate that an antibody binds exclusively to its intended target since, as noted above, an antibody binds to any polypeptide displaying the epitope(s) to which the antibody binds. Rather, an antibody "specifically binds" if its affinity for its intended target is about 5-fold greater when compared to its affinity for a non-target molecule which does not display the appropriate epitope(s). Preferably the affinity of the antibody will be at least about 5 fold, preferably 10 fold, more preferably 25-fold, even more preferably 50-fold, and most preferably 100-fold or more, greater for a target molecule than its affinity for a non-target molecule. In preferred embodiments, Preferred antibodies bind with affinities of at least about $10^7$ $M^{-1}$, and preferably between about $10^8$ $M^{-1}$ to about $10^9$ $M^{-1}$, about $10^9$ $M^{-1}$ to about $10^{10}$ $M^{-1}$, or about $10^{10}$ $M^{-1}$ to about $10^{12}$ $M^{-1}$.

Affinity is calculated as $K_d = k_{off}/k_{on}$ ($k_{off}$ is the dissociation rate constant, $K_{on}$ is the association rate constant and $K_d$ is the equilibrium constant). Affinity can be determined at equilibrium by measuring the fraction bound (r) of labeled ligand at various concentrations (c). The data are graphed using the Scatchard equation: $r/c=K(n-r)$: where r=moles of bound ligand/mole of receptor at equilibrium; c=free ligand concentration at equilibrium; K=equilibrium association constant; and n=number of ligand binding sites per receptor molecule. By graphical analysis, r/c is plotted on the Y-axis versus r on the X-axis, thus producing a Scatchard plot. Antibody affinity measurement by Scatchard analysis is well known in the art. See, e.g., van Erp et al., *J. Immunoassay* 12: 425-43, 1991; Nelson and Griswold, *Comput. Methods Programs Biomed.* 27: 65-8, 1988.

The term "epitope" refers to an antigenic determinant capable of specific binding to an antibody. Epitopes usually consist of chemically active surface groupings of molecules such as amino acids or sugar side chains and usually have specific three dimensional structural characteristics, as well as specific charge characteristics. Conformational and non-conformational epitopes are distinguished in that the binding to the former but not the latter is lost in the presence of denaturing solvents.

Numerous publications discuss the use of phage display technology to produce and screen libraries of polypeptides for binding to a selected analyte. See, e.g, Cwirla et al., *Proc. Natl. Acad. Sci. USA* 87, 6378-82, 1990; Devlin et al., *Science* 249, 404-6, 1990, Scott and Smith, *Science* 249, 386-88, 1990; and Ladner et al., U.S. Pat. No. 5,571,698. A basic concept of phage display methods is the establishment of a physical association between DNA encoding a polypeptide to be screened and the polypeptide. This physical association is provided by the phage particle, which displays a polypeptide as part of a capsid enclosing the phage genome which encodes the polypeptide. The establishment of a physical association between polypeptides and their genetic material allows simultaneous mass screening of very large numbers of phage bearing different polypeptides. Phage displaying a polypeptide with affinity to a target bind to the target and these phage are enriched by affinity screening to the target. The identity of polypeptides displayed from these phage can be determined from their respective genomes. Using these methods a polypeptide identified as having a binding affinity for a desired target can then be synthesized in bulk by conventional means. See, e.g., U.S. Pat. No. 6,057,098, which is hereby incorporated in its entirety, including all tables, figures, and claims.

The antibodies that are generated by these methods may then be selected by first screening for affinity and specificity with the purified polypeptide of interest and, if required, comparing the results to the affinity and specificity of the antibodies with polypeptides that are desired to be excluded from binding. The screening procedure can involve immobilization of the purified polypeptides in separate wells of microtiter plates. The solution containing a potential antibody or groups of antibodies is then placed into the respective microtiter wells and incubated for about 30 min to 2 h. The microtiter wells are then washed and a labeled secondary antibody (for example, an anti-mouse antibody conjugated to alkaline phosphatase if the raised antibodies are mouse antibodies) is added to the wells and incubated for about 30 min and then washed. Substrate is added to the wells and a color reaction will appear where antibody to the immobilized polypeptide(s) are present.

The antibodies so identified may then be further analyzed for affinity and specificity in the assay design selected. In the development of immunoassays for a target protein, the purified target protein acts as a standard with which to judge the sensitivity and specificity of the immunoassay using the antibodies that have been selected. Because the binding affinity of various antibodies may differ; certain antibody pairs (e.g., in sandwich assays) may interfere with one another sterically, etc., assay performance of an antibody may be a more important measure than absolute affinity and specificity of an antibody.

While the present application describes antibody-based binding assays in detail, alternatives to antibodies as binding species in assays are well known in the art. These include receptors for a particular target, aptamers, etc. Aptamers are oligonucleic acid or peptide molecules that bind to a specific target molecule. Aptamers are usually created by selecting them from a large random sequence pool, but natural aptamers also exist. High-affinity aptamers containing modified nucleotides conferring improved characteristics on the ligand, such as improved in vivo stability or improved delivery characteristics. Examples of such modifications include chemical substitutions at the ribose and/or phosphate and/or base positions, and may include amino acid side chain functionalities.

Assay Correlations

The term "correlating" as used herein in reference to the use of biomarkers refers to comparing the presence or amount of the biomarker(s) in a patient to its presence or amount in persons known to suffer from, or known to be at risk of, a given condition; or in persons known to be free of a given condition. Often, this takes the form of comparing an assay result in the form of a biomarker concentration to a predetermined threshold selected to be indicative of the occurrence or nonoccurrence of a disease or the likelihood of some future outcome.

Selecting a diagnostic threshold involves, among other things, consideration of the probability of disease, distribution of true and false diagnoses at different test thresholds, and estimates of the consequences of treatment (or a failure to treat) based on the diagnosis. For example, when considering administering a specific therapy which is highly efficacious and has a low level of risk, few tests are needed because clinicians can accept substantial diagnostic uncertainty. On the other hand, in situations where treatment options are less effective and more risky, clinicians often need a higher degree of diagnostic certainty. Thus, cost/benefit analysis is involved in selecting a diagnostic threshold.

Suitable thresholds may be determined in a variety of ways. For example, one recommended diagnostic threshold for the diagnosis of acute myocardial infarction using cardiac troponin is the 97.5th percentile of the concentration seen in a normal population. Another method may be to look at serial samples from the same patient, where a prior "baseline" result is used to monitor for temporal changes in a biomarker level.

Population studies may also be used to select a decision threshold. Receiver Operating Characteristic ("ROC") arose from the field of signal detection theory developed during World War II for the analysis of radar images, and ROC analysis is often used to select a threshold able to best distinguish a "diseased" subpopulation from a "nondiseased" subpopulation. A false positive in this case occurs when the person tests positive, but actually does not have the disease. A false negative, on the other hand, occurs when the person tests negative, suggesting they are healthy, when they actually do have the disease. To draw a ROC curve, the true positive rate (TPR) and false positive rate (FPR) are determined as the decision threshold is varied continuously. Since TPR is equivalent with sensitivity and FPR is equal to 1−specificity, the ROC graph is sometimes called the sensitivity vs (1−specificity) plot. A perfect test will have an area under the ROC curve of 1.0; a random test will have an area of 0.5. A threshold is selected to provide an acceptable level of specificity and sensitivity.

In this context, "diseased" is meant to refer to a population having one characteristic (the presence of a disease or condition or the occurrence of some outcome) and "nondiseased" is meant to refer to a population lacking the characteristic. While a single decision threshold is the simplest application of such a method, multiple decision thresholds may be used. For example, below a first threshold, the absence of disease may be assigned with relatively high confidence, and above a second threshold the presence of disease may also be assigned with relatively high confidence. Between the two thresholds may be considered indeterminate. This is meant to be exemplary in nature only.

In addition to threshold comparisons, other methods for correlating assay results to a patient classification (occurrence or nonoccurrence of disease, likelihood of an outcome, etc.) include decision trees, rule sets, Bayesian methods, and neural network methods. These methods can produce probability values representing the degree to which a subject belongs to one classification out of a plurality of classifications.

Measures of test accuracy may be obtained as described in Fischer et al., *Intensive Care Med.* 29: 1043-51, 2003, and used to determine the effectiveness of a given biomarker. These measures include sensitivity and specificity, predictive values, likelihood ratios, diagnostic odds ratios, and ROC curve areas. The area under the curve ("AUC") of a ROC plot is equal to the probability that a classifier will rank a randomly chosen positive instance higher than a randomly chosen negative one. The area under the ROC curve may be thought of as equivalent to the Mann-Whitney U test, which tests for the median difference between scores obtained in the two groups considered if the groups are of continuous data, or to the Wilcoxon test of ranks.

As discussed above, suitable tests may exhibit one or more of the following results on these various measures: a specificity of greater than 0.5, preferably at least 0.6, more preferably at least 0.7, still more preferably at least 0.8, even more preferably at least 0.9 and most preferably at least 0.95, with a corresponding sensitivity greater than 0.2, preferably greater than 0.3, more preferably greater than 0.4, still more preferably at least 0.5, even more preferably 0.6, yet more preferably greater than 0.7, still more preferably greater than 0.8, more preferably greater than 0.9, and most preferably greater than 0.95; a sensitivity of greater than 0.5, preferably at least 0.6, more preferably at least 0.7, still more preferably at least 0.8, even more preferably at least 0.9 and most preferably at least 0.95, with a corresponding specificity greater than 0.2, preferably greater than 0.3, more preferably greater than 0.4, still more preferably at least 0.5, even more preferably 0.6, yet more preferably greater than 0.7, still more preferably greater than 0.8, more preferably greater than 0.9, and most preferably greater than 0.95; at least 75% sensitivity, combined with at least 75% specificity; a ROC curve area of greater than 0.5, preferably at least 0.6, more preferably 0.7, still more preferably at least 0.8, even more preferably at least 0.9, and most preferably at least 0.95; an odds ratio different from 1, preferably at least about 2 or more or about 0.5 or less, more preferably at least about 3 or more or about 0.33 or less, still more preferably at least about 4 or more or about 0.25 or less, even more preferably at least about 5 or more or about 0.2 or less, and most preferably at least about 10 or more or about 0.1 or less; a positive likelihood ratio (calculated as sensitivity/(1-specificity)) of greater than 1, at least 2, more preferably at least 3, still more preferably at least 5, and most preferably at least 10; and or a negative likelihood ratio (calculated as (1-sensitivity)/specificity) of less than 1, less than or equal to 0.5, more preferably less than or equal to 0.3, and most preferably less than or equal to 0.1

Additional clinical indicia may be combined with the kidney injury marker assay result(s) of the present invention. These include other biomarkers related to renal status. Examples include the following, which recite the common biomarker name, followed by the Swiss-Prot entry number for that biomarker or its parent: Actin (P68133); Adenosine deaminase binding protein (DPP4, P27487); Alpha-1-acid glycoprotein 1 (P02763); Alpha-1-microglobulin (P02760); Albumin (P02768); Angiotensinogenase (Renin, P00797); Annexin A2 (P07355); Beta-glucuronidase (P08236); B-2-microglobulin (P61679); Beta-galactosidase (P16278); BMP-7 (P18075); Brain natriuretic peptide (proBNP, BNP-32, NTproBNP; P16860); Calcium-binding protein Beta (S100-beta, P04271); Carbonic anhydrase (Q16790); Casein Kinase 2 (P68400); Ceruloplasmin (P00450); Clusterin (P10909); Complement C3 (P01024); Cysteine-rich protein (CYR61, O00622); Cytochrome C (P99999); Epidermal growth factor (EGF, P01133); Endothelin-1 (P05305); Exosomal Fetuin-A (P02765); Fatty acid-binding protein, heart (FABP3, P05413); Fatty acid-binding protein, liver (P07148); Ferritin (light chain, P02793; heavy chain P02794); Fructose-1,6-biphosphatase (P09467); GRO-alpha (CXCL1, (P09341); Growth Hormone (P01241); Hepatocyte growth factor (P14210); Insulin-like growth factor I (P01343); Immunoglobulin G; Immunoglobulin Light Chains (Kappa and Lambda); Interferon gamma (P01308); Lysozyme (P61626); Interleukin-1alpha (P01583); Interleukin-2 (P60568); Interleukin-4 (P60568); Interleukin-9 (P15248); Interleukin-12p40 (P29460); Interleukin-13 (P35225); Interleukin-16 (Q14005); L1 cell adhesion molecule (P32004); Lactate dehydrogenase (P00338); Leucine Aminopeptidase (P28838); Meprin A-alpha subunit (Q16819); Meprin A-beta subunit (Q16820); Midkine (P21741); MIP2-alpha (CXCL2, P19875); MMP-2 (P08253); MMP-9 (P14780); Netrin-1 (O95631); Neutral endopeptidase (P08473); Osteopontin (P10451); Renal papillary antigen 1 (RPA1); Renal papillary antigen 2 (RPA2); Retinol binding protein (P09455); Ribonuclease; S100 calcium-binding protein A6 (P06703); Serum Amyloid P Component (P02743); Sodium/Hydrogen exchanger isoform (NHE3, P48764); Spermidine/spermine N1-acetyltransferase (P21673); TGF-Beta1 (P01137); Transferrin (P02787); Trefoil factor 3 (TFF3, Q07654); Toll-Like protein 4 (O00206); Total protein; Tubulointerstitial nephritis antigen (Q9UJW2); Uromodulin (Tamm-Horsfall protein, P07911).

For purposes of risk stratification, Adiponectin (Q15848); Alkaline phosphatase (P05186); Aminopeptidase N (P15144); CalbindinD28k (P05937); Cystatin C (P01034); δ subunit of FIFO ATPase (P03928); Gamma-glutamyltransferase (P19440); GSTa (alpha-glutathione-S-transferase, P08263); GSTpi (Glutathione-S-transferase P; GST class-pi; P09211); IGFBP-1 (P08833); IGFBP-2 (P18065); IGFBP-6 (P24592); Integral membrane protein 1 (Itm1, P46977); Interleukin-6 (P05231); Interleukin-8 (P10145); Interleukin-18 (Q14116); IP-10 (10 kDa interferon-gamma-induced protein, P02778); IRPR (IFRD1, O00458); Isovaleryl-CoA dehydrogenase (IVD, P26440); I-TAC/CXCL11 (O14625); Keratin 19 (P08727); Kim-1 (Hepatitis A virus cellular receptor 1, O43656); L-arginine:glycine amidinotransferase (P50440); Leptin (P41159); Lipocalin2 (NGAL, P80188); MCP-1 (P13500); MIG (Gamma-interferon-induced monokine Q07325); MIP-1a (P10147); MIP-3a (P78556); MIP-1beta (P13236); MIP-1d (Q16663); NAG (N-acetyl-beta-D-glucosaminidase, P54802); Organic ion transporter (OCT2, O15244); Osteoprotegerin (O14788); P8 protein (O60356); Plasminogen activator inhibitor 1 (PAI-1, P05121); ProANP(1-98) (P01160); Protein phosphatase 1-beta (PPI-beta, P62140); Rab GDI-beta (P50395); Renal kallikrein (Q86U61); RT1.B-1 (alpha) chain of the integral membrane protein (Q5Y7A8); Soluble tumor necrosis factor receptor superfamily member 1A (sTNFR-I, P19438); Soluble tumor necrosis factor receptor superfamily member 1B (sTNFR-II, P20333); Tissue inhibitor of metalloproteinases 3 (TIMP-3, P35625); uPAR (Q03405) may be combined with the kidney injury marker assay result(s) of the present invention.

Other clinical indicia which may be combined with the kidney injury marker assay result(s) of the present invention includes demographic information (e.g., weight, sex, age, race), medical history (e.g., family history, type of surgery, pre-existing disease such as aneurism, congestive heart failure, preeclampsia, eclampsia, diabetes mellitus, hypertension, coronary artery disease, proteinuria, renal insufficiency, or sepsis, type of toxin exposure such as NSAIDs, cyclosporines, tacrolimus, aminoglycosides, foscarnet, ethylene glycol, hemoglobin, myoglobin, ifosfamide, heavy metals, methotrexate, radiopaque contrast agents, or streptozotocin), clinical variables (e.g., blood pressure, temperature, respiration rate), risk scores (APACHE score, PREDICT score, TIMI Risk Score for UA/NSTEMI, Framingham Risk Score), a urine total protein measurement, a glomerular filtration rate, an estimated glomerular filtration rate, a urine production rate, a serum or plasma creatinine concentration, a renal papillary antigen 1 (RPA1)

measurement; a renal papillary antigen 2 (RPA2) measurement; a urine creatinine concentration, a fractional excretion of sodium, a urine sodium concentration, a urine creatinine to serum or plasma creatinine ratio, a urine specific gravity, a urine osmolality, a urine urea nitrogen to plasma urea nitrogen ratio, a plasma BUN to creatinine ratio, and/or a renal failure index calculated as urine sodium/(urine creatinine/plasma creatinine). Other measures of renal function which may be combined with the kidney injury marker assay result(s) are described hereinafter and in Harrison's Principles of Internal Medicine, 17$^{th}$ Ed., McGraw Hill, New York, pages 1741-1830, and Current Medical Diagnosis & Treatment 2008, 47$^{th}$ Ed, McGraw Hill, New York, pages 785-815, each of which are hereby incorporated by reference in their entirety.

Combining assay results/clinical indicia in this manner can comprise the use of multivariate logistical regression, log linear modeling, neural network analysis, n-of-m analysis, decision tree analysis, etc. This list is not meant to be limiting.

Diagnosis of Acute Renal Failure

As noted above, the terms "acute renal (or kidney) injury" and "acute renal (or kidney) failure" as used herein are defined in part in terms of changes in serum creatinine from a baseline value. Most definitions of ARF have common elements, including the use of serum creatinine and, often, urine output. Patients may present with renal dysfunction without an available baseline measure of renal function for use in this comparison. In such an event, one may estimate a baseline serum creatinine value by assuming the patient initially had a normal GFR. Glomerular filtration rate (GFR) is the volume of fluid filtered from the renal (kidney) glomerular capillaries into the Bowman's capsule per unit time. Glomerular filtration rate (GFR) can be calculated by measuring any chemical that has a steady level in the blood, and is freely filtered but neither reabsorbed nor secreted by the kidneys. GFR is typically expressed in units of ml/min:

$$GFR = \frac{\text{Urine Concentration} \times \text{Urine Flow}}{\text{Plasma Concentration}}$$

By normalizing the GFR to the body surface area, a GFR of approximately 75-100 ml/min per 1.73 m$^2$ can be assumed. The rate therefore measured is the quantity of the substance in the urine that originated from a calculable volume of blood.

There are several different techniques used to calculate or estimate the glomerular filtration rate (GFR or eGFR). In clinical practice, however, creatinine clearance is used to measure GFR. Creatinine is produced naturally by the body (creatinine is a metabolite of creatine, which is found in muscle). It is freely filtered by the glomerulus, but also actively secreted by the renal tubules in very small amounts such that creatinine clearance overestimates actual GFR by 10-20%. This margin of error is acceptable considering the ease with which creatinine clearance is measured.

Creatinine clearance (CCr) can be calculated if values for creatinine's urine concentration ($U_{Cr}$), urine flow rate (V), and creatinine's plasma concentration ($P_{Cr}$) are known. Since the product of urine concentration and urine flow rate yields creatinine's excretion rate, creatinine clearance is also said to be its excretion rate ($U_{Cr} \times V$) divided by its plasma concentration. This is commonly represented mathematically as:

$$C_{Cr} = \frac{U_{Cr} \times V}{P_{Cr}}$$

Commonly a 24 hour urine collection is undertaken, from empty-bladder one morning to the contents of the bladder the following morning, with a comparative blood test then taken:

$$C_{Cr} = \frac{U_{Cr} \times 24\text{- hour volume}}{P_{Cr} \times 24 \times 60 \text{ mins}}$$

To allow comparison of results between people of different sizes, the CCr is often corrected for the body surface area (BSA) and expressed compared to the average sized man as ml/min/1.73 m2. While most adults have a BSA that approaches 1.7 (1.6-1.9), extremely obese or slim patients should have their CCr corrected for their actual BSA:

$$C_{Cr\text{- corrected}} = \frac{C_{Cr} \times 1.73}{BSA}$$

The accuracy of a creatinine clearance measurement (even when collection is complete) is limited because as glomerular filtration rate (GFR) falls creatinine secretion is increased, and thus the rise in serum creatinine is less. Thus, creatinine excretion is much greater than the filtered load, resulting in a potentially large overestimation of the GFR (as much as a twofold difference). However, for clinical purposes it is important to determine whether renal function is stable or getting worse or better. This is often determined by monitoring serum creatinine alone. Like creatinine clearance, the serum creatinine will not be an accurate reflection of GFR in the non-steady-state condition of ARF. Nonetheless, the degree to which serum creatinine changes from baseline will reflect the change in GFR. Serum creatinine is readily and easily measured and it is specific for renal function.

For purposes of determining urine output on a Urine output on a mL/kg/hr basis, hourly urine collection measurement is adequate. In the case where, for example, only a cumulative 24-h output was available and no patient weights are provided, minor modifications of the RIFLE urine output criteria have been described. For example, Bagshaw et al., *Nephrol. Dial. Transplant.* 23: 1203-1210, 2008, assumes an average patient weight of 70 kg, and patients are assigned a RIFLE classification based on the following: <35 mL/h (Risk), <21 mL/h (Injury) or <4 mL/h (Failure).

Selecting a Treatment Regimen

Once a diagnosis is obtained, the clinician can readily select a treatment regimen that is compatible with the diagnosis, such as initiating renal replacement therapy, withdrawing delivery of compounds that are known to be damaging to the kidney, kidney transplantation, delaying or avoiding procedures that are known to be damaging to the kidney, modifying diuretic administration, initiating goal directed therapy, etc. The skilled artisan is aware of appropriate treatments for numerous diseases discussed in relation to the methods of diagnosis described herein. See, e.g., Merck Manual of Diagnosis and Therapy, 17th Ed. Merck Research Laboratories, Whitehouse Station, N.J., 1999. In addition, since the methods and compositions described herein provide prognostic information, the markers of the present invention may be used to monitor a course of treatment. For example, improved or worsened prognostic state may indicate that a particular treatment is or is not efficacious.

One skilled in the art readily appreciates that the present invention is well adapted to carry out the objects and obtain the ends and advantages mentioned, as well as those inherent therein. The examples provided herein are representative of preferred embodiments, are exemplary, and are not intended as limitations on the scope of the invention.

Example 1

Contrast-Induced Nephropathy Sample Collection

The objective of this sample collection study is to collect samples of plasma and urine and clinical data from patients before and after receiving intravascular contrast media. Approximately 250 adults undergoing radiographic/angiographic procedures involving intravascular administration of iodinated contrast media are enrolled. To be enrolled in the study, each patient must meet all of the following inclusion criteria and none of the following exclusion criteria:
Inclusion Criteria
males and females 18 years of age or older;
undergoing a radiographic/angiographic procedure (such as a CT scan or coronary intervention) involving the intravascular administration of contrast media;
expected to be hospitalized for at least 48 hours after contrast administration.
able and willing to provide written informed consent for study participation and to comply with all study procedures.
Exclusion Criteria
renal transplant recipients;
acutely worsening renal function prior to the contrast procedure;
already receiving dialysis (either acute or chronic) or in imminent need of dialysis at enrollment;
expected to undergo a major surgical procedure (such as involving cardiopulmonary bypass) or an additional imaging procedure with contrast media with significant risk for further renal insult within the 48 hrs following contrast administration;
participation in an interventional clinical study with an experimental therapy within the previous 30 days;
known infection with human immunodeficiency virus (HIV) or a hepatitis virus.

Immediately prior to the first contrast administration (and after any pre-procedure hydration), an EDTA anti-coagulated blood sample (10 mL) and a urine sample (10 mL) are collected from each patient. Blood and urine samples are then collected at 4 (±0.5), 8 (±1), 24 (±2) 48 (±2), and 72 (±2) hrs following the last administration of contrast media during the index contrast procedure. Blood is collected via direct venipuncture or via other available venous access, such as an existing femoral sheath, central venous line, peripheral intravenous line or hep-lock. These study blood samples are processed to plasma at the clinical site, frozen and shipped to Astute Medical, Inc., San Diego, Calif. The study urine samples are frozen and shipped to Astute Medical, Inc.

Serum creatinine is assessed at the site immediately prior to the first contrast administration (after any pre-procedure hydration) and at 4 (±0.5), 8 (±1), 24 (±2) and 48 (±2)), and 72 (±2) hours following the last administration of contrast (ideally at the same time as the study samples are obtained). In addition, each patient's status is evaluated through day 30 with regard to additional serum and urine creatinine measurements, a need for dialysis, hospitalization status, and adverse clinical outcomes (including mortality).

Prior to contrast administration, each patient is assigned a risk based on the following assessment: systolic blood pressure <80 mm Hg=5 points; intra-arterial balloon pump=5 points; congestive heart failure (Class III-IV or history of pulmonary edema)=5 points; age >75 yrs=4 points; hematocrit level <39% for men, <35% for women=3 points; diabetes=3 points; contrast media volume=1 point for each 100 mL; serum creatinine level >1.5 g/dL=4 points OR estimated GFR 40-60 mL/min/1.73 m$^2$=2 points, 20-40 mL/min/1.73 m$^2$=4 points, <20 mL/min/1.73 m$^2$=6 points. The risks assigned are as follows: risk for CIN and dialysis: 5 or less total points=risk of CIN—7.5%, risk of dialysis—0.04%; 6-10 total points=risk of CIN—14%, risk of dialysis—0.12%; 11-16 total points=risk of CIN—26.1%, risk of dialysis—1.09%; >16 total points=risk of CIN—57.3%, risk of dialysis—12.8%.

Example 2

Cardiac Surgery Sample Collection

The objective of this sample collection study is to collect samples of plasma and urine and clinical data from patients before and after undergoing cardiovascular surgery, a procedure known to be potentially damaging to kidney function. Approximately 900 adults undergoing such surgery are enrolled. To be enrolled in the study, each patient must meet all of the following inclusion criteria and none of the following exclusion criteria:
Inclusion Criteria
males and females 18 years of age or older;
undergoing cardiovascular surgery;
Toronto/Ottawa Predictive Risk Index for Renal Replacement risk score of at least 2 (Wijeysundera et al., *JAMA* 297: 1801-9, 2007); and
able and willing to provide written informed consent for study participation and to comply with all study procedures.
Exclusion Criteria
known pregnancy;
previous renal transplantation;
acutely worsening renal function prior to enrollment (e.g., any category of RIFLE criteria);
already receiving dialysis (either acute or chronic) or in imminent need of dialysis at enrollment;
currently enrolled in another clinical study or expected to be enrolled in another clinical study within 7 days of cardiac surgery that involves drug infusion or a therapeutic intervention for AKI;
known infection with human immunodeficiency virus (HIV) or a hepatitis virus.

Within 3 hours prior to the first incision (and after any pre-procedure hydration), an EDTA anti-coagulated blood sample (10 mL), whole blood (3 mL), and a urine sample (35 mL) are collected from each patient. Blood and urine samples are then collected at 3 (±0.5), 6 (±0.5), 12 (±1), 24 (±2) and 48 (±2) hrs following the procedure and then daily on days 3 through 7 if the subject remains in the hospital. Blood is collected via direct venipuncture or via other available venous access, such as an existing femoral sheath, central venous line, peripheral intravenous line or hep-lock. These study blood samples are frozen and shipped to Astute Medical, Inc., San Diego, Calif. The study urine samples are frozen and shipped to Astute Medical, Inc.

Example 3

Acutely Ill Subject Sample Collection

The objective of this study is to collect samples from acutely ill patients. Approximately 1900 adults expected to be in the ICU for at least 48 hours will be enrolled. To be enrolled in the study, each patient must meet all of the following inclusion criteria and none of the following exclusion criteria:

Inclusion Criteria
males and females 18 years of age or older;
Study population 1: approximately 300 patients that have at least one of:
shock (SBP<90 mmHg and/or need for vasopressor support to maintain MAP>60 mmHg and/or documented drop in SBP of at least 40 mmHg); and
sepsis;
Study population 2: approximately 300 patients that have at least one of:
IV antibiotics ordered in computerized physician order entry (CPOE) within 24 hours of enrollment;
contrast media exposure within 24 hours of enrollment;
increased Intra-Abdominal Pressure with acute decompensated heart failure; and
severe trauma as the primary reason for ICU admission and likely to be hospitalized in the ICU for 48 hours after enrollment;
Study population 3: approximately 300 patients expected to be hospitalized through acute care setting (ICU or ED) with a known risk factor for acute renal injury (e.g. sepsis, hypotension/shock (Shock=systolic BP<90 mmHg and/or the need for vasopressor support to maintain a MAP>60 mmHg and/or a documented drop in SBP>40 mmHg), major trauma, hemorrhage, or major surgery); and/or expected to be hospitalized to the ICU for at least 24 hours after enrollment;
Study population 4: approximately 1000 patients that are 21 years of age or older, within 24 hours of being admitted into the ICU, expected to have an indwelling urinary catheter for at least 48 hours after enrollment, and have at least one of the following acute conditions within 24 hours prior to enrollment:
(i) respiratory SOFA score of ≥2 (PaO2/FiO2<300), (ii) cardiovascular SOFA score of ≥1 (MAP<70 mm Hg and/or any vasopressor required).

Exclusion Criteria
known pregnancy;
institutionalized individuals;
previous renal transplantation;
known acutely worsening renal function prior to enrollment (e.g., any category of RIFLE criteria);
received dialysis (either acute or chronic) within 5 days prior to enrollment or in imminent need of dialysis at the time of enrollment;
known infection with human immunodeficiency virus (HIV) or a hepatitis virus;
meets any of the following:
(i) active bleeding with an anticipated need for >4 units PRBC in a day;
(ii) hemoglobin <7 g/dL;
(iii) any other condition that in the physician's opinion would contraindicate drawing serial blood samples for clinical study purposes;
meets only the SBP<90 mmHg inclusion criterion set forth above, and does not have shock in the attending physician's or principal investigator's opinion;

After obtaining informed consent, an EDTA anti-coagulated blood sample (10 mL) and a urine sample (25-50 mL) are collected from each patient. Blood and urine samples are then collected at 4 (±0.5) and 8 (±1) hours after contrast administration (if applicable); at 12 (±1), 24 (±2), 36 (±2), 48 (±2), 60 (±2), 72 (±2), and 84 (±2) hours after enrollment, and thereafter daily up to day 7 to day 14 while the subject is hospitalized. Blood is collected via direct venipuncture or via other available venous access, such as an existing femoral sheath, central venous line, peripheral intravenous line or hep-lock. These study blood samples are processed to plasma at the clinical site, frozen and shipped to Astute Medical, Inc., San Diego, Calif. The study urine samples are frozen and shipped to Astute Medical, Inc.

Example 4

Immunoassay Format

Analytes are measured using standard sandwich enzyme immunoassay techniques. A first antibody which binds the analyte is immobilized in wells of a 96 well polystyrene microplate. Analyte standards and test samples are pipetted into the appropriate wells and any analyte present is bound by the immobilized antibody. After washing away any unbound substances, a horseradish peroxidase-conjugated second antibody which binds the analyte is added to the wells, thereby forming sandwich complexes with the analyte (if present) and the first antibody. Following a wash to remove any unbound antibody-enzyme reagent, a substrate solution comprising tetramethylbenzidine and hydrogen peroxide is added to the wells. Color develops in proportion to the amount of analyte present in the sample. The color development is stopped and the intensity of the color is measured at 540 nm or 570 nm. An analyte concentration is assigned to the test sample by comparison to a standard curve determined from the analyte standards.

Units for the concentrations reported in the following data tables are as follows: Heat shock 70 kDa protein 1—pg/mL, Alpha-1-antitrypsin Neutrophil elastase complex—pg/mL, Stromelysin-1:Metalloproteinase inhibitor 2 complex—pg/mL, Insulin-like growth factor 1 receptor—ng/mL, Myeloid differentiation primary response protein MyD88—ng/mL, Neuronal cell adhesion molecule—ng/mL, and Tumor necrosis factor ligand superfamily member 10—pg/mL. In the case of those kidney injury markers which are membrane proteins as described herein, the assays used in these examples detect soluble forms thereof.

Example 5

Apparently Healthy Donor and Chronic Disease Patient Samples

Human urine samples from donors with no known chronic or acute disease ("Apparently Healthy Donors") were purchased from two vendors (Golden West Biologicals, Inc., 27625 Commerce Center Dr., Temecula, Calif. 92590 and Virginia Medical Research, Inc., 915 First Colonial Rd., Virginia Beach, Va. 23454). The urine samples were shipped and stored frozen at less than −20° C. The vendors supplied demographic information for the individual donors including gender, race (Black/White), smoking status and age.

Human urine samples from donors with various chronic diseases ("Chronic Disease Patients") including congestive heart failure, coronary artery disease, chronic kidney disease, chronic obstructive pulmonary disease, diabetes mellitus and hypertension were purchased from Virginia Medical Research, Inc., 915 First Colonial Rd., Virginia Beach, Va. 23454. The urine samples were shipped and stored frozen at less than −20 degrees centigrade. The vendor provided a case report form for each individual donor with age, gender, race (Black/White), smoking status and alcohol use, height, weight, chronic disease(s) diagnosis, current medications and previous surgeries.

Example 6

Use of Kidney Injury Markers for Evaluating Renal Status in Patients

Patients from the intensive care unit (ICU) were enrolled in the following study. Each patient was classified by kidney status as non-injury (0), risk of injury (R), injury (I), and failure (F) according to the maximum stage reached within 7 days of enrollment as determined by the RIFLE criteria. EDTA anti-coagulated blood samples (10 mL) and a urine samples (25-30 mL) were collected from each patient at enrollment, 4 (±0.5) and 8 (±1) hours after contrast administration (if applicable); at 12 (±1), 24 (±2), and 48 (±2) hours after enrollment, and thereafter daily up to day 7 to day 14 while the subject is hospitalized. Markers were each measured by standard immunoassay methods using commercially available assay reagents in the urine samples and the plasma component of the blood samples collected.

Two cohorts were defined to represent a "diseased" and a "normal" population. While these terms are used for convenience, "diseased" and "normal" simply represent two cohorts for comparison (say RIFLE 0 vs RIFLE R, I and F; RIFLE 0 vs RIFLE R; RIFLE 0 and R vs RIFLE I and F; etc.). The time "prior max stage" represents the time at which a sample is collected, relative to the time a particular patient reaches the lowest disease stage as defined for that cohort, binned into three groups which are +/−12 hours. For example, "24 hr prior" which uses 0 vs R, I, F as the two cohorts would mean 24 hr (+/−12 hours) prior to reaching stage R (or I if no sample at R, or F if no sample at R or I).

A receiver operating characteristic (ROC) curve was generated for each biomarker measured and the area under each ROC curve (AUC) is determined Patients in Cohort 2 were also separated according to the reason for adjudication to cohort 2 as being based on serum creatinine measurements (sCr), being based on urine output (UO), or being based on either serum creatinine measurements or urine output. Using the same example discussed above (0 vs R, I, F), for those patients adjudicated to stage R, I, or F on the basis of serum creatinine measurements alone, the stage 0 cohort may include patients adjudicated to stage R, I, or F on the basis of urine output; for those patients adjudicated to stage R, I, or F on the basis of urine output alone, the stage 0 cohort may include patients adjudicated to stage R, I, or F on the basis of serum creatinine measurements; and for those patients adjudicated to stage R, I, or F on the basis of serum creatinine measurements or urine output, the stage 0 cohort contains only patients in stage 0 for both serum creatinine measurements and urine output. Also, in the data for patients adjudicated on the basis of serum creatinine measurements or urine output, the adjudication method which yielded the most severe RIFLE stage is used.

The ability to distinguish cohort 1 from Cohort 2 was determined using ROC analysis. SE is the standard error of the AUC, n is the number of sample or individual patients ("pts," as indicated). Standard errors are calculated as described in Hanley, J. A., and McNeil, B. J., The meaning and use of the area under a receiver operating characteristic (ROC) curve. Radiology (1982) 143: 29-36; p values are calculated with a two-tailed Z-test. An AUC<0.5 is indicative of a negative going marker for the comparison, and an AUC>0.5 is indicative of a positive going marker for the comparison.

Various threshold (or "cutoff") concentrations were selected, and the associated sensitivity and specificity for distinguishing cohort 1 from cohort 2 are determined OR is the odds ratio calculated for the particular cutoff concentration, and 95% CI is the confidence interval for the odds ratio.

TABLE 1

Comparison of marker levels in urine samples collected from Cohort 1 (patients that did not progress beyond RIFLE stage 0) and in urine samples collected from subjects at 0, 24 hours, and 48 hours prior to reaching stage R, I or F in Cohort 2.

Stromelysin-1:Metalloproteinase inhibitor 2 complex

| | 0 hr prior to AKI stage | | 24 hr prior to AKI stage | | 48 hr prior to AKI stage | |
| --- | --- | --- | --- | --- | --- | --- |
| | Cohort 1 | Cohort 2 | Cohort 1 | Cohort 2 | Cohort 1 | Cohort 2 |
| sCr or UO | | | | | | |
| Median | 0.487 | 0.237 | 0.487 | 0.487 | 0.487 | 0.362 |
| Average | 328 | 5.13 | 328 | 22.4 | 328 | 0.362 |
| Stdev | 1910 | 21.0 | 1910 | 65.2 | 1910 | 0.176 |
| p (t-test) | | 0.47 | | 0.49 | | 0.81 |
| Min | 0.237 | 0.237 | 0.237 | 0.237 | 0.237 | 0.237 |
| Max | 13900 | 91.7 | 13900 | 267 | 13900 | 0.487 |
| n (Samp) | 53 | 19 | 53 | 19 | 53 | 2 |
| n (Patient) | 42 | 19 | 42 | 19 | 42 | 2 |
| sCr only | | | | | | |
| Median | 0.487 | 0.487 | 0.487 | 0.487 | 0.487 | 0.487 |
| Average | 193 | 0.387 | 193 | 111 | 193 | 0.487 |
| Stdev | 1440 | 0.137 | 1440 | 235 | 1440 | 0 |
| p (t-test) | | 0.77 | | 0.90 | | 0.85 |
| Min | 0.237 | 0.237 | 0.237 | 0.237 | 0.237 | 0.487 |
| Max | 13900 | 0.487 | 13900 | 530 | 13900 | 0.487 |

TABLE 1-continued

Comparison of marker levels in urine samples collected from Cohort 1
(patients that did not progress beyond RIFLE stage 0) and in urine samples collected
from subjects at 0, 24 hours, and 48 hours prior to reaching stage R, I or F in Cohort 2.

|  | | | | | | |
|---|---|---|---|---|---|---|
| n (Samp) | 93 | 5 | 93 | 5 | 93 | 2 |
| n (Patient) | 73 | 5 | 73 | 5 | 73 | 2 |
| UO only | | | | | | |
| Median | 0.487 | 0.237 | 0.487 | 0.487 | 0.487 | 0.487 |
| Average | 348 | 6.40 | 348 | 117 | 348 | 0.425 |
| Stdev | 2070 | 23.6 | 2070 | 431 | 2070 | 0.125 |
| p (t-test) | | 0.53 | | 0.62 | | 0.74 |
| Min | 0.237 | 0.237 | 0.237 | 0.237 | 0.237 | 0.237 |
| Max | 13900 | 91.7 | 13900 | 1930 | 13900 | 0.487 |
| n (Samp) | 45 | 15 | 45 | 20 | 45 | 4 |
| n (Patient) | 35 | 15 | 35 | 20 | 35 | 4 |

|  | 0 hr prior to AKI stage | | | 24 hr prior to AKI stage | | | 48 hr prior to AKI stage | | |
|---|---|---|---|---|---|---|---|---|---|
|  | sCr or UO | sCr only | UO only | sCr or UO | sCr only | UO only | sCr or UO | sCr only | UO only |
| AUC | 0.32 | 0.47 | 0.39 | 0.44 | 0.57 | 0.58 | 0.35 | 0.63 | 0.54 |
| SE | 0.075 | 0.14 | 0.087 | 0.078 | 0.14 | 0.079 | 0.22 | 0.21 | 0.15 |
| p | 0.015 | 0.80 | 0.20 | 0.46 | 0.60 | 0.33 | 0.50 | 0.55 | 0.82 |
| nCohort 1 | 53 | 93 | 45 | 53 | 93 | 45 | 53 | 93 | 45 |
| nCohort 2 | 19 | 5 | 15 | 19 | 5 | 20 | 2 | 2 | 4 |
| Cutoff 1 | 0 | 0 | 0 | 0 | 0 | 0.237 | 0 | 0.237 | 0.237 |
| Sens 1 | 100% | 100% | 100% | 100% | 100% | 70% | 100% | 100% | 75% |
| Spec 1 | 0% | 0% | 0% | 0% | 0% | 49% | 0% | 44% | 49% |
| Cutoff 2 | 0 | 0 | 0 | 0 | 0 | 0 | 0 | 0.237 | 0 |
| Sens 2 | 100% | 100% | 100% | 100% | 100% | 100% | 100% | 100% | 100% |
| Spec 2 | 0% | 0% | 0% | 0% | 0% | 0% | 0% | 44% | 0% |
| Cutoff 3 | 0 | 0 | 0 | 0 | 0 | 0 | 0 | 0.237 | 0 |
| Sens 3 | 100% | 100% | 100% | 100% | 100% | 100% | 100% | 100% | 100% |
| Spec 3 | 0% | 0% | 0% | 0% | 0% | 0% | 0% | 44% | 0% |
| Cutoff 4 | 0.487 | 0.487 | 0.487 | 0.487 | 0.487 | 0.487 | 0.487 | 0.487 | 0.487 |
| Sens 4 | 5% | 0% | 7% | 21% | 40% | 25% | 0% | 0% | 0% |
| Spec 4 | 77% | 82% | 78% | 77% | 82% | 78% | 77% | 82% | 78% |
| Cutoff 5 | 85.2 | 0.487 | 3.84 | 85.2 | 0.487 | 3.84 | 85.2 | 0.487 | 3.84 |
| Sens 5 | 5% | 0% | 7% | 11% | 40% | 25% | 0% | 0% | 0% |
| Spec 5 | 81% | 82% | 80% | 81% | 82% | 80% | 81% | 82% | 80% |
| Cutoff 6 | 201 | 154 | 201 | 201 | 154 | 201 | 201 | 154 | 201 |
| Sens 6 | 0% | 0% | 0% | 5% | 20% | 10% | 0% | 0% | 0% |
| Spec 6 | 91% | 90% | 93% | 91% | 90% | 93% | 91% | 90% | 93% |
| OR Quart 2 | 1.0 | >3.6 | 5.1 | 0.70 | 0.96 | >27 | >0 | >2.1 | 0 |
| p Value | 1.0 | <0.29 | 0.17 | 0.67 | 0.98 | <0.0044 | <na | <0.56 | na |
| 95% CI of | 0.058 | >0.35 | 0.50 | 0.13 | 0.057 | >2.8 | >na | >0.18 | na |
| OR Quart 2 | 17 | na | 52 | 3.7 | 16 | na | na | na | na |
| OR Quart 3 | 34 | >1.0 | 12 | 1.3 | 1.0 | >7.3 | >1.1 | >0 | 3.7 |
| p Value | 0.0021 | <0.98 | 0.030 | 0.70 | 1.0 | <0.088 | <0.96 | <na | 0.29 |
| 95% CI of | 3.6 | >0.062 | 1.3 | 0.30 | 0.059 | >0.74 | >0.061 | >na | 0.32 |
| OR Quart 3 | 320 | na | 120 | 6.1 | 17 | na | na | na | 42 |
| OR Quart 4 | 6.5 | >1.1 | 3.5 | 2.2 | 2.0 | >6.7 | >1.2 | >0 | 0 |
| p Value | 0.10 | <0.95 | 0.30 | 0.28 | 0.58 | <0.10 | <0.92 | <na | na |
| 95% CI of | 0.68 | >0.064 | 0.32 | 0.52 | 0.17 | >0.69 | >0.066 | >na | na |
| OR Quart4 | 63 | na | 38 | 9.6 | 24 | na | na | na | na |

Heat shock 70 kDa protein 1

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| sCr or UO | | | | | | |
| Median | 277 | 424 | 277 | 499 | 277 | 225 |
| Average | 558 | 408 | 558 | 702 | 558 | 700 |
| Stdev | 1110 | 392 | 1110 | 906 | 1110 | 897 |
| p (t-test) | | 0.58 | | 0.62 | | 0.83 |
| Min | 0.297 | 0.335 | 0.297 | 0.335 | 0.297 | 140 |
| Max | 7800 | 1680 | 7800 | 3860 | 7800 | 1730 |
| n (Samp) | 51 | 18 | 51 | 18 | 51 | 3 |
| n (Patient) | 41 | 18 | 41 | 18 | 41 | 3 |
| sCr only | | | | | | |
| Median | 286 | 459 | 286 | 982 | 286 | 774 |
| Average | 535 | 863 | 535 | 861 | 535 | 774 |
| Stdev | 943 | 767 | 943 | 592 | 943 | 776 |
| p (t-test) | | 0.45 | | 0.45 | | 0.72 |
| Min | 0.297 | 217 | 0.297 | 335 | 0.297 | 225 |

TABLE 1-continued

Comparison of marker levels in urine samples collected from Cohort 1
(patients that did not progress beyond RIFLE stage 0) and in urine samples collected
from subjects at 0, 24 hours, and 48 hours prior to reaching stage R, I or F in Cohort 2.

| | | | | | | |
|---|---|---|---|---|---|---|
| Max | 7800 | 1710 | 7800 | 1600 | 7800 | 1320 |
| n (Samp) | 90 | 5 | 90 | 5 | 90 | 2 |
| n (Patient) | 71 | 5 | 71 | 5 | 71 | 2 |
| UO only | | | | | | |
| Median | 224 | 424 | 224 | 435 | 224 | 1680 |
| Average | 553 | 339 | 553 | 1260 | 553 | 1170 |
| Stdev | 1190 | 258 | 1190 | 2690 | 1190 | 801 |
| p (t-test) | | 0.51 | | 0.15 | | 0.27 |
| Min | 0.297 | 0.335 | 0.297 | 0.335 | 0.297 | 140 |
| Max | 7800 | 812 | 7800 | 11800 | 7800 | 1820 |
| n (Samp) | 45 | 14 | 45 | 19 | 45 | 5 |
| n (Patient) | 35 | 14 | 35 | 19 | 35 | 5 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.52 | 0.68 | 0.53 | 0.57 | 0.70 | 0.64 | 0.57 | 0.69 | 0.78 |
| SE | 0.080 | 0.14 | 0.090 | 0.080 | 0.13 | 0.079 | 0.18 | 0.21 | 0.13 |
| p | 0.85 | 0.17 | 0.77 | 0.37 | 0.13 | 0.079 | 0.70 | 0.36 | 0.025 |
| nCohort 1 | 51 | 90 | 45 | 51 | 90 | 45 | 51 | 90 | 45 |
| nCohort 2 | 18 | 5 | 14 | 18 | 5 | 19 | 3 | 2 | 5 |
| Cutoff 1 | 210 | 245 | 99.4 | 151 | 627 | 180 | 117 | 224 | 401 |
| Sens 1 | 72% | 80% | 71% | 72% | 80% | 74% | 100% | 100% | 80% |
| Spec 1 | 39% | 47% | 36% | 29% | 73% | 44% | 29% | 43% | 67% |
| Cutoff 2 | 60.6 | 245 | 47.5 | 117 | 627 | 135 | 117 | 224 | 401 |
| Sens 2 | 83% | 80% | 86% | 83% | 80% | 84% | 100% | 100% | 80% |
| Spec 2 | 20% | 47% | 24% | 29% | 73% | 38% | 29% | 43% | 67% |
| Cutoff 3 | 20.7 | 210 | 23.5 | 0.297 | 0.297 | 99.4 | 117 | 224 | 135 |
| Sens 3 | 94% | 100% | 93% | 100% | 100% | 95% | 100% | 100% | 100% |
| Spec 3 | 10% | 41% | 16% | 2% | 1% | 36% | 29% | 43% | 38% |
| Cutoff 4 | 574 | 545 | 512 | 574 | 545 | 512 | 574 | 545 | 512 |
| Sens 4 | 17% | 40% | 21% | 44% | 80% | 42% | 33% | 50% | 60% |
| Spec 4 | 71% | 70% | 71% | 71% | 70% | 71% | 71% | 70% | 71% |
| Cutoff 5 | 755 | 763 | 664 | 755 | 763 | 664 | 755 | 763 | 664 |
| Sens 5 | 11% | 40% | 14% | 33% | 60% | 32% | 33% | 50% | 60% |
| Spec 5 | 80% | 80% | 80% | 80% | 80% | 80% | 80% | 80% | 80% |
| Cutoff 6 | 1020 | 1020 | 1320 | 1020 | 1020 | 1320 | 1020 | 1020 | 1320 |
| Sens 6 | 6% | 40% | 0% | 17% | 40% | 16% | 33% | 50% | 60% |
| Spec 6 | 90% | 90% | 91% | 90% | 90% | 91% | 90% | 90% | 91% |
| OR Quart 2 | 1.0 | >2.1 | 0.56 | 1.9 | 0 | 6.8 | >2.2 | >1.0 | >1.0 |
| p Value | 1.0 | <0.56 | 0.57 | 0.42 | na | 0.099 | <0.55 | <0.98 | <1.0 |
| 95% CI of | 0.20 | >0.18 | 0.079 | 0.38 | na | 0.69 | >0.17 | >0.062 | >0.056 |
| OR Quart 2 | 4.9 | na | 4.0 | 9.9 | na | 67 | na | na | na |
| OR Quart 3 | 2.3 | >1.0 | 3.2 | 1.4 | 0.96 | 12 | >0 | >0 | >1.1 |
| p Value | 0.28 | <1.0 | 0.16 | 0.67 | 0.98 | 0.033 | <na | <na | <0.95 |
| 95% CI of | 0.52 | >0.059 | 0.63 | 0.27 | 0.056 | 1.2 | >na | >na | >0.061 |
| OR Quart 3 | 10.0 | na | 16 | 7.7 | 16 | 110 | na | na | na |
| OR Quart 4 | 0.65 | >2.1 | 0.56 | 2.3 | 3.1 | 9.0 | >1.0 | >1.0 | >3.6 |
| p Value | 0.61 | <0.56 | 0.57 | 0.30 | 0.34 | 0.057 | <1.0 | <0.98 | <0.30 |
| 95% CI of | 0.12 | >0.18 | 0.079 | 0.48 | 0.30 | 0.94 | >0.056 | >0.062 | >0.32 |
| OR Quart 4 | 3.5 | na | 4.0 | 11 | 33 | 87 | na | na | na |

Insulin-like growth factor 1 receptor

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| sCr or UO | | | | | | |
| Median | 0.0103 | 0.0103 | 0.0103 | 0.0169 | nd | nd |
| Average | 0.0275 | 0.0137 | 0.0275 | 0.0405 | nd | nd |
| Stdev | 0.0922 | 0.0113 | 0.0922 | 0.0818 | nd | nd |
| p (t-test) | | 0.54 | | 0.59 | nd | nd |
| Min | 0.000123 | 0.000172 | 0.000123 | 0.000172 | nd | nd |
| Max | 0.679 | 0.0423 | 0.679 | 0.365 | nd | nd |
| n (Samp) | 54 | 17 | 54 | 19 | nd | nd |
| n (Patient) | 43 | 17 | 43 | 19 | nd | nd |
| sCr only | | | | | | |
| Median | 0.0103 | 0.00132 | 0.0103 | 0.0381 | 0.0103 | 0.0292 |
| Average | 0.0278 | 0.00733 | 0.0278 | 0.0354 | 0.0278 | 0.0292 |
| Stdev | 0.0804 | 0.00927 | 0.0804 | 0.0263 | 0.0804 | 0 |
| p (t-test) | | 0.57 | | 0.83 | | 0.98 |

TABLE 1-continued

Comparison of marker levels in urine samples collected from Cohort 1
(patients that did not progress beyond RIFLE stage 0) and in urine samples collected
from subjects at 0, 24 hours, and 48 hours prior to reaching stage R, I or F in Cohort 2.

| | | | | | | |
|---|---|---|---|---|---|---|
| Min | 0.000123 | 0.000172 | 0.000123 | 0.000519 | 0.000123 | 0.0292 |
| Max | 0.679 | 0.0197 | 0.679 | 0.0680 | 0.679 | 0.0292 |
| n (Samp) | 91 | 5 | 91 | 5 | 91 | 2 |
| n (Patient) | 73 | 5 | 73 | 5 | 73 | 2 |
| UO only | | | | | | |
| Median | 0.0103 | 0.0169 | 0.0103 | 0.0115 | 0.0103 | 0.0150 |
| Average | 0.0292 | 0.0166 | 0.0292 | 0.0335 | 0.0292 | 0.0200 |
| Stdev | 0.0988 | 0.0108 | 0.0988 | 0.0799 | 0.0988 | 0.0216 |
| p (t-test) | | 0.65 | | 0.86 | | 0.87 |
| Min | 0.000123 | 0.000519 | 0.000123 | 0.000172 | 0.000123 | 0.00132 |
| Max | 0.679 | 0.0423 | 0.679 | 0.365 | 0.679 | 0.0436 |
| n (Samp) | 47 | 13 | 47 | 20 | 47 | 3 |
| n (Patient) | 37 | 13 | 37 | 20 | 37 | 3 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.50 | 0.34 | 0.59 | 0.59 | 0.72 | 0.56 | nd | 0.81 | 0.63 |
| SE | 0.081 | 0.14 | 0.092 | 0.078 | 0.13 | 0.078 | nd | 0.19 | 0.18 |
| p | 0.98 | 0.25 | 0.33 | 0.23 | 0.10 | 0.47 | nd | 0.093 | 0.48 |
| nCohort 1 | 54 | 91 | 47 | 54 | 91 | 47 | nd | 91 | 47 |
| nCohort 2 | 17 | 5 | 13 | 19 | 5 | 20 | nd | 2 | 3 |
| Cutoff 1 | 0.00573 | 0.000172 | 0.00454 | 0.00132 | 0.0169 | 0.00454 | nd | 0.0254 | 0.000519 |
| Sens 1 | 76% | 80% | 92% | 74% | 80% | 70% | nd | 100% | 100% |
| Spec 1 | 30% | 11% | 36% | 26% | 67% | 36% | nd | 79% | 30% |
| Cutoff 2 | 0.000519 | 0.000172 | 0.00454 | 0.000172 | 0.0169 | 0.000519 | nd | 0.0254 | 0.000519 |
| Sens 2 | 82% | 80% | 92% | 89% | 80% | 85% | nd | 100% | 100% |
| Spec 2 | 20% | 11% | 36% | 13% | 67% | 30% | nd | 79% | 30% |
| Cutoff 3 | 0.000172 | 0.000123 | 0.00454 | 0.000123 | 0.000172 | 0.000172 | nd | 0.0254 | 0.000519 |
| Sens 3 | 94% | 100% | 92% | 100% | 100% | 90% | nd | 100% | 100% |
| Spec 3 | 13% | 2% | 36% | 4% | 11% | 19% | nd | 79% | 30% |
| Cutoff 4 | 0.0169 | 0.0197 | 0.0169 | 0.0169 | 0.0197 | 0.0169 | nd | 0.0197 | 0.0169 |
| Sens 4 | 35% | 0% | 46% | 47% | 60% | 35% | nd | 100% | 33% |
| Spec 4 | 72% | 71% | 70% | 72% | 71% | 70% | nd | 71% | 70% |
| Cutoff 5 | 0.0292 | 0.0292 | 0.0292 | 0.0292 | 0.0292 | 0.0292 | nd | 0.0292 | 0.0292 |
| Sens 5 | 6% | 0% | 8% | 32% | 60% | 15% | nd | 0% | 33% |
| Spec 5 | 85% | 84% | 85% | 85% | 84% | 85% | nd | 84% | 85% |
| Cutoff 6 | 0.0388 | 0.0423 | 0.0388 | 0.0388 | 0.0423 | 0.0388 | nd | 0.0423 | 0.0388 |
| Sens 6 | 6% | 0% | 8% | 21% | 40% | 10% | nd | 0% | 33% |
| Spec 6 | 93% | 92% | 91% | 93% | 92% | 91% | nd | 92% | 91% |
| OR Quart 2 | 1.2 | >2.2 | 7.0 | 1.0 | 0 | 3.8 | nd | >0 | >1.0 |
| p Value | 0.77 | <0.54 | 0.097 | 1.0 | na | 0.14 | nd | <na | <1.0 |
| 95% CI of | 0.27 | >0.18 | 0.71 | 0.21 | na | 0.64 | nd | >na | >0.056 |
| OR Quart 2 | 5.7 | na | 69 | 4.8 | na | 23 | nd | na | na |
| OR Quart 3 | 0.93 | >0 | 3.5 | 1.0 | 1.0 | 3.8 | nd | >0 | >1.1 |
| p Value | 0.93 | <na | 0.30 | 1.0 | 1.0 | 0.14 | nd | <na | <0.95 |
| 95% CI of | 0.19 | >na | 0.32 | 0.21 | 0.059 | 0.64 | nd | >na | >0.061 |
| OR Quart 3 | 4.5 | na | 38 | 4.8 | 17 | 23 | nd | na | na |
| OR Quart 4 | 0.93 | >3.4 | 5.1 | 2.0 | 3.3 | 3.8 | nd | >2.1 | >1.0 |
| p Value | 0.93 | <0.30 | 0.17 | 0.33 | 0.32 | 0.14 | nd | <0.56 | <1.0 |
| 95% CI of | 0.19 | >0.33 | 0.50 | 0.48 | 0.32 | 0.64 | nd | >0.18 | >0.056 |
| OR Quart 4 | 4.5 | na | 52 | 8.7 | 34 | 23 | nd | na | na |

| Interstitial collagenase:Metalloproteinase inhibitor 2 complex | | | | | | |
|---|---|---|---|---|---|---|
| | 0 hr prior to AKI stage | | 24 hr prior to AKI stage | | 48 hr prior to AKI stage | |
| | Cohort 1 | Cohort 2 | Cohort 1 | Cohort 2 | Cohort 1 | Cohort 2 |
| sCr or UO | | | | | | |
| Median | 0.233 | 0.233 | 0.233 | 0.233 | 0.233 | 0.231 |
| Average | 315 | 0.967 | 315 | 18.9 | 315 | 0.231 |
| Stdev | 2200 | 3.21 | 2200 | 68.2 | 2200 | 0.00389 |
| p (t-test) | | 0.54 | | 0.56 | | 0.84 |
| Min | 0.228 | 0.228 | 0.228 | 0.228 | 0.228 | 0.228 |
| Max | 16000 | 14.2 | 16000 | 297 | 16000 | 0.233 |
| n (Samp) | 53 | 19 | 53 | 19 | 53 | 2 |
| n (Patient) | 42 | 19 | 42 | 19 | 42 | 2 |
| sCr only | | | | | | |
| Median | 0.233 | 0.233 | 0.233 | 0.233 | 0.233 | 0.228 |
| Average | 184 | 4.37 | 184 | 6.08 | 184 | 0.228 |
| Stdev | 1660 | 6.22 | 1660 | 13.1 | 1660 | 0 |

TABLE 1-continued

Comparison of marker levels in urine samples collected from Cohort 1
(patients that did not progress beyond RIFLE stage 0) and in urine samples collected
from subjects at 0, 24 hours, and 48 hours prior to reaching stage R, I or F in Cohort 2.

|  |  |  |  |  |  |  |
|---|---|---|---|---|---|---|
| p (t-test) |  | 0.81 |  | 0.81 |  | 0.88 |
| Min | 0.228 | 0.228 | 0.228 | 0.228 | 0.228 | 0.228 |
| Max | 16000 | 14.2 | 16000 | 29.5 | 16000 | 0.228 |
| n (Samp) | 93 | 5 | 93 | 5 | 93 | 2 |
| n (Patient) | 73 | 5 | 73 | 5 | 73 | 2 |
| UO only |  |  |  |  |  |  |
| Median | 0.233 | 0.233 | 0.233 | 0.233 | 0.233 | 0.231 |
| Average | 360 | 0.232 | 360 | 37.2 | 360 | 3.72 |
| Stdev | 2380 | 0.00268 | 2380 | 105 | 2380 | 6.99 |
| p (t-test) |  | 0.56 |  | 0.55 |  | 0.77 |
| Min | 0.228 | 0.228 | 0.228 | 0.228 | 0.228 | 0.228 |
| Max | 16000 | 0.233 | 16000 | 384 | 16000 | 14.2 |
| n (Samp) | 45 | 15 | 45 | 20 | 45 | 4 |
| n (Patient) | 35 | 15 | 35 | 20 | 35 | 4 |

|  | 0 hr prior to AKI stage | | | 24 hr prior to AKI stage | | | 48 hr prior to AKI stage | | |
|---|---|---|---|---|---|---|---|---|---|
|  | sCr or UO | sCr only | UO only | sCr or UO | sCr only | UO only | sCr or UO | sCr only | UO only |
| AUC | 0.50 | 0.61 | 0.40 | 0.58 | 0.56 | 0.50 | 0.42 | 0.18 | 0.42 |
| SE | 0.078 | 0.14 | 0.087 | 0.078 | 0.14 | 0.078 | 0.22 | 0.18 | 0.16 |
| p | 0.96 | 0.41 | 0.25 | 0.33 | 0.65 | 0.98 | 0.71 | 0.086 | 0.63 |
| nCohort 1 | 53 | 93 | 45 | 53 | 93 | 45 | 53 | 93 | 45 |
| nCohort 2 | 19 | 5 | 15 | 19 | 5 | 20 | 2 | 2 | 4 |
| Cutoff 1 | 0 | 0.228 | 0 | 0.228 | 0.228 | 0 | 0 | 0 | 0 |
| Sens 1 | 100% | 80% | 100% | 74% | 80% | 100% | 100% | 100% | 100% |
| Spec 1 | 0% | 37% | 0% | 45% | 37% | 0% | 0% | 0% | 0% |
| Cutoff 2 | 0 | 0.228 | 0 | 0 | 0.228 | 0 | 0 | 0 | 0 |
| Sens 2 | 100% | 80% | 100% | 100% | 80% | 100% | 100% | 100% | 100% |
| Spec 2 | 0% | 37% | 0% | 0% | 37% | 0% | 0% | 0% | 0% |
| Cutoff 3 | 0 | 0 | 0 | 0 | 0 | 0 | 0 | 0 | 0 |
| Sens 3 | 100% | 100% | 100% | 100% | 100% | 100% | 100% | 100% | 100% |
| Spec 3 | 0% | 0% | 0% | 0% | 0% | 0% | 0% | 0% | 0% |
| Cutoff 4 | 0.233 | 0.233 | 0.233 | 0.233 | 0.233 | 0.233 | 0.233 | 0.233 | 0.233 |
| Sens 4 | 5% | 40% | 0% | 26% | 20% | 30% | 0% | 0% | 25% |
| Spec 4 | 77% | 78% | 73% | 77% | 78% | 73% | 77% | 78% | 73% |
| Cutoff 5 | 2.99 | 2.13 | 2.99 | 2.99 | 2.13 | 2.99 | 2.99 | 2.13 | 2.99 |
| Sens 5 | 5% | 40% | 0% | 21% | 20% | 25% | 0% | 0% | 25% |
| Spec 5 | 81% | 81% | 80% | 81% | 81% | 80% | 81% | 81% | 80% |
| Cutoff 6 | 30.3 | 18.5 | 18.5 | 30.3 | 18.5 | 18.5 | 30.3 | 18.5 | 18.5 |
| Sens 6 | 0% | 0% | 0% | 11% | 20% | 15% | 0% | 0% | 0% |
| Spec 6 | 91% | 90% | 93% | 91% | 90% | 93% | 91% | 90% | 93% |
| OR Quart 2 | 0.12 | >1.0 | >10 | 0 | >1.0 | 0.43 | >1.1 | >0 | 1.1 |
| p Value | 0.061 | <1.0 | <0.047 | na | <1.0 | 0.27 | <0.96 | <na | 0.95 |
| 95% CI of | 0.012 | >0.059 | >1.0 | na | >0.059 | 0.095 | >0.061 | >na | 0.061 |
| OR Quart 2 | 1.1 | na | na | na | na | 1.9 | na | na | 20 |
| OR Quart 3 | 3.1 | >2.2 | >5.5 | 2.6 | >3.4 | 0.30 | >0 | >0 | 0 |
| p Value | 0.100 | <0.54 | <0.15 | 0.18 | <0.30 | 0.14 | <na | <na | na |
| 95% CI of | 0.80 | >0.18 | >0.53 | 0.65 | >0.33 | 0.060 | >na | >na | na |
| OR Quart 3 | 12 | na | na | 10 | na | 1.5 | na | na | na |
| OR Quart 4 | 0.12 | >2.1 | >7.5 | 1.0 | >1.0 | 0.70 | >1.2 | >2.3 | 2.4 |
| p Value | 0.061 | <0.56 | <0.085 | 1.0 | <1.0 | 0.62 | <0.92 | <0.51 | 0.50 |
| 95% CI of | 0.012 | >0.18 | >0.76 | 0.23 | >0.059 | 0.17 | >0.066 | >0.19 | 0.19 |
| OR Quart 4 | 1.1 | na | na | 4.3 | na | 2.8 | na | na | 31 |

72 kDa type IV collagenase:Metalloproteinase inhibitor 2 complex

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| sCr or UO |  |  |  |  |  |  |
| Median | 63.6 | 11.3 | 63.6 | 82.5 | nd | nd |
| Average | 610 | 807 | 610 | 1160 | nd | nd |
| Stdev | 2290 | 2050 | 2290 | 3840 | nd | nd |
| p (t-test) |  | 0.74 |  | 0.48 | nd | nd |
| Min | 1.15 | 1.15 | 1.15 | 1.15 | nd | nd |
| Max | 16000 | 8520 | 16000 | 16000 | nd | nd |
| n (Samp) | 50 | 19 | 50 | 17 | nd | nd |
| n (Patient) | 40 | 19 | 40 | 17 | nd | nd |
| sCr only |  |  |  |  |  |  |
| Median | 34.8 | 29.2 | 34.8 | 292 | 34.8 | 918 |
| Average | 736 | 628 | 736 | 509 | 736 | 918 |

TABLE 1-continued

Comparison of marker levels in urine samples collected from Cohort 1
(patients that did not progress beyond RIFLE stage 0) and in urine samples collected
from subjects at 0, 24 hours, and 48 hours prior to reaching stage R, I or F in Cohort 2.

|  | | | | | | |
|---|---|---|---|---|---|---|
| Stdev | 2550 | 1220 | 2550 | 670 | 2550 | 1230 |
| p (t-test) | | 0.92 | | 0.86 | | 0.92 |
| Min | 1.15 | 1.19 | 1.15 | 1.19 | 1.15 | 51.6 |
| Max | 16000 | 3060 | 16000 | 1450 | 16000 | 1780 |
| n (Samp) | 88 | 6 | 88 | 4 | 88 | 2 |
| n (Patient) | 72 | 6 | 72 | 4 | 72 | 2 |
| UO only | | | | | | |
| Median | 21.1 | 1.19 | 21.1 | 158 | 21.1 | 3060 |
| Average | 607 | 816 | 607 | 1240 | 607 | 4730 |
| Stdev | 2400 | 2210 | 2400 | 3680 | 2400 | 5730 |
| p (t-test) | | 0.77 | | 0.41 | | 0.012 |
| Min | 1.15 | 1.15 | 1.15 | 1.15 | 1.15 | 30.3 |
| Max | 16000 | 8520 | 16000 | 16000 | 16000 | 11100 |
| n (Samp) | 45 | 15 | 45 | 19 | 45 | 3 |
| n (Patient) | 35 | 15 | 35 | 19 | 35 | 3 |

|  | 0 hr prior to AKI stage | | | 24 hr prior to AKI stage | | | 48 hr prior to AKI stage | | |
|---|---|---|---|---|---|---|---|---|---|
|  | sCr or UO | sCr only | UO only | sCr or UO | sCr only | UO only | sCr or UO | sCr only | UO only |
| AUC | 0.52 | 0.59 | 0.53 | 0.54 | 0.64 | 0.55 | nd | 0.72 | 0.82 |
| SE | 0.079 | 0.13 | 0.087 | 0.082 | 0.15 | 0.080 | nd | 0.21 | 0.15 |
| p | 0.85 | 0.49 | 0.73 | 0.62 | 0.37 | 0.51 | nd | 0.30 | 0.033 |
| nCohort 1 | 50 | 88 | 45 | 50 | 88 | 45 | nd | 88 | 45 |
| nCohort 2 | 19 | 6 | 15 | 17 | 4 | 19 | nd | 2 | 3 |
| Cutoff 1 | 1.15 | 1.19 | 1.15 | 1.15 | 36.4 | 1.15 | nd | 36.4 | 21.1 |
| Sens 1 | 95% | 83% | 93% | 88% | 75% | 79% | nd | 100% | 100% |
| Spec 1 | 24% | 45% | 20% | 24% | 51% | 20% | nd | 51% | 51% |
| Cutoff 2 | 1.15 | 1.19 | 1.15 | 1.15 | 1.15 | 0 | nd | 36.4 | 21.1 |
| Sens 2 | 95% | 83% | 93% | 88% | 100% | 100% | nd | 100% | 100% |
| Spec 2 | 24% | 45% | 20% | 24% | 18% | 0% | nd | 51% | 51% |
| Cutoff 3 | 1.15 | 1.15 | 1.15 | 0 | 1.15 | 0 | nd | 36.4 | 21.1 |
| Sens 3 | 95% | 100% | 93% | 100% | 100% | 100% | nd | 100% | 100% |
| Spec 3 | 24% | 18% | 20% | 0% | 18% | 0% | nd | 51% | 51% |
| Cutoff 4 | 189 | 295 | 189 | 189 | 295 | 189 | nd | 295 | 189 |
| Sens 4 | 32% | 33% | 33% | 41% | 50% | 42% | nd | 50% | 67% |
| Spec 4 | 70% | 70% | 71% | 70% | 70% | 71% | nd | 70% | 71% |
| Cutoff 5 | 462 | 579 | 419 | 462 | 579 | 419 | nd | 579 | 419 |
| Sens 5 | 21% | 33% | 20% | 18% | 25% | 26% | nd | 50% | 67% |
| Spec 5 | 80% | 81% | 80% | 80% | 81% | 80% | nd | 81% | 80% |
| Cutoff 6 | 1190 | 1230 | 1190 | 1190 | 1230 | 1190 | nd | 1230 | 1190 |
| Sens 6 | 16% | 17% | 13% | 12% | 25% | 16% | nd | 50% | 67% |
| Spec 6 | 90% | 91% | 91% | 90% | 91% | 91% | nd | 91% | 91% |
| OR Quart 2 | 4.1 | >4.6 | 12 | 1.8 | >1.0 | 1.0 | nd | >0 | >1.1 |
| p Value | 0.076 | <0.19 | 0.030 | 0.48 | <0.98 | 1.0 | nd | <na | <0.95 |
| 95% CI of | 0.86 | >0.47 | 1.3 | 0.35 | >0.062 | 0.20 | nd | >na | >0.061 |
| OR Quart 2 | 20 | na | 120 | 9.2 | na | 5.0 | nd | na | na |
| OR Quart 3 | 1.0 | >0 | 3.5 | 1.8 | >1.0 | 1.8 | nd | >1.0 | >0 |
| p Value | 1.0 | <na | 0.30 | 0.48 | <0.98 | 0.45 | nd | <0.97 | <na |
| 95% CI of | 0.17 | >na | 0.32 | 0.35 | >0.062 | 0.39 | nd | >0.061 | >na |
| OR Quart 3 | 5.8 | na | 38 | 9.2 | na | 8.2 | nd | na | na |
| OR Quart 4 | 1.8 | >2.1 | 5.1 | 1.3 | >2.2 | 1.4 | nd | >1.0 | >2.4 |
| p Value | 0.48 | <0.56 | 0.17 | 0.74 | <0.53 | 0.69 | nd | <1.0 | <0.50 |
| 95% CI of | 0.36 | >0.18 | 0.50 | 0.25 | >0.18 | 0.29 | nd | >0.059 | >0.19 |
| OR Quart 4 | 9.1 | na | 52 | 7.2 | na | 6.4 | nd | na | na |

Neural cell adhesion molecule 1

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| sCr or UO | | | | | | |
| Median | 2300 | 3540 | 2300 | 2640 | 2300 | 2890 |
| Average | 2930 | 3880 | 2930 | 4210 | 2930 | 3140 |
| Stdev | 2240 | 4050 | 2240 | 6650 | 2240 | 1810 |
| p (t-test) | | 7.5E−4 | | 6.1E−4 | | 0.55 |
| Min | 6.83 | 221 | 6.83 | 216 | 6.83 | 293 |
| Max | 22000 | 40700 | 22000 | 55700 | 22000 | 6560 |
| n (Samp) | 460 | 117 | 460 | 125 | 460 | 45 |
| n (Patient) | 223 | 117 | 223 | 125 | 223 | 45 |

TABLE 1-continued

Comparison of marker levels in urine samples collected from Cohort 1
(patients that did not progress beyond RIFLE stage 0) and in urine samples collected
from subjects at 0, 24 hours, and 48 hours prior to reaching stage R, I or F in Cohort 2.

| sCr only | | | | | | |
|---|---|---|---|---|---|---|
| Median | 2840 | 2320 | 2840 | 2390 | 2840 | 1990 |
| Average | 3480 | 2560 | 3480 | 3160 | 3480 | 2390 |
| Stdev | 3360 | 1650 | 3360 | 2380 | 3360 | 1630 |
| p (t-test) | | 0.087 | | 0.52 | | 0.11 |
| Min | 6.83 | 221 | 6.83 | 216 | 6.83 | 387 |
| Max | 55700 | 6210 | 55700 | 10800 | 55700 | 6110 |
| n (Samp) | 1008 | 39 | 1008 | 45 | 1008 | 25 |
| n (Patient) | 374 | 39 | 374 | 45 | 374 | 25 |
| UO only | | | | | | |
| Median | 2410 | 3860 | 2410 | 3060 | 2410 | 2880 |
| Average | 3010 | 4670 | 3010 | 4630 | 3010 | 3260 |
| Stdev | 2070 | 4820 | 2070 | 7120 | 2070 | 1990 |
| p (t-test) | | 9.0E−8 | | 4.0E−5 | | 0.44 |
| Min | 173 | 506 | 173 | 224 | 173 | 293 |
| Max | 11700 | 40700 | 11700 | 55700 | 11700 | 9700 |
| n (Samp) | 432 | 107 | 432 | 116 | 432 | 43 |
| n (Patient) | 172 | 107 | 172 | 116 | 172 | 43 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.61 | 0.40 | 0.66 | 0.56 | 0.46 | 0.58 | 0.56 | 0.37 | 0.56 |
| SE | 0.030 | 0.049 | 0.031 | 0.030 | 0.045 | 0.031 | 0.046 | 0.061 | 0.047 |
| p | 3.7E−4 | 0.044 | 6.1E−7 | 0.042 | 0.42 | 0.014 | 0.19 | 0.031 | 0.22 |
| nCohort 1 | 460 | 1008 | 432 | 460 | 1008 | 432 | 460 | 1008 | 432 |
| nCohort 2 | 117 | 39 | 107 | 125 | 45 | 116 | 45 | 25 | 43 |
| Cutoff 1 | 2270 | 1090 | 2690 | 1950 | 1680 | 2040 | 2150 | 1190 | 2250 |
| Sens 1 | 70% | 72% | 70% | 70% | 71% | 71% | 71% | 72% | 72% |
| Spec 1 | 50% | 12% | 55% | 41% | 25% | 40% | 47% | 14% | 45% |
| Cutoff 2 | 1550 | 994 | 2000 | 1250 | 1110 | 1560 | 1500 | 1110 | 1650 |
| Sens 2 | 80% | 82% | 80% | 80% | 80% | 80% | 80% | 80% | 81% |
| Spec 2 | 30% | 10% | 39% | 20% | 13% | 29% | 28% | 13% | 31% |
| Cutoff 3 | 994 | 615 | 1450 | 898 | 883 | 986 | 485 | 491 | 881 |
| Sens 3 | 91% | 92% | 91% | 90% | 91% | 91% | 91% | 92% | 91% |
| Spec 3 | 13% | 4% | 26% | 10% | 8% | 12% | 3% | 2% | 9% |
| Cutoff 4 | 3540 | 4070 | 3650 | 3540 | 4070 | 3650 | 3540 | 4070 | 3650 |
| Sens 4 | 50% | 18% | 54% | 37% | 31% | 39% | 38% | 16% | 35% |
| Spec 4 | 70% | 70% | 70% | 70% | 70% | 70% | 70% | 70% | 70% |
| Cutoff 5 | 4180 | 4960 | 4430 | 4180 | 4960 | 4430 | 4180 | 4960 | 4430 |
| Sens 5 | 31% | 8% | 33% | 30% | 20% | 31% | 31% | 8% | 26% |
| Spec 5 | 80% | 80% | 80% | 80% | 80% | 80% | 80% | 80% | 80% |
| Cutoff 6 | 5630 | 6470 | 6000 | 5630 | 6470 | 6000 | 5630 | 6470 | 6000 |
| Sens 6 | 17% | 0% | 23% | 20% | 9% | 20% | 9% | 0% | 9% |
| Spec 6 | 90% | 90% | 90% | 90% | 90% | 90% | 90% | 90% | 90% |
| OR Quart 2 | 1.1 | 1.5 | 1.3 | 0.87 | 0.72 | 1.3 | 0.65 | 1.0 | 1.1 |
| p Value | 0.87 | 0.43 | 0.47 | 0.65 | 0.49 | 0.35 | 0.43 | 1.00 | 0.80 |
| 95% CI of | 0.55 | 0.53 | 0.63 | 0.49 | 0.29 | 0.72 | 0.22 | 0.25 | 0.40 |
| OR Quart 2 | 2.1 | 4.3 | 2.8 | 1.6 | 1.8 | 2.5 | 1.9 | 4.1 | 3.3 |
| OR Quart 3 | 1.8 | 1.5 | 2.9 | 0.87 | 1.2 | 1.3 | 1.9 | 1.8 | 2.3 |
| p Value | 0.050 | 0.43 | 0.0021 | 0.65 | 0.67 | 0.43 | 0.15 | 0.36 | 0.083 |
| 95% CI of | 1.00 | 0.53 | 1.5 | 0.49 | 0.53 | 0.69 | 0.80 | 0.51 | 0.90 |
| OR Quart 3 | 3.4 | 4.3 | 5.7 | 1.6 | 2.7 | 2.4 | 4.5 | 6.1 | 5.8 |
| OR Quart 4 | 2.6 | 2.6 | 3.7 | 1.7 | 1.2 | 2.1 | 1.6 | 2.6 | 1.9 |
| p Value | 0.0015 | 0.052 | 9.9E−5 | 0.048 | 0.67 | 0.015 | 0.29 | 0.11 | 0.17 |
| 95% CI of | 1.4 | 0.99 | 1.9 | 1.0 | 0.53 | 1.2 | 0.67 | 0.80 | 0.75 |
| OR Quart 4 | 4.7 | 6.8 | 7.3 | 3.0 | 2.7 | 3.7 | 3.9 | 8.3 | 5.1 |

Tumor necrosis factor ligand superfamily member 10

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| sCr or UO | | | | | | |
| Median | 0.0285 | 0.0335 | 0.0285 | 0.0324 | 0.0285 | 0.0287 |
| Average | 2.78 | 1.92 | 2.78 | 2.63 | 2.78 | 1.54 |
| Stdev | 9.69 | 7.52 | 9.69 | 13.7 | 9.69 | 6.36 |
| p (t-test) | | 0.37 | | 0.89 | | 0.39 |
| Min | 0.0110 | 0.0110 | 0.0110 | 0.0110 | 0.0110 | 0.0110 |
| Max | 92.3 | 63.9 | 92.3 | 134 | 92.3 | 41.7 |

TABLE 1-continued

Comparison of marker levels in urine samples collected from Cohort 1
(patients that did not progress beyond RIFLE stage 0) and in urine samples collected
from subjects at 0, 24 hours, and 48 hours prior to reaching stage R, I or F in Cohort 2.

| | | | | | | |
|---|---|---|---|---|---|---|
| n (Samp) | 449 | 115 | 449 | 124 | 449 | 47 |
| n (Patient) | 222 | 115 | 222 | 124 | 222 | 47 |
| sCr only | | | | | | |
| Median | 0.0285 | 0.0257 | 0.0285 | 0.0317 | 0.0285 | 0.0287 |
| Average | 2.84 | 0.930 | 2.84 | 1.03 | 2.84 | 2.16 |
| Stdev | 11.0 | 3.19 | 11.0 | 3.99 | 11.0 | 8.53 |
| p (t-test) | | 0.30 | | 0.27 | | 0.76 |
| Min | 0.0110 | 0.0139 | 0.0110 | 0.0139 | 0.0110 | 0.0110 |
| Max | 159 | 13.9 | 159 | 24.4 | 159 | 41.7 |
| n (Samp) | 997 | 36 | 997 | 45 | 997 | 24 |
| n (Patient) | 379 | 36 | 379 | 45 | 379 | 24 |
| UO only | | | | | | |
| Median | 0.0287 | 0.0335 | 0.0287 | 0.0312 | 0.0287 | 0.0287 |
| Average | 3.05 | 3.56 | 3.05 | 3.58 | 3.05 | 0.744 |
| Stdev | 10.6 | 13.1 | 10.6 | 17.5 | 10.6 | 2.23 |
| p (t-test) | | 0.67 | | 0.68 | | 0.15 |
| Min | 0.0110 | 0.0110 | 0.0110 | 0.0110 | 0.0110 | 0.0139 |
| Max | 92.3 | 79.6 | 92.3 | 134 | 92.3 | 12.3 |
| n (Samp) | 419 | 107 | 419 | 115 | 419 | 44 |
| n (Patient) | 175 | 107 | 175 | 115 | 175 | 44 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.52 | 0.42 | 0.50 | 0.52 | 0.52 | 0.50 | 0.49 | 0.50 | 0.46 |
| SE | 0.030 | 0.051 | 0.031 | 0.030 | 0.044 | 0.030 | 0.045 | 0.060 | 0.047 |
| p | 0.58 | 0.11 | 0.97 | 0.49 | 0.68 | 0.99 | 0.80 | 0.99 | 0.45 |
| nCohort 1 | 449 | 997 | 419 | 449 | 997 | 419 | 449 | 997 | 419 |
| nCohort 2 | 115 | 36 | 107 | 124 | 45 | 115 | 47 | 24 | 44 |
| Cutoff 1 | 0.0239 | 0.0217 | 0.0247 | 0.0237 | 0.0247 | 0.0239 | 0.0217 | 0.0239 | 0.0227 |
| Sens 1 | 70% | 72% | 71% | 73% | 71% | 70% | 74% | 71% | 70% |
| Spec 1 | 38% | 22% | 40% | 35% | 41% | 34% | 27% | 37% | 26% |
| Cutoff 2 | 0.0205 | 0.0162 | 0.0159 | 0.0217 | 0.0217 | 0.0227 | 0.0205 | 0.0205 | 0.0205 |
| Sens 2 | 80% | 83% | 86% | 82% | 82% | 81% | 83% | 88% | 84% |
| Spec 2 | 22% | 15% | 16% | 27% | 22% | 26% | 22% | 18% | 19% |
| Cutoff 3 | 0.0139 | 0.0110 | 0.0139 | 0.0147 | 0.0147 | 0.0147 | 0.0110 | 0.0139 | 0.0147 |
| Sens 3 | 93% | 100% | 92% | 91% | 91% | 90% | 98% | 92% | 91% |
| Spec 3 | 8% | 4% | 7% | 14% | 11% | 12% | 4% | 7% | 12% |
| Cutoff 4 | 0.0526 | 0.0439 | 0.0526 | 0.0526 | 0.0439 | 0.0526 | 0.0526 | 0.0439 | 0.0526 |
| Sens 4 | 16% | 17% | 17% | 19% | 18% | 20% | 19% | 21% | 18% |
| Spec 4 | 73% | 73% | 72% | 73% | 73% | 72% | 73% | 73% | 72% |
| Cutoff 5 | 1.17 | 0.327 | 1.42 | 1.17 | 0.327 | 1.42 | 1.17 | 0.327 | 1.42 |
| Sens 5 | 14% | 11% | 15% | 14% | 13% | 16% | 13% | 17% | 11% |
| Spec 5 | 80% | 80% | 80% | 80% | 80% | 80% | 80% | 80% | 80% |
| Cutoff 6 | 6.80 | 6.49 | 8.01 | 6.80 | 6.49 | 8.01 | 6.80 | 6.49 | 8.01 |
| Sens 6 | 9% | 6% | 7% | 6% | 4% | 5% | 4% | 4% | 2% |
| Spec 6 | 90% | 90% | 90% | 90% | 90% | 90% | 90% | 90% | 90% |
| OR Quart 2 | 1.0 | 1.3 | 2.7 | 1.7 | 0.62 | 1.8 | 2.3 | 0.66 | 2.5 |
| p Value | 1.0 | 0.58 | 0.0019 | 0.076 | 0.34 | 0.053 | 0.063 | 0.53 | 0.054 |
| 95% CI of | 0.54 | 0.46 | 1.4 | 0.95 | 0.24 | 0.99 | 0.96 | 0.18 | 0.98 |
| OR Quart 2 | 1.8 | 3.9 | 5.0 | 3.1 | 1.6 | 3.2 | 5.6 | 2.4 | 6.3 |
| OR Quart 3 | 2.3 | 1.5 | 1.4 | 2.7 | 1.9 | 1.6 | 1.6 | 1.5 | 1.6 |
| p Value | 0.0030 | 0.43 | 0.31 | 7.0E−4 | 0.10 | 0.10 | 0.35 | 0.43 | 0.33 |
| 95% CI of | 1.3 | 0.53 | 0.72 | 1.5 | 0.89 | 0.91 | 0.61 | 0.53 | 0.61 |
| OR Quart 3 | 4.0 | 4.3 | 2.7 | 4.8 | 4.0 | 3.0 | 3.9 | 4.3 | 4.4 |
| OR Quart 4 | 0.68 | 2.2 | 1.6 | 0.94 | 0.62 | 0.96 | 1.3 | 0.83 | 1.5 |
| p Value | 0.25 | 0.11 | 0.18 | 0.85 | 0.34 | 0.89 | 0.63 | 0.76 | 0.44 |
| 95% CI of | 0.35 | 0.84 | 0.81 | 0.49 | 0.24 | 0.50 | 0.48 | 0.25 | 0.54 |
| OR Quart 4 | 1.3 | 6.0 | 3.0 | 1.8 | 1.6 | 1.8 | 3.3 | 2.7 | 4.0 |

Myeloid differentiation primary response protein MyD88

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| sCr or UO | | | | | | |
| Median | 0.000533 | 0.000171 | 0.000533 | 0.000533 | 0.000533 | 0.000165 |
| Average | 0.0182 | 0.0146 | 0.0182 | 0.0138 | 0.0182 | 0.000900 |
| Stdev | 0.0708 | 0.0619 | 0.0708 | 0.0330 | 0.0708 | 0.00127 |
| p (t-test) | | 0.79 | | 0.73 | | 0.68 |
| Min | 0.000126 | 0.000126 | 0.000126 | 0.000126 | 0.000126 | 0.000165 |

TABLE 1-continued

Comparison of marker levels in urine samples collected from Cohort 1
(patients that did not progress beyond RIFLE stage 0) and in urine samples collected
from subjects at 0, 24 hours, and 48 hours prior to reaching stage R, I or F in Cohort 2.

|  |  |  |  |  |  |  |
|---|---|---|---|---|---|---|
| Max | 0.671 | 0.371 | 0.671 | 0.171 | 0.671 | 0.00237 |
| n (Samp) | 98 | 36 | 98 | 33 | 98 | 3 |
| n (Patient) | 64 | 36 | 64 | 33 | 64 | 3 |
| sCr only |  |  |  |  |  |  |
| Median | 0.000533 | 0.000171 | 0.000533 | 0.000165 | 0.000533 | 0.000165 |
| Average | 0.0184 | 0.00598 | 0.0184 | 0.00792 | 0.0184 | 0.00225 |
| Stdev | 0.0636 | 0.0133 | 0.0636 | 0.0140 | 0.0636 | 0.00419 |
| p (t-test) |  | 0.52 |  | 0.59 |  | 0.61 |
| Min | 0.000126 | 0.000126 | 0.000126 | 0.000126 | 0.000126 | 0.000126 |
| Max | 0.671 | 0.0400 | 0.671 | 0.0359 | 0.671 | 0.00853 |
| n (Samp) | 192 | 11 | 192 | 11 | 192 | 4 |
| n (Patient) | 114 | 11 | 114 | 11 | 114 | 4 |
| UO only |  |  |  |  |  |  |
| Median | 0.000533 | 0.000352 | 0.000533 | 0.000533 | 0.000533 | 0.000533 |
| Average | 0.0113 | 0.0169 | 0.0113 | 0.0134 | 0.0113 | 0.00485 |
| Stdev | 0.0229 | 0.0676 | 0.0229 | 0.0332 | 0.0229 | 0.0101 |
| p (t-test) |  | 0.48 |  | 0.68 |  | 0.50 |
| Min | 0.000126 | 0.000126 | 0.000126 | 0.000126 | 0.000126 | 0.000165 |
| Max | 0.106 | 0.371 | 0.106 | 0.171 | 0.106 | 0.0253 |
| n (Samp) | 99 | 30 | 99 | 34 | 99 | 6 |
| n (Patient) | 61 | 30 | 61 | 34 | 61 | 6 |

|  | 0 hr prior to AKI stage | | | 24 hr prior to AKI stage | | | 48 hr prior to AKI stage | | |
|---|---|---|---|---|---|---|---|---|---|
|  | sCr or UO | sCr only | UO only | sCr or UO | sCr only | UO only | sCr or UO | sCr only | UO only |
| AUC | 0.42 | 0.42 | 0.45 | 0.55 | 0.41 | 0.55 | 0.39 | 0.31 | 0.51 |
| SE | 0.057 | 0.092 | 0.061 | 0.059 | 0.093 | 0.058 | 0.18 | 0.15 | 0.12 |
| p | 0.17 | 0.41 | 0.39 | 0.37 | 0.31 | 0.37 | 0.54 | 0.21 | 0.92 |
| nCohort 1 | 98 | 192 | 99 | 98 | 192 | 99 | 98 | 192 | 99 |
| nCohort 2 | 36 | 11 | 30 | 33 | 11 | 34 | 3 | 4 | 6 |
| Cutoff 1 | 0.000126 | 0.000126 | 0.000126 | 0.000171 | 0.000126 | 0.000171 | 0.000126 | 0.000126 | 0.000126 |
| Sens 1 | 86% | 91% | 87% | 73% | 73% | 74% | 100% | 75% | 100% |
| Spec 1 | 8% | 11% | 9% | 40% | 11% | 42% | 8% | 11% | 9% |
| Cutoff 2 | 0.000126 | 0.000126 | 0.000126 | 0.000126 | 0 | 0.000126 | 0.000126 | 0 | 0.000126 |
| Sens 2 | 86% | 91% | 87% | 94% | 100% | 94% | 100% | 100% | 100% |
| Spec 2 | 8% | 11% | 9% | 8% | 0% | 9% | 8% | 0% | 9% |
| Cutoff 3 | 0 | 0.000126 | 0 | 0.000126 | 0 | 0.000126 | 0.000126 | 0 | 0.000126 |
| Sens 3 | 100% | 91% | 100% | 94% | 100% | 94% | 100% | 100% | 100% |
| Spec 3 | 0% | 11% | 0% | 8% | 0% | 9% | 8% | 0% | 9% |
| Cutoff 4 | 0.000533 | 0.00237 | 0.00309 | 0.000533 | 0.00237 | 0.00309 | 0.000533 | 0.00237 | 0.00309 |
| Sens 4 | 22% | 18% | 27% | 33% | 27% | 26% | 33% | 25% | 17% |
| Spec 4 | 71% | 70% | 71% | 71% | 70% | 71% | 71% | 70% | 71% |
| Cutoff 5 | 0.0212 | 0.0190 | 0.0212 | 0.0212 | 0.0190 | 0.0212 | 0.0212 | 0.0190 | 0.0212 |
| Sens 5 | 14% | 18% | 13% | 18% | 18% | 18% | 0% | 0% | 17% |
| Spec 5 | 81% | 80% | 81% | 81% | 80% | 81% | 81% | 80% | 81% |
| Cutoff 6 | 0.0484 | 0.0394 | 0.0393 | 0.0484 | 0.0394 | 0.0393 | 0.0484 | 0.0394 | 0.0393 |
| Sens 6 | 3% | 9% | 3% | 6% | 0% | 12% | 0% | 0% | 0% |
| Spec 6 | 91% | 90% | 91% | 91% | 90% | 91% | 91% | 90% | 91% |
| OR Quart 2 | 0.12 | 0 | 1.3 | 3.0 | 0 | 3.2 | >1.1 | >1.0 | 1.0 |
| p Value | 0.055 | na | 0.71 | 0.048 | na | 0.055 | <0.96 | <0.99 | 1.0 |
| 95% CI of | 0.014 | na | 0.37 | 1.0 | na | 0.98 | >0.064 | >0.062 | 0.13 |
| OR Quart 2 | 1.0 | na | 4.3 | 8.8 | na | 10 | na | na | 7.7 |
| OR Quart 3 | 3.4 | 3.9 | 0.64 | 0.23 | 1.4 | 2.1 | >2.3 | >2.1 | 0.48 |
| p Value | 0.024 | 0.10 | 0.53 | 0.083 | 0.70 | 0.23 | <0.52 | <0.55 | 0.56 |
| 95% CI of | 1.2 | 0.77 | 0.16 | 0.044 | 0.29 | 0.62 | >0.19 | >0.18 | 0.041 |
| OR Quart 3 | 10.0 | 20 | 2.5 | 1.2 | 6.4 | 7.1 | na | na | 5.6 |
| OR Quart 4 | 2.2 | 1.0 | 3.1 | 1.3 | 1.4 | 1.7 | >0 | >1.0 | 0.46 |
| p Value | 0.16 | 0.98 | 0.051 | 0.61 | 0.68 | 0.39 | <na | <0.99 | 0.54 |
| 95% CI of | 0.74 | 0.14 | 0.99 | 0.43 | 0.30 | 0.50 | >na | >0.062 | 0.039 |
| OR Quart 4 | 6.6 | 7.5 | 9.5 | 4.2 | 6.6 | 5.9 | na | na | 5.4 |

TABLE 2

Comparison of marker levels in urine samples collected from Cohort 1 (patients that did not progress beyond RIFLE stage 0 or R) and in urine samples collected from subjects at 0, 24 hours, and 48 hours prior to reaching stage I or F in Cohort 2.

| | Stromelysin-1:Metalloproteinase inhibitor 2 complex | | | |
|---|---|---|---|---|
| | 24 hr prior to AKI stage | | 48 hr prior to AKI stage | |
| | Cohort 1 | Cohort 2 | Cohort 1 | Cohort 2 |
| sCr or UO | | | | |
| Median | 0.487 | 0.487 | nd | nd |
| Average | 202 | 23.1 | nd | nd |
| Stdev | 1420 | 69.4 | nd | nd |
| p (t-test) | | 0.63 | nd | nd |
| Min | 0.237 | 0.237 | nd | nd |
| Max | 13900 | 267 | nd | nd |
| n (Samp) | 97 | 15 | nd | nd |
| n (Patient) | 74 | 15 | nd | nd |
| sCr only | | | | |
| Median | 0.487 | 10.9 | nd | nd |
| Average | 181 | 181 | nd | nd |
| Stdev | 1340 | 303 | nd | nd |
| p (t-test) | | 1.00 | nd | nd |
| Min | 0.237 | 0.487 | nd | nd |
| Max | 13900 | 530 | nd | nd |
| n (Samp) | 110 | 3 | nd | nd |
| n (Patient) | 85 | 3 | nd | nd |
| UO only | | | | |
| Median | 0.237 | 0.487 | 0.237 | 5.71 |
| Average | 217 | 24.0 | 217 | 5.71 |
| Stdev | 1550 | 72.0 | 1550 | 7.39 |
| p (t-test) | | 0.64 | | 0.85 |
| Min | 0.237 | 0.237 | 0.237 | 0.487 |
| Max | 13900 | 267 | 13900 | 10.9 |
| n (Samp) | 82 | 14 | 82 | 2 |
| n (Patient) | 62 | 14 | 62 | 2 |

| | 24 hr prior to AKI stage | | | 48 hr prior to AKI stage | | |
|---|---|---|---|---|---|---|
| | sCr or UO | sCr only | UO only | sCr or UO | sCr only | UO only |
| AUC | 0.63 | 0.80 | 0.63 | nd | nd | 0.77 |
| SE | 0.082 | 0.15 | 0.085 | nd | nd | 0.20 |
| p | 0.12 | 0.048 | 0.12 | nd | nd | 0.18 |
| nCohort 1 | 97 | 110 | 82 | nd | nd | 82 |
| nCohort 2 | 15 | 3 | 14 | nd | nd | 2 |
| Cutoff 1 | 0.237 | 0.237 | 0.237 | nd | nd | 0.237 |
| Sens 1 | 87% | 100% | 79% | nd | nd | 100% |
| Spec 1 | 45% | 44% | 55% | nd | nd | 55% |
| Cutoff 2 | 0.237 | 0.237 | 0 | nd | nd | 0.237 |
| Sens 2 | 87% | 100% | 100% | nd | nd | 100% |
| Spec 2 | 45% | 44% | 0% | nd | nd | 55% |
| Cutoff 3 | 0 | 0.237 | 0 | nd | nd | 0.237 |
| Sens 3 | 100% | 100% | 100% | nd | nd | 100% |
| Spec 3 | 0% | 44% | 0% | nd | nd | 55% |
| Cutoff 4 | 0.487 | 0.487 | 0.487 | nd | nd | 0.487 |
| Sens 4 | 20% | 67% | 14% | nd | nd | 50% |
| Spec 4 | 81% | 82% | 83% | nd | nd | 83% |
| Cutoff 5 | 0.487 | 0.487 | 0.487 | nd | nd | 0.487 |
| Sens 5 | 20% | 67% | 14% | nd | nd | 50% |
| Spec 5 | 81% | 82% | 83% | nd | nd | 83% |
| Cutoff 6 | 154 | 123 | 118 | nd | nd | 118 |
| Sens 6 | 7% | 33% | 7% | nd | nd | 0% |
| Spec 6 | 91% | 90% | 90% | nd | nd | 90% |
| OR Quart 2 | >21 | >1.0 | 2.1 | nd | nd | >0 |
| p Value | <0.0051 | <0.98 | 0.56 | nd | nd | <na |
| 95% CI of | >2.5 | >0.062 | 0.18 | nd | nd | >na |
| OR Quart 2 | na | na | 25 | nd | nd | na |
| OR Quart 3 | >0 | >0 | 14 | nd | nd | >1.0 |
| p Value | <na | <na | 0.018 | nd | nd | <0.97 |
| 95% CI of | >na | >na | 1.6 | nd | nd | >0.061 |
| OR Quart 3 | na | na | 120 | nd | nd | na |
| OR Quart 4 | >3.4 | >2.1 | 2.1 | nd | nd | >1.0 |
| p Value | <0.31 | <0.56 | 0.56 | nd | nd | <0.97 |

TABLE 2-continued

Comparison of marker levels in urine samples collected from Cohort 1 (patients that did not progress beyond RIFLE stage 0 or R) and in urine samples collected from subjects at 0, 24 hours, and 48 hours prior to reaching stage I or F in Cohort 2.

| | | | | | | |
|---|---|---|---|---|---|---|
| 95% CI of | >0.33 | >0.18 | 0.18 | nd | nd | >0.061 |
| OR Quart 4 | na | na | 25 | nd | nd | na |

Heat shock 70 kDa protein 1

| | | 24 hr prior to AKI stage | | 48 hr prior to AKI stage | |
|---|---|---|---|---|---|
| | | Cohort 1 | Cohort 2 | Cohort 1 | Cohort 2 |
| sCr or UO | | | | | |
| | Median | 257 | 658 | nd | nd |
| | Average | 500 | 1700 | nd | nd |
| | Stdev | 872 | 3070 | nd | nd |
| | p (t-test) | | 0.0023 | nd | nd |
| | Min | 0.297 | 0.335 | nd | nd |
| | Max | 7800 | 11800 | nd | nd |
| | n (Samp) | 95 | 14 | nd | nd |
| | n (Patient) | 73 | 14 | nd | nd |
| sCr only | | | | | |
| | Median | 283 | 1510 | nd | nd |
| | Average | 534 | 1440 | nd | nd |
| | Stdev | 897 | 318 | nd | nd |
| | p (t-test) | | 0.085 | nd | nd |
| | Min | 0.297 | 1090 | nd | nd |
| | Max | 7800 | 1710 | nd | nd |
| | n (Samp) | 107 | 3 | nd | nd |
| | n (Patient) | 83 | 3 | nd | nd |
| UO only | | | | | |
| | Median | 225 | 435 | 225 | 1660 |
| | Average | 503 | 1590 | 503 | 1660 |
| | Stdev | 930 | 3220 | 930 | 215 |
| | p (t-test) | | 0.014 | | 0.083 |
| | Min | 0.297 | 0.335 | 0.297 | 1510 |
| | Max | 7800 | 11800 | 7800 | 1820 |
| | n (Samp) | 82 | 13 | 82 | 2 |
| | n (Patient) | 62 | 13 | 62 | 2 |

| | 24 hr prior to AKI stage | | | 48 hr prior to AKI stage | | |
|---|---|---|---|---|---|---|
| | sCr or UO | sCr only | UO only | sCr or UO | sCr only | UO only |
| AUC | 0.70 | 0.93 | 0.62 | nd | nd | 0.96 |
| SE | 0.082 | 0.10 | 0.088 | nd | nd | 0.10 |
| p | 0.015 | 2.3E−5 | 0.17 | nd | nd | 5.5E−6 |
| nCohort 1 | 95 | 107 | 82 | nd | nd | 82 |
| nCohort 2 | 14 | 3 | 13 | nd | nd | 2 |
| Cutoff 1 | 401 | 1040 | 246 | nd | nd | 1340 |
| Sens 1 | 71% | 100% | 77% | nd | nd | 100% |
| Spec 1 | 60% | 91% | 52% | nd | nd | 94% |
| Cutoff 2 | 246 | 1040 | 125 | nd | nd | 1340 |
| Sens 2 | 86% | 100% | 85% | nd | nd | 100% |
| Spec 2 | 49% | 91% | 33% | nd | nd | 94% |
| Cutoff 3 | 125 | 1040 | 23.5 | nd | nd | 1340 |
| Sens 3 | 93% | 100% | 92% | nd | nd | 100% |
| Spec 3 | 29% | 91% | 12% | nd | nd | 94% |
| Cutoff 4 | 529 | 545 | 512 | nd | nd | 512 |
| Sens 4 | 57% | 100% | 46% | nd | nd | 100% |
| Spec 4 | 71% | 70% | 71% | nd | nd | 71% |
| Cutoff 5 | 755 | 770 | 755 | nd | nd | 755 |
| Sens 5 | 50% | 100% | 38% | nd | nd | 100% |
| Spec 5 | 80% | 80% | 80% | nd | nd | 80% |
| Cutoff 6 | 1020 | 1040 | 1020 | nd | nd | 1020 |
| Sens 6 | 36% | 100% | 23% | nd | nd | 100% |
| Spec 6 | 91% | 91% | 90% | nd | nd | 90% |
| OR Quart 2 | 2.1 | >0 | 0.95 | nd | nd | >0 |
| p Value | 0.56 | <na | 0.96 | nd | nd | <na |
| 95% CI of | 0.18 | >na | 0.12 | nd | nd | >na |
| OR Quart 2 | 24 | na | 7.4 | nd | nd | na |
| OR Quart 3 | 4.5 | >0 | 2.1 | nd | nd | >0 |
| p Value | 0.19 | <na | 0.42 | nd | nd | <na |
| 95% CI of | 0.47 | >na | 0.35 | nd | nd | >na |
| OR Quart 3 | 43 | na | 13 | nd | nd | na |
| OR Quart 4 | 8.7 | >3.2 | 2.8 | nd | nd | >2.2 |

TABLE 2-continued

Comparison of marker levels in urine samples collected from Cohort 1 (patients that did not progress beyond RIFLE stage 0 or R) and in urine samples collected from subjects at 0, 24 hours, and 48 hours prior to reaching stage I or F in Cohort 2.

| | | | | | | |
|---|---|---|---|---|---|---|
| p Value | 0.051 | <0.32 | 0.26 | nd | nd | <0.53 |
| 95% CI of | 0.99 | >0.32 | 0.48 | nd | nd | >0.19 |
| OR Quart 4 | 76 | na | 16 | nd | nd | na |

Insulin-like growth factor 1 receptor

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| sCr or UO | | | | | | |
| Median | 0.0103 | 0.0170 | 0.0103 | 0.0197 | nd | nd |
| Average | 0.0238 | 0.0170 | 0.0238 | 0.0407 | nd | nd |
| Stdev | 0.0708 | 0.0233 | 0.0708 | 0.0903 | nd | nd |
| p (t-test) | | 0.89 | | 0.41 | nd | nd |
| Min | 0.000123 | 0.000519 | 0.000123 | 0.00132 | nd | nd |
| Max | 0.679 | 0.0335 | 0.679 | 0.365 | nd | nd |
| n (Samp) | 95 | 2 | 95 | 15 | nd | nd |
| n (Patient) | 74 | 2 | 74 | 15 | nd | nd |
| sCr only | | | | | | |
| Median | nd | nd | 0.0103 | 0.0197 | nd | nd |
| Average | nd | nd | 0.0263 | 0.0160 | nd | nd |
| Stdev | nd | nd | 0.0743 | 0.00637 | nd | nd |
| p (t-test) | nd | nd | | 0.81 | nd | nd |
| Min | nd | nd | 0.000123 | 0.00862 | nd | nd |
| Max | nd | nd | 0.679 | 0.0197 | nd | nd |
| n (Samp) | nd | nd | 108 | 3 | nd | nd |
| n (Patient) | nd | nd | 85 | 3 | nd | nd |
| UO only | | | | | | |
| Median | nd | nd | 0.0103 | 0.0150 | 0.0103 | 0.0261 |
| Average | nd | nd | 0.0248 | 0.0422 | 0.0248 | 0.0261 |
| Stdev | nd | nd | 0.0761 | 0.0935 | 0.0761 | 0.0247 |
| p (t-test) | nd | nd | | 0.45 | | 0.98 |
| Min | nd | nd | 0.000123 | 0.00132 | 0.000123 | 0.00862 |
| Max | nd | nd | 0.679 | 0.365 | 0.679 | 0.0436 |
| n (Samp) | nd | nd | 82 | 14 | 82 | 2 |
| n (Patient) | nd | nd | 64 | 14 | 64 | 2 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.51 | nd | nd | 0.62 | 0.57 | 0.62 | nd | nd | 0.65 |
| SE | 0.21 | nd | nd | 0.082 | 0.17 | 0.085 | nd | nd | 0.21 |
| p | 0.96 | nd | nd | 0.16 | 0.68 | 0.16 | nd | nd | 0.48 |
| nCohort 1 | 95 | nd | nd | 95 | 108 | 82 | nd | nd | 82 |
| nCohort 2 | 2 | nd | nd | 15 | 3 | 14 | nd | nd | 2 |
| Cutoff 1 | 0.000172 | nd | nd | 0.00862 | 0.00573 | 0.00862 | nd | nd | 0.00454 |
| Sens 1 | 100% | nd | nd | 80% | 100% | 79% | nd | nd | 100% |
| Spec 1 | 13% | nd | nd | 40% | 31% | 44% | nd | nd | 34% |
| Cutoff 2 | 0.000172 | nd | nd | 0.00862 | 0.00573 | 0.00454 | nd | nd | 0.00454 |
| Sens 2 | 100% | nd | nd | 80% | 100% | 86% | nd | nd | 100% |
| Spec 2 | 13% | nd | nd | 40% | 31% | 34% | nd | nd | 34% |
| Cutoff 3 | 0.000172 | nd | nd | 0.00132 | 0.00573 | 0.00132 | nd | nd | 0.00454 |
| Sens 3 | 100% | nd | nd | 93% | 100% | 93% | nd | nd | 100% |
| Spec 3 | 13% | nd | nd | 27% | 31% | 32% | nd | nd | 34% |
| Cutoff 4 | 0.0197 | nd | nd | 0.0197 | 0.0197 | 0.0197 | nd | nd | 0.0197 |
| Sens 4 | 50% | nd | nd | 40% | 0% | 43% | nd | nd | 50% |
| Spec 4 | 73% | nd | nd | 73% | 70% | 72% | nd | nd | 72% |
| Cutoff 5 | 0.0292 | nd | nd | 0.0292 | 0.0292 | 0.0292 | nd | nd | 0.0292 |
| Sens 5 | 50% | nd | nd | 13% | 0% | 14% | nd | nd | 50% |
| Spec 5 | 83% | nd | nd | 83% | 82% | 83% | nd | nd | 83% |
| Cutoff 6 | 0.0423 | nd | nd | 0.0423 | 0.0423 | 0.0423 | nd | nd | 0.0423 |
| Sens 6 | 0% | nd | nd | 7% | 0% | 7% | nd | nd | 50% |
| Spec 6 | 92% | nd | nd | 92% | 91% | 91% | nd | nd | 91% |
| OR Quart 2 | 0 | nd | nd | 4.3 | >1.0 | >8.0 | nd | nd | >1.0 |
| p Value | na | nd | nd | 0.20 | <1.0 | <0.064 | nd | nd | <0.97 |
| 95% CI of | na | nd | nd | 0.45 | >0.059 | >0.88 | nd | nd | >0.061 |
| OR Quart 2 | na | nd | nd | 42 | na | na | nd | nd | na |
| OR Quart 3 | 0 | nd | nd | 5.9 | >2.1 | >3.4 | nd | nd | >0 |
| p Value | na | nd | nd | 0.12 | <0.56 | <0.30 | nd | nd | <na |
| 95% CI of | na | nd | nd | 0.64 | >0.18 | >0.33 | nd | nd | >na |
| OR Quart 3 | na | nd | nd | 54 | na | na | nd | nd | na |

TABLE 2-continued

Comparison of marker levels in urine samples collected from Cohort
1 (patients that did not progress beyond RIFLE stage 0 or R) and in urine samples
collected from subjects at 0, 24 hours, and 48 hours prior to reaching stage I or F in Cohort 2.

| | | | | | | | | | |
|---|---|---|---|---|---|---|---|---|---|
| OR Quart 4 | 0.96 | nd | nd | 5.7 | >0 | >6.3 | nd | nd | >1.0 |
| p Value | 0.98 | nd | nd | 0.13 | <na | <0.11 | nd | nd | <0.97 |
| 95% CI of | 0.057 | nd | nd | 0.61 | >na | >0.68 | nd | nd | >0.061 |
| OR Quart 4 | 16 | nd | nd | 52 | na | na | nd | nd | na |

Alpha-1-antitrypsin Neutrophil elastase complex

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| sCr or UO | | | | | | |
| Median | 16.2 | 272 | 16.2 | 43.9 | 16.2 | 10.7 |
| Average | 65.3 | 222 | 65.3 | 168 | 65.3 | 39.0 |
| Stdev | 120 | 142 | 120 | 184 | 120 | 44.5 |
| p (t-test) | | 0.013 | | 0.011 | | 0.57 |
| Min | 0.946 | 14.8 | 0.946 | 2.36 | 0.946 | 1.04 |
| Max | 400 | 329 | 400 | 400 | 400 | 97.9 |
| n (Samp) | 93 | 4 | 93 | 12 | 93 | 7 |
| n (Patient) | 67 | 4 | 67 | 12 | 67 | 7 |
| sCr only | | | | | | |
| Median | 17.7 | 154 | 17.7 | 206 | 17.7 | 5.41 |
| Average | 73.1 | 154 | 73.1 | 206 | 73.1 | 136 |
| Stdev | 124 | 196 | 124 | 274 | 124 | 229 |
| p (t-test) | | 0.37 | | 0.14 | | 0.40 |
| Min | 0.946 | 14.8 | 0.946 | 12.3 | 0.946 | 1.23 |
| Max | 400 | 292 | 400 | 400 | 400 | 400 |
| n (Samp) | 117 | 2 | 117 | 2 | 117 | 3 |
| n (Patient) | 83 | 2 | 83 | 2 | 83 | 3 |
| UO only | | | | | | |
| Median | 17.3 | 252 | 17.3 | 55.1 | 17.3 | 38.5 |
| Average | 80.5 | 198 | 80.5 | 172 | 80.5 | 46.8 |
| Stdev | 137 | 165 | 137 | 176 | 137 | 43.7 |
| p (t-test) | | 0.15 | | 0.048 | | 0.55 |
| Min | 1.27 | 12.7 | 1.27 | 2.36 | 1.27 | 1.04 |
| Max | 400 | 329 | 400 | 400 | 400 | 97.9 |
| n (Samp) | 80 | 3 | 80 | 11 | 80 | 6 |
| n (Patient) | 59 | 3 | 59 | 11 | 59 | 6 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.79 | 0.67 | 0.71 | 0.70 | 0.68 | 0.69 | 0.45 | 0.39 | 0.53 |
| SE | 0.14 | 0.21 | 0.17 | 0.088 | 0.21 | 0.093 | 0.12 | 0.18 | 0.12 |
| p | 0.032 | 0.43 | 0.22 | 0.024 | 0.38 | 0.043 | 0.64 | 0.54 | 0.80 |
| nCohort 1 | 93 | 117 | 80 | 93 | 117 | 80 | 93 | 117 | 80 |
| nCohort 2 | 4 | 2 | 3 | 12 | 2 | 11 | 7 | 3 | 6 |
| Cutoff 1 | 245 | 14.5 | 12.7 | 18.0 | 12.2 | 20.3 | 5.27 | 1.04 | 10.4 |
| Sens 1 | 75% | 100% | 100% | 75% | 100% | 73% | 71% | 100% | 83% |
| Spec 1 | 89% | 44% | 42% | 55% | 41% | 59% | 23% | 2% | 34% |
| Cutoff 2 | 14.5 | 14.5 | 12.7 | 16.2 | 12.2 | 18.0 | 1.04 | 1.04 | 10.4 |
| Sens 2 | 100% | 100% | 100% | 83% | 100% | 82% | 86% | 100% | 83% |
| Spec 2 | 49% | 44% | 42% | 51% | 41% | 52% | 1% | 2% | 34% |
| Cutoff 3 | 14.5 | 14.5 | 12.7 | 12.2 | 12.2 | 16.2 | 0.946 | 1.04 | 0 |
| Sens 3 | 100% | 100% | 100% | 92% | 100% | 91% | 100% | 100% | 100% |
| Spec 3 | 49% | 44% | 42% | 45% | 41% | 48% | 1% | 2% | 0% |
| Cutoff 4 | 31.8 | 42.5 | 31.9 | 31.8 | 42.5 | 31.9 | 31.8 | 42.5 | 31.9 |
| Sens 4 | 75% | 50% | 67% | 58% | 50% | 64% | 43% | 33% | 50% |
| Spec 4 | 71% | 70% | 70% | 71% | 70% | 70% | 71% | 70% | 70% |
| Cutoff 5 | 57.4 | 76.0 | 76.0 | 57.4 | 76.0 | 76.0 | 57.4 | 76.0 | 76.0 |
| Sens 5 | 75% | 50% | 67% | 42% | 50% | 45% | 43% | 33% | 33% |
| Spec 5 | 81% | 80% | 80% | 81% | 80% | 80% | 81% | 80% | 80% |
| Cutoff 6 | 347 | 347 | 400 | 347 | 347 | 400 | 347 | 347 | 400 |
| Sens 6 | 0% | 0% | 0% | 33% | 50% | 0% | 0% | 33% | 0% |
| Spec 6 | 90% | 91% | 100% | 90% | 91% | 100% | 90% | 91% | 100% |
| OR Quart 2 | >1.0 | >1.0 | >1.0 | 2.1 | >1.0 | 2.0 | 0 | 0 | 2.0 |
| p Value | <0.98 | <1.0 | <1.0 | 0.56 | <1.0 | 0.58 | na | na | 0.58 |
| 95% CI of | >0.062 | >0.060 | >0.058 | 0.18 | >0.060 | 0.17 | na | na | 0.17 |
| OR Quart 2 | na | na | na | 25 | na | 24 | na | na | 24 |
| OR Quart 3 | >0 | >0 | >0 | 3.3 | >0 | 3.1 | 0.31 | 0 | 0 |
| p Value | <na | <na | <na | 0.32 | <na | 0.34 | 0.32 | na | na |
| 95% CI of | >na | >na | >na | 0.32 | >na | 0.30 | 0.030 | na | na |

TABLE 2-continued

Comparison of marker levels in urine samples collected from Cohort
1 (patients that did not progress beyond RIFLE stage 0 or R) and in urine samples
collected from subjects at 0, 24 hours, and 48 hours prior to reaching stage I or F in Cohort 2.

| | | | | | | | | | |
|---|---|---|---|---|---|---|---|---|---|
| OR Quart 3 | na | na | na | 34 | na | 33 | 3.2 | na | na |
| OR Quart 4 | >3.3 | >1.0 | >2.1 | 7.1 | >1.0 | 5.8 | 1.0 | 2.1 | 3.2 |
| p Value | <0.32 | <1.0 | <0.56 | 0.079 | <1.0 | 0.12 | 1.0 | 0.56 | 0.34 |
| 95% CI of | >0.32 | >0.060 | >0.18 | 0.80 | >0.060 | 0.62 | 0.18 | 0.18 | 0.30 |
| OR Quart 4 | na | na | na | 64 | na | 55 | 5.5 | 24 | 33 |

Interstitial collagenase:Metalloproteinase inhibitor 2 complex

| | 24 hr prior to AKI stage | | 48 hr prior to AKI stage | |
|---|---|---|---|---|
| | Cohort 1 | Cohort 2 | Cohort 1 | Cohort 2 |
| sCr or UO | | | | |
| Median | 0.233 | 0.233 | | |
| Average | 177 | 26.6 | | |
| Stdev | 1620 | 76.2 | | |
| p (t-test) | | 0.72 | | |
| Min | 0.228 | 0.228 | | |
| Max | 16000 | 297 | | |
| n (Samp) | 97 | 15 | | |
| n (Patient) | 74 | 15 | | |
| sCr only | | | | |
| Median | 0.233 | 6.97 | | |
| Average | 159 | 12.2 | | |
| Stdev | 1530 | 15.3 | | |
| p (t-test) | | 0.87 | | |
| Min | 0.228 | 0.233 | | |
| Max | 16000 | 29.5 | | |
| n (Samp) | 110 | 3 | | |
| n (Patient) | 85 | 3 | | |
| UO only | | | | |
| Median | 0.233 | 0.233 | 0.233 | 0.231 |
| Average | 202 | 28.0 | 202 | 0.231 |
| Stdev | 1770 | 78.9 | 1770 | 0.00389 |
| p (t-test) | | 0.71 | | 0.87 |
| Min | 0.228 | 0.228 | 0.228 | 0.228 |
| Max | 16000 | 297 | 16000 | 0.233 |
| n (Samp) | 82 | 14 | 82 | 2 |
| n (Patient) | 62 | 14 | 62 | 2 |

| | 24 hr prior to AKI stage | | | 48 hr prior to AKI stage | | |
|---|---|---|---|---|---|---|
| | sCr or UO | sCr only | UO only | sCr or UO | sCr only | UO only |
| AUC | 0.55 | 0.78 | 0.51 | nd | nd | 0.34 |
| SE | 0.082 | 0.16 | 0.084 | nd | nd | 0.21 |
| p | 0.51 | 0.079 | 0.94 | nd | nd | 0.47 |
| nCohort 1 | 97 | 110 | 82 | nd | nd | 82 |
| nCohort 2 | 15 | 3 | 14 | nd | nd | 2 |
| Cutoff 1 | 0 | 0.228 | 0 | nd | nd | 0 |
| Sens 1 | 100% | 100% | 100% | nd | nd | 100% |
| Spec 1 | 0% | 37% | 0% | nd | nd | 0% |
| Cutoff 2 | 0 | 0.228 | 0 | nd | nd | 0 |
| Sens 2 | 100% | 100% | 100% | nd | nd | 100% |
| Spec 2 | 0% | 37% | 0% | nd | nd | 0% |
| Cutoff 3 | 0 | 0.228 | 0 | nd | nd | 0 |
| Sens 3 | 100% | 100% | 100% | nd | nd | 100% |
| Spec 3 | 0% | 37% | 0% | nd | nd | 0% |
| Cutoff 4 | 0.233 | 0.233 | 0.233 | nd | nd | 0.233 |
| Sens 4 | 40% | 67% | 36% | nd | nd | 0% |
| Spec 4 | 81% | 79% | 79% | nd | nd | 79% |
| Cutoff 5 | 0.233 | 1.35 | 1.26 | nd | nd | 1.26 |
| Sens 5 | 40% | 67% | 36% | nd | nd | 0% |
| Spec 5 | 81% | 80% | 80% | nd | nd | 80% |
| Cutoff 6 | 18.2 | 18.5 | 10.7 | nd | nd | 10.7 |
| Sens 6 | 20% | 33% | 21% | nd | nd | 0% |
| Spec 6 | 91% | 91% | 90% | nd | nd | 90% |
| OR Quart 2 | 0.17 | >0 | 1.0 | nd | nd | >0 |
| p Value | 0.12 | <na | 1.0 | nd | nd | <na |
| 95% CI of | 0.019 | >na | 0.22 | nd | nd | >na |
| OR Quart 2 | 1.6 | na | 4.6 | nd | nd | na |
| OR Quart 3 | 0.55 | >1.0 | 0.22 | nd | nd | >1.0 |
| p Value | 0.45 | <0.98 | 0.19 | nd | nd | <0.97 |

TABLE 2-continued

Comparison of marker levels in urine samples collected from Cohort
1 (patients that did not progress beyond RIFLE stage 0 or R) and in urine samples
collected from subjects at 0, 24 hours, and 48 hours prior to reaching stage I or F in Cohort 2.

| | | | | | | | |
|---|---|---|---|---|---|---|---|
| 95% CI of | 0.12 | >0.062 | 0.022 | nd | nd | | >0.061 |
| OR Quart 3 | 2.6 | na | 2.1 | nd | nd | | na |
| OR Quart 4 | 1.3 | >2.1 | 1.3 | nd | nd | | >1.0 |
| p Value | 0.74 | <0.56 | 0.71 | nd | nd | | <0.97 |
| 95% CI of | 0.33 | >0.18 | 0.31 | nd | nd | | >0.061 |
| OR Quart 4 | 4.7 | na | 5.6 | nd | nd | | na |

72 kDa type IV collagenase:Metalloproteinase inhibitor 2 complex

| | 24 hr prior to AKI stage | | 48 hr prior to AKI stage | |
|---|---|---|---|---|
| | Cohort 1 | Cohort 2 | Cohort 1 | Cohort 2 |
| sCr or UO | | | | |
| Median | 28.1 | 269 | nd | nd |
| Average | 585 | 1600 | nd | nd |
| Stdev | 1940 | 4100 | nd | nd |
| p (t-test) | | 0.12 | nd | nd |
| Min | 1.15 | 1.15 | nd | nd |
| Max | 16000 | 16000 | nd | nd |
| n (Samp) | 91 | 15 | nd | nd |
| n (Patient) | 72 | 15 | nd | nd |
| sCr only | | | | |
| Median | 30.3 | 527 | nd | nd |
| Average | 817 | 447 | nd | nd |
| Stdev | 2580 | 245 | nd | nd |
| p (t-test) | | 0.81 | nd | nd |
| Min | 1.15 | 171 | nd | nd |
| Max | 16000 | 642 | nd | nd |
| n (Samp) | 105 | 3 | nd | nd |
| n (Patient) | 84 | 3 | nd | nd |
| UO only | | | | |
| Median | 16.2 | 231 | 16.2 | 5640 |
| Average | 624 | 1660 | 624 | 5640 |
| Stdev | 2060 | 4240 | 2060 | 7740 |
| p (t-test) | | 0.15 | | 0.0023 |
| Min | 1.15 | 1.15 | 1.15 | 171 |
| Max | 16000 | 16000 | 16000 | 11100 |
| n (Samp) | 80 | 14 | 80 | 2 |
| n (Patient) | 63 | 14 | 63 | 2 |

| | 24 hr prior to AKI stage | | | 48 hr prior to AKI stage | | |
|---|---|---|---|---|---|---|
| | sCr or UO | sCr only | UO only | sCr or UO | sCr only | UO only |
| AUC | 0.60 | 0.75 | 0.57 | nd | nd | 0.83 |
| SE | 0.083 | 0.17 | 0.086 | nd | nd | 0.18 |
| p | 0.22 | 0.14 | 0.40 | nd | nd | 0.066 |
| nCohort 1 | 91 | 105 | 80 | nd | nd | 80 |
| nCohort 2 | 15 | 3 | 14 | nd | nd | 2 |
| Cutoff 1 | 1.15 | 164 | 1.15 | nd | nd | 164 |
| Sens 1 | 80% | 100% | 79% | nd | nd | 100% |
| Spec 1 | 18% | 65% | 15% | nd | nd | 68% |
| Cutoff 2 | 1.15 | 164 | 0 | nd | nd | 164 |
| Sens 2 | 80% | 100% | 100% | nd | nd | 100% |
| Spec 2 | 18% | 65% | 0% | nd | nd | 68% |
| Cutoff 3 | 0 | 164 | 0 | nd | nd | 164 |
| Sens 3 | 100% | 100% | 100% | nd | nd | 100% |
| Spec 3 | 0% | 65% | 0% | nd | nd | 68% |
| Cutoff 4 | 189 | 295 | 227 | nd | nd | 227 |
| Sens 4 | 60% | 67% | 50% | nd | nd | 50% |
| Spec 4 | 70% | 70% | 70% | nd | nd | 70% |
| Cutoff 5 | 579 | 595 | 579 | nd | nd | 579 |
| Sens 5 | 33% | 33% | 29% | nd | nd | 50% |
| Spec 5 | 80% | 80% | 80% | nd | nd | 80% |
| Cutoff 6 | 1380 | 1700 | 1380 | nd | nd | 1380 |
| Sens 6 | 20% | 0% | 21% | nd | nd | 50% |
| Spec 6 | 90% | 90% | 90% | nd | nd | 90% |
| OR Quart 2 | 0.21 | >0 | 0.61 | nd | nd | >0 |
| p Value | 0.18 | <na | 0.60 | nd | nd | <na |
| 95% CI of | 0.022 | >na | 0.092 | nd | nd | >na |
| OR Quart 2 | 2.0 | na | 4.0 | nd | nd | na |
| OR Quart 3 | 1.0 | >1.0 | 1.4 | nd | nd | >1.1 |

TABLE 2-continued

Comparison of marker levels in urine samples collected from Cohort
1 (patients that did not progress beyond RIFLE stage 0 or R) and in urine samples
collected from subjects at 0, 24 hours, and 48 hours prior to reaching stage I or F in Cohort 2.

| | | | | | | | |
|---|---|---|---|---|---|---|---|
| p Value | 1.0 | <0.98 | 0.68 | nd | nd | <0.97 |
| 95% CI of | 0.22 | >0.062 | 0.28 | nd | nd | >0.061 |
| OR Quart 3 | 4.5 | na | 7.1 | nd | nd | na |
| OR Quart 4 | 1.6 | >2.2 | 1.8 | nd | nd | >1.0 |
| p Value | 0.53 | <0.54 | 0.48 | nd | nd | <1.0 |
| 95% CI of | 0.39 | >0.18 | 0.37 | nd | nd | >0.058 |
| OR Quart 4 | 6.4 | na | 8.4 | nd | nd | na |

Neural cell adhesion molecule 1

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| sCr or UO | | | | | | |
| Median | 2660 | 3570 | 2660 | 2810 | 2660 | 2310 |
| Average | 3280 | 3960 | 3280 | 4330 | 3280 | 2870 |
| Stdev | 2980 | 2720 | 2980 | 6820 | 2980 | 2250 |
| p (t-test) | | 0.087 | | 0.014 | | 0.39 |
| Min | 6.83 | 85.5 | 6.83 | 375 | 6.83 | 138 |
| Max | 48400 | 15000 | 48400 | 55700 | 48400 | 9700 |
| n (Samp) | 923 | 60 | 923 | 68 | 923 | 38 |
| n (Patient) | 359 | 60 | 359 | 68 | 359 | 38 |
| sCr only | | | | | | |
| Median | 2820 | 2420 | 2820 | 2620 | 2820 | 2470 |
| Average | 3470 | 2380 | 3470 | 3790 | 3470 | 3290 |
| Stdev | 3270 | 1460 | 3270 | 2950 | 3270 | 2340 |
| p (t-test) | | 0.20 | | 0.68 | | 0.83 |
| Min | 6.83 | 301 | 6.83 | 921 | 6.83 | 932 |
| Max | 55700 | 4670 | 55700 | 10800 | 55700 | 8410 |
| n (Samp) | 1219 | 15 | 1219 | 18 | 1219 | 16 |
| n (Patient) | 439 | 15 | 439 | 18 | 439 | 16 |
| UO only | | | | | | |
| Median | 2740 | 4130 | 2740 | 3060 | 2740 | 2460 |
| Average | 3340 | 4790 | 3340 | 4830 | 3340 | 2990 |
| Stdev | 2980 | 4070 | 2980 | 7620 | 2980 | 2240 |
| p (t-test) | | 6.9E-4 | | 0.0014 | | 0.50 |
| Min | 0.234 | 85.5 | 0.234 | 375 | 0.234 | 138 |
| Max | 48400 | 26600 | 48400 | 55700 | 48400 | 9700 |
| n (Samp) | 819 | 55 | 819 | 61 | 819 | 34 |
| n (Patient) | 285 | 55 | 285 | 61 | 285 | 34 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.59 | 0.39 | 0.64 | 0.54 | 0.52 | 0.55 | 0.44 | 0.48 | 0.46 |
| SE | 0.040 | 0.078 | 0.041 | 0.037 | 0.070 | 0.039 | 0.049 | 0.073 | 0.052 |
| p | 0.029 | 0.15 | 8.7E-4 | 0.30 | 0.73 | 0.24 | 0.24 | 0.83 | 0.41 |
| nCohort 1 | 923 | 1219 | 819 | 923 | 1219 | 819 | 923 | 1219 | 819 |
| nCohort 2 | 60 | 15 | 55 | 68 | 18 | 61 | 38 | 16 | 34 |
| Cutoff 1 | 2430 | 1120 | 2720 | 2030 | 2080 | 2030 | 1250 | 1050 | 1650 |
| Sens 1 | 70% | 73% | 71% | 71% | 72% | 70% | 71% | 75% | 71% |
| Spec 1 | 46% | 14% | 50% | 36% | 35% | 34% | 17% | 12% | 26% |
| Cutoff 2 | 1680 | 848 | 2290 | 1210 | 1700 | 1220 | 957 | 965 | 1180 |
| Sens 2 | 80% | 80% | 80% | 81% | 83% | 80% | 82% | 81% | 82% |
| Spec 2 | 28% | 8% | 41% | 16% | 26% | 15% | 11% | 10% | 15% |
| Cutoff 3 | 873 | 615 | 1220 | 1040 | 1080 | 1040 | 402 | 950 | 402 |
| Sens 3 | 90% | 93% | 91% | 91% | 94% | 90% | 92% | 94% | 91% |
| Spec 3 | 8% | 4% | 15% | 13% | 12% | 11% | 2% | 10% | 2% |
| Cutoff 4 | 3890 | 4060 | 3930 | 3890 | 4060 | 3930 | 3890 | 4060 | 3930 |
| Sens 4 | 45% | 7% | 53% | 38% | 39% | 41% | 26% | 38% | 26% |
| Spec 4 | 70% | 70% | 70% | 70% | 70% | 70% | 70% | 70% | 70% |
| Cutoff 5 | 4730 | 4960 | 4750 | 4730 | 4960 | 4750 | 4730 | 4960 | 4750 |
| Sens 5 | 35% | 0% | 44% | 28% | 28% | 31% | 21% | 25% | 21% |
| Spec 5 | 80% | 80% | 80% | 80% | 80% | 80% | 80% | 80% | 80% |
| Cutoff 6 | 6230 | 6520 | 6280 | 6230 | 6520 | 6280 | 6230 | 6520 | 6280 |
| Sens 6 | 20% | 0% | 24% | 16% | 17% | 18% | 8% | 6% | 9% |
| Spec 6 | 90% | 90% | 90% | 90% | 90% | 90% | 90% | 90% | 90% |
| OR Quart 2 | 0.65 | 6.1 | 1.7 | 1.1 | 2.0 | 1.2 | 0.49 | 0.40 | 0.66 |
| p Value | 0.36 | 0.094 | 0.25 | 0.72 | 0.32 | 0.56 | 0.20 | 0.27 | 0.44 |
| 95% CI of | 0.26 | 0.73 | 0.67 | 0.56 | 0.50 | 0.59 | 0.17 | 0.076 | 0.23 |
| OR Quart 2 | 1.6 | 51 | 4.5 | 2.3 | 8.1 | 2.7 | 1.5 | 2.1 | 1.9 |

TABLE 2-continued

Comparison of marker levels in urine samples collected from Cohort 1 (patients that did not progress beyond RIFLE stage 0 or R) and in urine samples collected from subjects at 0, 24 hours, and 48 hours prior to reaching stage I or F in Cohort 2.

| | | | | | | | | | |
|---|---|---|---|---|---|---|---|---|---|
| OR Quart 3 | 1.5 | 2.0 | 1.8 | 0.93 | 1.3 | 0.84 | 1.1 | 0.80 | 1.1 |
| p Value | 0.27 | 0.57 | 0.25 | 0.84 | 0.70 | 0.67 | 0.82 | 0.74 | 0.81 |
| 95% CI of | 0.72 | 0.18 | 0.68 | 0.44 | 0.30 | 0.37 | 0.46 | 0.21 | 0.45 |
| OR Quart 3 | 3.3 | 22 | 4.5 | 2.0 | 6.0 | 1.9 | 2.7 | 3.0 | 2.8 |
| OR Quart 4 | 1.9 | 6.1 | 3.7 | 1.5 | 1.7 | 1.7 | 1.2 | 1.0 | 1.0 |
| p Value | 0.082 | 0.094 | 0.0029 | 0.24 | 0.48 | 0.16 | 0.66 | 1.00 | 0.99 |
| 95% CI of | 0.92 | 0.73 | 1.6 | 0.76 | 0.40 | 0.82 | 0.52 | 0.29 | 0.39 |
| OR Quart 4 | 3.9 | 51 | 8.8 | 3.0 | 7.1 | 3.4 | 2.9 | 3.5 | 2.6 |

Myeloid differentiation primary response protein MyD88

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| sCr or UO | | | | | | |
| Median | 0.000533 | 0.000352 | 0.000533 | 0.000533 | 0.000533 | 0.00237 |
| Average | 0.0158 | 0.0168 | 0.0158 | 0.0123 | 0.0158 | 0.00355 |
| Stdev | 0.0587 | 0.0263 | 0.0587 | 0.0363 | 0.0587 | 0.00366 |
| p (t-test) | | 0.96 | | 0.78 | | 0.64 |
| Min | 0.000126 | 0.000126 | 0.000126 | 0.000126 | 0.000126 | 0.000171 |
| Max | 0.671 | 0.0804 | 0.671 | 0.171 | 0.671 | 0.00853 |
| n (Samp) | 197 | 10 | 197 | 23 | 197 | 5 |
| n (Patient) | 118 | 10 | 118 | 23 | 118 | 5 |
| sCr only | | | | | | |
| Median | nd | nd | 0.000533 | 0.000168 | nd | nd |
| Average | nd | nd | 0.0165 | 0.000259 | nd | nd |
| Stdev | nd | nd | 0.0575 | 0.000183 | nd | nd |
| p (t-test) | nd | nd | | 0.57 | nd | nd |
| Min | nd | nd | 0.000126 | 0.000165 | nd | nd |
| Max | nd | nd | 0.671 | 0.000533 | nd | nd |
| n (Samp) | nd | nd | 239 | 4 | nd | nd |
| n (Patient) | nd | nd | 138 | 4 | nd | nd |
| UO only | | | | | | |
| Median | 0.000533 | 0.000352 | 0.000533 | 0.000533 | 0.000533 | 0.00145 |
| Average | 0.0131 | 0.0168 | 0.0131 | 0.0128 | 0.0131 | 0.00305 |
| Stdev | 0.0363 | 0.0263 | 0.0363 | 0.0370 | 0.0363 | 0.00350 |
| p (t-test) | | 0.75 | | 0.97 | | 0.50 |
| Min | 0.000126 | 0.000126 | 0.000126 | 0.000126 | 0.000126 | 0.000171 |
| Max | 0.371 | 0.0804 | 0.371 | 0.171 | 0.371 | 0.00853 |
| n (Samp) | 181 | 10 | 181 | 22 | 181 | 6 |
| n (Patient) | 105 | 10 | 105 | 22 | 105 | 6 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.54 | nd | 0.53 | 0.46 | 0.34 | 0.46 | 0.62 | nd | 0.60 |
| SE | 0.095 | nd | 0.096 | 0.065 | 0.15 | 0.066 | 0.14 | nd | 0.12 |
| p | 0.71 | nd | 0.74 | 0.49 | 0.28 | 0.56 | 0.36 | nd | 0.42 |
| nCohort 1 | 197 | nd | 181 | 197 | 239 | 181 | 197 | nd | 181 |
| nCohort 2 | 10 | nd | 10 | 23 | 4 | 22 | 5 | nd | 6 |
| Cutoff 1 | 0.000165 | nd | 0.000165 | 0.000126 | 0.000126 | 0.000126 | 0.000171 | nd | 0.000171 |
| Sens 1 | 80% | nd | 80% | 91% | 100% | 91% | 80% | nd | 83% |
| Spec 1 | 35% | nd | 33% | 10% | 10% | 10% | 42% | nd | 41% |
| Cutoff 2 | 0.000165 | nd | 0.000165 | 0.000126 | 0.000126 | 0.000126 | 0.000171 | nd | 0.000171 |
| Sens 2 | 80% | nd | 80% | 91% | 100% | 91% | 80% | nd | 83% |
| Spec 2 | 35% | nd | 33% | 10% | 10% | 10% | 42% | nd | 41% |
| Cutoff 3 | 0 | nd | 0 | 0.000126 | 0.000126 | 0.000126 | 0.000165 | nd | 0.000165 |
| Sens 3 | 100% | nd | 100% | 91% | 100% | 91% | 100% | nd | 100% |
| Spec 3 | 0% | nd | 0% | 10% | 10% | 10% | 35% | nd | 33% |
| Cutoff 4 | 0.00167 | nd | 0.00309 | 0.00167 | 0.00309 | 0.00309 | 0.00167 | nd | 0.00309 |
| Sens 4 | 40% | nd | 40% | 22% | 0% | 23% | 60% | nd | 33% |
| Spec 4 | 70% | nd | 70% | 70% | 70% | 70% | 70% | nd | 70% |
| Cutoff 5 | 0.0184 | nd | 0.0188 | 0.0184 | 0.0188 | 0.0188 | 0.0184 | nd | 0.0188 |
| Sens 5 | 40% | nd | 40% | 17% | 0% | 18% | 0% | nd | 0% |
| Spec 5 | 80% | nd | 80% | 80% | 80% | 80% | 80% | nd | 80% |
| Cutoff 6 | 0.0387 | nd | 0.0366 | 0.0387 | 0.0393 | 0.0366 | 0.0387 | nd | 0.0366 |
| Sens 6 | 10% | nd | 10% | 9% | 0% | 9% | 0% | nd | 0% |
| Spec 6 | 90% | nd | 90% | 90% | 90% | 90% | 90% | nd | 90% |
| OR Quart 2 | 2.0 | nd | 1.5 | 0 | >1.0 | 0.38 | >1.0 | nd | >3.1 |
| p Value | 0.42 | nd | 0.67 | na | <0.99 | 0.26 | <1.0 | nd | <0.33 |
| 95% CI of | 0.36 | nd | 0.24 | na | >0.062 | 0.069 | >0.061 | nd | >0.31 |

TABLE 2-continued

Comparison of marker levels in urine samples collected from Cohort 1 (patients that did not progress beyond RIFLE stage 0 or R) and in urine samples collected from subjects at 0, 24 hours, and 48 hours prior to reaching stage I or F in Cohort 2.

| OR Quart 2 | 12 | nd | 9.4 | na | na | 2.0 | na | nd | na |
|---|---|---|---|---|---|---|---|---|---|
| OR Quart 3 | 0 | nd | 0.48 | 3.1 | >3.2 | 1.2 | >3.2 | nd | >3.1 |
| p Value | na | nd | 0.55 | 0.046 | <0.33 | 0.75 | <0.32 | nd | <0.33 |
| 95% CI of | na | nd | 0.042 | 1.0 | >0.32 | 0.35 | >0.32 | nd | >0.31 |
| OR Quart 3 | na | nd | 5.5 | 9.4 | na | 4.3 | na | nd | na |
| OR Quart 4 | 2.0 | nd | 2.0 | 1.0 | >0 | 2.0 | >1.0 | nd | >0 |
| p Value | 0.42 | nd | 0.42 | 1.0 | <na | 0.24 | <1.0 | nd | <na |
| 95% CI of | 0.36 | nd | 0.36 | 0.27 | >na | 0.63 | >0.061 | nd | >na |
| OR Quart 4 | 12 | nd | 12 | 3.7 | na | 6.5 | na | nd | na |

TABLE 3

Comparison of marker levels in urine samples collected within 12 hours of reaching stage R from Cohort 1 (patients that reached, but did not progress beyond, RIFLE stage R) and from Cohort 2 (patients that reached RIFLE stage I or F).
Tumor necrosis factor ligand superfamily member 10

|  | sCr or UO | | sCr only | | UO only | |
|---|---|---|---|---|---|---|
|  | Cohort 1 | Cohort 2 | Cohort 1 | Cohort 2 | Cohort 1 | Cohort 2 |
| Median | 0.0287 | 0.0287 | 0.0257 | 0.0285 | 0.0335 | 0.0286 |
| Average | 1.65 | 2.49 | 0.779 | 0.732 | 2.34 | 2.49 |
| Stdev | 7.15 | 8.75 | 2.82 | 1.39 | 8.97 | 9.35 |
| p (t-test) |  | 0.53 |  | 0.96 |  | 0.93 |
| Min | 0.0110 | 0.0110 | 0.0139 | 0.0139 | 0.0110 | 0.0110 |
| Max | 63.9 | 50.6 | 13.9 | 3.82 | 63.9 | 50.6 |
| n (Samp) | 121 | 43 | 47 | 11 | 99 | 30 |
| n (Patient) | 121 | 43 | 47 | 11 | 99 | 30 |

| At Enrollment | | | |
|---|---|---|---|
|  | sCr or UO | sCr only | UO only |
| AUC | 0.53 | 0.59 | 0.49 |
| SE | 0.052 | 0.099 | 0.061 |
| p | 0.61 | 0.36 | 0.88 |
| nCohort 1 | 121 | 47 | 99 |
| nCohort 2 | 43 | 11 | 30 |
| Cutoff 1 | 0.0239 | 0.0237 | 0.0239 |
| Sens 1 | 77% | 73% | 73% |
| Spec 1 | 35% | 47% | 32% |
| Cutoff 2 | 0.0227 | 0.0227 | 0.0227 |
| Sens 2 | 84% | 82% | 83% |
| Spec 2 | 30% | 38% | 28% |
| Cutoff 3 | 0.0159 | 0.0139 | 0.0159 |
| Sens 3 | 91% | 91% | 90% |
| Spec 3 | 15% | 6% | 15% |
| Cutoff 4 | 0.0439 | 0.0363 | 0.0439 |
| Sens 4 | 26% | 36% | 20% |
| Spec 4 | 73% | 74% | 73% |
| Cutoff 5 | 0.0526 | 0.0439 | 0.0526 |
| Sens 5 | 21% | 36% | 17% |
| Spec 5 | 85% | 81% | 84% |
| Cutoff 6 | 1.70 | 2.23 | 1.70 |
| Sens 6 | 16% | 18% | 17% |
| Spec 6 | 90% | 91% | 91% |
| OR Quart 2 | 2.8 | 0.92 | 1.3 |
| p Value | 0.050 | 0.94 | 0.71 |
| 95% CI of | 1.00 | 0.11 | 0.37 |
| OR Quart 2 | 7.9 | 7.6 | 4.3 |
| OR Quart 3 | 1.6 | 1.6 | 3.1 |
| p Value | 0.42 | 0.62 | 0.051 |
| 95% CI of | 0.53 | 0.23 | 0.99 |
| OR Quart 3 | 4.6 | 12 | 9.5 |
| OR Quart 4 | 1.8 | 2.2 | 0.64 |
| p Value | 0.29 | 0.42 | 0.53 |
| 95% CI of | 0.61 | 0.33 | 0.16 |
| OR Quart 4 | 5.2 | 14 | 2.5 |

TABLE 4

Comparison of the maximum marker levels in urine samples collected from Cohort 1 (patients that did not progress beyond RIFLE stage 0) and the maximum values in urine samples collected from subjects between enrollment and 0, 24 hours, and 48 hours prior to reaching stage F in Cohort 2.

Stromelysin-1:Metalloproteinase inhibitor 2 complex

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| sCr or UO | | | | | | |
| Median | 0.487 | 0.487 | 0.487 | 0.487 | 0.487 | 0.487 |
| Average | 400 | 101 | 400 | 101 | 400 | 0.487 |
| Stdev | 2140 | 197 | 2140 | 197 | 2140 | 0 |
| p (t-test) |  | 0.70 |  | 0.70 |  | 0.75 |
| Min | 0.237 | 0.487 | 0.237 | 0.487 | 0.237 | 0.487 |
| Max | 13900 | 530 | 13900 | 530 | 13900 | 0.487 |
| n (Samp) | 42 | 8 | 42 | 8 | 42 | 3 |
| n (Patient) | 42 | 8 | 42 | 8 | 42 | 3 |

TABLE 4-continued

Comparison of the maximum marker levels in urine samples
collected from Cohort 1 (patients that did not progress beyond RIFLE stage 0) and the
maximum values in urine samples collected from subjects between enrollment and 0, 24
hours, and 48 hours prior to reaching stage F in Cohort 2.

| sCr only | | | | | | |
|---|---|---|---|---|---|---|
| Median | 0.487 | 5.71 | 0.487 | 5.71 | nd | nd |
| Average | 238 | 136 | 238 | 136 | nd | nd |
| Stdev | 1630 | 263 | 1630 | 263 | nd | nd |
| p (t-test) | | 0.90 | | 0.90 | nd | nd |
| Min | 0.237 | 0.487 | 0.237 | 0.487 | nd | nd |
| Max | 13900 | 530 | 13900 | 530 | nd | nd |
| n (Samp) | 73 | 4 | 73 | 4 | nd | nd |
| n (Patient) | 73 | 4 | 73 | 4 | nd | nd |
| UO only | | | | | | |
| Median | 0.487 | 0.487 | 0.487 | 0.487 | 0.487 | 0.487 |
| Average | 435 | 53.8 | 435 | 53.8 | 435 | 0.487 |
| Stdev | 2350 | 119 | 2350 | 119 | 2350 | 0 |
| p (t-test) | | 0.72 | | 0.72 | | 0.75 |
| Min | 0.237 | 0.487 | 0.237 | 0.487 | 0.237 | 0.487 |
| Max | 13900 | 267 | 13900 | 267 | 13900 | 0.487 |
| n (Samp) | 35 | 5 | 35 | 5 | 35 | 3 |
| n (Patient) | 35 | 5 | 35 | 5 | 35 | 3 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.68 | 0.76 | 0.69 | 0.68 | 0.76 | 0.69 | 0.56 | nd | 0.63 |
| SE | 0.11 | 0.14 | 0.14 | 0.11 | 0.14 | 0.14 | 0.18 | nd | 0.18 |
| p | 0.11 | 0.076 | 0.17 | 0.11 | 0.076 | 0.17 | 0.74 | nd | 0.48 |
| nCohort 1 | 42 | 73 | 35 | 42 | 73 | 35 | 42 | nd | 35 |
| nCohort 2 | 8 | 4 | 5 | 8 | 4 | 5 | 3 | nd | 3 |
| Cutoff 1 | 0.237 | 0.237 | 0.237 | 0.237 | 0.237 | 0.237 | 0.237 | nd | 0.237 |
| Sens 1 | 100% | 100% | 100% | 100% | 100% | 100% | 100% | nd | 100% |
| Spec 1 | 31% | 42% | 46% | 31% | 42% | 46% | 31% | nd | 46% |
| Cutoff 2 | 0.237 | 0.237 | 0.237 | 0.237 | 0.237 | 0.237 | 0.237 | nd | 0.237 |
| Sens 2 | 100% | 100% | 100% | 100% | 100% | 100% | 100% | nd | 100% |
| Spec 2 | 31% | 42% | 46% | 31% | 42% | 46% | 31% | nd | 46% |
| Cutoff 3 | 0.237 | 0.237 | 0.237 | 0.237 | 0.237 | 0.237 | 0.237 | nd | 0.237 |
| Sens 3 | 100% | 100% | 100% | 100% | 100% | 100% | 100% | nd | 100% |
| Spec 3 | 31% | 42% | 46% | 31% | 42% | 46% | 31% | nd | 46% |
| Cutoff 4 | 0.487 | 0.487 | 0.487 | 0.487 | 0.487 | 0.487 | 0.487 | nd | 0.487 |
| Sens 4 | 38% | 50% | 20% | 38% | 50% | 20% | 0% | nd | 0% |
| Spec 4 | 81% | 82% | 80% | 81% | 82% | 80% | 81% | nd | 80% |
| Cutoff 5 | 0.487 | 0.487 | 0.487 | 0.487 | 0.487 | 0.487 | 0.487 | nd | 0.487 |
| Sens 5 | 38% | 50% | 20% | 38% | 50% | 20% | 0% | nd | 0% |
| Spec 5 | 81% | 82% | 80% | 81% | 82% | 80% | 81% | nd | 80% |
| Cutoff 6 | 261 | 154 | 201 | 261 | 154 | 201 | 261 | nd | 201 |
| Sens 6 | 25% | 25% | 20% | 25% | 25% | 20% | 0% | nd | 0% |
| Spec 6 | 90% | 90% | 91% | 90% | 90% | 91% | 90% | nd | 91% |
| OR Quart 2 | >7.5 | >2.2 | >6.7 | >7.5 | >2.2 | >6.7 | >4.1 | nd | >3.9 |
| p Value | <0.090 | <0.53 | <0.12 | <0.090 | <0.53 | <0.12 | <0.25 | nd | <0.28 |
| 95% CI of OR Quart 2 | >0.73 | >0.19 | >0.60 | >0.73 | >0.19 | >0.60 | >0.36 | nd | >0.33 |
| | na | na | na | na | na | na | na | nd | na |
| OR Quart 3 | >0 | >0 | >0 | >0 | >0 | >0 | >0 | nd | >0 |
| p Value | <na | <na | <na | <na | <na | <na | <na | nd | <na |
| 95% CI of OR Quart 3 | >na | >na | >na | >na | >na | >na | >na | nd | >na |
| | na | na | na | na | na | na | na | nd | na |
| OR Quart 4 | >3.6 | >2.1 | >1.1 | >3.6 | >2.1 | >1.1 | >0 | nd | >0 |
| p Value | <0.30 | <0.56 | <0.94 | <0.30 | <0.56 | <0.94 | <na | nd | <na |
| 95% CI of OR Quart4 | >0.32 | >0.18 | >0.060 | >0.32 | >0.18 | >0.060 | >na | nd | >na |
| | na | na | na | na | na | na | na | nd | na |

| Heat shock 70 kDa protein 1 | | | | | |
|---|---|---|---|---|---|
| | 0 hr prior to AKI stage | | 24 hr prior to AKI stage | | 48 hr prior to AKI stage | |
| | Cohort 1 | Cohort 2 | Cohort 1 | Cohort 2 | Cohort 1 | Cohort 2 |
| sCr or UO | | | | | | |
| Median | 338 | 1320 | 338 | 1320 | 338 | 1320 |
| Average | 633 | 2600 | 633 | 2600 | 633 | 4450 |
| Stdev | 1230 | 4080 | 1230 | 4080 | 1230 | 6370 |
| p (t-test) | | 0.013 | | 0.013 | | 0.0012 |
| Min | 0.297 | 250 | 0.297 | 250 | 0.297 | 250 |

TABLE 4-continued

Comparison of the maximum marker levels in urine samples
collected from Cohort 1 (patients that did not progress beyond RIFLE stage 0) and the
maximum values in urine samples collected from subjects between enrollment and 0, 24
hours, and 48 hours prior to reaching stage F in Cohort 2.

|  |  |  |  |  |  |  |
|---|---|---|---|---|---|---|
| Max | 7800 | 11800 | 7800 | 11800 | 7800 | 11800 |
| n (Samp) | 41 | 7 | 41 | 7 | 41 | 3 |
| n (Patient) | 41 | 7 | 41 | 7 | 41 | 3 |
| sCr only |  |  |  |  |  |  |
| Median | 408 | 1300 | 408 | 1300 | nd | nd |
| Average | 620 | 1140 | 620 | 1140 | nd | nd |
| Stdev | 1040 | 648 | 1040 | 648 | nd | nd |
| p (t-test) |  | 0.33 |  | 0.33 | nd | nd |
| Min | 0.297 | 250 | 0.297 | 250 | nd | nd |
| Max | 7800 | 1710 | 7800 | 1710 | nd | nd |
| n (Samp) | 71 | 4 | 71 | 4 | nd | nd |
| n (Patient) | 71 | 4 | 71 | 4 | nd | nd |
| UO only |  |  |  |  |  |  |
| Median | 277 | 934 | 277 | 934 | 277 | 1320 |
| Average | 664 | 3480 | 664 | 3480 | 664 | 4450 |
| Stdev | 1330 | 5560 | 1330 | 5560 | 1330 | 6370 |
| p (t-test) |  | 0.013 |  | 0.013 |  | 0.0031 |
| Min | 0.297 | 250 | 0.297 | 250 | 0.297 | 250 |
| Max | 7800 | 11800 | 7800 | 11800 | 7800 | 11800 |
| n (Samp) | 35 | 4 | 35 | 4 | 35 | 3 |
| n (Patient) | 35 | 4 | 35 | 4 | 35 | 3 |

|  | 0 hr prior to AKI stage | | | 24 hr prior to AKI stage | | | 48 hr prior to AKI stage | | |
|---|---|---|---|---|---|---|---|---|---|
|  | sCr or UO | sCr only | UO only | sCr or UO | sCr only | UO only | sCr or UO | sCr only | UO only |
| AUC | 0.83 | 0.80 | 0.75 | 0.83 | 0.80 | 0.75 | 0.79 | nd | 0.79 |
| SE | 0.099 | 0.14 | 0.15 | 0.099 | 0.14 | 0.15 | 0.16 | nd | 0.16 |
| p | 8.2E−4 | 0.027 | 0.084 | 8.2E−4 | 0.027 | 0.084 | 0.066 | nd | 0.077 |
| nCohort 1 | 41 | 71 | 35 | 41 | 71 | 35 | 41 | nd | 35 |
| nCohort 2 | 7 | 4 | 4 | 7 | 4 | 4 | 3 | nd | 3 |
| Cutoff 1 | 1020 | 1040 | 512 | 1020 | 1040 | 512 | 245 | nd | 225 |
| Sens 1 | 71% | 75% | 75% | 71% | 75% | 75% | 100% | nd | 100% |
| Spec 1 | 88% | 90% | 66% | 88% | 90% | 66% | 46% | nd | 49% |
| Cutoff 2 | 512 | 245 | 225 | 512 | 245 | 225 | 245 | nd | 225 |
| Sens 2 | 86% | 100% | 100% | 86% | 100% | 100% | 100% | nd | 100% |
| Spec 2 | 66% | 41% | 49% | 66% | 41% | 49% | 46% | nd | 49% |
| Cutoff 3 | 245 | 245 | 225 | 245 | 245 | 225 | 245 | nd | 225 |
| Sens 3 | 100% | 100% | 100% | 100% | 100% | 100% | 100% | nd | 100% |
| Spec 3 | 46% | 41% | 49% | 46% | 41% | 49% | 46% | nd | 49% |
| Cutoff 4 | 596 | 627 | 596 | 596 | 627 | 596 | 596 | nd | 596 |
| Sens 4 | 71% | 75% | 50% | 71% | 75% | 50% | 67% | nd | 67% |
| Spec 4 | 71% | 70% | 71% | 71% | 70% | 71% | 71% | nd | 71% |
| Cutoff 5 | 811 | 812 | 755 | 811 | 812 | 755 | 811 | nd | 755 |
| Sens 5 | 71% | 75% | 50% | 71% | 75% | 50% | 67% | nd | 67% |
| Spec 5 | 80% | 80% | 80% | 80% | 80% | 80% | 80% | nd | 80% |
| Cutoff 6 | 1150 | 1040 | 1340 | 1150 | 1040 | 1340 | 1150 | nd | 1340 |
| Sens 6 | 57% | 75% | 25% | 57% | 75% | 25% | 67% | nd | 33% |
| Spec 6 | 90% | 90% | 91% | 90% | 90% | 91% | 90% | nd | 91% |
| OR Quart 2 | >1.1 | >1.0 | >1.0 | >1.1 | >1.0 | >1.0 | >1.1 | nd | >1.0 |
| p Value | <0.95 | <1.0 | <1.0 | <0.95 | <1.0 | <1.0 | <0.95 | nd | <1.0 |
| 95% CI of | >0.061 | >0.058 | >0.054 | >0.061 | >0.058 | >0.054 | >0.060 | nd | >0.054 |
| OR Quart 2 | na | na | na | na | na | na | na | nd | na |
| OR Quart 3 | >1.1 | >0 | >1.0 | >1.1 | >0 | >1.0 | >0 | nd | >0 |
| p Value | <0.95 | <na | <1.0 | <0.95 | <na | <1.0 | <na | nd | <na |
| 95% CI of | >0.061 | >na | >0.054 | >0.061 | >na | >0.054 | >na | nd | >na |
| OR Quart 3 | na | na | na | na | na | na | na | nd | na |
| OR Quart 4 | >8.6 | >3.4 | >2.2 | >8.6 | >3.4 | >2.2 | >2.4 | nd | >2.2 |
| p Value | <0.072 | <0.31 | <0.54 | <0.072 | <0.31 | <0.54 | <0.49 | nd | <0.54 |
| 95% CI of | >0.83 | >0.32 | >0.17 | >0.83 | >0.32 | >0.17 | >0.19 | nd | >0.17 |
| OR Quart 4 | na | na | na | na | na | na | na | nd | na |

Interstitial collagenase:Metalloproteinase inhibitor 2 complex

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| sCr or UO |  |  |  |  |  |  |
| Median | 0.233 | 6.57 | 0.233 | 6.57 | 0.233 | 0.228 |
| Average | 396 | 48.1 | 396 | 48.1 | 396 | 2.21 |

TABLE 4-continued

Comparison of the maximum marker levels in urine samples
collected from Cohort 1 (patients that did not progress beyond RIFLE stage 0) and the
maximum values in urine samples collected from subjects between enrollment and 0, 24
hours, and 48 hours prior to reaching stage F in Cohort 2.

|  |  |  |  |  |  |  |
|---|---|---|---|---|---|---|
| Stdev | 2470 | 102 | 2470 | 102 | 2470 | 3.43 |
| p (t-test) |  | 0.69 |  | 0.69 |  | 0.79 |
| Min | 0.228 | 0.228 | 0.228 | 0.228 | 0.228 | 0.228 |
| Max | 16000 | 297 | 16000 | 297 | 16000 | 6.17 |
| n (Samp) | 42 | 8 | 42 | 8 | 42 | 3 |
| n (Patient) | 42 | 8 | 42 | 8 | 42 | 3 |
| sCr only |  |  |  |  |  |  |
| Median | 0.233 | 6.57 | 0.233 | 6.57 | nd | nd |
| Average | 233 | 10.7 | 233 | 10.7 | nd | nd |
| Stdev | 1870 | 12.9 | 1870 | 12.9 | nd | nd |
| p (t-test) |  | 0.81 |  | 0.81 | nd | nd |
| Min | 0.228 | 0.233 | 0.228 | 0.233 | nd | nd |
| Max | 16000 | 29.5 | 16000 | 29.5 | nd | nd |
| n (Samp) | 73 | 4 | 73 | 4 | nd | nd |
| n (Patient) | 73 | 4 | 73 | 4 | nd | nd |
| UO only |  |  |  |  |  |  |
| Median | 0.233 | 6.17 | 0.233 | 6.17 | 0.233 | 0.228 |
| Average | 462 | 69.6 | 462 | 69.6 | 462 | 2.21 |
| Stdev | 2700 | 129 | 2700 | 129 | 2700 | 3.43 |
| p (t-test) |  | 0.75 |  | 0.75 |  | 0.77 |
| Min | 0.228 | 0.228 | 0.228 | 0.228 | 0.228 | 0.228 |
| Max | 16000 | 297 | 16000 | 297 | 16000 | 6.17 |
| n (Samp) | 35 | 5 | 35 | 5 | 35 | 3 |
| n (Patient) | 35 | 5 | 35 | 5 | 35 | 3 |

|  | 0 hr prior to AKI stage | | | 24 hr prior to AKI stage | | | 48 hr prior to AKI stage | | |
|---|---|---|---|---|---|---|---|---|---|
|  | sCr or UO | sCr only | UO only | sCr or UO | sCr only | UO only | sCr or UO | sCr only | UO only |
| AUC | 0.68 | 0.77 | 0.59 | 0.68 | 0.77 | 0.59 | 0.41 | nd | 0.35 |
| SE | 0.11 | 0.14 | 0.14 | 0.11 | 0.14 | 0.14 | 0.18 | nd | 0.18 |
| p | 0.12 | 0.055 | 0.51 | 0.12 | 0.055 | 0.51 | 0.63 | nd | 0.41 |
| nCohort 1 | 42 | 73 | 35 | 42 | 73 | 35 | 42 | nd | 35 |
| nCohort 2 | 8 | 4 | 5 | 8 | 4 | 5 | 3 | nd | 3 |
| Cutoff 1 | 0.228 | 5.57 | 0 | 0.228 | 5.57 | 0 | 0 | nd | 0 |
| Sens 1 | 75% | 75% | 100% | 75% | 75% | 100% | 100% | nd | 100% |
| Spec 1 | 45% | 79% | 0% | 45% | 79% | 0% | 0% | nd | 0% |
| Cutoff 2 | 0 | 0.228 | 0 | 0 | 0.228 | 0 | 0 | nd | 0 |
| Sens 2 | 100% | 100% | 100% | 100% | 100% | 100% | 100% | nd | 100% |
| Spec 2 | 0% | 36% | 0% | 0% | 36% | 0% | 0% | nd | 0% |
| Cutoff 3 | 0 | 0.228 | 0 | 0 | 0.228 | 0 | 0 | nd | 0 |
| Sens 3 | 100% | 100% | 100% | 100% | 100% | 100% | 100% | nd | 100% |
| Spec 3 | 0% | 36% | 0% | 0% | 36% | 0% | 0% | nd | 0% |
| Cutoff 4 | 0.233 | 0.233 | 0.233 | 0.233 | 0.233 | 0.233 | 0.233 | nd | 0.233 |
| Sens 4 | 62% | 75% | 60% | 62% | 75% | 60% | 33% | nd | 33% |
| Spec 4 | 76% | 75% | 71% | 76% | 75% | 71% | 76% | nd | 71% |
| Cutoff 5 | 6.97 | 6.17 | 7.29 | 6.97 | 6.17 | 7.29 | 6.97 | nd | 7.29 |
| Sens 5 | 38% | 50% | 40% | 38% | 50% | 40% | 0% | nd | 0% |
| Spec 5 | 81% | 82% | 80% | 81% | 82% | 80% | 81% | nd | 80% |
| Cutoff 6 | 30.3 | 30.3 | 18.5 | 30.3 | 30.3 | 18.5 | 30.3 | nd | 18.5 |
| Sens 6 | 25% | 0% | 40% | 25% | 0% | 40% | 0% | nd | 0% |
| Spec 6 | 90% | 90% | 91% | 90% | 90% | 91% | 90% | nd | 91% |
| OR Quart 2 | 0 | >0 | 0 | 0 | >0 | 0 | 0 | nd | 0 |
| p Value | na | <na | na | na | <na | na | na | nd | na |
| 95% CI of | na | >na | na | na | >na | na | na | nd | na |
| OR Quart 2 | na | na | na | na | na | na | na | nd | na |
| OR Quart 3 | 1.0 | >1.1 | 0.44 | 1.0 | >1.1 | 0.44 | 0 | nd | 0 |
| p Value | 1.0 | <0.97 | 0.54 | 1.0 | <0.97 | 0.54 | na | nd | na |
| 95% CI of | 0.12 | >0.061 | 0.034 | 0.12 | >0.061 | 0.034 | na | nd | na |
| OR Quart 3 | 8.6 | na | 5.9 | 8.6 | na | 5.9 | na | nd | na |
| OR Quart 4 | 2.2 | >3.4 | 1.0 | 2.2 | >3.4 | 1.0 | 2.4 | nd | 2.6 |
| p Value | 0.42 | <0.31 | 1.0 | 0.42 | <0.31 | 1.0 | 0.49 | nd | 0.48 |
| 95% CI of | 0.33 | >0.32 | 0.11 | 0.33 | >0.32 | 0.11 | 0.19 | nd | 0.19 |
| OR Quart 4 | 15 | na | 8.9 | 15 | na | 8.9 | 32 | nd | 34 |

TABLE 4-continued

Comparison of the maximum marker levels in urine samples
collected from Cohort 1 (patients that did not progress beyond RIFLE stage 0) and the
maximum values in urine samples collected from subjects between enrollment and 0, 24
hours, and 48 hours prior to reaching stage F in Cohort 2.

72 kDa type IV collagenase:Metalloproteinase inhibitor 2 complex

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| sCr or UO | | | | | | |
| Median | 117 | 411 | 117 | 411 | 117 | 269 |
| Average | 756 | 2460 | 756 | 2460 | 756 | 685 |
| Stdev | 2540 | 5500 | 2540 | 5500 | 2540 | 961 |
| p (t-test) |  | 0.17 |  | 0.17 |  | 0.96 |
| Min | 1.15 | 1.15 | 1.15 | 1.15 | 1.15 | 1.15 |
| Max | 16000 | 16000 | 16000 | 16000 | 16000 | 1780 |
| n (Samp) | 40 | 8 | 40 | 8 | 40 | 3 |
| n (Patient) | 40 | 8 | 40 | 8 | 40 | 3 |
| sCr only | | | | | | |
| Median | 110 | 398 | 110 | 398 | nd | nd |
| Average | 889 | 402 | 889 | 402 | nd | nd |
| Stdev | 2800 | 219 | 2800 | 219 | nd | nd |
| p (t-test) |  | 0.73 |  | 0.73 | nd | nd |
| Min | 1.15 | 171 | 1.15 | 171 | nd | nd |
| Max | 16000 | 642 | 16000 | 642 | nd | nd |
| n (Samp) | 72 | 4 | 72 | 4 | nd | nd |
| n (Patient) | 72 | 4 | 72 | 4 | nd | nd |
| UO only | | | | | | |
| Median | 57.4 | 295 | 57.4 | 295 | 57.4 | 269 |
| Average | 772 | 3670 | 772 | 3670 | 772 | 685 |
| Stdev | 2710 | 6930 | 2710 | 6930 | 2710 | 961 |
| p (t-test) |  | 0.083 |  | 0.083 |  | 0.96 |
| Min | 1.15 | 1.15 | 1.15 | 1.15 | 1.15 | 1.15 |
| Max | 16000 | 16000 | 16000 | 16000 | 16000 | 1780 |
| n (Samp) | 35 | 5 | 35 | 5 | 35 | 3 |
| n (Patient) | 35 | 5 | 35 | 5 | 35 | 3 |

|  | 0 hr prior to AKI stage | | | 24 hr prior to AKI stage | | | 48 hr prior to AKI stage | | |
|---|---|---|---|---|---|---|---|---|---|
|  | sCr or UO | sCr only | UO only | sCr or UO | sCr only | UO only | sCr or UO | sCr only | UO only |
| AUC | 0.68 | 0.69 | 0.68 | 0.68 | 0.69 | 0.68 | 0.56 | nd | 0.57 |
| SE | 0.11 | 0.15 | 0.14 | 0.11 | 0.15 | 0.14 | 0.18 | nd | 0.18 |
| p | 0.099 | 0.21 | 0.21 | 0.099 | 0.21 | 0.21 | 0.73 | nd | 0.69 |
| nCohort 1 | 40 | 72 | 35 | 40 | 72 | 35 | 40 | nd | 35 |
| nCohort 2 | 8 | 4 | 5 | 8 | 4 | 5 | 3 | nd | 3 |
| Cutoff 1 | 234 | 234 | 234 | 234 | 234 | 234 | 0 | nd | 0 |
| Sens 1 | 75% | 75% | 80% | 75% | 75% | 80% | 100% | nd | 100% |
| Spec 1 | 68% | 64% | 69% | 68% | 64% | 69% | 0% | nd | 0% |
| Cutoff 2 | 164 | 164 | 234 | 164 | 164 | 234 | 0 | nd | 0 |
| Sens 2 | 88% | 100% | 80% | 88% | 100% | 80% | 100% | nd | 100% |
| Spec 2 | 57% | 57% | 69% | 57% | 57% | 69% | 0% | nd | 0% |
| Cutoff 3 | 0 | 164 | 0 | 0 | 164 | 0 | 0 | nd | 0 |
| Sens 3 | 100% | 100% | 100% | 100% | 100% | 100% | 100% | nd | 100% |
| Spec 3 | 0% | 57% | 0% | 0% | 57% | 0% | 0% | nd | 0% |
| Cutoff 4 | 398 | 419 | 398 | 398 | 419 | 398 | 398 | nd | 398 |
| Sens 4 | 50% | 50% | 40% | 50% | 50% | 40% | 33% | nd | 33% |
| Spec 4 | 70% | 71% | 71% | 70% | 71% | 71% | 70% | nd | 71% |
| Cutoff 5 | 615 | 656 | 579 | 615 | 656 | 579 | 615 | nd | 579 |
| Sens 5 | 38% | 0% | 40% | 38% | 0% | 40% | 33% | nd | 33% |
| Spec 5 | 80% | 81% | 80% | 80% | 81% | 80% | 80% | nd | 80% |
| Cutoff 6 | 1230 | 1380 | 1230 | 1230 | 1380 | 1230 | 1230 | nd | 1230 |
| Sens 6 | 25% | 0% | 40% | 25% | 0% | 40% | 33% | nd | 33% |
| Spec 6 | 90% | 90% | 91% | 90% | 90% | 91% | 90% | nd | 91% |
| OR Quart 2 | 0 | >0 | 0 | 0 | >0 | 0 | 0 | nd | 0 |
| p Value | na | <na | na | na | <na | na | na | nd | na |
| 95% CI of | na | >na | na | na | >na | na | na | nd | na |
| OR Quart 2 | na | na | na | na | na | na | na | nd | na |
| OR Quart 3 | 5.5 | >3.6 | 2.2 | 5.5 | >3.6 | 2.2 | 0.90 | nd | 1.0 |
| p Value | 0.16 | <0.29 | 0.54 | 0.16 | <0.29 | 0.54 | 0.94 | nd | 1.0 |
| 95% CI of | 0.51 | >0.34 | 0.17 | 0.51 | >0.34 | 0.17 | 0.049 | nd | 0.053 |
| OR Quart 3 | 59 | na | 30 | 59 | na | 30 | 17 | nd | 19 |
| OR Quart 4 | 3.7 | >1.1 | 2.2 | 3.7 | >1.1 | 2.2 | 0.90 | nd | 0.89 |
| p Value | 0.29 | <0.97 | 0.54 | 0.29 | <0.97 | 0.54 | 0.94 | nd | 0.94 |

TABLE 4-continued

Comparison of the maximum marker levels in urine samples collected from Cohort 1 (patients that did not progress beyond RIFLE stage 0) and the maximum values in urine samples collected from subjects between enrollment and 0, 24 hours, and 48 hours prior to reaching stage F in Cohort 2.

| 95% CI of | 0.32 | >0.061 | 0.17 | 0.32 | >0.061 | 0.17 | 0.049 | nd | 0.047 |
|---|---|---|---|---|---|---|---|---|---|
| OR Quart 4 | 42 | na | 30 | 42 | na | 30 | 17 | nd | 17 |

Neural cell adhesion molecule 1

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| sCr or UO | | | | | | |
| Median | 2820 | 4940 | 2820 | 4490 | 2820 | 3900 |
| Average | 3370 | 6950 | 3370 | 6450 | 3370 | 4660 |
| Stdev | 2580 | 9680 | 2580 | 9690 | 2580 | 2330 |
| p (t-test) | | 1.0E−5 | | 1.4E−4 | | 0.053 |
| Min | 6.83 | 171 | 6.83 | 171 | 6.83 | 1650 |
| Max | 22000 | 55700 | 22000 | 55700 | 22000 | 9700 |
| n (Samp) | 223 | 30 | 223 | 30 | 223 | 16 |
| n (Patient) | 223 | 30 | 223 | 30 | 223 | 16 |
| sCr only | | | | | | |
| Median | 3740 | 4080 | 3740 | 4080 | 3740 | 5050 |
| Average | 4470 | 4560 | 4470 | 4510 | 4470 | 5290 |
| Stdev | 4470 | 2180 | 4470 | 2210 | 4470 | 1870 |
| p (t-test) | | 0.95 | | 0.97 | | 0.63 |
| Min | 6.83 | 171 | 6.83 | 171 | 6.83 | 3280 |
| Max | 55700 | 7860 | 55700 | 7860 | 55700 | 7860 |
| n (Samp) | 374 | 13 | 374 | 13 | 374 | 7 |
| n (Patient) | 374 | 13 | 374 | 13 | 374 | 7 |
| UO only | | | | | | |
| Median | 3220 | 5250 | 3220 | 5050 | 3220 | 4490 |
| Average | 3650 | 8910 | 3650 | 8250 | 3650 | 4750 |
| Stdev | 2320 | 11500 | 2320 | 11500 | 2320 | 2360 |
| p (t-test) | | 2.8E−7 | | 6.5E−6 | | 0.090 |
| Min | 485 | 1700 | 485 | 1120 | 485 | 1650 |
| Max | 11700 | 55700 | 11700 | 55700 | 11700 | 9700 |
| n (Samp) | 172 | 23 | 172 | 23 | 172 | 14 |
| n (Patient) | 172 | 23 | 172 | 23 | 172 | 14 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.73 | 0.58 | 0.75 | 0.68 | 0.57 | 0.69 | 0.69 | 0.67 | 0.65 |
| SE | 0.054 | 0.084 | 0.061 | 0.056 | 0.084 | 0.064 | 0.076 | 0.11 | 0.082 |
| p | 1.9E−5 | 0.34 | 3.2E−5 | 0.0016 | 0.38 | 0.0035 | 0.013 | 0.13 | 0.074 |
| nCohort 1 | 223 | 374 | 172 | 223 | 374 | 172 | 223 | 374 | 172 |
| nCohort 2 | 30 | 13 | 23 | 30 | 13 | 23 | 16 | 7 | 14 |
| Cutoff 1 | 3720 | 3410 | 3960 | 3110 | 3250 | 3110 | 3250 | 3970 | 3280 |
| Sens 1 | 70% | 77% | 74% | 70% | 77% | 74% | 75% | 71% | 71% |
| Spec 1 | 65% | 46% | 65% | 57% | 44% | 49% | 59% | 56% | 52% |
| Cutoff 2 | 3250 | 3250 | 3280 | 2440 | 2870 | 2460 | 3110 | 3720 | 2690 |
| Sens 2 | 80% | 85% | 83% | 80% | 85% | 83% | 81% | 86% | 86% |
| Spec 2 | 59% | 44% | 52% | 43% | 37% | 39% | 57% | 50% | 43% |
| Cutoff 3 | 2210 | 2200 | 2690 | 1740 | 2200 | 1740 | 1700 | 3250 | 1700 |
| Sens 3 | 90% | 92% | 91% | 90% | 92% | 91% | 94% | 100% | 93% |
| Spec 3 | 41% | 27% | 43% | 27% | 27% | 22% | 26% | 44% | 21% |
| Cutoff 4 | 3940 | 5270 | 4360 | 3940 | 5270 | 4360 | 3940 | 5270 | 4360 |
| Sens 4 | 63% | 31% | 65% | 57% | 31% | 61% | 50% | 29% | 50% |
| Spec 4 | 70% | 70% | 70% | 70% | 70% | 70% | 70% | 70% | 70% |
| Cutoff 5 | 4960 | 6450 | 5580 | 4960 | 6450 | 5580 | 4960 | 6450 | 5580 |
| Sens 5 | 50% | 23% | 48% | 47% | 23% | 43% | 38% | 29% | 36% |
| Spec 5 | 80% | 80% | 80% | 80% | 80% | 80% | 80% | 80% | 80% |
| Cutoff 6 | 6160 | 7760 | 6670 | 6160 | 7760 | 6670 | 6160 | 7760 | 6670 |
| Sens 6 | 33% | 15% | 35% | 30% | 15% | 35% | 25% | 29% | 21% |
| Spec 6 | 90% | 90% | 90% | 90% | 90% | 90% | 90% | 90% | 90% |
| OR Quart 2 | 1.5 | 4.1 | 4.2 | 2.1 | 4.1 | 1.3 | 2.0 | >2.0 | 0.98 |
| p Value | 0.65 | 0.21 | 0.21 | 0.31 | 0.21 | 0.72 | 0.58 | <0.56 | 0.98 |
| 95% CI of | 0.25 | 0.45 | 0.45 | 0.50 | 0.45 | 0.28 | 0.18 | >0.18 | 0.13 |
| OR Quart 2 | 9.5 | 37 | 39 | 8.8 | 37 | 6.3 | 23 | na | 7.3 |
| OR Quart 3 | 5.1 | 5.2 | 7.8 | 2.1 | 5.2 | 2.1 | 6.4 | >3.1 | 2.7 |
| p Value | 0.043 | 0.14 | 0.059 | 0.31 | 0.14 | 0.32 | 0.089 | <0.33 | 0.25 |
| 95% CI of | 1.1 | 0.59 | 0.93 | 0.50 | 0.59 | 0.49 | 0.75 | >0.32 | 0.49 |

TABLE 4-continued

Comparison of the maximum marker levels in urine samples collected from Cohort 1 (patients that did not progress beyond RIFLE stage 0) and the maximum values in urine samples collected from subjects between enrollment and 0, 24 hours, and 48 hours prior to reaching stage F in Cohort 2.

| | | | | | | | | | |
|---|---|---|---|---|---|---|---|---|---|
| OR Quart 3 | 25 | 45 | 66 | 8.8 | 45 | 8.9 | 55 | na | 15 |
| OR Quart 4 | 10 | 3.0 | 14 | 6.1 | 3.0 | 3.8 | 7.7 | >2.0 | 2.6 |
| p Value | 0.0027 | 0.34 | 0.014 | 0.0061 | 0.34 | 0.052 | 0.061 | <0.57 | 0.27 |
| 95% CI of | 2.2 | 0.31 | 1.7 | 1.7 | 0.31 | 0.99 | 0.91 | >0.18 | 0.48 |
| OR Quart 4 | 46 | 30 | 110 | 22 | 30 | 15 | 64 | na | 14 |

Tumor necrosis factor ligand superfamily member 10

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| sCr or UO | | | | | | |
| Median | 0.0363 | 0.348 | 0.0363 | 0.338 | 0.0363 | 0.336 |
| Average | 4.58 | 11.4 | 4.58 | 10.8 | 4.58 | 1.86 |
| Stdev | 13.0 | 31.2 | 13.0 | 31.3 | 13.0 | 2.64 |
| p (t-test) | | 0.032 | | 0.048 | | 0.40 |
| Min | 0.0110 | 0.0159 | 0.0110 | 0.0159 | 0.0110 | 0.0159 |
| Max | 92.3 | 134 | 92.3 | 134 | 92.3 | 8.63 |
| n (Samp) | 222 | 30 | 222 | 30 | 222 | 16 |
| n (Patient) | 222 | 30 | 222 | 30 | 222 | 16 |
| sCr only | | | | | | |
| Median | 0.0410 | 0.0597 | 0.0410 | 0.0410 | 0.0410 | 0.636 |
| Average | 5.75 | 2.45 | 5.75 | 2.45 | 5.75 | 2.67 |
| Stdev | 16.4 | 3.54 | 16.4 | 3.54 | 16.4 | 3.52 |
| p (t-test) | | 0.47 | | 0.47 | | 0.62 |
| Min | 0.0110 | 0.0159 | 0.0110 | 0.0159 | 0.0110 | 0.0159 |
| Max | 159 | 9.58 | 159 | 9.58 | 159 | 8.63 |
| n (Samp) | 379 | 13 | 379 | 13 | 379 | 7 |
| n (Patient) | 379 | 13 | 379 | 13 | 379 | 7 |
| UO only | | | | | | |
| Median | 0.0439 | 1.51 | 0.0439 | 0.670 | 0.0439 | 0.336 |
| Average | 5.67 | 17.5 | 5.67 | 13.4 | 5.67 | 1.74 |
| Stdev | 15.3 | 37.7 | 15.3 | 35.4 | 15.3 | 2.70 |
| p (t-test) | | 0.0059 | | 0.064 | | 0.34 |
| Min | 0.0110 | 0.0217 | 0.0110 | 0.0217 | 0.0110 | 0.0239 |
| Max | 92.3 | 134 | 92.3 | 134 | 92.3 | 9.58 |
| n (Samp) | 175 | 23 | 175 | 23 | 175 | 14 |
| n (Patient) | 175 | 23 | 175 | 23 | 175 | 14 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.63 | 0.55 | 0.63 | 0.61 | 0.52 | 0.61 | 0.59 | 0.56 | 0.56 |
| SE | 0.057 | 0.084 | 0.066 | 0.058 | 0.082 | 0.066 | 0.077 | 0.11 | 0.082 |
| p | 0.020 | 0.51 | 0.050 | 0.047 | 0.84 | 0.10 | 0.24 | 0.60 | 0.49 |
| nCohort 1 | 222 | 379 | 175 | 222 | 379 | 175 | 222 | 379 | 175 |
| nCohort 2 | 30 | 13 | 23 | 30 | 13 | 23 | 16 | 7 | 14 |
| Cutoff 1 | 0.0335 | 0.0257 | 0.0335 | 0.0285 | 0.0239 | 0.0335 | 0.0285 | 0.0392 | 0.0335 |
| Sens 1 | 70% | 77% | 74% | 70% | 85% | 74% | 75% | 71% | 71% |
| Spec 1 | 48% | 31% | 39% | 41% | 27% | 39% | 41% | 49% | 39% |
| Cutoff 2 | 0.0257 | 0.0239 | 0.0285 | 0.0239 | 0.0239 | 0.0285 | 0.0247 | 0.0217 | 0.0247 |
| Sens 2 | 80% | 85% | 83% | 80% | 85% | 83% | 81% | 86% | 86% |
| Spec 2 | 39% | 27% | 34% | 39% | 27% | 34% | 39% | 20% | 30% |
| Cutoff 3 | 0.0239 | 0.0217 | 0.0239 | 0.0239 | 0.0217 | 0.0239 | 0.0237 | 0.0147 | 0.0239 |
| Sens 3 | 90% | 92% | 91% | 90% | 92% | 91% | 94% | 100% | 93% |
| Spec 3 | 38% | 20% | 30% | 38% | 20% | 30% | 38% | 8% | 30% |
| Cutoff 4 | 0.775 | 1.53 | 1.42 | 0.775 | 1.53 | 1.42 | 0.775 | 1.53 | 1.42 |
| Sens 4 | 47% | 38% | 52% | 47% | 38% | 43% | 44% | 43% | 36% |
| Spec 4 | 70% | 70% | 70% | 70% | 70% | 70% | 70% | 70% | 70% |
| Cutoff 5 | 4.08 | 5.16 | 4.69 | 4.08 | 5.16 | 4.69 | 4.08 | 5.16 | 4.69 |
| Sens 5 | 27% | 23% | 30% | 23% | 23% | 22% | 12% | 29% | 7% |
| Spec 5 | 80% | 80% | 80% | 80% | 80% | 80% | 80% | 80% | 80% |
| Cutoff 6 | 11.8 | 16.4 | 15.0 | 11.8 | 16.4 | 15.0 | 11.8 | 16.4 | 15.0 |
| Sens 6 | 13% | 0% | 22% | 10% | 0% | 13% | 0% | 0% | 0% |
| Spec 6 | 90% | 90% | 90% | 90% | 90% | 90% | 90% | 90% | 90% |
| OR Quart 2 | 12 | 1.5 | 4.5 | 6.5 | 2.0 | 4.5 | 4.1 | 0 | >8.2 |
| p Value | 0.021 | 0.65 | 0.067 | 0.019 | 0.42 | 0.067 | 0.21 | na | <0.053 |
| 95% CI of | 1.4 | 0.25 | 0.90 | 1.4 | 0.37 | 0.90 | 0.45 | na | >0.97 |
| OR Quart 2 | 94 | 9.3 | 22 | 30 | 11 | 22 | 38 | na | na |

TABLE 4-continued

Comparison of the maximum marker levels in urine samples collected from Cohort 1 (patients that did not progress beyond RIFLE stage 0) and the maximum values in urine samples collected from subjects between enrollment and 0, 24 hours, and 48 hours prior to reaching stage F in Cohort 2.

| OR Quart 3 | 7.8 | 2.0 | 2.1 | 3.2 | 1.5 | 3.3 | 5.4 | 1.5 | >3.2 |
|---|---|---|---|---|---|---|---|---|---|
| p Value | 0.059 | 0.42 | 0.41 | 0.16 | 0.65 | 0.16 | 0.13 | 0.65 | <0.32 |
| 95% CI of | 0.92 | 0.37 | 0.36 | 0.62 | 0.25 | 0.63 | 0.61 | 0.25 | >0.32 |
| OR Quart 3 | 65 | 11 | 12 | 17 | 9.3 | 17 | 47 | 9.3 | na |
| OR Quart 4 | 15 | 2.0 | 5.2 | 6.5 | 2.0 | 3.8 | 6.4 | 0.99 | >4.3 |
| p Value | 0.011 | 0.42 | 0.043 | 0.019 | 0.42 | 0.11 | 0.089 | 0.99 | <0.20 |
| 95% CI of | 1.8 | 0.37 | 1.1 | 1.4 | 0.37 | 0.75 | 0.75 | 0.14 | >0.46 |
| OR Quart 4 | 120 | 11 | 25 | 30 | 11 | 19 | 55 | 7.2 | na |

TABLE 5

Comparison of marker levels in EDTA samples collected from Cohort 1 (patients that did not progress beyond RIFLE stage 0) and in EDTA samples collected from subjects at 0, 24 hours, and 48 hours prior to reaching stage R, I or F in Cohort 2.

Heat shock 70 kDa protein 1

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| sCr or UO | | | | | | |
| Median | 641 | 1370 | 641 | 1200 | 641 | 2350 |
| Average | 1400 | 2760 | 1400 | 1990 | 1400 | 2240 |
| Stdev | 2010 | 3320 | 2010 | 2130 | 2010 | 2100 |
| p (t-test) | | 0.057 | | 0.25 | | 0.26 |
| Min | 0.288 | 0.288 | 0.288 | 128 | 0.288 | 54.3 |
| Max | 10000 | 10700 | 10000 | 9450 | 10000 | 6660 |
| n (Samp) | 54 | 14 | 54 | 24 | 54 | 9 |
| n (Patient) | 53 | 14 | 53 | 24 | 53 | 9 |
| sCr only | | | | | | |
| Median | 840 | 1950 | 840 | 1240 | 840 | 1720 |
| Average | 1580 | 2450 | 1580 | 1240 | 1580 | 1470 |
| Stdev | 2190 | 1690 | 2190 | 1030 | 2190 | 1030 |
| p (t-test) | | 0.50 | | 0.83 | | 0.93 |
| Min | 0.288 | 1070 | 0.288 | 514 | 0.288 | 340 |
| Max | 10700 | 4330 | 10700 | 1970 | 10700 | 2350 |
| n (Samp) | 111 | 3 | 111 | 2 | 111 | 3 |
| n (Patient) | 93 | 3 | 93 | 2 | 93 | 3 |
| UO only | | | | | | |
| Median | 641 | 1370 | 641 | 1220 | 641 | 963 |
| Average | 1390 | 2740 | 1390 | 2040 | 1390 | 2010 |
| Stdev | 1860 | 3550 | 1860 | 2110 | 1860 | 2200 |
| p (t-test) | | 0.073 | | 0.18 | | 0.38 |
| Min | 0.288 | 0.288 | 0.288 | 128 | 0.288 | 54.3 |
| Max | 10000 | 10700 | 10000 | 9450 | 10000 | 6660 |
| n (Samp) | 48 | 12 | 48 | 25 | 48 | 9 |
| n (Patient) | 44 | 12 | 44 | 25 | 44 | 9 |

|  | 0 hr prior to AKI stage | | | 24 hr prior to AKI stage | | | 48 hr prior to AKI stage | | |
|---|---|---|---|---|---|---|---|---|---|
|  | sCr or UO | sCr only | UO only | sCr or UO | sCr only | UO only | sCr or UO | sCr only | UO only |
| AUC | 0.61 | 0.75 | 0.58 | 0.66 | 0.59 | 0.66 | 0.65 | 0.62 | 0.59 |
| SE | 0.088 | 0.17 | 0.095 | 0.070 | 0.21 | 0.070 | 0.11 | 0.18 | 0.11 |
| p | 0.21 | 0.13 | 0.43 | 0.023 | 0.69 | 0.025 | 0.16 | 0.49 | 0.39 |
| nCohort 1 | 54 | 111 | 48 | 54 | 111 | 48 | 54 | 111 | 48 |
| nCohort 2 | 14 | 3 | 12 | 24 | 2 | 25 | 9 | 3 | 9 |
| Cutoff 1 | 705 | 1000 | 387 | 837 | 507 | 837 | 500 | 336 | 310 |
| Sens 1 | 71% | 100% | 75% | 71% | 100% | 72% | 78% | 100% | 78% |
| Spec 1 | 54% | 56% | 42% | 56% | 41% | 54% | 44% | 31% | 38% |
| Cutoff 2 | 0.288 | 1000 | 0.288 | 514 | 507 | 664 | 310 | 336 | 248 |
| Sens 2 | 86% | 100% | 83% | 83% | 100% | 80% | 89% | 100% | 89% |
| Spec 2 | 4% | 56% | 4% | 46% | 41% | 52% | 37% | 31% | 29% |
| Cutoff 3 | 0 | 1000 | 0 | 310 | 507 | 310 | 48.9 | 336 | 48.9 |
| Sens 3 | 100% | 100% | 100% | 92% | 100% | 92% | 100% | 100% | 100% |
| Spec 3 | 0% | 56% | 0% | 37% | 41% | 38% | 11% | 31% | 12% |
| Cutoff 4 | 1370 | 1500 | 1500 | 1370 | 1500 | 1500 | 1370 | 1500 | 1500 |
| Sens 4 | 50% | 67% | 42% | 46% | 50% | 48% | 56% | 67% | 44% |

TABLE 5-continued

Comparison of marker levels in EDTA samples collected from
Cohort 1 (patients that did not progress beyond RIFLE stage 0) and in EDTA samples
collected from subjects at 0, 24 hours, and 48 hours prior to reaching stage R, I or F in Cohort 2.

| | | | | | | | | | |
|---|---|---|---|---|---|---|---|---|---|
| Spec 4 | 70% | 70% | 71% | 70% | 70% | 71% | 70% | 70% | 71% |
| Cutoff 5 | 2700 | 2550 | 2700 | 2700 | 2550 | 2700 | 2700 | 2550 | 2700 |
| Sens 5 | 36% | 33% | 33% | 21% | 0% | 24% | 33% | 0% | 33% |
| Spec 5 | 81% | 80% | 81% | 81% | 80% | 81% | 81% | 80% | 81% |
| Cutoff 6 | 3540 | 3540 | 3630 | 3540 | 3540 | 3630 | 3540 | 3540 | 3630 |
| Sens 6 | 29% | 33% | 25% | 12% | 0% | 12% | 11% | 0% | 11% |
| Spec 6 | 91% | 90% | 92% | 91% | 90% | 92% | 91% | 90% | 92% |
| OR Quart 2 | 0.62 | >0 | 0.62 | 3.6 | >1.0 | 5.1 | 2.0 | >1.0 | 3.5 |
| p Value | 0.63 | <na | 0.63 | 0.15 | <0.98 | 0.068 | 0.59 | <1.0 | 0.30 |
| 95% CI of | 0.090 | >na | 0.087 | 0.63 | >0.062 | 0.89 | 0.16 | >0.060 | 0.32 |
| OR Quart 2 | 4.3 | na | 4.3 | 21 | na | 29 | 25 | na | 39 |
| OR Quart 3 | 1.0 | >1.0 | 1.0 | 5.0 | >0 | 6.4 | 0.93 | >0 | 1.0 |
| p Value | 1.0 | <0.98 | 1.0 | 0.071 | <na | 0.036 | 0.96 | <na | 1.0 |
| 95% CI of | 0.17 | >0.062 | 0.17 | 0.87 | >na | 1.1 | 0.053 | >na | 0.056 |
| OR Quart 3 | 5.8 | na | 6.0 | 28 | na | 36 | 16 | na | 18 |
| OR Quart 4 | 2.5 | >2.1 | 1.5 | 7.0 | >1.0 | 5.8 | 6.4 | >2.1 | 4.7 |
| p Value | 0.25 | <0.56 | 0.67 | 0.026 | <1.0 | 0.046 | 0.11 | <0.56 | 0.19 |
| 95% CI of | 0.52 | >0.18 | 0.26 | 1.3 | >0.060 | 1.0 | 0.65 | >0.18 | 0.46 |
| OR Quart 4 | 13 | na | 8.0 | 38 | na | 33 | 63 | na | 49 |

Insulin-like growth factor 1 receptor

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| sCr or UO | | | | | | |
| Median | 0.0498 | 0.0502 | 0.0498 | 0.0556 | 0.0498 | 0.0331 |
| Average | 0.207 | 0.622 | 0.207 | 0.470 | 0.207 | 0.899 |
| Stdev | 0.797 | 3.22 | 0.797 | 2.43 | 0.797 | 4.04 |
| p (t-test) | | 0.28 | | 0.38 | | 0.15 |
| Min | 9.84E-5 | 0.000208 | 9.84E-5 | 0.000211 | 9.84E-5 | 0.000208 |
| Max | 6.23 | 18.2 | 6.23 | 14.8 | 6.23 | 19.4 |
| n (Samp) | 79 | 32 | 79 | 37 | 79 | 23 |
| n (Patient) | 70 | 32 | 70 | 37 | 70 | 23 |
| sCr only | | | | | | |
| Median | 0.0498 | 0.0255 | 0.0498 | 0.0595 | 0.0498 | 0.0398 |
| Average | 0.124 | 2.30 | 0.124 | 1.92 | 0.124 | 2.20 |
| Stdev | 0.523 | 6.44 | 0.523 | 5.22 | 0.523 | 6.46 |
| p (t-test) | | 1.0E-5 | | 1.4E-5 | | 2.5E-5 |
| Min | 9.84E-5 | 0.000208 | 9.84E-5 | 0.000211 | 9.84E-5 | 0.0214 |
| Max | 6.23 | 18.2 | 6.23 | 14.8 | 6.23 | 19.4 |
| n (Samp) | 187 | 8 | 187 | 8 | 187 | 9 |
| n (Patient) | 126 | 8 | 126 | 8 | 126 | 9 |
| UO only | | | | | | |
| Median | 0.0498 | 0.0572 | 0.0498 | 0.0556 | 0.0498 | 0.0354 |
| Average | 0.233 | 0.808 | 0.233 | 0.589 | 0.233 | 0.0641 |
| Stdev | 0.851 | 3.96 | 0.851 | 3.27 | 0.851 | 0.126 |
| p (t-test) | | 0.25 | | 0.39 | | 0.42 |
| Min | 0.000208 | 0.000208 | 0.000208 | 0.000211 | 0.000208 | 0.000208 |
| Max | 6.23 | 21.0 | 6.23 | 20.5 | 6.23 | 0.543 |
| n (Samp) | 69 | 28 | 69 | 39 | 69 | 17 |
| n (Patient) | 57 | 28 | 57 | 39 | 57 | 17 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.48 | 0.34 | 0.51 | 0.55 | 0.50 | 0.55 | 0.40 | 0.49 | 0.38 |
| SE | 0.061 | 0.11 | 0.065 | 0.058 | 0.10 | 0.058 | 0.070 | 0.099 | 0.080 |
| p | 0.72 | 0.14 | 0.82 | 0.37 | 0.98 | 0.35 | 0.17 | 0.93 | 0.14 |
| nCohort 1 | 79 | 187 | 69 | 79 | 187 | 69 | 79 | 187 | 69 |
| nCohort 2 | 32 | 8 | 28 | 37 | 8 | 39 | 23 | 9 | 17 |
| Cutoff 1 | 0.0219 | 0.0137 | 0.0398 | 0.0373 | 0.00497 | 0.0373 | 0.0212 | 0.0283 | 0.0212 |
| Sens 1 | 72% | 75% | 71% | 73% | 75% | 74% | 83% | 78% | 76% |
| Spec 1 | 28% | 14% | 46% | 43% | 9% | 43% | 24% | 28% | 23% |
| Cutoff 2 | 0.0178 | 0.000208 | 0.0212 | 0.0251 | 0.000211 | 0.0325 | 0.0212 | 0.0219 | 0.000224 |
| Sens 2 | 81% | 88% | 82% | 81% | 88% | 82% | 83% | 89% | 82% |
| Spec 2 | 20% | 3% | 23% | 28% | 5% | 39% | 24% | 23% | 7% |
| Cutoff 3 | 0.0134 | 0.000172 | 0.0134 | 0.00497 | 0.000208 | 0.0178 | 0.000208 | 0.0212 | 0.000208 |
| Sens 3 | 91% | 100% | 93% | 92% | 100% | 92% | 96% | 100% | 94% |
| Spec 3 | 16% | 1% | 14% | 10% | 3% | 22% | 3% | 18% | 3% |
| Cutoff 4 | 0.0839 | 0.0729 | 0.0839 | 0.0839 | 0.0729 | 0.0839 | 0.0839 | 0.0729 | 0.0839 |

TABLE 5-continued

Comparison of marker levels in EDTA samples collected from
Cohort 1 (patients that did not progress beyond RIFLE stage 0) and in EDTA samples
collected from subjects at 0, 24 hours, and 48 hours prior to reaching stage R, I or F in Cohort 2.

| Sens 4 | 16% | 12% | 21% | 27% | 25% | 26% | 9% | 33% | 6% |
|---|---|---|---|---|---|---|---|---|---|
| Spec 4 | 73% | 70% | 72% | 73% | 70% | 72% | 73% | 70% | 72% |
| Cutoff 5 | 0.0986 | 0.0876 | 0.101 | 0.0986 | 0.0876 | 0.101 | 0.0986 | 0.0876 | 0.101 |
| Sens 5 | 12% | 12% | 14% | 24% | 25% | 21% | 9% | 22% | 6% |
| Spec 5 | 81% | 80% | 81% | 81% | 80% | 81% | 81% | 80% | 81% |
| Cutoff 6 | 0.135 | 0.133 | 0.176 | 0.135 | 0.133 | 0.176 | 0.135 | 0.133 | 0.176 |
| Sens 6 | 12% | 12% | 7% | 14% | 25% | 5% | 9% | 11% | 6% |
| Spec 6 | 91% | 90% | 91% | 91% | 90% | 91% | 91% | 90% | 91% |
| OR Quart 2 | 2.0 | 1.0 | 1.0 | 1.4 | 0 | 2.1 | 3.8 | 0.49 | 8.4 |
| p Value | 0.24 | 1.0 | 1.0 | 0.56 | na | 0.24 | 0.13 | 0.57 | 0.060 |
| 95% CI of | 0.62 | 0.061 | 0.27 | 0.44 | na | 0.62 | 0.69 | 0.043 | 0.91 |
| OR Quart 2 | 6.7 | 16 | 3.7 | 4.5 | na | 6.8 | 21 | 5.6 | 77 |
| OR Quart 3 | 1.5 | 2.0 | 2.1 | 1.9 | 0.98 | 3.2 | 6.4 | 2.1 | 6.2 |
| p Value | 0.54 | 0.57 | 0.22 | 0.26 | 0.98 | 0.050 | 0.028 | 0.41 | 0.11 |
| 95% CI of | 0.43 | 0.18 | 0.63 | 0.62 | 0.19 | 1.00 | 1.2 | 0.36 | 0.66 |
| OR Quart 3 | 5.0 | 23 | 7.3 | 6.0 | 5.1 | 11 | 33 | 12 | 58 |
| OR Quart 4 | 1.5 | 4.4 | 0.95 | 1.7 | 0.64 | 2.1 | 3.8 | 1.0 | 6.6 |
| p Value | 0.49 | 0.20 | 0.94 | 0.39 | 0.63 | 0.24 | 0.13 | 1.0 | 0.10 |
| 95% CI of | 0.45 | 0.47 | 0.26 | 0.53 | 0.10 | 0.62 | 0.69 | 0.14 | 0.70 |
| OR Quart 4 | 5.2 | 41 | 3.5 | 5.2 | 4.0 | 6.8 | 21 | 7.4 | 62 |

Neural cell adhesion molecule 1

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| sCr or UO | | | | | | |
| Median | 183000 | 192000 | 183000 | 180000 | 183000 | 172000 |
| Average | 191000 | 193000 | 191000 | 185000 | 191000 | 179000 |
| Stdev | 79300 | 67000 | 79300 | 78800 | 79300 | 59800 |
| p (t-test) | | 0.83 | | 0.64 | | 0.48 |
| Min | 1370 | 63300 | 1370 | 190 | 1370 | 49200 |
| Max | 520000 | 371000 | 520000 | 506000 | 520000 | 297000 |
| n (Samp) | 122 | 52 | 122 | 55 | 122 | 25 |
| n (Patient) | 88 | 52 | 88 | 55 | 88 | 25 |
| sCr only | | | | | | |
| Median | 181000 | 199000 | 181000 | 210000 | 181000 | 179000 |
| Average | 184000 | 200000 | 184000 | 227000 | 184000 | 180000 |
| Stdev | 70200 | 62800 | 70200 | 97800 | 70200 | 54800 |
| p (t-test) | | 0.38 | | 0.030 | | 0.87 |
| Min | 190 | 118000 | 190 | 129000 | 190 | 108000 |
| Max | 520000 | 316000 | 520000 | 506000 | 520000 | 280000 |
| n (Samp) | 291 | 16 | 291 | 14 | 291 | 9 |
| n (Patient) | 164 | 16 | 164 | 14 | 164 | 9 |
| UO only | | | | | | |
| Median | 180000 | 182000 | 180000 | 180000 | 180000 | 172000 |
| Average | 189000 | 187000 | 189000 | 176000 | 189000 | 178000 |
| Stdev | 81700 | 69000 | 81700 | 63300 | 81700 | 59400 |
| p (t-test) | | 0.92 | | 0.32 | | 0.57 |
| Min | 1080 | 63300 | 1080 | 190 | 1080 | 49200 |
| Max | 520000 | 371000 | 520000 | 337000 | 520000 | 297000 |
| n (Samp) | 124 | 43 | 124 | 57 | 124 | 23 |
| n (Patient) | 81 | 43 | 81 | 57 | 81 | 23 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.53 | 0.58 | 0.50 | 0.48 | 0.64 | 0.48 | 0.48 | 0.49 | 0.49 |
| SE | 0.048 | 0.077 | 0.051 | 0.047 | 0.082 | 0.047 | 0.064 | 0.099 | 0.066 |
| p | 0.59 | 0.30 | 0.98 | 0.72 | 0.098 | 0.63 | 0.71 | 0.90 | 0.84 |
| nCohort 1 | 122 | 291 | 124 | 122 | 291 | 124 | 122 | 291 | 124 |
| nCohort 2 | 52 | 16 | 43 | 55 | 14 | 57 | 25 | 9 | 23 |
| Cutoff 1 | 152000 | 160000 | 141000 | 151000 | 175000 | 144000 | 147000 | 144000 | 147000 |
| Sens 1 | 71% | 75% | 72% | 71% | 71% | 70% | 72% | 78% | 74% |
| Spec 1 | 32% | 37% | 23% | 32% | 46% | 25% | 27% | 26% | 28% |
| Cutoff 2 | 134000 | 125000 | 130000 | 133000 | 164000 | 123000 | 125000 | 115000 | 125000 |
| Sens 2 | 81% | 81% | 81% | 80% | 86% | 81% | 80% | 89% | 83% |
| Spec 2 | 20% | 17% | 19% | 20% | 39% | 12% | 14% | 14% | 15% |
| Cutoff 3 | 106000 | 118000 | 105000 | 107000 | 133000 | 107000 | 115000 | 107000 | 115000 |
| Sens 3 | 90% | 94% | 91% | 91% | 93% | 91% | 92% | 100% | 91% |
| Spec 3 | 9% | 14% | 9% | 10% | 21% | 10% | 11% | 11% | 12% |

TABLE 5-continued

Comparison of marker levels in EDTA samples collected from
Cohort 1 (patients that did not progress beyond RIFLE stage 0) and in EDTA samples
collected from subjects at 0, 24 hours, and 48 hours prior to reaching stage R, I or F in Cohort 2.

| Cutoff 4 | 212000 | 207000 | 209000 | 212000 | 207000 | 209000 | 212000 | 207000 | 209000 |
|---|---|---|---|---|---|---|---|---|---|
| Sens 4 | 31% | 44% | 33% | 29% | 50% | 25% | 32% | 22% | 35% |
| Spec 4 | 70% | 70% | 70% | 70% | 70% | 70% | 70% | 70% | 70% |
| Cutoff 5 | 227000 | 227000 | 228000 | 227000 | 227000 | 228000 | 227000 | 227000 | 228000 |
| Sens 5 | 25% | 38% | 21% | 25% | 43% | 23% | 32% | 22% | 35% |
| Spec 5 | 80% | 80% | 81% | 80% | 80% | 81% | 80% | 80% | 81% |
| Cutoff 6 | 262000 | 262000 | 257000 | 262000 | 262000 | 257000 | 262000 | 262000 | 257000 |
| Sens 6 | 13% | 12% | 14% | 7% | 14% | 9% | 8% | 11% | 9% |
| Spec 6 | 90% | 90% | 90% | 90% | 90% | 90% | 90% | 90% | 90% |
| OR Quart 2 | 0.87 | 0.48 | 0.66 | 0.75 | 2.1 | 1.1 | 0.32 | 1.0 | 0.21 |
| p Value | 0.76 | 0.41 | 0.41 | 0.53 | 0.41 | 0.77 | 0.11 | 1.0 | 0.058 |
| 95% CI of | 0.34 | 0.085 | 0.24 | 0.30 | 0.37 | 0.47 | 0.078 | 0.14 | 0.041 |
| OR Quart 2 | 2.2 | 2.7 | 1.8 | 1.9 | 12 | 2.8 | 1.3 | 7.3 | 1.1 |
| OR Quart 3 | 0.89 | 0.99 | 0.86 | 0.75 | 1.0 | 0.74 | 0.85 | 1.5 | 0.85 |
| p Value | 0.81 | 0.98 | 0.75 | 0.53 | 1.0 | 0.52 | 0.77 | 0.65 | 0.77 |
| 95% CI of | 0.35 | 0.24 | 0.33 | 0.30 | 0.14 | 0.29 | 0.27 | 0.25 | 0.27 |
| OR Quart 3 | 2.3 | 4.1 | 2.2 | 1.9 | 7.3 | 1.9 | 2.6 | 9.4 | 2.6 |
| OR Quart 4 | 1.2 | 1.5 | 0.86 | 1.1 | 3.1 | 1.4 | 0.88 | 1.0 | 0.72 |
| p Value | 0.70 | 0.53 | 0.75 | 0.76 | 0.17 | 0.46 | 0.82 | 1.0 | 0.59 |
| 95% CI of | 0.48 | 0.41 | 0.33 | 0.48 | 0.61 | 0.58 | 0.28 | 0.14 | 0.22 |
| OR Quart 4 | 2.9 | 5.6 | 2.2 | 2.7 | 16 | 3.3 | 2.7 | 7.3 | 2.3 |

Tumor necrosis factor ligand superfamily member 10

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| sCr or UO | | | | | | |
| Median | 0.0228 | 0.0313 | 0.0228 | 0.0239 | 0.0228 | 0.0313 |
| Average | 8.36 | 2.81 | 8.36 | 4.03 | 8.36 | 6.36 |
| Stdev | 43.2 | 6.38 | 43.2 | 9.01 | 43.2 | 14.2 |
| p (t-test) | | 0.40 | | 0.54 | | 0.85 |
| Min | 0.0162 | 0.0162 | 0.0162 | 0.0162 | 0.0162 | 0.0162 |
| Max | 292 | 31.9 | 292 | 35.0 | 292 | 44.8 |
| n (Samp) | 95 | 43 | 95 | 39 | 95 | 17 |
| n (Patient) | 69 | 43 | 69 | 39 | 69 | 17 |
| sCr only | | | | | | |
| Median | 0.0313 | 0.0315 | 0.0313 | 0.0228 | 0.0313 | 4.67 |
| Average | 6.23 | 2.84 | 6.23 | 5.61 | 6.23 | 13.8 |
| Stdev | 29.8 | 9.15 | 29.8 | 11.2 | 29.8 | 18.7 |
| p (t-test) | | 0.70 | | 0.93 | | 0.45 |
| Min | 0.0162 | 0.0162 | 0.0162 | 0.0162 | 0.0162 | 0.0162 |
| Max | 292 | 31.9 | 292 | 35.0 | 292 | 44.8 |
| n (Samp) | 223 | 12 | 223 | 18 | 223 | 9 |
| n (Patient) | 138 | 12 | 138 | 18 | 138 | 9 |
| UO only | | | | | | |
| Median | 0.0313 | 0.0313 | 0.0313 | 0.0313 | 0.0313 | 0.0313 |
| Average | 9.24 | 2.29 | 9.24 | 4.53 | 9.24 | 0.671 |
| Stdev | 42.8 | 4.74 | 42.8 | 16.5 | 42.8 | 2.10 |
| p (t-test) | | 0.32 | | 0.51 | | 0.46 |
| Min | 0.0162 | 0.0162 | 0.0162 | 0.0162 | 0.0162 | 0.0162 |
| Max | 292 | 16.7 | 292 | 98.4 | 292 | 7.88 |
| n (Samp) | 98 | 38 | 98 | 39 | 98 | 14 |
| n (Patient) | 67 | 38 | 67 | 39 | 67 | 14 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.51 | 0.49 | 0.47 | 0.52 | 0.44 | 0.47 | 0.65 | 0.70 | 0.49 |
| SE | 0.053 | 0.086 | 0.056 | 0.055 | 0.073 | 0.055 | 0.077 | 0.099 | 0.083 |
| p | 0.82 | 0.90 | 0.54 | 0.69 | 0.41 | 0.55 | 0.051 | 0.043 | 0.94 |
| nCohort 1 | 95 | 223 | 98 | 95 | 223 | 98 | 95 | 223 | 98 |
| nCohort 2 | 43 | 12 | 38 | 39 | 18 | 39 | 17 | 9 | 14 |
| Cutoff 1 | 0.0162 | 0.0205 | 0.0197 | 0.0197 | 0.0162 | 0.0197 | 0.0247 | 0.0313 | 0.0269 |
| Sens 1 | 81% | 75% | 71% | 79% | 83% | 77% | 88% | 78% | 79% |
| Spec 1 | 15% | 24% | 21% | 25% | 13% | 21% | 53% | 54% | 47% |
| Cutoff 2 | 0.0162 | 0.0162 | 0.0162 | 0.0162 | 0.0162 | 0.0162 | 0.0247 | 0.0205 | 0.0197 |
| Sens 2 | 81% | 83% | 82% | 85% | 83% | 82% | 88% | 89% | 86% |
| Spec 2 | 15% | 13% | 10% | 15% | 13% | 10% | 53% | 24% | 21% |
| Cutoff 3 | 0 | 0 | 0 | 0 | 0 | 0 | 0.0162 | 0 | 0.0162 |
| Sens 3 | 100% | 100% | 100% | 100% | 100% | 100% | 94% | 100% | 93% |

TABLE 5-continued

Comparison of marker levels in EDTA samples collected from
Cohort 1 (patients that did not progress beyond RIFLE stage 0) and in EDTA samples
collected from subjects at 0, 24 hours, and 48 hours prior to reaching stage R, I or F in Cohort 2.

| Spec 3      | 0%     | 0%    | 0%     | 0%     | 0%    | 0%     | 15%    | 0%    | 10%    |
|-------------|--------|-------|--------|--------|-------|--------|--------|-------|--------|
| Cutoff 4    | 0.0317 | 0.171 | 0.0363 | 0.0317 | 0.171 | 0.0363 | 0.0317 | 0.171 | 0.0363 |
| Sens 4      | 30%    | 25%   | 26%    | 28%    | 22%   | 26%    | 41%    | 56%   | 14%    |
| Spec 4      | 73%    | 70%   | 71%    | 73%    | 70%   | 71%    | 73%    | 70%   | 71%    |
| Cutoff 5    | 0.328  | 3.32  | 1.53   | 0.328  | 3.32  | 1.53   | 0.328  | 3.32  | 1.53   |
| Sens 5      | 30%    | 8%    | 21%    | 28%    | 22%   | 21%    | 35%    | 56%   | 7%     |
| Spec 5      | 80%    | 80%   | 81%    | 80%    | 80%   | 81%    | 80%    | 80%   | 81%    |
| Cutoff 6    | 4.64   | 10.8  | 7.32   | 4.64   | 10.8  | 7.32   | 4.64   | 10.8  | 7.32   |
| Sens 6      | 19%    | 8%    | 16%    | 21%    | 22%   | 10%    | 29%    | 33%   | 7%     |
| Spec 6      | 91%    | 90%   | 91%    | 91%    | 90%   | 91%    | 91%    | 90%   | 91%    |
| OR Quart 2  | 0.54   | 2.1   | 0.85   | 1.1    | 0.75  | 0.90   | 1.6    | 1.0   | 2.2    |
| p Value     | 0.26   | 0.41  | 0.78   | 0.85   | 0.71  | 0.85   | 0.64   | 1.0   | 0.40   |
| 95% CI of   | 0.19   | 0.36  | 0.28   | 0.38   | 0.16  | 0.31   | 0.24   | 0.061 | 0.36   |
| OR Quart 2  | 1.6    | 12    | 2.6    | 3.2    | 3.5   | 2.6    | 10     | 16    | 13     |
| OR Quart 3  | 0.76   | 1.5   | 0.85   | 1.0    | 1.3   | 0.77   | 2.8    | 2.0   | 3.5    |
| p Value     | 0.60   | 0.65  | 0.78   | 1.0    | 0.71  | 0.63   | 0.24   | 0.57  | 0.14   |
| 95% CI of   | 0.28   | 0.25  | 0.28   | 0.34   | 0.33  | 0.26   | 0.50   | 0.18  | 0.65   |
| OR Quart 3  | 2.1    | 9.5   | 2.6    | 3.0    | 5.1   | 2.3    | 16     | 23    | 19     |
| OR Quart 4  | 1.1    | 1.6   | 1.7    | 1.3    | 1.6   | 1.4    | 4.3    | 5.4   | 1.0    |
| p Value     | 0.87   | 0.64  | 0.30   | 0.65   | 0.49  | 0.55   | 0.086  | 0.13  | 1.0    |
| 95% CI of   | 0.41   | 0.25  | 0.61   | 0.45   | 0.42  | 0.49   | 0.81   | 0.61  | 0.13   |
| OR Quart 4  | 2.9    | 9.7   | 4.8    | 3.6    | 5.9   | 3.8    | 23     | 48    | 7.6    |

Myeloid differentiation primary response protein MyD88

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| sCr or UO | | | | | | |
| Median      | 0.000368 | 0.000245 | 0.000368 | 0.000368 | 0.000368 | 0.000457 |
| Average     | 0.00255  | 0.00199  | 0.00255  | 0.000350 | 0.00255  | 0.00458  |
| Stdev       | 0.0181   | 0.00785  | 0.0181   | 9.42E-5  | 0.0181   | 0.0138   |
| p (t-test)  |          | 0.86     |          | 0.46     |          | 0.72     |
| Min         | 0.000224 | 0.000224 | 0.000224 | 0.000224 | 0.000224 | 0.000224 |
| Max         | 0.171    | 0.0441   | 0.171    | 0.000457 | 0.171    | 0.0463   |
| n (Samp)    | 90       | 33       | 90       | 37       | 90       | 11       |
| n (Patient) | 63       | 33       | 63       | 37       | 63       | 11       |
| sCr only    |          |          |          |          |          |          |
| Median      | 0.000368 | 0.000245 | 0.000368 | 0.000224 | 0.000368 | 0.000457 |
| Average     | 0.00184  | 0.000291 | 0.00184  | 0.000301 | 0.00184  | 0.000368 |
| Stdev       | 0.0129   | 8.43E-5  | 0.0129   | 0.000121 | 0.0129   | 0.000122 |
| p (t-test)  |          | 0.72     |          | 0.77     |          | 0.80     |
| Min         | 0.000126 | 0.000224 | 0.000126 | 0.000224 | 0.000126 | 0.000224 |
| Max         | 0.171    | 0.000457 | 0.171    | 0.000457 | 0.171    | 0.000457 |
| n (Samp)    | 202      | 9        | 202      | 6        | 202      | 5        |
| n (Patient) | 121      | 9        | 121      | 6        | 121      | 5        |
| UO only     |          |          |          |          |          |          |
| Median      | 0.000332 | 0.000245 | 0.000332 | 0.000368 | 0.000332 | 0.000457 |
| Average     | 0.00450  | 0.00230  | 0.00450  | 0.000348 | 0.00450  | 0.00456  |
| Stdev       | 0.0265   | 0.00850  | 0.0265   | 9.37E-5  | 0.0265   | 0.0138   |
| p (t-test)  |          | 0.67     |          | 0.34     |          | 0.99     |
| Min         | 0.000224 | 0.000224 | 0.000224 | 0.000224 | 0.000224 | 0.000224 |
| Max         | 0.194    | 0.0441   | 0.194    | 0.000457 | 0.194    | 0.0463   |
| n (Samp)    | 94       | 28       | 94       | 38       | 94       | 11       |
| n (Patient) | 58       | 28       | 58       | 38       | 58       | 11       |

|  | 0 hr prior to AKI stage | | | 24 hr prior to AKI stage | | | 48 hr prior to AKI stage | | |
|---|---|---|---|---|---|---|---|---|---|
|  | sCr or UO | sCr only | UO only | sCr or UO | sCr only | UO only | sCr or UO | sCr only | UO only |
| AUC      | 0.42     | 0.40     | 0.45  | 0.53     | 0.36     | 0.55     | 0.71     | 0.60     | 0.68     |
| SE       | 0.059    | 0.10     | 0.063 | 0.057    | 0.12     | 0.056    | 0.091    | 0.14     | 0.093    |
| p        | 0.17     | 0.35     | 0.44  | 0.63     | 0.26     | 0.34     | 0.022    | 0.47     | 0.053    |
| nCohort 1| 90       | 202      | 94    | 90       | 202      | 94       | 90       | 202      | 94       |
| nCohort 2| 33       | 9        | 28    | 37       | 6        | 38       | 11       | 5        | 11       |
| Cutoff 1 | 0        | 0.000224 | 0     | 0.000224 | 0.000126 | 0.000224 | 0.000296 | 0.000224 | 0.000296 |
| Sens 1   | 100%     | 78%      | 100%  | 81%      | 100%     | 84%      | 91%      | 80%      | 82%      |
| Spec 1   | 0%       | 24%      | 0%    | 21%      | 0%       | 24%      | 43%      | 24%      | 50%      |
| Cutoff 2 | 0        | 0.000126 | 0     | 0.000224 | 0.000126 | 0.000224 | 0.000296 | 0.000224 | 0.000296 |
| Sens 2   | 100%     | 100%     | 100%  | 81%      | 100%     | 84%      | 91%      | 80%      | 82%      |
| Spec 2   | 0%       | 0%       | 0%    | 21%      | 0%       | 24%      | 43%      | 24%      | 50%      |
| Cutoff 3 | 0        | 0.000126 | 0     | 0        | 0.000126 | 0        | 0.000296 | 0.000126 | 0.000224 |

TABLE 5-continued

Comparison of marker levels in EDTA samples collected from
Cohort 1 (patients that did not progress beyond RIFLE stage 0) and in EDTA samples
collected from subjects at 0, 24 hours, and 48 hours prior to reaching stage R, I or F in Cohort 2.

| Sens 3 | 100% | 100% | 100% | 100% | 100% | 100% | 91% | 100% | 91% |
|---|---|---|---|---|---|---|---|---|---|
| Spec 3 | 0% | 0% | 0% | 0% | 0% | 0% | 43% | 0% | 24% |
| Cutoff 4 | 0.000368 | 0.000368 | 0.000368 | 0.000368 | 0.000368 | 0.000368 | 0.000368 | 0.000368 | 0.000368 |
| Sens 4 | 18% | 11% | 18% | 32% | 33% | 32% | 64% | 60% | 55% |
| Spec 4 | 71% | 72% | 72% | 71% | 72% | 72% | 71% | 72% | 72% |
| Cutoff 5 | 0.000457 | 0.000457 | 0.000457 | 0.000457 | 0.000457 | 0.000457 | 0.000457 | 0.000457 | 0.000457 |
| Sens 5 | 6% | 0% | 7% | 0% | 0% | 0% | 9% | 0% | 9% |
| Spec 5 | 96% | 96% | 95% | 96% | 96% | 95% | 96% | 96% | 95% |
| Cutoff 6 | 0.000457 | 0.000457 | 0.000457 | 0.000457 | 0.000457 | 0.000457 | 0.000457 | 0.000457 | 0.000457 |
| Sens 6 | 6% | 0% | 7% | 0% | 0% | 0% | 9% | 0% | 9% |
| Spec 6 | 96% | 96% | 95% | 96% | 96% | 95% | 96% | 96% | 95% |
| OR Quart 2 | 1.5 | 0 | 1.9 | 1.5 | 0 | 1.2 | 0 | 0.98 | 1.0 |
| p Value | 0.52 | na | 0.32 | 0.46 | na | 0.78 | na | 0.99 | 1.0 |
| 95% CI of | 0.42 | na | 0.54 | 0.51 | na | 0.39 | na | 0.060 | 0.059 |
| OR Quart 2 | 5.4 | na | 6.6 | 4.5 | na | 3.5 | na | 16 | 17 |
| OR Quart 3 | 2.5 | 6.6 | 1.8 | 1.3 | 0 | 1.6 | 11 | 0.98 | 3.3 |
| p Value | 0.14 | 0.085 | 0.35 | 0.63 | na | 0.42 | 0.029 | 0.99 | 0.32 |
| 95% CI of | 0.73 | 0.77 | 0.52 | 0.44 | na | 0.53 | 1.3 | 0.060 | 0.32 |
| OR Quart 3 | 8.4 | 57 | 6.3 | 3.9 | na | 4.6 | 99 | 16 | 34 |
| OR Quart 4 | 3.0 | 2.1 | 1.6 | 0.96 | 2.1 | 1.4 | 2.0 | 2.0 | 7.1 |
| p Value | 0.075 | 0.55 | 0.48 | 0.94 | 0.41 | 0.58 | 0.58 | 0.58 | 0.079 |
| 95% CI of | 0.90 | 0.18 | 0.44 | 0.31 | 0.36 | 0.46 | 0.17 | 0.18 | 0.80 |
| OR Quart 4 | 10 | 24 | 5.7 | 3.0 | 12 | 4.0 | 24 | 23 | 64 |

TABLE 6

Comparison of marker levels in EDTA samples collected from
Cohort 1 (patients that did not progress beyond RIFLE stage 0 or R) and in EDTA
samples collected from subjects at 0, 24 hours, and 48 hours prior to reaching stage I or F
in Cohort 2.

| | Heat shock 70 kDa protein 1 | | | |
|---|---|---|---|---|
| | 24 hr prior to AKI stage | | 48 hr prior to AKI stage | |
| | Cohort 1 | Cohort 2 | Cohort 1 | Cohort 2 |
| sCr or UO | | | | |
| Median | 934 | 840 | 934 | 928 |
| Average | 1680 | 957 | 1680 | 967 |
| Stdev | 2210 | 694 | 2210 | 860 |
| p (t-test) | | 0.33 | | 0.44 |
| Min | 0.288 | 16.7 | 0.288 | 0.288 |
| Max | 10700 | 2280 | 10700 | 1970 |
| n (Samp) | 113 | 9 | 113 | 6 |
| n (Patient) | 92 | 9 | 92 | 6 |
| UO only | | | | |
| Median | 934 | 840 | 934 | 336 |
| Average | 1650 | 957 | 1650 | 817 |
| Stdev | 2190 | 694 | 2190 | 870 |
| p (t-test) | | 0.35 | | 0.40 |
| Min | 0.288 | 16.7 | 0.288 | 0.288 |
| Max | 10700 | 2280 | 10700 | 1970 |
| n (Samp) | 99 | 9 | 99 | 5 |
| n (Patient) | 77 | 9 | 77 | 5 |

| | 24 hr prior to AKI stage | | | 48 hr prior to AKI stage | | |
|---|---|---|---|---|---|---|
| | sCr or UO | sCr only | UO only | sCr or UO | sCr only | UO only |
| AUC | 0.46 | nd | 0.47 | 0.44 | nd | 0.39 |
| SE | 0.10 | nd | 0.10 | 0.12 | nd | 0.14 |
| p | 0.73 | nd | 0.75 | 0.66 | nd | 0.44 |
| nCohort 1 | 113 | nd | 99 | 113 | nd | 99 |
| nCohort 2 | 9 | nd | 9 | 6 | nd | 5 |
| Cutoff 1 | 705 | nd | 664 | 252 | nd | 252 |
| Sens 1 | 78% | nd | 78% | 83% | nd | 80% |
| Spec 1 | 44% | nd | 44% | 23% | nd | 25% |
| Cutoff 2 | 114 | nd | 114 | 252 | nd | 252 |
| Sens 2 | 89% | nd | 89% | 83% | nd | 80% |
| Spec 2 | 15% | nd | 16% | 23% | nd | 25% |

TABLE 6-continued

Comparison of marker levels in EDTA samples collected from
Cohort 1 (patients that did not progress beyond RIFLE stage 0 or R) and in EDTA
samples collected from subjects at 0, 24 hours, and 48 hours prior to reaching stage I or F
in Cohort 2.

| | | | | | | |
|---|---|---|---|---|---|---|
| Cutoff 3 | 4.58 | nd | 4.58 | 0 | nd | 0 |
| Sens 3 | 100% | nd | 100% | 100% | nd | 100% |
| Spec 3 | 6% | nd | 7% | 0% | nd | 0% |
| Cutoff 4 | 1620 | nd | 1610 | 1620 | nd | 1610 |
| Sens 4 | 11% | nd | 11% | 33% | nd | 20% |
| Spec 4 | 71% | nd | 71% | 71% | nd | 71% |
| Cutoff 5 | 2930 | nd | 2930 | 2930 | nd | 2930 |
| Sens 5 | 0% | nd | 0% | 0% | nd | 0% |
| Spec 5 | 81% | nd | 81% | 81% | nd | 81% |
| Cutoff 6 | 3970 | nd | 4330 | 3970 | nd | 4330 |
| Sens 6 | 0% | nd | 0% | 0% | nd | 0% |
| Spec 6 | 90% | nd | 91% | 90% | nd | 91% |
| OR Quart 2 | 3.3 | nd | 3.2 | 2.1 | nd | >2.2 |
| p Value | 0.31 | nd | 0.32 | 0.56 | nd | <0.54 |
| 95% CI of | 0.33 | nd | 0.32 | 0.18 | nd | >0.18 |
| OR Quart 2 | 34 | nd | 33 | 24 | nd | na |
| OR Quart 3 | 3.2 | nd | 3.2 | 1.0 | nd | >2.2 |
| p Value | 0.32 | nd | 0.32 | 1.0 | nd | <0.54 |
| 95% CI of | 0.32 | nd | 0.32 | 0.060 | nd | >0.18 |
| OR Quart 3 | 33 | nd | 33 | 17 | nd | na |
| OR Quart 4 | 2.1 | nd | 2.1 | 2.1 | nd | >1.0 |
| p Value | 0.54 | nd | 0.56 | 0.54 | nd | <0.98 |
| 95% CI of | 0.18 | nd | 0.18 | 0.18 | nd | >0.062 |
| OR Quart 4 | 25 | nd | 24 | 25 | nd | na |

Insulin-like growth factor 1 receptor

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| sCr or UO | | | | | | |
| Median | 0.0484 | 0.0572 | 0.0484 | 0.0619 | 0.0484 | 0.0426 |
| Average | 0.346 | 2.67 | 0.346 | 0.938 | 0.346 | 1.38 |
| Stdev | 2.22 | 6.87 | 2.22 | 3.58 | 2.22 | 5.00 |
| p (t-test) | | 0.017 | | 0.32 | | 0.13 |
| Min | 9.84E−5 | 0.0144 | 9.84E−5 | 0.000211 | 9.84E−5 | 0.000211 |
| Max | 21.0 | 18.2 | 21.0 | 14.8 | 21.0 | 19.4 |
| n (Samp) | 183 | 7 | 183 | 17 | 183 | 15 |
| n (Patient) | 122 | 7 | 122 | 17 | 122 | 15 |
| sCr only | | | | | | |
| Median | 0.0498 | 0.0888 | 0.0498 | 7.45 | 0.0498 | 0.0596 |
| Average | 0.300 | 6.12 | 0.300 | 7.45 | 0.300 | 4.90 |
| Stdev | 2.01 | 10.5 | 2.01 | 10.4 | 2.01 | 9.70 |
| p (t-test) | | 1.2E−5 | | 3.9E−6 | | 9.6E−5 |
| Min | 9.84E−5 | 0.0144 | 9.84E−5 | 0.0742 | 9.84E−5 | 0.0214 |
| Max | 21.0 | 18.2 | 21.0 | 14.8 | 21.0 | 19.4 |
| n (Samp) | 222 | 3 | 222 | 2 | 222 | 4 |
| n (Patient) | 145 | 3 | 145 | 2 | 145 | 4 |
| UO only | | | | | | |
| Median | 0.0498 | 0.0572 | 0.0498 | 0.0572 | 0.0498 | 0.0449 |
| Average | 0.393 | 0.0892 | 0.393 | 0.0668 | 0.393 | 0.102 |
| Stdev | 2.37 | 0.0767 | 2.37 | 0.0525 | 2.37 | 0.149 |
| p (t-test) | | 0.80 | | 0.57 | | 0.67 |
| Min | 0.000208 | 0.0390 | 0.000208 | 0.000211 | 0.000208 | 0.000211 |
| Max | 21.0 | 0.204 | 21.0 | 0.192 | 21.0 | 0.543 |
| n (Samp) | 159 | 4 | 159 | 17 | 159 | 12 |
| n (Patient) | 102 | 4 | 102 | 17 | 102 | 12 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.65 | 0.65 | 0.62 | 0.60 | 0.85 | 0.54 | 0.54 | 0.59 | 0.52 |
| SE | 0.11 | 0.17 | 0.15 | 0.075 | 0.17 | 0.075 | 0.079 | 0.15 | 0.088 |
| p | 0.19 | 0.38 | 0.42 | 0.17 | 0.038 | 0.61 | 0.58 | 0.55 | 0.80 |
| nCohort 1 | 183 | 222 | 159 | 183 | 222 | 159 | 183 | 222 | 159 |
| nCohort 2 | 7 | 3 | 4 | 17 | 2 | 17 | 15 | 4 | 12 |
| Cutoff 1 | 0.0556 | 0.0137 | 0.0556 | 0.0407 | 0.0729 | 0.0373 | 0.0219 | 0.0390 | 0.0219 |
| Sens 1 | 71% | 100% | 75% | 71% | 100% | 71% | 73% | 75% | 75% |
| Spec 1 | 60% | 15% | 57% | 44% | 72% | 40% | 25% | 41% | 23% |
| Cutoff 2 | 0.0373 | 0.0137 | 0.0373 | 0.0297 | 0.0729 | 0.0253 | 0.0212 | 0.0212 | 0.0212 |

TABLE 6-continued

Comparison of marker levels in EDTA samples collected from Cohort 1 (patients that did not progress beyond RIFLE stage 0 or R) and in EDTA samples collected from subjects at 0, 24 hours, and 48 hours prior to reaching stage I or F in Cohort 2.

| | | | | | | | | | |
|---|---|---|---|---|---|---|---|---|---|
| Sens 2 | 86% | 100% | 100% | 82% | 100% | 82% | 93% | 100% | 92% |
| Spec 2 | 42% | 15% | 40% | 33% | 72% | 25% | 21% | 20% | 18% |
| Cutoff 3 | 0.0137 | 0.0137 | 0.0373 | 0.00949 | 0.0729 | 0.00497 | 0.0212 | 0.0212 | 0.0212 |
| Sens 3 | 100% | 100% | 100% | 94% | 100% | 94% | 93% | 100% | 92% |
| Spec 3 | 15% | 15% | 40% | 11% | 72% | 9% | 21% | 20% | 18% |
| Cutoff 4 | 0.0692 | 0.0699 | 0.0729 | 0.0692 | 0.0699 | 0.0729 | 0.0692 | 0.0699 | 0.0729 |
| Sens 4 | 43% | 67% | 25% | 41% | 100% | 35% | 40% | 50% | 42% |
| Spec 4 | 71% | 71% | 70% | 71% | 71% | 70% | 71% | 71% | 70% |
| Cutoff 5 | 0.0839 | 0.0839 | 0.0839 | 0.0839 | 0.0839 | 0.0839 | 0.0839 | 0.0839 | 0.0839 |
| Sens 5 | 43% | 67% | 25% | 29% | 50% | 29% | 33% | 25% | 33% |
| Spec 5 | 80% | 80% | 81% | 80% | 80% | 81% | 80% | 80% | 81% |
| Cutoff 6 | 0.129 | 0.133 | 0.134 | 0.129 | 0.133 | 0.134 | 0.129 | 0.133 | 0.134 |
| Sens 6 | 29% | 33% | 25% | 18% | 50% | 12% | 20% | 25% | 17% |
| Spec 6 | 90% | 90% | 91% | 90% | 90% | 91% | 90% | 90% | 91% |
| OR Quart 2 | 0.98 | 0 | >1.0 | 2.1 | >0 | 1.4 | 1.2 | 0.98 | 1.3 |
| p Value | 0.99 | na | <1.0 | 0.41 | <na | 0.69 | 0.75 | 0.99 | 0.72 |
| 95% CI of | 0.059 | na | >0.060 | 0.36 | >na | 0.29 | 0.32 | 0.060 | 0.28 |
| OR Quart 2 | 16 | na | na | 12 | na | 6.5 | 5.0 | 16 | 6.4 |
| OR Quart 3 | 2.0 | 0 | >2.1 | 2.7 | >1.0 | 1.8 | 0.23 | 1.0 | 0.31 |
| p Value | 0.56 | na | <0.56 | 0.26 | <0.99 | 0.46 | 0.20 | 1.0 | 0.32 |
| 95% CI of | 0.18 | na | >0.18 | 0.49 | >0.062 | 0.39 | 0.025 | 0.061 | 0.031 |
| OR Quart 3 | 23 | na | na | 14 | na | 7.8 | 2.2 | 16 | 3.1 |
| OR Quart 4 | 3.1 | 2.0 | >1.0 | 3.3 | >1.0 | 1.8 | 1.2 | 0.98 | 1.3 |
| p Value | 0.34 | 0.58 | <1.0 | 0.16 | <0.99 | 0.46 | 0.75 | 0.99 | 0.72 |
| 95% CI of | 0.31 | 0.18 | >0.060 | 0.63 | >0.062 | 0.39 | 0.32 | 0.060 | 0.28 |
| OR Quart 4 | 31 | 23 | na | 17 | na | 7.8 | 5.0 | 16 | 6.4 |

Neural cell adhesion molecule 1

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| sCr or UO | | | | | | |
| Median | 184000 | 178000 | 184000 | 185000 | 184000 | 156000 |
| Average | 189000 | 187000 | 189000 | 191000 | 189000 | 158000 |
| Stdev | 70300 | 63200 | 70300 | 93000 | 70300 | 51300 |
| p (t-test) | | 0.90 | | 0.91 | | 0.060 |
| Min | 791 | 93200 | 791 | 190 | 791 | 49200 |
| Max | 520000 | 316000 | 520000 | 506000 | 520000 | 280000 |
| n (Samp) | 285 | 16 | 285 | 28 | 285 | 19 |
| n (Patient) | 163 | 16 | 163 | 28 | 163 | 19 |
| sCr only | | | | | | |
| Median | 181000 | 243000 | 181000 | 232000 | 181000 | 175000 |
| Average | 184000 | 236000 | 184000 | 295000 | 184000 | 190000 |
| Stdev | 68800 | 73300 | 68800 | 135000 | 68800 | 53400 |
| p (t-test) | | 0.14 | | 5.0E−4 | | 0.86 |
| Min | 190 | 140000 | 190 | 160000 | 190 | 140000 |
| Max | 520000 | 316000 | 520000 | 506000 | 520000 | 280000 |
| n (Samp) | 356 | 4 | 356 | 5 | 356 | 5 |
| n (Patient) | 197 | 4 | 197 | 5 | 197 | 5 |
| UO only | | | | | | |
| Median | 183000 | 172000 | 183000 | 177000 | 183000 | 156000 |
| Average | 188000 | 168000 | 188000 | 169000 | 188000 | 155000 |
| Stdev | 72400 | 51800 | 72400 | 65000 | 72400 | 47600 |
| p (t-test) | | 0.32 | | 0.19 | | 0.058 |
| Min | 791 | 93200 | 791 | 190 | 791 | 49200 |
| Max | 520000 | 282000 | 520000 | 331000 | 520000 | 230000 |
| n (Samp) | 261 | 13 | 261 | 26 | 261 | 17 |
| n (Patient) | 143 | 13 | 143 | 26 | 143 | 17 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.49 | 0.73 | 0.41 | 0.48 | 0.79 | 0.43 | 0.36 | 0.51 | 0.36 |
| SE | 0.075 | 0.15 | 0.085 | 0.058 | 0.12 | 0.061 | 0.070 | 0.13 | 0.074 |
| p | 0.92 | 0.12 | 0.29 | 0.79 | 0.015 | 0.25 | 0.041 | 0.91 | 0.052 |
| nCohort 1 | 285 | 356 | 261 | 285 | 356 | 261 | 285 | 356 | 261 |
| nCohort 2 | 16 | 4 | 13 | 28 | 5 | 26 | 19 | 5 | 17 |
| Cutoff 1 | 152000 | 230000 | 133000 | 158000 | 230000 | 130000 | 139000 | 166000 | 144000 |
| Sens 1 | 75% | 75% | 77% | 71% | 80% | 73% | 74% | 80% | 71% |

TABLE 6-continued

Comparison of marker levels in EDTA samples collected from
Cohort 1 (patients that did not progress beyond RIFLE stage 0 or R) and in EDTA
samples collected from subjects at 0, 24 hours, and 48 hours prior to reaching stage I or F
in Cohort 2.

| | | | | | | | | | |
|---|---|---|---|---|---|---|---|---|---|
| Spec 1 | 30% | 81% | 21% | 32% | 81% | 19% | 21% | 41% | 26% |
| Cutoff 2 | 133000 | 140000 | 121000 | 125000 | 230000 | 121000 | 107000 | 166000 | 107000 |
| Sens 2 | 81% | 100% | 85% | 82% | 80% | 81% | 84% | 80% | 82% |
| Spec 2 | 19% | 24% | 14% | 14% | 81% | 14% | 8% | 41% | 9% |
| Cutoff 3 | 95600 | 140000 | 95600 | 91800 | 160000 | 91800 | 91800 | 140000 | 91800 |
| Sens 3 | 94% | 100% | 92% | 93% | 100% | 92% | 95% | 100% | 94% |
| Spec 3 | 6% | 24% | 6% | 5% | 37% | 5% | 5% | 24% | 5% |
| Cutoff 4 | 214000 | 207000 | 214000 | 214000 | 207000 | 214000 | 214000 | 207000 | 214000 |
| Sens 4 | 25% | 75% | 8% | 29% | 80% | 19% | 11% | 20% | 12% |
| Spec 4 | 70% | 71% | 70% | 70% | 71% | 70% | 70% | 71% | 70% |
| Cutoff 5 | 233000 | 228000 | 233000 | 233000 | 228000 | 233000 | 233000 | 228000 | 233000 |
| Sens 5 | 19% | 75% | 8% | 14% | 80% | 12% | 5% | 20% | 0% |
| Spec 5 | 80% | 80% | 80% | 80% | 80% | 80% | 80% | 80% | 80% |
| Cutoff 6 | 266000 | 262000 | 265000 | 266000 | 262000 | 265000 | 266000 | 262000 | 265000 |
| Sens 6 | 12% | 25% | 8% | 11% | 40% | 4% | 5% | 20% | 0% |
| Spec 6 | 90% | 90% | 90% | 90% | 90% | 90% | 90% | 90% | 90% |
| OR Quart 2 | 0.75 | 0 | 3.1 | 1.0 | >1.0 | 2.1 | 2.1 | 2.0 | 1.5 |
| p Value | 0.71 | na | 0.33 | 0.98 | <0.99 | 0.24 | 0.41 | 0.57 | 0.64 |
| 95% CI of | 0.16 | na | 0.32 | 0.34 | >0.062 | 0.61 | 0.37 | 0.18 | 0.25 |
| OR Quart 2 | 3.5 | na | 31 | 3.0 | na | 7.4 | 12 | 23 | 9.5 |
| OR Quart 3 | 1.3 | 0 | 5.3 | 0.86 | >0 | 1.3 | 3.8 | 1.0 | 3.8 |
| p Value | 0.72 | na | 0.13 | 0.79 | <na | 0.73 | 0.11 | 1.0 | 0.11 |
| 95% CI of | 0.33 | na | 0.60 | 0.27 | >na | 0.33 | 0.75 | 0.062 | 0.76 |
| OR Quart 3 | 5.0 | na | 47 | 2.7 | na | 4.9 | 19 | 16 | 19 |
| OR Quart 4 | 1.0 | 3.1 | 4.2 | 1.2 | >4.1 | 2.5 | 3.2 | 0.99 | 2.7 |
| p Value | 0.98 | 0.34 | 0.20 | 0.77 | <0.21 | 0.15 | 0.17 | 0.99 | 0.25 |
| 95% CI of | 0.24 | 0.31 | 0.46 | 0.40 | >0.45 | 0.72 | 0.62 | 0.061 | 0.50 |
| OR Quart 4 | 4.2 | 30 | 39 | 3.4 | na | 8.4 | 16 | 16 | 14 |

Myeloid differentiation primary response protein MyD88

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| sCr or UO | | | | | | |
| Median | 0.000368 | 0.000245 | 0.000368 | 0.000368 | 0.000368 | 0.000368 |
| Average | 0.00279 | 0.000236 | 0.00279 | 0.000326 | 0.00279 | 0.000351 |
| Stdev | 0.0186 | 1.14E−5 | 0.0186 | 9.54E−5 | 0.0186 | 0.000109 |
| p (t-test) | | 0.68 | | 0.59 | | 0.70 |
| Min | 0.000126 | 0.000224 | 0.000126 | 0.000224 | 0.000126 | 0.000224 |
| Max | 0.194 | 0.000245 | 0.194 | 0.000457 | 0.194 | 0.000457 |
| n (Samp) | 203 | 9 | 203 | 17 | 203 | 9 |
| n (Patient) | 120 | 9 | 120 | 17 | 120 | 9 |
| sCr only | | | | | | |
| Median | nd | nd | nd | nd | 0.000368 | 0.000340 |
| Average | nd | nd | nd | nd | 0.00235 | 0.000340 |
| Stdev | nd | nd | nd | nd | 0.0169 | 0.000165 |
| p (t-test) | nd | nd | nd | nd | | 0.87 |
| Min | nd | nd | nd | nd | 0.000126 | 0.000224 |
| Max | nd | nd | nd | nd | 0.194 | 0.000457 |
| n (Samp) | nd | nd | nd | nd | 246 | 2 |
| n (Patient) | nd | nd | nd | nd | 142 | 2 |
| UO only | | | | | | |
| Median | 0.000368 | 0.000245 | 0.000368 | 0.000368 | 0.000368 | 0.000307 |
| Average | 0.00296 | 0.000236 | 0.00296 | 0.000326 | 0.00296 | 0.000337 |
| Stdev | 0.0193 | 1.14E−5 | 0.0193 | 9.54E−5 | 0.0193 | 0.000108 |
| p (t-test) | | 0.67 | | 0.57 | | 0.70 |
| Min | 0.000126 | 0.000224 | 0.000126 | 0.000224 | 0.000126 | 0.000224 |
| Max | 0.194 | 0.000245 | 0.194 | 0.000457 | 0.194 | 0.000457 |
| n (Samp) | 189 | 9 | 189 | 17 | 189 | 8 |
| n (Patient) | 106 | 9 | 106 | 17 | 106 | 8 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.24 | nd | 0.25 | 0.47 | nd | 0.48 | 0.56 | 0.48 | 0.54 |
| SE | 0.095 | nd | 0.096 | 0.074 | nd | 0.074 | 0.10 | 0.21 | 0.11 |
| p | 0.0060 | nd | 0.0098 | 0.73 | nd | 0.82 | 0.54 | 0.94 | 0.74 |
| nCohort 1 | 203 | nd | 189 | 203 | nd | 189 | 203 | 246 | 189 |
| nCohort 2 | 9 | nd | 9 | 17 | nd | 17 | 9 | 2 | 8 |

TABLE 6-continued

Comparison of marker levels in EDTA samples collected from
Cohort 1 (patients that did not progress beyond RIFLE stage 0 or R) and in EDTA
samples collected from subjects at 0, 24 hours, and 48 hours prior to reaching stage I or F
in Cohort 2.

|  |  |  |  |  |  |  |  |  |  |
|---|---|---|---|---|---|---|---|---|---|
| Cutoff 1 | 0.000126 | nd | 0.000126 | 0.000224 | nd | 0.000224 | 0.000224 | 0.000126 | 0.000224 |
| Sens 1 | 100% | nd | 100% | 76% | nd | 76% | 89% | 100% | 88% |
| Spec 1 | 0% | nd | 1% | 23% | nd | 24% | 23% | 0% | 24% |
| Cutoff 2 | 0.000126 | nd | 0.000126 | 0.000126 | nd | 0.000126 | 0.000224 | 0.000126 | 0.000224 |
| Sens 2 | 100% | nd | 100% | 100% | nd | 100% | 89% | 100% | 88% |
| Spec 2 | 0% | nd | 1% | 0% | nd | 1% | 23% | 0% | 24% |
| Cutoff 3 | 0.000126 | nd | 0.000126 | 0.000126 | nd | 0.000126 | 0.000126 | 0.000126 | 0.000126 |
| Sens 3 | 100% | nd | 100% | 100% | nd | 100% | 100% | 100% | 100% |
| Spec 3 | 0% | nd | 1% | 0% | nd | 1% | 0% | 0% | 1% |
| Cutoff 4 | 0.000368 | nd | 0.000368 | 0.000368 | nd | 0.000368 | 0.000368 | 0.000368 | 0.000368 |
| Sens 4 | 0% | nd | 0% | 24% | nd | 24% | 44% | 50% | 38% |
| Spec 4 | 71% | nd | 71% | 71% | nd | 71% | 71% | 73% | 71% |
| Cutoff 5 | 0.000457 | nd | 0.000457 | 0.000457 | nd | 0.000457 | 0.000457 | 0.000457 | 0.000457 |
| Sens 5 | 0% | nd | 0% | 0% | nd | 0% | 0% | 0% | 0% |
| Spec 5 | 96% | nd | 95% | 96% | nd | 95% | 96% | 96% | 95% |
| Cutoff 6 | 0.000457 | nd | 0.000457 | 0.000457 | nd | 0.000457 | 0.000457 | 0.000457 | 0.000457 |
| Sens 6 | 0% | nd | 0% | 0% | nd | 0% | 0% | 0% | 0% |
| Spec 6 | 96% | nd | 95% | 96% | nd | 95% | 96% | 96% | 95% |
| OR Quart 2 | >0 | nd | >0 | 0.32 | nd | 1.3 | 4.2 | 0 | 3.1 |
| p Value | <na | nd | <na | 0.33 | nd | 0.70 | 0.20 | na | 0.33 |
| 95% CI of | >na | nd | >na | 0.032 | nd | 0.33 | 0.46 | na | 0.31 |
| OR Quart 2 | na | nd | na | 3.2 | nd | 5.2 | 39 | na | 31 |
| OR Quart 3 | >5.5 | nd | >5.6 | 3.4 | nd | 1.0 | 0 | 0 | 1.0 |
| p Value | <0.12 | nd | <0.12 | 0.080 | nd | 1.0 | na | na | 1.0 |
| 95% CI of | >0.62 | nd | >0.63 | 0.87 | nd | 0.24 | na | na | 0.061 |
| OR Quart 3 | na | nd | na | 13 | nd | 4.2 | na | na | 16 |
| OR Quart 4 | >4.3 | nd | >4.4 | 1.4 | nd | 1.0 | 4.2 | 1.0 | 3.1 |
| p Value | <0.20 | nd | <0.19 | 0.70 | nd | 0.98 | 0.20 | 1.0 | 0.34 |
| 95% CI of | >0.47 | nd | >0.48 | 0.29 | nd | 0.24 | 0.46 | 0.061 | 0.31 |
| OR Quart 4 | na | nd | na | 6.4 | nd | 4.3 | 39 | 16 | 31 |

TABLE 7

Comparison of marker levels in EDTA samples collected within 12
hours of reaching stage R from Cohort 1 (patients that reached, but did not progress
beyond, RIFLE stage R) and from Cohort 2 (patients that reached RIFLE stage I or F).

| | Insulin-like growth factor 1 receptor | | | | | |
|---|---|---|---|---|---|---|
| | sCr or UO | | sCr only | | UO only | |
| | Cohort 1 | Cohort 2 | Cohort 1 | Cohort 2 | Cohort 1 | Cohort 2 |
| Median | 0.0447 | 0.0717 | nd | nd | 0.0478 | 0.0804 |
| Average | 0.574 | 0.103 | nd | nd | 0.707 | 0.0835 |
| Stdev | 3.27 | 0.114 | nd | nd | 3.71 | 0.0515 |
| p (t-test) | | 0.62 | nd | nd | | 0.62 |
| Min | 0.000208 | 0.0214 | nd | nd | 0.000208 | 0.0214 |
| Max | 20.5 | 0.432 | nd | nd | 21.0 | 0.192 |
| n (Samp) | 39 | 12 | nd | nd | 32 | 9 |
| n (Patient) | 39 | 12 | nd | nd | 32 | 9 |

| | At Enrollment | | |
|---|---|---|---|
| | sCr or UO | sCr only | UO only |
| AUC | 0.66 | nd | 0.71 |
| SE | 0.095 | nd | 0.11 |
| p | 0.088 | nd | 0.047 |
| nCohort 1 | 39 | nd | 32 |
| nCohort 2 | 12 | nd | 9 |
| Cutoff 1 | 0.0331 | nd | 0.0545 |
| Sens 1 | 75% | nd | 78% |
| Spec 1 | 31% | nd | 59% |
| Cutoff 2 | 0.0292 | nd | 0.0214 |
| Sens 2 | 83% | nd | 89% |
| Spec 2 | 28% | nd | 25% |
| Cutoff 3 | 0.0214 | nd | 0.0179 |
| Sens 3 | 92% | nd | 100% |
| Spec 3 | 26% | nd | 19% |
| Cutoff 4 | 0.0608 | nd | 0.0608 |
| Sens 4 | 58% | nd | 67% |

TABLE 7-continued

Comparison of marker levels in EDTA samples collected within 12 hours of reaching stage R from Cohort 1 (patients that reached, but did not progress beyond, RIFLE stage R) and from Cohort 2 (patients that reached RIFLE stage I or F).

| | | | |
|---|---|---|---|
| Spec 4 | 72% | nd | 72% |
| Cutoff 5 | 0.0692 | nd | 0.0668 |
| Sens 5 | 50% | nd | 67% |
| Spec 5 | 82% | nd | 81% |
| Cutoff 6 | 0.0945 | nd | 0.0839 |
| Sens 6 | 33% | nd | 44% |
| Spec 6 | 92% | nd | 91% |
| OR Quart 2 | 0.91 | nd | 0 |
| p Value | 0.93 | nd | na |
| 95% CI of | 0.11 | nd | na |
| OR Quart 2 | 7.7 | nd | na |
| OR Quart 3 | 0.91 | nd | 1.0 |
| p Value | 0.93 | nd | 1.0 |
| 95% CI of | 0.11 | nd | 0.11 |
| OR Quart 3 | 7.7 | nd | 8.9 |
| OR Quart 4 | 4.3 | nd | 3.3 |
| p Value | 0.13 | nd | 0.23 |
| 95% CI of | 0.66 | nd | 0.47 |
| OR Quart 4 | 28 | nd | 23 |

Tumor necrosis factor ligand superfamily member 10

| | sCr or UO | | sCr only | | UO only | |
|---|---|---|---|---|---|---|
| | Cohort 1 | Cohort 2 | Cohort 1 | Cohort 2 | Cohort 1 | Cohort 2 |
| Median | 0.0315 | 0.0228 | nd | nd | 0.0315 | 0.0228 |
| Average | 6.86 | 1.36 | nd | nd | 2.72 | 1.74 |
| Stdev | 27.8 | 5.65 | nd | nd | 5.07 | 6.41 |
| p (t-test) | | 0.41 | nd | nd | | 0.58 |
| Min | 0.0162 | 0.0162 | nd | nd | 0.0162 | 0.0162 |
| Max | 172 | 24.0 | nd | nd | 16.7 | 24.0 |
| n (Samp) | 38 | 18 | nd | nd | 32 | 14 |
| n (Patient) | 38 | 18 | nd | nd | 32 | 14 |

| | At Enrollment | | |
|---|---|---|---|
| | sCr or UO | sCr only | UO only |
| AUC | 0.28 | nd | 0.29 |
| SE | 0.078 | nd | 0.088 |
| p | 0.0054 | nd | 0.017 |
| nCohort 1 | 38 | nd | 32 |
| nCohort 2 | 18 | nd | 14 |
| Cutoff 1 | 0.0197 | nd | 0.0197 |
| Sens 1 | 72% | nd | 71% |
| Spec 1 | 18% | nd | 16% |
| Cutoff 2 | 0 | nd | 0 |
| Sens 2 | 100% | nd | 100% |
| Spec 2 | 0% | nd | 0% |
| Cutoff 3 | 0 | nd | 0 |
| Sens 3 | 100% | nd | 100% |
| Spec 3 | 0% | nd | 0% |
| Cutoff 4 | 0.601 | nd | 0.444 |
| Sens 4 | 6% | nd | 7% |
| Spec 4 | 71% | nd | 72% |
| Cutoff 5 | 6.98 | nd | 6.98 |
| Sens 5 | 6% | nd | 7% |
| Spec 5 | 82% | nd | 81% |
| Cutoff 6 | 13.4 | nd | 10.8 |
| Sens 6 | 6% | nd | 7% |
| Spec 6 | 92% | nd | 91% |
| OR Quart 2 | 2.2 | nd | 0.50 |
| p Value | 0.55 | nd | 0.59 |
| 95% CI of | 0.17 | nd | 0.039 |
| OR Quart 2 | 27 | nd | 6.4 |
| OR Quart 3 | 17 | nd | 5.0 |
| p Value | 0.015 | nd | 0.096 |
| 95% CI of | 1.8 | nd | 0.75 |
| OR Quart 3 | 170 | nd | 33 |
| OR Quart 4 | 13 | nd | 4.2 |
| p Value | 0.028 | nd | 0.15 |
| 95% CI of | 1.3 | nd | 0.61 |
| OR Quart 4 | 130 | nd | 29 |

TABLE 8

Comparison of the maximum marker levels in EDTA samples
collected from Cohort 1 (patients that did not progress beyond RIFLE stage 0) and the
maximum values in EDTA samples collected from subjects between enrollment and 0, 24
hours, and 48 hours prior to reaching stage F in Cohort 2.

Heat shock 70 kDa protein 1

|  | 0 hr prior to AKI stage | | 24 hr prior to AKI stage | |
|---|---|---|---|---|
|  | Cohort 1 | Cohort 2 | Cohort 1 | Cohort 2 |
| sCr or UO | | | | |
| Median | 618 | 2280 | 618 | 2280 |
| Average | 1400 | 2650 | 1400 | 2650 |
| Stdev | 2030 | 2030 | 2030 | 2030 |
| p (t-test) | | 0.30 | | 0.30 |
| Min | 0.288 | 840 | 0.288 | 840 |
| Max | 10000 | 4840 | 10000 | 4840 |
| n (Samp) | 53 | 3 | 53 | 3 |
| n (Patient) | 53 | 3 | 53 | 3 |
| UO only | | | | |
| Median | 641 | 1560 | 641 | 1560 |
| Average | 1410 | 1560 | 1410 | 1560 |
| Stdev | 1930 | 1020 | 1930 | 1020 |
| p (t-test) | | 0.92 | | 0.92 |
| Min | 0.288 | 840 | 0.288 | 840 |
| Max | 10000 | 2280 | 10000 | 2280 |
| n (Samp) | 44 | 2 | 44 | 2 |
| n (Patient) | 44 | 2 | 44 | 2 |

|  | 0 hr prior to AKI stage | | | 24 hr prior to AKI stage | | |
|---|---|---|---|---|---|---|
|  | sCr or UO | sCr only | UO only | sCr or UO | sCr only | UO only |
| AUC | 0.77 | nd | 0.66 | 0.77 | nd | 0.66 |
| SE | 0.16 | nd | 0.22 | 0.16 | nd | 0.22 |
| p | 0.093 | nd | 0.46 | 0.093 | nd | 0.46 |
| nCohort 1 | 53 | nd | 44 | 53 | nd | 44 |
| nCohort 2 | 3 | nd | 2 | 3 | nd | 2 |
| Cutoff 1 | 837 | nd | 837 | 837 | nd | 837 |
| Sens 1 | 100% | nd | 100% | 100% | nd | 100% |
| Spec 1 | 57% | nd | 55% | 57% | nd | 55% |
| Cutoff 2 | 837 | nd | 837 | 837 | nd | 837 |
| Sens 2 | 100% | nd | 100% | 100% | nd | 100% |
| Spec 2 | 57% | nd | 55% | 57% | nd | 55% |
| Cutoff 3 | 837 | nd | 837 | 837 | nd | 837 |
| Sens 3 | 100% | nd | 100% | 100% | nd | 100% |
| Spec 3 | 57% | nd | 55% | 57% | nd | 55% |
| Cutoff 4 | 1370 | nd | 1370 | 1370 | nd | 1370 |
| Sens 4 | 67% | nd | 50% | 67% | nd | 50% |
| Spec 4 | 72% | nd | 70% | 72% | nd | 70% |
| Cutoff 5 | 2700 | nd | 2860 | 2700 | nd | 2860 |
| Sens 5 | 33% | nd | 0% | 33% | nd | 0% |
| Spec 5 | 81% | nd | 82% | 81% | nd | 82% |
| Cutoff 6 | 3540 | nd | 3630 | 3540 | nd | 3630 |
| Sens 6 | 33% | nd | 0% | 33% | nd | 0% |
| Spec 6 | 91% | nd | 91% | 91% | nd | 91% |
| OR Quart 2 | >0 | nd | >0 | >0 | nd | >0 |
| p Value | <na | nd | <na | <na | nd | <na |
| 95% CI of | >na | nd | >na | >na | nd | >na |
| OR Quart 2 | na | nd | na | na | nd | na |
| OR Quart 3 | >1.1 | nd | >1.1 | >1.1 | nd | >1.1 |
| p Value | <0.96 | nd | <0.95 | <0.96 | nd | <0.95 |
| 95% CI of | >0.061 | nd | >0.060 | >0.061 | nd | >0.060 |
| OR Quart 3 | na | nd | na | na | nd | na |
| OR Quart 4 | >2.3 | nd | >1.0 | >2.3 | nd | >1.0 |
| p Value | <0.51 | nd | <1.0 | <0.51 | nd | <1.0 |
| 95% CI of | >0.19 | nd | >0.055 | >0.19 | nd | >0.055 |
| OR Quart 4 | na | nd | na | na | nd | na |

TABLE 8-continued

Comparison of the maximum marker levels in EDTA samples collected from Cohort 1 (patients that did not progress beyond RIFLE stage 0) and the maximum values in EDTA samples collected from subjects between enrollment and 0, 24 hours, and 48 hours prior to reaching stage F in Cohort 2.

| | Neural cell adhesion molecule 1 | | | | | |
|---|---|---|---|---|---|---|
| | 0 hr prior to AKI stage | | 24 hr prior to AKI stage | | 48 hr prior to AKI stage | |
| | Cohort 1 | Cohort 2 | Cohort 1 | Cohort 2 | Cohort 1 | Cohort 2 |
| sCr or UO | | | | | | |
| Median | 184000 | 172000 | 184000 | 172000 | 184000 | 167000 |
| Average | 188000 | 180000 | 188000 | 177000 | 188000 | 165000 |
| Stdev | 79000 | 49600 | 79000 | 44400 | 79000 | 20800 |
| p (t-test) | | 0.78 | | 0.69 | | 0.57 |
| Min | 1370 | 111000 | 1370 | 111000 | 1370 | 140000 |
| Max | 520000 | 256000 | 520000 | 245000 | 520000 | 187000 |
| n (Samp) | 88 | 8 | 88 | 8 | 88 | 4 |
| n (Patient) | 88 | 8 | 88 | 8 | 88 | 4 |
| sCr only | | | | | | |
| Median | 181000 | 177000 | 181000 | 177000 | 181000 | 167000 |
| Average | 187000 | 188000 | 187000 | 181000 | 187000 | 165000 |
| Stdev | 75100 | 49800 | 75100 | 38000 | 75100 | 23700 |
| p (t-test) | | 0.98 | | 0.88 | | 0.61 |
| Min | 190 | 140000 | 190 | 140000 | 190 | 140000 |
| Max | 520000 | 256000 | 520000 | 230000 | 520000 | 187000 |
| n (Samp) | 164 | 4 | 164 | 4 | 164 | 3 |
| n (Patient) | 164 | 4 | 164 | 4 | 164 | 3 |
| UO only | | | | | | |
| Median | 180000 | 162000 | 180000 | 162000 | 180000 | 158000 |
| Average | 187000 | 166000 | 187000 | 166000 | 187000 | 158000 |
| Stdev | 85300 | 45100 | 85300 | 45100 | 85300 | 18300 |
| p (t-test) | | 0.56 | | 0.56 | | 0.56 |
| Min | 1080 | 111000 | 1080 | 111000 | 1080 | 140000 |
| Max | 520000 | 245000 | 520000 | 245000 | 520000 | 176000 |
| n (Samp) | 81 | 6 | 81 | 6 | 81 | 3 |
| n (Patient) | 81 | 6 | 81 | 6 | 81 | 3 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.47 | 0.50 | 0.41 | 0.47 | 0.48 | 0.41 | 0.39 | 0.38 | 0.36 |
| SE | 0.11 | 0.15 | 0.13 | 0.11 | 0.15 | 0.13 | 0.15 | 0.17 | 0.18 |
| p | 0.80 | 0.99 | 0.47 | 0.75 | 0.92 | 0.47 | 0.48 | 0.49 | 0.43 |
| nCohort 1 | 88 | 164 | 81 | 88 | 164 | 81 | 88 | 164 | 81 |
| nCohort 2 | 8 | 4 | 6 | 8 | 4 | 6 | 4 | 3 | 3 |
| Cutoff 1 | 158000 | 165000 | 139000 | 158000 | 165000 | 139000 | 158000 | 139000 | 139000 |
| Sens 1 | 75% | 75% | 83% | 75% | 75% | 83% | 75% | 100% | 100% |
| Spec 1 | 36% | 40% | 25% | 36% | 40% | 25% | 36% | 22% | 25% |
| Cutoff 2 | 139000 | 139000 | 139000 | 139000 | 139000 | 139000 | 139000 | 139000 | 139000 |
| Sens 2 | 88% | 100% | 83% | 88% | 100% | 83% | 100% | 100% | 100% |
| Spec 2 | 24% | 22% | 25% | 24% | 22% | 25% | 24% | 22% | 25% |
| Cutoff 3 | 107000 | 139000 | 107000 | 107000 | 139000 | 107000 | 139000 | 139000 | 139000 |
| Sens 3 | 100% | 100% | 100% | 100% | 100% | 100% | 100% | 100% | 100% |
| Spec 3 | 11% | 22% | 12% | 11% | 22% | 12% | 24% | 22% | 25% |
| Cutoff 4 | 216000 | 217000 | 214000 | 216000 | 217000 | 214000 | 216000 | 217000 | 214000 |
| Sens 4 | 25% | 25% | 17% | 25% | 25% | 17% | 0% | 0% | 0% |
| Spec 4 | 70% | 70% | 70% | 70% | 70% | 70% | 70% | 70% | 70% |
| Cutoff 5 | 227000 | 230000 | 227000 | 227000 | 230000 | 227000 | 227000 | 230000 | 227000 |
| Sens 5 | 25% | 25% | 17% | 25% | 0% | 17% | 0% | 0% | 0% |
| Spec 5 | 81% | 80% | 80% | 81% | 80% | 80% | 81% | 80% | 80% |
| Cutoff 6 | 272000 | 272000 | 258000 | 272000 | 272000 | 258000 | 272000 | 272000 | 258000 |
| Sens 6 | 0% | 0% | 0% | 0% | 0% | 0% | 0% | 0% | 0% |
| Spec 6 | 91% | 90% | 90% | 91% | 90% | 90% | 91% | 90% | 90% |
| OR Quart 2 | 0.48 | 1.0 | 0 | 0.48 | 1.0 | 0 | >1.0 | >1.0 | >0 |
| p Value | 0.56 | 1.0 | na | 0.56 | 1.0 | na | <0.98 | <0.99 | <na |
| 95% CI of | 0.040 | 0.060 | na | 0.040 | 0.060 | na | >0.062 | >0.062 | >na |
| OR Quart 2 | 5.7 | 17 | na | 5.7 | 17 | na | na | na | na |
| OR Quart 3 | 1.6 | 1.0 | 4.7 | 1.6 | 1.0 | 4.7 | >2.2 | >1.0 | >2.2 |
| p Value | 0.64 | 1.0 | 0.19 | 0.64 | 1.0 | 0.19 | <0.53 | <0.99 | <0.53 |
| 95% CI of | 0.24 | 0.060 | 0.48 | 0.24 | 0.060 | 0.48 | >0.18 | >0.062 | >0.19 |
| OR Quart 3 | 10 | 17 | 46 | 10 | 17 | 46 | na | na | na |
| OR Quart 4 | 1.0 | 1.0 | 1.0 | 1.0 | 1.0 | 1.0 | >1.0 | >1.0 | >1.0 |

TABLE 8-continued

Comparison of the maximum marker levels in EDTA samples collected from Cohort 1 (patients that did not progress beyond RIFLE stage 0) and the maximum values in EDTA samples collected from subjects between enrollment and 0, 24 hours, and 48 hours prior to reaching stage F in Cohort 2.

| p Value | 1.0 | 1.0 | 0.97 | 1.0 | 1.0 | 0.97 | <0.98 | <0.97 | <0.97 |
|---|---|---|---|---|---|---|---|---|---|
| 95% CI of | 0.13 | 0.060 | 0.061 | 0.13 | 0.060 | 0.061 | >0.062 | >0.064 | >0.061 |
| OR Quart 4 | 7.7 | 17 | 18 | 7.7 | 17 | 18 | na | na | na |

Tumor necrosis factor ligand superfamily member 10

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| sCr or UO | | | | | | |
| Median | 0.0228 | 0.0271 | 0.0228 | 0.0271 | 0.0228 | 0.0228 |
| Average | 11.3 | 3.14 | 11.3 | 3.14 | 11.3 | 2.39 |
| Stdev | 50.4 | 7.16 | 50.4 | 7.16 | 50.4 | 5.88 |
| p (t-test) | | 0.58 | | 0.58 | | 0.64 |
| Min | 0.0162 | 0.0162 | 0.0162 | 0.0162 | 0.0162 | 0.0162 |
| Max | 292 | 20.9 | 292 | 20.9 | 292 | 15.7 |
| n (Samp) | 69 | 12 | 69 | 12 | 69 | 7 |
| n (Patient) | 69 | 12 | 69 | 12 | 69 | 7 |
| sCr only | | | | | | |
| Median | 0.0313 | 0.0228 | 0.0313 | 0.0228 | 0.0313 | 0.0228 |
| Average | 9.00 | 2.64 | 9.00 | 2.64 | 9.00 | 5.25 |
| Stdev | 37.6 | 6.40 | 37.6 | 6.40 | 37.6 | 9.06 |
| p (t-test) | | 0.68 | | 0.68 | | 0.86 |
| Min | 0.0162 | 0.0162 | 0.0162 | 0.0162 | 0.0162 | 0.0162 |
| Max | 292 | 15.7 | 292 | 15.7 | 292 | 15.7 |
| n (Samp) | 138 | 6 | 138 | 6 | 138 | 3 |
| n (Patient) | 138 | 6 | 138 | 6 | 138 | 3 |
| UO only | | | | | | |
| Median | 0.0313 | 0.0271 | 0.0313 | 0.0271 | 0.0313 | 0.0228 |
| Average | 13.0 | 2.74 | 13.0 | 2.74 | 13.0 | 0.173 |
| Stdev | 51.4 | 7.33 | 51.4 | 7.33 | 51.4 | 0.367 |
| p (t-test) | | 0.58 | | 0.58 | | 0.55 |
| Min | 0.0162 | 0.0162 | 0.0162 | 0.0162 | 0.0162 | 0.0162 |
| Max | 292 | 20.9 | 292 | 20.9 | 292 | 0.921 |
| n (Samp) | 67 | 8 | 67 | 8 | 67 | 6 |
| n (Patient) | 67 | 8 | 67 | 8 | 67 | 6 |

|  | 0 hr prior to AKI stage | | | 24 hr prior to AKI stage | | | 48 hr prior to AKI stage | | |
|---|---|---|---|---|---|---|---|---|---|
|  | sCr or UO | sCr only | UO only | sCr or UO | sCr only | UO only | sCr or UO | sCr only | UO only |
| AUC | 0.50 | 0.37 | 0.44 | 0.50 | 0.37 | 0.44 | 0.48 | 0.41 | 0.35 |
| SE | 0.091 | 0.12 | 0.11 | 0.091 | 0.12 | 0.11 | 0.12 | 0.18 | 0.13 |
| p | 0.96 | 0.30 | 0.59 | 0.96 | 0.30 | 0.59 | 0.85 | 0.60 | 0.25 |
| nCohort 1 | 69 | 138 | 67 | 69 | 138 | 67 | 69 | 138 | 67 |
| nCohort 2 | 12 | 6 | 8 | 12 | 6 | 8 | 7 | 3 | 6 |
| Cutoff 1 | 0.0197 | 0.0205 | 0.0197 | 0.0197 | 0.0205 | 0.0197 | 0.0197 | 0 | 0.0197 |
| Sens 1 | 92% | 83% | 88% | 92% | 83% | 88% | 86% | 100% | 83% |
| Spec 1 | 17% | 14% | 12% | 17% | 14% | 12% | 17% | 0% | 12% |
| Cutoff 2 | 0.0197 | 0.0205 | 0.0197 | 0.0197 | 0.0205 | 0.0197 | 0.0197 | 0 | 0.0197 |
| Sens 2 | 92% | 83% | 88% | 92% | 83% | 88% | 86% | 100% | 83% |
| Spec 2 | 17% | 14% | 12% | 17% | 14% | 12% | 17% | 0% | 12% |
| Cutoff 3 | 0.0197 | 0 | 0 | 0.0197 | 0 | 0 | 0 | 0 | 0 |
| Sens 3 | 92% | 100% | 100% | 92% | 100% | 100% | 100% | 100% | 100% |
| Spec 3 | 17% | 0% | 0% | 17% | 0% | 0% | 0% | 0% | 0% |
| Cutoff 4 | 0.0392 | 0.921 | 0.0591 | 0.0392 | 0.921 | 0.0591 | 0.0392 | 0.921 | 0.0591 |
| Sens 4 | 25% | 17% | 25% | 25% | 17% | 25% | 29% | 33% | 17% |
| Spec 4 | 71% | 70% | 70% | 71% | 70% | 70% | 71% | 70% | 70% |
| Cutoff 5 | 2.12 | 3.82 | 3.20 | 2.12 | 3.82 | 3.20 | 2.12 | 3.82 | 3.20 |
| Sens 5 | 17% | 17% | 12% | 17% | 17% | 12% | 14% | 33% | 0% |
| Spec 5 | 81% | 80% | 81% | 81% | 80% | 81% | 81% | 80% | 81% |
| Cutoff 6 | 5.31 | 15.7 | 23.0 | 5.31 | 15.7 | 23.0 | 5.31 | 15.7 | 23.0 |
| Sens 6 | 17% | 0% | 0% | 17% | 0% | 0% | 14% | 0% | 0% |
| Spec 6 | 91% | 91% | 91% | 91% | 91% | 91% | 91% | 91% | 91% |
| OR Quart 2 | 6.3 | 0 | 2.1 | 6.3 | 0 | 2.1 | 0.47 | 0 | >2.4 |
| p Value | 0.11 | na | 0.55 | 0.11 | na | 0.55 | 0.55 | na | <0.50 |
| 95% CI of | 0.67 | na | 0.18 | 0.67 | na | 0.18 | 0.039 | na | >0.20 |
| OR Quart 2 | 60 | na | 26 | 60 | na | 26 | 5.7 | na | na |
| OR Quart 3 | 3.4 | 4.4 | 1.0 | 3.4 | 4.4 | 1.0 | 1.6 | 1.0 | >0 |
| p Value | 0.31 | 0.20 | 1.0 | 0.31 | 0.20 | 1.0 | 0.63 | 0.98 | <na |
| 95% CI of | 0.32 | 0.46 | 0.058 | 0.32 | 0.46 | 0.058 | 0.23 | 0.062 | >na |

TABLE 8-continued

Comparison of the maximum marker levels in EDTA samples collected from Cohort 1 (patients that did not progress beyond RIFLE stage 0) and the maximum values in EDTA samples collected from subjects between enrollment and 0, 24 hours, and 48 hours prior to reaching stage F in Cohort 2.

| | | | | | | | | | |
|---|---|---|---|---|---|---|---|---|---|
| OR Quart 3 | 35 | 41 | 17 | 35 | 41 | 17 | 11 | 17 | na |
| OR Quart 4 | 3.2 | 1.0 | 5.1 | 3.2 | 1.0 | 5.1 | 0.47 | 1.0 | >5.4 |
| p Value | 0.34 | 1.0 | 0.16 | 0.34 | 1.0 | 0.16 | 0.55 | 0.98 | <0.15 |
| 95% CI of | 0.30 | 0.060 | 0.52 | 0.30 | 0.060 | 0.52 | 0.039 | 0.062 | >0.55 |
| OR Quart 4 | 33 | 17 | 51 | 33 | 17 | 51 | 5.7 | 17 | na |

TABLE 9

Comparison of marker levels in urine samples collected from Cohort 1 (patients that did not progress beyond RIFLE stage 0, R, or I) and in urine samples collected from Cohort 2 (subjects who progress to RIFLE stage F) at 0, 24 hours, and 48 hours prior to the subject reaching RIFLE stage I.

Stromelysin-1:Metalloproteinase inhibitor 2 complex

| | 24 hr prior to AKI stage | |
|---|---|---|
| | Cohort 1 | Cohort 2 |
| sCr or UO | | |
| Median | 0.487 | 0.487 |
| Average | 177 | 40.1 |
| Stdev | 1320 | 100 |
| p (t-test) | | 0.79 |
| Min | 0.237 | 0.487 |
| Max | 13900 | 267 |
| n (Samp) | 113 | 7 |
| n (Patient) | 87 | 7 |
| sCr only | | |
| Median | 0.487 | 10.9 |
| Average | 171 | 181 |
| Stdev | 1290 | 303 |
| p (t-test) | | 0.99 |
| Min | 0.237 | 0.487 |
| Max | 13900 | 530 |
| n (Samp) | 118 | 3 |
| n (Patient) | 91 | 3 |
| UO only | | |
| Median | 0.237 | 0.487 |
| Average | 190 | 53.8 |
| Stdev | 1430 | 119 |
| p (t-test) | | 0.83 |
| Min | 0.237 | 0.487 |
| Max | 13900 | 267 |
| n (Samp) | 96 | 5 |
| n (Patient) | 74 | 5 |

| | 24 hr prior to AKI stage | | |
|---|---|---|---|
| | sCr or UO | sCr only | UO only |
| AUC | 0.71 | 0.81 | 0.73 |
| SE | 0.11 | 0.15 | 0.13 |
| p | 0.063 | 0.046 | 0.081 |
| nCohort 1 | 113 | 118 | 96 |
| nCohort 2 | 7 | 3 | 5 |
| Cutoff 1 | 0.237 | 0.237 | 0.237 |
| Sens 1 | 100% | 100% | 100% |
| Spec 1 | 45% | 43% | 52% |
| Cutoff 2 | 0.237 | 0.237 | 0.237 |
| Sens 2 | 100% | 100% | 100% |
| Spec 2 | 45% | 43% | 52% |
| Cutoff 3 | 0.237 | 0.237 | 0.237 |
| Sens 3 | 100% | 100% | 100% |
| Spec 3 | 45% | 43% | 52% |
| Cutoff 4 | 0.487 | 0.487 | 0.487 |
| Sens 4 | 29% | 67% | 20% |
| Spec 4 | 82% | 82% | 82% |
| Cutoff 5 | 0.487 | 0.487 | 0.487 |

TABLE 9-continued

Comparison of marker levels in urine samples collected from Cohort 1 (patients that did not progress beyond RIFLE stage 0, R, or I) and in urine samples collected from Cohort 2 (subjects who progress to RIFLE stage F) at 0, 24 hours, and 48 hours prior to the subject reaching RIFLE stage I.

| | | | |
|---|---|---|---|
| Sens 5 | 29% | 67% | 20% |
| Spec 5 | 82% | 82% | 82% |
| Cutoff 6 | 123 | 154 | 118 |
| Sens 6 | 14% | 33% | 20% |
| Spec 6 | 90% | 91% | 91% |
| OR Quart 2 | >6.0 | >1.0 | >0 |
| p Value | <0.11 | <0.98 | <na |
| 95% CI of | >0.66 | >0.062 | >na |
| OR Quart 2 | na | na | na |
| OR Quart 3 | >0 | >0 | >4.8 |
| p Value | <na | <na | <0.18 |
| 95% CI of | >na | >na | >0.49 |
| OR Quart 3 | na | na | na |
| OR Quart 4 | >2.1 | >2.1 | >1.0 |
| p Value | <0.54 | <0.56 | <1.0 |
| 95% CI of | >0.18 | >0.18 | >0.059 |
| OR Quart 4 | na | na | na |

Heat shock 70 kDa protein 1

| | 24 hr prior to AKI stage | |
|---|---|---|
| | Cohort 1 | Cohort 2 |
| sCr or UO | | |
| Median | 277 | 1420 |
| Average | 581 | 2850 |
| Stdev | 1100 | 4410 |
| p (t-test) | | 2.0E−4 |
| Min | 0.297 | 250 |
| Max | 7800 | 11800 |
| n (Samp) | 111 | 6 |
| n (Patient) | 86 | 6 |
| sCr only | | |
| Median | 289 | 1510 |
| Average | 686 | 1440 |
| Stdev | 1500 | 318 |
| p (t-test) | | 0.39 |
| Min | 0.297 | 1090 |
| Max | 11800 | 1710 |
| n (Samp) | 115 | 3 |
| n (Patient) | 89 | 3 |
| UO only | | |
| Median | 267 | 934 |
| Average | 617 | 3480 |
| Stdev | 1170 | 5560 |
| p (t-test) | | 3.5E−4 |
| Min | 0.297 | 250 |
| Max | 7800 | 11800 |
| n (Samp) | 96 | 4 |
| n (Patient) | 74 | 4 |

| | 24 hr prior to AKI stage | | |
|---|---|---|---|
| | sCr or UO | sCr only | UO only |
| AUC | 0.83 | 0.92 | 0.77 |
| SE | 0.10 | 0.11 | 0.14 |
| p | 0.0018 | 1.9E−4 | 0.055 |
| nCohort 1 | 111 | 115 | 96 |
| nCohort 2 | 6 | 3 | 4 |
| Cutoff 1 | 529 | 1040 | 529 |
| Sens 1 | 83% | 100% | 75% |
| Spec 1 | 70% | 89% | 70% |
| Cutoff 2 | 529 | 1040 | 246 |
| Sens 2 | 83% | 100% | 100% |
| Spec 2 | 70% | 89% | 49% |
| Cutoff 3 | 246 | 1040 | 246 |
| Sens 3 | 100% | 100% | 100% |
| Spec 3 | 48% | 89% | 49% |
| Cutoff 4 | 529 | 596 | 574 |
| Sens 4 | 83% | 100% | 50% |

TABLE 9-continued

Comparison of marker levels in urine samples collected from Cohort 1 (patients that did not progress beyond RIFLE stage 0, R, or I) and in urine samples collected from Cohort 2 (subjects who progress to RIFLE stage F) at 0, 24 hours, and 48 hours prior to the subject reaching RIFLE stage I.

| | | | |
|---|---|---|---|
| Spec 4 | 70% | 70% | 71% |
| Cutoff 5 | 770 | 782 | 782 |
| Sens 5 | 67% | 100% | 50% |
| Spec 5 | 80% | 80% | 80% |
| Cutoff 6 | 1040 | 1320 | 1340 |
| Sens 6 | 67% | 67% | 25% |
| Spec 6 | 90% | 91% | 91% |
| OR Quart 2 | >1.0 | >0 | >1.0 |
| p Value | <0.98 | <na | <0.98 |
| 95% CI of | >0.062 | >na | >0.062 |
| OR Quart 2 | na | na | na |
| OR Quart 3 | >1.0 | >0 | >1.0 |
| p Value | <0.98 | <na | <0.98 |
| 95% CI of | >0.062 | >na | >0.062 |
| OR Quart 3 | na | na | na |
| OR Quart 4 | >4.5 | >3.2 | >2.2 |
| p Value | <0.19 | <0.32 | <0.54 |
| 95% CI of | >0.47 | >0.32 | >0.18 |
| OR Quart 4 | na | na | na |

Insulin-like growth factor 1 receptor 24 hr prior to AKI stage

| | Cohort 1 | Cohort 2 |
|---|---|---|
| sCr or UO | | |
| Median | 0.0103 | 0.0103 |
| Average | 0.0227 | 0.0647 |
| Stdev | 0.0655 | 0.132 |
| p (t-test) | | 0.13 |
| Min | 0.000123 | 0.00862 |
| Max | 0.679 | 0.365 |
| n (Samp) | 112 | 7 |
| n (Patient) | 88 | 7 |
| sCr only | | |
| Median | 0.0103 | 0.0197 |
| Average | 0.0261 | 0.0160 |
| Stdev | 0.0718 | 0.00637 |
| p (t-test) | | 0.81 |
| Min | 0.000123 | 0.00862 |
| Max | 0.679 | 0.0197 |
| n (Samp) | 117 | 3 |
| n (Patient) | 92 | 3 |
| UO only | | |
| Median | 0.0103 | 0.0103 |
| Average | 0.0239 | 0.0849 |
| Stdev | 0.0705 | 0.157 |
| p (t-test) | | 0.083 |
| Min | 0.000123 | 0.0103 |
| Max | 0.679 | 0.365 |
| n (Samp) | 96 | 5 |
| n (Patient) | 76 | 5 |

24 hr prior to AKI stage

| | sCr or UO | sCr only | UO only |
|---|---|---|---|
| AUC | 0.61 | 0.57 | 0.65 |
| SE | 0.12 | 0.17 | 0.14 |
| p | 0.34 | 0.71 | 0.28 |
| nCohort 1 | 112 | 117 | 96 |
| nCohort 2 | 7 | 3 | 5 |
| Cutoff 1 | 0.00862 | 0.00573 | 0.00862 |
| Sens 1 | 86% | 100% | 100% |
| Spec 1 | 41% | 32% | 44% |
| Cutoff 2 | 0.00862 | 0.00573 | 0.00862 |
| Sens 2 | 86% | 100% | 100% |
| Spec 2 | 41% | 32% | 44% |
| Cutoff 3 | 0.00573 | 0.00573 | 0.00862 |
| Sens 3 | 100% | 100% | 100% |
| Spec 3 | 33% | 32% | 44% |

TABLE 9-continued

Comparison of marker levels in urine samples collected from Cohort 1 (patients that did not progress beyond RIFLE stage 0, R, or I) and in urine samples collected from Cohort 2 (subjects who progress to RIFLE stage F) at 0, 24 hours, and 48 hours prior to the subject reaching RIFLE stage I.

| | | | |
|---|---|---|---|
| Cutoff 4 | 0.0197 | 0.0211 | 0.0211 |
| Sens 4 | 29% | 0% | 40% |
| Spec 4 | 71% | 71% | 72% |
| Cutoff 5 | 0.0292 | 0.0292 | 0.0292 |
| Sens 5 | 14% | 0% | 20% |
| Spec 5 | 82% | 81% | 82% |
| Cutoff 6 | 0.0423 | 0.0423 | 0.0423 |
| Sens 6 | 14% | 0% | 20% |
| Spec 6 | 92% | 91% | 92% |
| OR Quart 2 | >4.5 | >1.0 | >1.0 |
| p Value | <0.19 | <0.98 | <0.98 |
| 95% CI of | >0.47 | >0.062 | >0.062 |
| OR Quart 2 | na | na | na |
| OR Quart 3 | >1.0 | >2.1 | >2.2 |
| p Value | <1.0 | <0.54 | <0.54 |
| 95% CI of | >0.060 | >0.18 | >0.18 |
| OR Quart 3 | na | na | na |
| OR Quart 4 | >2.1 | >0 | >2.1 |
| p Value | <0.56 | <na | <0.56 |
| 95% CI of | >0.18 | >na | >0.18 |
| OR Quart 4 | na | na | na |

Interstitial collagenase:Metalloproteinase inhibitor2 complex

| | 24 hr prior to AKI stage | |
|---|---|---|
| | Cohort 1 | Cohort 2 |
| sCr or UO | | |
| Median | 0.233 | 6.17 |
| Average | 152 | 50.7 |
| Stdev | 1510 | 110 |
| p (t-test) | | 0.86 |
| Min | 0.228 | 0.228 |
| Max | 16000 | 297 |
| n (Samp) | 113 | 7 |
| n (Patient) | 87 | 7 |
| sCr only | | |
| Median | 0.233 | 6.97 |
| Average | 149 | 12.2 |
| Stdev | 1470 | 15.3 |
| p (t-test) | | 0.87 |
| Min | 0.228 | 0.233 |
| Max | 16000 | 29.5 |
| n (Samp) | 118 | 3 |
| n (Patient) | 91 | 3 |
| UO only | | |
| Median | 0.233 | 6.17 |
| Average | 173 | 69.6 |
| Stdev | 1630 | 129 |
| p (t-test) | | 0.89 |
| Min | 0.228 | 0.228 |
| Max | 16000 | 297 |
| n (Samp) | 96 | 5 |
| n (Patient) | 74 | 5 |

| | 24 hr prior to AKI stage | | |
|---|---|---|---|
| | sCr or UO | sCr only | UO only |
| AUC | 0.66 | 0.79 | 0.62 |
| SE | 0.12 | 0.16 | 0.14 |
| p | 0.17 | 0.072 | 0.37 |
| nCohort 1 | 113 | 118 | 96 |
| nCohort 2 | 7 | 3 | 5 |
| Cutoff 1 | 0.228 | 0.228 | 0 |
| Sens 1 | 71% | 100% | 100% |
| Spec 1 | 38% | 39% | 0% |
| Cutoff 2 | 0 | 0.228 | 0 |
| Sens 2 | 100% | 100% | 100% |
| Spec 2 | 0% | 39% | 0% |
| Cutoff 3 | 0 | 0.228 | 0 |

TABLE 9-continued

Comparison of marker levels in urine samples collected from Cohort 1 (patients that did not progress beyond RIFLE stage 0, R, or I) and in urine samples collected from Cohort 2 (subjects who progress to RIFLE stage F) at 0, 24 hours, and 48 hours prior to the subject reaching RIFLE stage I.

| | | | |
|---|---|---|---|
| Sens 3 | 100% | 100% | 100% |
| Spec 3 | 0% | 39% | 0% |
| Cutoff 4 | 0.233 | 0.233 | 0.233 |
| Sens 4 | 57% | 67% | 60% |
| Spec 4 | 80% | 79% | 79% |
| Cutoff 5 | 1.26 | 1.35 | 1.26 |
| Sens 5 | 57% | 67% | 60% |
| Spec 5 | 81% | 81% | 80% |
| Cutoff 6 | 14.2 | 18.5 | 10.7 |
| Sens 6 | 29% | 33% | 40% |
| Spec 6 | 90% | 92% | 91% |
| OR Quart 2 | >2.1 | >0 | 0 |
| p Value | <0.54 | <na | na |
| 95% CI of | >0.18 | >na | na |
| OR Quart 2 | na | na | na |
| OR Quart 3 | >1.0 | >1.0 | 0 |
| p Value | <0.98 | <0.98 | na |
| 95% CI of | >0.062 | >0.062 | na |
| OR Quart 3 | na | na | na |
| OR Quart 4 | >4.6 | >2.1 | 1.5 |
| p Value | <0.18 | <0.56 | 0.67 |
| 95% CI of | >0.48 | >0.18 | 0.23 |
| OR Quart 4 | na | na | 9.8 |

72 kDa type IV collagenase:Metalloproteinase inhibitor 2 complex

| | 24 hr prior to AKI stage | |
|---|---|---|
| | Cohort 1 | Cohort 2 |
| sCr or UO | | |
| Median | 29.2 | 295 |
| Average | 793 | 2740 |
| Stdev | 2550 | 5880 |
| p (t-test) | | 0.081 |
| Min | 1.15 | 1.15 |
| Max | 16000 | 16000 |
| n (Samp) | 108 | 7 |
| n (Patient) | 86 | 7 |
| sCr only | | |
| Median | 30.3 | 527 |
| Average | 926 | 447 |
| Stdev | 2880 | 245 |
| p (t-test) | | 0.77 |
| Min | 1.15 | 171 |
| Max | 16000 | 642 |
| n (Samp) | 113 | 3 |
| n (Patient) | 90 | 3 |
| UO only | | |
| Median | 28.1 | 295 |
| Average | 868 | 3670 |
| Stdev | 2710 | 6930 |
| p (t-test) | | 0.044 |
| Min | 1.15 | 1.15 |
| Max | 16000 | 16000 |
| n (Samp) | 95 | 5 |
| n (Patient) | 76 | 5 |

| | 24 hr prior to AKI stage | | |
|---|---|---|---|
| | sCr or UO | sCr only | UO only |
| AUC | 0.70 | 0.74 | 0.67 |
| SE | 0.11 | 0.17 | 0.14 |
| p | 0.081 | 0.16 | 0.21 |
| nCohort 1 | 108 | 113 | 95 |
| nCohort 2 | 7 | 3 | 5 |
| Cutoff 1 | 234 | 164 | 234 |
| Sens 1 | 71% | 100% | 80% |
| Spec 1 | 71% | 65% | 69% |
| Cutoff 2 | 164 | 164 | 234 |
| Sens 2 | 86% | 100% | 80% |

TABLE 9-continued

Comparison of marker levels in urine samples collected from Cohort 1 (patients that did not progress beyond RIFLE stage 0, R, or I) and in urine samples collected from Cohort 2 (subjects who progress to RIFLE stage F) at 0, 24 hours, and 48 hours prior to the subject reaching RIFLE stage I.

| | | | |
|---|---|---|---|
| Spec 2 | 67% | 65% | 69% |
| Cutoff 3 | 0 | 164 | 0 |
| Sens 3 | 100% | 100% | 100% |
| Spec 3 | 0% | 65% | 0% |
| Cutoff 4 | 227 | 365 | 365 |
| Sens 4 | 71% | 67% | 40% |
| Spec 4 | 70% | 71% | 71% |
| Cutoff 5 | 595 | 656 | 595 |
| Sens 5 | 43% | 0% | 40% |
| Spec 5 | 81% | 81% | 80% |
| Cutoff 6 | 1700 | 1780 | 1700 |
| Sens 6 | 29% | 0% | 40% |
| Spec 6 | 91% | 90% | 91% |
| OR Quart 2 | 0 | >0 | 0 |
| p Value | na | <na | na |
| 95% CI of | na | >na | na |
| OR Quart 2 | na | na | na |
| OR Quart 3 | 3.1 | >1.0 | 2.1 |
| p Value | 0.34 | <0.98 | 0.56 |
| 95% CI of | 0.30 | >0.062 | 0.18 |
| OR Quart 3 | 32 | na | 25 |
| OR Quart 4 | 3.1 | >2.1 | 2.1 |
| p Value | 0.34 | <0.54 | 0.56 |
| 95% CI of | 0.30 | >0.18 | 0.18 |
| OR Quart 4 | 32 | na | 25 |

Neural cell adhesion molecule 1

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| sCr or UO | | | | | | |
| Median | 2720 | 3990 | 2720 | 2690 | 2720 | 2100 |
| Average | 3340 | 4390 | 3340 | 6270 | 3340 | 2870 |
| Stdev | 2880 | 3520 | 2880 | 11900 | 2880 | 2900 |
| p (t-test) | | 0.093 | | 5.4E−5 | | 0.60 |
| Min | 0.234 | 171 | 0.234 | 375 | 0.234 | 138 |
| Max | 48400 | 15000 | 48400 | 55700 | 48400 | 9700 |
| n (Samp) | 1261 | 22 | 1261 | 20 | 1261 | 10 |
| n (Patient) | 450 | 22 | 450 | 20 | 450 | 10 |
| sCr only | | | | | | |
| Median | 2780 | 2260 | 2780 | 3970 | 2780 | 3900 |
| Average | 3450 | 2670 | 3450 | 3650 | 3450 | 3740 |
| Stdev | 3260 | 2170 | 3260 | 2070 | 3260 | 2410 |
| p (t-test) | | 0.50 | | 0.90 | | 0.86 |
| Min | 0.234 | 171 | 0.234 | 1090 | 0.234 | 963 |
| Max | 55700 | 6800 | 55700 | 5590 | 55700 | 6210 |
| n (Samp) | 1325 | 8 | 1325 | 4 | 1325 | 4 |
| n (Patient) | 465 | 8 | 465 | 4 | 465 | 4 |
| UO only | | | | | | |
| Median | 2840 | 4560 | 2840 | 4560 | 2840 | 3280 |
| Average | 3410 | 6830 | 3410 | 8190 | 3410 | 3570 |
| Stdev | 2840 | 6750 | 2840 | 12900 | 2840 | 3190 |
| p (t-test) | | 1.4E−5 | | 3.0E−10 | | 0.88 |
| Min | 0.234 | 416 | 0.234 | 375 | 0.234 | 346 |
| Max | 48400 | 26600 | 48400 | 55700 | 48400 | 9700 |
| n (Samp) | 1116 | 14 | 1116 | 19 | 1116 | 7 |
| n (Patient) | 364 | 14 | 364 | 19 | 364 | 7 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.59 | 0.42 | 0.70 | 0.55 | 0.58 | 0.62 | 0.40 | 0.57 | 0.48 |
| SE | 0.064 | 0.11 | 0.079 | 0.067 | 0.15 | 0.069 | 0.095 | 0.15 | 0.11 |
| p | 0.16 | 0.44 | 0.010 | 0.45 | 0.59 | 0.084 | 0.32 | 0.65 | 0.88 |
| nCohort 1 | 1261 | 1325 | 1116 | 1261 | 1325 | 1116 | 1261 | 1325 | 1116 |
| nCohort 2 | 22 | 8 | 14 | 20 | 4 | 19 | 10 | 4 | 7 |
| Cutoff 1 | 2200 | 1340 | 3860 | 2030 | 2870 | 2080 | 1180 | 2560 | 1650 |
| Sens 1 | 73% | 75% | 71% | 70% | 75% | 74% | 70% | 75% | 71% |

TABLE 9-continued

Comparison of marker levels in urine samples collected from Cohort 1 (patients that did not progress beyond RIFLE stage 0, R, or I) and in urine samples collected from Cohort 2 (subjects who progress to RIFLE stage F) at 0, 24 hours, and 48 hours prior to the subject reaching RIFLE stage I.

| | | | | | | | | | |
|---|---|---|---|---|---|---|---|---|---|
| Spec 1 | 39% | 19% | 67% | 35% | 52% | 34% | 16% | 46% | 24% |
| Cutoff 2 | 1340 | 623 | 2310 | 1740 | 1090 | 1740 | 957 | 957 | 1180 |
| Sens 2 | 82% | 88% | 86% | 80% | 100% | 84% | 80% | 100% | 86% |
| Spec 2 | 20% | 5% | 39% | 28% | 14% | 26% | 11% | 10% | 14% |
| Cutoff 3 | 623 | 169 | 1490 | 1110 | 1090 | 1110 | 341 | 957 | 325 |
| Sens 3 | 91% | 100% | 93% | 90% | 100% | 95% | 90% | 100% | 100% |
| Spec 3 | 5% | 0% | 21% | 15% | 14% | 13% | 1% | 10% | 1% |
| Cutoff 4 | 3940 | 4040 | 4060 | 3940 | 4040 | 4060 | 3940 | 4040 | 4060 |
| Sens 4 | 55% | 12% | 57% | 45% | 50% | 58% | 20% | 50% | 29% |
| Spec 4 | 70% | 70% | 70% | 70% | 70% | 70% | 70% | 70% | 70% |
| Cutoff 5 | 4850 | 4930 | 4910 | 4850 | 4930 | 4910 | 4850 | 4930 | 4910 |
| Sens 5 | 41% | 12% | 43% | 35% | 50% | 42% | 20% | 50% | 29% |
| Spec 5 | 80% | 80% | 80% | 80% | 80% | 80% | 80% | 80% | 80% |
| Cutoff 6 | 6440 | 6520 | 6470 | 6440 | 6520 | 6470 | 6440 | 6520 | 6470 |
| Sens 6 | 23% | 12% | 29% | 20% | 0% | 32% | 10% | 0% | 14% |
| Spec 6 | 90% | 90% | 90% | 90% | 90% | 90% | 90% | 90% | 90% |
| OR Quart 2 | 0.33 | 2.0 | 0.50 | 1.5 | 0 | 1.7 | 1.0 | 1.0 | 1.0 |
| p Value | 0.17 | 0.57 | 0.57 | 0.53 | na | 0.48 | 1.0 | 1.0 | 1.0 |
| 95% CI of | 0.066 | 0.18 | 0.045 | 0.42 | na | 0.40 | 0.14 | 0.062 | 0.14 |
| OR Quart 2 | 1.6 | 22 | 5.5 | 5.4 | na | 7.1 | 7.1 | 16 | 7.1 |
| OR Quart 3 | 0.83 | 2.0 | 2.0 | 0.50 | 1.0 | 0.33 | 1.0 | 0 | 0 |
| p Value | 0.76 | 0.57 | 0.42 | 0.42 | 1.0 | 0.34 | 1.0 | na | na |
| 95% CI of | 0.25 | 0.18 | 0.37 | 0.090 | 0.062 | 0.034 | 0.14 | na | na |
| OR Quart 3 | 2.7 | 22 | 11 | 2.7 | 16 | 3.2 | 7.1 | na | na |
| OR Quart 4 | 1.5 | 3.0 | 3.6 | 2.0 | 2.0 | 3.4 | 2.0 | 2.0 | 1.5 |
| p Value | 0.44 | 0.34 | 0.12 | 0.26 | 0.57 | 0.065 | 0.42 | 0.57 | 0.65 |
| 95% CI of | 0.53 | 0.31 | 0.73 | 0.60 | 0.18 | 0.93 | 0.37 | 0.18 | 0.25 |
| OR Quart 4 | 4.3 | 29 | 17 | 6.8 | 22 | 13 | 11 | 22 | 9.1 |

Tumor necrosis factor ligand superfamily member 10

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| sCr or UO | | | | | | |
| Median | 0.0285 | 0.0287 | 0.0285 | 0.0387 | 0.0285 | 0.0287 |
| Average | 2.55 | 7.89 | 2.55 | 9.52 | 2.55 | 0.125 |
| Stdev | 9.75 | 24.9 | 9.75 | 30.0 | 9.75 | 0.289 |
| p (t-test) | | 0.017 | | 0.0029 | | 0.46 |
| Min | 0.0110 | 0.0139 | 0.0110 | 0.0110 | 0.0110 | 0.0205 |
| Max | 159 | 113 | 159 | 134 | 159 | 0.894 |
| n (Samp) | 1234 | 21 | 1234 | 20 | 1234 | 9 |
| n (Patient) | 456 | 21 | 456 | 20 | 456 | 9 |
| sCr only | | | | | | |
| Median | 0.0285 | 0.0243 | 0.0285 | 1.57 | 0.0285 | 0.0287 |
| Average | 2.78 | 1.22 | 2.78 | 1.66 | 2.78 | 0.0300 |
| Stdev | 10.9 | 3.38 | 10.9 | 1.89 | 10.9 | 0.00805 |
| p (t-test) | | 0.69 | | 0.84 | | 0.62 |
| Min | 0.0110 | 0.0139 | 0.0110 | 0.0227 | 0.0110 | 0.0217 |
| Max | 159 | 9.58 | 159 | 3.47 | 159 | 0.0410 |
| n (Samp) | 1294 | 8 | 1294 | 4 | 1294 | 4 |
| n (Patient) | 471 | 8 | 471 | 4 | 471 | 4 |
| UO only | | | | | | |
| Median | 0.0285 | 0.0311 | 0.0285 | 0.0410 | 0.0285 | 0.0363 |
| Average | 2.57 | 13.5 | 2.57 | 15.4 | 2.57 | 0.153 |
| Stdev | 9.97 | 27.1 | 9.97 | 38.8 | 9.97 | 0.327 |
| p (t-test) | | 8.5E−5 | | 6.1E−7 | | 0.52 |
| Min | 0.0110 | 0.0139 | 0.0110 | 0.0110 | 0.0110 | 0.0205 |
| Max | 159 | 79.6 | 159 | 134 | 159 | 0.894 |
| n (Samp) | 1092 | 14 | 1092 | 19 | 1092 | 7 |
| n (Patient) | 372 | 14 | 372 | 19 | 372 | 7 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.57 | 0.45 | 0.59 | 0.61 | 0.58 | 0.61 | 0.46 | 0.49 | 0.48 |
| SE | 0.066 | 0.11 | 0.081 | 0.068 | 0.15 | 0.069 | 0.099 | 0.15 | 0.11 |
| p | 0.30 | 0.61 | 0.25 | 0.12 | 0.59 | 0.098 | 0.72 | 0.95 | 0.85 |
| nCohort 1 | 1234 | 1294 | 1092 | 1234 | 1294 | 1092 | 1234 | 1294 | 1092 |

TABLE 9-continued

Comparison of marker levels in urine samples collected from Cohort 1 (patients that did not progress beyond RIFLE stage 0, R, or I) and in urine samples collected from Cohort 2 (subjects who progress to RIFLE stage F) at 0, 24 hours, and 48 hours prior to the subject reaching RIFLE stage I.

| nCohort 2 | 21 | 8 | 14 | 20 | 4 | 19 | 9 | 4 | 7 |
|---|---|---|---|---|---|---|---|---|---|
| Cutoff 1 | 0.0247 | 0.0239 | 0.0285 | 0.0247 | 0.0239 | 0.0247 | 0.0217 | 0.0285 | 0.0237 |
| Sens 1 | 76% | 88% | 71% | 70% | 75% | 74% | 78% | 75% | 71% |
| Spec 1 | 41% | 33% | 51% | 41% | 33% | 40% | 22% | 52% | 28% |
| Cutoff 2 | 0.0239 | 0.0239 | 0.0247 | 0.0217 | 0.0217 | 0.0205 | 0.0205 | 0.0205 | 0.0217 |
| Sens 2 | 81% | 88% | 86% | 80% | 100% | 89% | 89% | 100% | 86% |
| Spec 2 | 37% | 33% | 40% | 22% | 22% | 17% | 19% | 18% | 21% |
| Cutoff 3 | 0.0239 | 0.0110 | 0.0110 | 0.0205 | 0.0217 | 0.0162 | 0.0162 | 0.0205 | 0.0162 |
| Sens 3 | 90% | 100% | 100% | 90% | 100% | 95% | 100% | 100% | 100% |
| Spec 3 | 34% | 3% | 3% | 19% | 22% | 14% | 15% | 18% | 14% |
| Cutoff 4 | 0.0439 | 0.0410 | 0.0439 | 0.0439 | 0.0410 | 0.0439 | 0.0439 | 0.0410 | 0.0439 |
| Sens 4 | 24% | 12% | 29% | 45% | 50% | 47% | 11% | 0% | 14% |
| Spec 4 | 74% | 70% | 74% | 74% | 70% | 74% | 74% | 70% | 74% |
| Cutoff 5 | 0.0597 | 0.0597 | 0.0597 | 0.0597 | 0.0597 | 0.0597 | 0.0597 | 0.0597 | 0.0597 |
| Sens 5 | 24% | 12% | 29% | 45% | 50% | 47% | 11% | 0% | 14% |
| Spec 5 | 80% | 80% | 81% | 80% | 80% | 81% | 80% | 80% | 81% |
| Cutoff 6 | 5.80 | 5.86 | 5.80 | 5.80 | 5.86 | 5.80 | 5.80 | 5.86 | 5.80 |
| Sens 6 | 19% | 12% | 29% | 15% | 0% | 16% | 0% | 0% | 0% |
| Spec 6 | 90% | 90% | 90% | 90% | 90% | 90% | 90% | 90% | 90% |
| OR Quart 2 | 3.0 | 1.0 | 1.00 | 0.39 | 1.00 | 0.20 | 4.0 | >3.0 | 3.0 |
| p Value | 0.18 | 1.00 | 1.00 | 0.27 | 1.00 | 0.14 | 0.21 | <0.34 | 0.34 |
| 95% CI of | 0.61 | 0.062 | 0.14 | 0.076 | 0.062 | 0.023 | 0.45 | >0.31 | 0.31 |
| OR Quart 2 | 15 | 16 | 7.1 | 2.1 | 16 | 1.7 | 36 | na | 29 |
| OR Quart 3 | 4.1 | 5.1 | 3.0 | 0.80 | 0 | 0.79 | 2.0 | >0 | 1.0 |
| p Value | 0.078 | 0.14 | 0.18 | 0.74 | na | 0.73 | 0.57 | <na | 1.0 |
| 95% CI of | 0.86 | 0.59 | 0.61 | 0.21 | na | 0.21 | 0.18 | >na | 0.062 |
| OR Quart 3 | 19 | 44 | 15 | 3.0 | na | 3.0 | 22 | na | 16 |
| OR Quart 4 | 2.5 | 1.0 | 2.0 | 1.8 | 2.0 | 1.8 | 2.0 | >1.0 | 2.0 |
| p Value | 0.27 | 1.00 | 0.42 | 0.29 | 0.57 | 0.29 | 0.57 | <1.00 | 0.57 |
| 95% CI of | 0.48 | 0.062 | 0.36 | 0.60 | 0.18 | 0.60 | 0.18 | >0.063 | 0.18 |
| OR Quart 4 | 13 | 16 | 11 | 5.5 | 22 | 5.5 | 22 | na | 22 |

Myeloid differentiation primary response protein MyD88

| | 0 hr prior to AKI stage | | 24 hr prior to AKI stage | |
|---|---|---|---|---|
| sCr or UO | Cohort 1 | Cohort 2 | Cohort 1 | Cohort 2 |
| Median | 0.000533 | 0.000146 | 0.000533 | 0.000165 |
| Average | 0.0162 | 0.000146 | 0.0162 | 0.00319 |
| Stdev | 0.0567 | 2.76E−5 | 0.0567 | 0.00825 |
| p (t-test) | | 0.69 | | 0.52 |
| Min | 0.000126 | 0.000126 | 0.000126 | 0.000165 |
| Max | 0.671 | 0.000165 | 0.671 | 0.0236 |
| n (Samp) | 247 | 2 | 247 | 8 |
| n (Patient) | 141 | 2 | 141 | 8 |

| | 24 hr prior to AKI stage | |
|---|---|---|
| | Cohort 1 | Cohort 2 |
| sCr only | | |
| Median | 0.000533 | 0.000165 |
| Average | 0.0159 | 0.000288 |
| Stdev | 0.0562 | 0.000213 |
| p (t-test) | | 0.63 |
| Min | 0.000126 | 0.000165 |
| Max | 0.671 | 0.000533 |
| n (Samp) | 252 | 3 |
| n (Patient) | 145 | 3 |
| UO only | | |
| Median | 0.000533 | 0.000165 |
| Average | 0.0141 | 0.000239 |
| Stdev | 0.0390 | 0.000165 |
| p (t-test) | | 0.43 |
| Min | 0.000126 | 0.000165 |
| Max | 0.371 | 0.000533 |
| n (Samp) | 233 | 5 |
| n (Patient) | 128 | 5 |

TABLE 9-continued

Comparison of marker levels in urine samples collected from Cohort 1 (patients that did not progress beyond RIFLE stage 0, R, or I) and in urine samples collected from Cohort 2 (subjects who progress to RIFLE stage F) at 0, 24 hours, and 48 hours prior to the subject reaching RIFLE stage I.

| | 0 hr prior to AKI stage | | | 24 hr prior to AKI stage | | |
|---|---|---|---|---|---|---|
| | sCr or UO | sCr only | UO only | sCr or UO | sCr only | UO only |
| AUC | 0.13 | nd | nd | 0.38 | 0.33 | 0.28 |
| SE | 0.16 | nd | nd | 0.11 | 0.17 | 0.13 |
| p | 0.027 | nd | nd | 0.25 | 0.33 | 0.093 |
| nCohort 1 | 247 | nd | nd | 247 | 252 | 233 |
| nCohort 2 | 2 | nd | nd | 8 | 3 | 5 |
| Cutoff 1 | 0 | nd | nd | 0.000126 | 0.000126 | 0.000126 |
| Sens 1 | 100% | nd | nd | 100% | 100% | 100% |
| Spec 1 | 0% | nd | nd | 11% | 10% | 12% |
| Cutoff 2 | 0 | nd | nd | 0.000126 | 0.000126 | 0.000126 |
| Sens 2 | 100% | nd | nd | 100% | 100% | 100% |
| Spec 2 | 0% | nd | nd | 11% | 10% | 12% |
| Cutoff 3 | 0 | nd | nd | 0.000126 | 0.000126 | 0.000126 |
| Sens 3 | 100% | nd | nd | 100% | 100% | 100% |
| Spec 3 | 0% | nd | nd | 11% | 10% | 12% |
| Cutoff 4 | 0.00247 | nd | nd | 0.00247 | 0.00237 | 0.00616 |
| Sens 4 | 0% | nd | nd | 12% | 0% | 0% |
| Spec 4 | 70% | nd | nd | 70% | 70% | 71% |
| Cutoff 5 | 0.0184 | nd | nd | 0.0184 | 0.0184 | 0.0190 |
| Sens 5 | 0% | nd | nd | 12% | 0% | 0% |
| Spec 5 | 80% | nd | nd | 80% | 81% | 80% |
| Cutoff 6 | 0.0393 | nd | nd | 0.0393 | 0.0387 | 0.0387 |
| Sens 6 | 0% | nd | nd | 0% | 0% | 0% |
| Spec 6 | 90% | nd | nd | 90% | 90% | 90% |
| OR Quart 2 | >0 | nd | nd | 2.0 | >0 | >1.0 |
| p Value | <na | nd | nd | 0.57 | <na | <0.98 |
| 95% CI of | >na | nd | nd | 0.18 | >na | >0.063 |
| OR Quart 2 | na | nd | nd | 23 | na | na |
| OR Quart 3 | >0 | nd | nd | 5.3 | >3.1 | >0 |
| p Value | <na | nd | nd | 0.13 | <0.33 | <na |
| 95% CI of | >na | nd | nd | 0.61 | >0.32 | >na |
| OR Quart 3 | na | nd | nd | 47 | na | na |
| OR Quart 4 | >2.1 | nd | nd | 0 | >0 | >4.4 |
| p Value | <0.55 | nd | nd | na | <na | <0.19 |
| 95% CI of | >0.19 | nd | nd | na | >na | >0.47 |
| OR Quart 4 | na | nd | nd | na | na | na |

TABLE 10

Comparison of marker levels in EDTA samples collected from Cohort 1 (patients that did not progress beyond RIFLE stage 0, R, or I) and in EDTA samples collected from Cohort 2 (subjects who progress to RIFLE stage F) at 0, 24 hours, and 48 hours prior to the subject reaching RIFLE stage I.

| Heat shock 70 kDa protein 1 | | |
|---|---|---|
| | 24 hr prior to AKI stage | |
| | Cohort 1 | Cohort 2 |
| sCr or UO | | |
| Median | 905 | 1560 |
| Average | 1560 | 1560 |
| Stdev | 2100 | 1020 |
| p (t-test) | | 1.00 |
| Min | 0.288 | 840 |
| Max | 10700 | 2280 |
| n (Samp) | 129 | 2 |
| n (Patient) | 106 | 2 |
| UO only | | |
| Median | 929 | 1560 |
| Average | 1550 | 1560 |
| Stdev | 2080 | 1020 |
| p (t-test) | | 1.00 |
| Min | 0.288 | 840 |

TABLE 10-continued

Comparison of marker levels in EDTA samples collected from Cohort 1
(patients that did not progress beyond RIFLE stage 0, R, or I) and in EDTA samples
collected from Cohort 2 (subjects who progress to RIFLE stage F) at 0, 24 hours,
and 48 hours prior to the subject reaching RIFLE stage I.

|  | Max | 10700 |  | 2280 |
|---|---|---|---|---|
|  | n (Samp) | 113 |  | 2 |
|  | n (Patient) | 90 |  | 2 |

| | 24 hr prior to AKI stage | | |
|---|---|---|---|
| | sCr or UO | sCr only | UO only |
| AUC | 0.64 | nd | 0.64 |
| SE | 0.21 | nd | 0.21 |
| p | 0.51 | nd | 0.52 |
| nCohort 1 | 129 | nd | 113 |
| nCohort 2 | 2 | nd | 2 |
| Cutoff 1 | 837 | nd | 837 |
| Sens 1 | 100% | nd | 100% |
| Spec 1 | 49% | nd | 49% |
| Cutoff 2 | 837 | nd | 837 |
| Sens 2 | 100% | nd | 100% |
| Spec 2 | 49% | nd | 49% |
| Cutoff 3 | 837 | nd | 837 |
| Sens 3 | 100% | nd | 100% |
| Spec 3 | 49% | nd | 49% |
| Cutoff 4 | 1560 | nd | 1560 |
| Sens 4 | 50% | nd | 50% |
| Spec 4 | 71% | nd | 71% |
| Cutoff 5 | 2550 | nd | 2550 |
| Sens 5 | 0% | nd | 0% |
| Spec 5 | 81% | nd | 81% |
| Cutoff 6 | 3630 | nd | 3540 |
| Sens 6 | 0% | nd | 0% |
| Spec 6 | 91% | nd | 90% |
| OR Quart 2 | >1.0 | nd | >1.0 |
| p Value | <1.0 | nd | <1.0 |
| 95% CI of | >0.060 | nd | >0.060 |
| OR Quart 2 | na | nd | na |
| OR Quart 3 | >0 | nd | >0 |
| p Value | <na | nd | <na |
| 95% CI of | >na | nd | >na |
| OR Quart 3 | na | nd | na |
| OR Quart 4 | >1.0 | nd | >1.0 |
| p Value | <1.0 | nd | <1.0 |
| 95% CI of | >0.060 | nd | >0.060 |
| OR Quart 4 | na | nd | na |

| | Insulin-like growth factor 1 receptor | | | | | |
|---|---|---|---|---|---|---|
| | 0 hr prior to AKI stage | | 24 hr prior to AKI stage | | 48 hr prior to AKI stage | |
| | Cohort 1 | Cohort 2 | Cohort 1 | Cohort 2 | Cohort 1 | Cohort 2 |
| sCr or UO | | | | | | |
| Median | 0.0484 | 0.0490 | 0.0484 | 0.0644 | 0.0484 | 0.0214 |
| Average | 0.521 | 0.0490 | 0.521 | 0.0732 | 0.521 | 0.0337 |
| Stdev | 2.80 | 0.0562 | 2.80 | 0.0681 | 2.80 | 0.0410 |
| p (t-test) | | 0.81 | | 0.75 | | 0.76 |
| Min | 9.84E−5 | 0.00927 | 9.84E−5 | 0.000211 | 9.84E−5 | 0.000211 |
| Max | 21.0 | 0.0888 | 21.0 | 0.164 | 21.0 | 0.0795 |
| n (Samp) | 229 | 2 | 229 | 4 | 229 | 3 |
| n (Patient) | 148 | 2 | 148 | 4 | 148 | 3 |
| UO only | | | | | | |
| Median | nd | nd | 0.0520 | 0.0319 | 0.0520 | 0.0108 |
| Average | nd | nd | 0.336 | 0.0570 | 0.336 | 0.0108 |
| Stdev | nd | nd | 2.14 | 0.0752 | 2.14 | 0.0150 |
| p (t-test) | nd | nd | | 0.80 | | 0.83 |
| Min | nd | nd | 0.000172 | 0.000211 | 0.000172 | 0.000211 |
| Max | nd | nd | 21.0 | 0.164 | 21.0 | 0.0214 |
| n (Samp) | nd | nd | 196 | 4 | 196 | 2 |
| n (Patient) | nd | nd | 124 | 4 | 124 | 2 |

TABLE 10-continued

Comparison of marker levels in EDTA samples collected from Cohort 1
(patients that did not progress beyond RIFLE stage 0, R, or I) and in EDTA samples
collected from Cohort 2 (subjects who progress to RIFLE stage F) at 0, 24 hours,
and 48 hours prior to the subject reaching RIFLE stage I.

|  | 0 hr prior to AKI stage | | | 24 hr prior to AKI stage | | | 48 hr prior to AKI stage | | |
| --- | --- | --- | --- | --- | --- | --- | --- | --- | --- |
|  | sCr or UO | sCr only | UO only | sCr or UO | sCr only | UO only | sCr or UO | sCr only | UO only |
| AUC | 0.46 | nd | nd | 0.56 | nd | 0.39 | 0.33 | nd | 0.11 |
| SE | 0.21 | nd | nd | 0.15 | nd | 0.15 | 0.17 | nd | 0.15 |
| p | 0.83 | nd | nd | 0.71 | nd | 0.47 | 0.32 | nd | 0.010 |
| nCohort 1 | 229 | nd | nd | 229 | nd | 196 | 229 | nd | 196 |
| nCohort 2 | 2 | nd | nd | 4 | nd | 4 | 3 | nd | 2 |
| Cutoff 1 | 0.00767 | nd | nd | 0.0535 | nd | 0.00497 | 0.000208 | nd | 0.000208 |
| Sens 1 | 100% | nd | nd | 75% | nd | 75% | 100% | nd | 100% |
| Spec 1 | 10% | nd | nd | 55% | nd | 9% | 3% | nd | 3% |
| Cutoff 2 | 0.00767 | nd | nd | 0.000208 | nd | 0.000208 | 0.000208 | nd | 0.000208 |
| Sens 2 | 100% | nd | nd | 100% | nd | 100% | 100% | nd | 100% |
| Spec 2 | 10% | nd | nd | 3% | nd | 3% | 3% | nd | 3% |
| Cutoff 3 | 0.00767 | nd | nd | 0.000208 | nd | 0.000208 | 0.000208 | nd | 0.000208 |
| Sens 3 | 100% | nd | nd | 100% | nd | 100% | 100% | nd | 100% |
| Spec 3 | 10% | nd | nd | 3% | nd | 3% | 3% | nd | 3% |
| Cutoff 4 | 0.0699 | nd | nd | 0.0699 | nd | 0.0769 | 0.0699 | nd | 0.0769 |
| Sens 4 | 50% | nd | nd | 50% | nd | 25% | 33% | nd | 0% |
| Spec 4 | 70% | nd | nd | 70% | nd | 70% | 70% | nd | 70% |
| Cutoff 5 | 0.0888 | nd | nd | 0.0888 | nd | 0.0888 | 0.0888 | nd | 0.0888 |
| Sens 5 | 0% | nd | nd | 25% | nd | 25% | 0% | nd | 0% |
| Spec 5 | 81% | nd | nd | 81% | nd | 81% | 81% | nd | 81% |
| Cutoff 6 | 0.135 | nd | nd | 0.135 | nd | 0.135 | 0.135 | nd | 0.135 |
| Sens 6 | 0% | nd | nd | 25% | nd | 25% | 0% | nd | 0% |
| Spec 6 | 90% | nd | nd | 90% | nd | 90% | 90% | nd | 90% |
| OR Quart 2 | 0 | nd | nd | 0 | nd | 1.0 | >1.0 | nd | >0 |
| p Value | na | nd | nd | na | nd | 1.0 | <0.99 | nd | <na |
| 95% CI of | na | nd | nd | na | nd | 0.061 | >0.062 | nd | >na |
| OR Quart 2 | na | nd | nd | na | nd | 16 | na | nd | na |
| OR Quart 3 | 0 | nd | nd | 2.0 | nd | 0 | >0 | nd | >0 |
| p Value | na | nd | nd | 0.57 | nd | na | <na | nd | <na |
| 95% CI of | na | nd | nd | 0.18 | nd | na | >na | nd | >na |
| OR Quart 3 | na | nd | nd | 23 | nd | na | na | nd | na |
| OR Quart 4 | 1.0 | nd | nd | 0.98 | nd | 2.0 | >2.1 | nd | >2.1 |
| p Value | 0.99 | nd | nd | 0.99 | nd | 0.57 | <0.56 | nd | <0.54 |
| 95% CI of | 0.062 | nd | nd | 0.060 | nd | 0.18 | >0.18 | nd | >0.19 |
| OR Quart 4 | 17 | nd | nd | 16 | nd | 23 | na | nd | na |

Neural cell adhesion molecule 1

|  | 0 hr prior to AKI stage | | 24 hr prior to AKI stage | | 48 hr prior to AKI stage | |
| --- | --- | --- | --- | --- | --- | --- |
| sCr or UO | Cohort 1 | Cohort 2 | Cohort 1 | Cohort 2 | Cohort 1 | Cohort 2 |
| Median | 181000 | 111000 | 181000 | 166000 | 181000 | 162000 |
| Average | 186000 | 154000 | 186000 | 177000 | 186000 | 163000 |
| Stdev | 72800 | 88700 | 72800 | 50000 | 72800 | 22700 |
| p (t-test) |  | 0.45 |  | 0.76 |  | 0.52 |
| Min | 190 | 96200 | 190 | 125000 | 190 | 140000 |
| Max | 520000 | 256000 | 520000 | 245000 | 520000 | 187000 |
| n (Samp) | 369 | 3 | 369 | 6 | 369 | 4 |
| n (Patient) | 201 | 3 | 201 | 6 | 201 | 4 |

|  | 48 hr prior to AKI stage | |
| --- | --- | --- |
| sCr only | Cohort 1 | Cohort 2 |
| Median | 181000 | 154000 |
| Average | 186000 | 154000 |
| Stdev | 72400 | 19300 |
| p (t-test) |  | 0.53 |
| Min | 190 | 140000 |
| Max | 520000 | 167000 |
| n (Samp) | 376 | 2 |
| n (Patient) | 205 | 2 |

TABLE 10-continued

Comparison of marker levels in EDTA samples collected from Cohort 1
(patients that did not progress beyond RIFLE stage 0, R, or I) and in EDTA samples
collected from Cohort 2 (subjects who progress to RIFLE stage F) at 0, 24 hours,
and 48 hours prior to the subject reaching RIFLE stage I.

| UO only | 24 hr prior to AKI stage | | 48 hr prior to AKI stage | |
|---|---|---|---|---|
| | Cohort 1 | Cohort 2 | Cohort 1 | Cohort 2 |
| Median | 180000 | 165000 | 180000 | 162000 |
| Average | 183000 | 164000 | 183000 | 162000 |
| Stdev | 70100 | 51300 | 70100 | 20600 |
| p (t-test) | | 0.55 | | 0.68 |
| Min | 190 | 111000 | 190 | 147000 |
| Max | 520000 | 245000 | 520000 | 176000 |
| n (Samp) | 339 | 5 | 339 | 2 |
| n (Patient) | 178 | 5 | 178 | 2 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.35 | nd | nd | 0.47 | nd | 0.40 | 0.38 | 0.32 | 0.39 |
| SE | 0.17 | nd | nd | 0.12 | nd | 0.14 | 0.15 | 0.21 | 0.21 |
| p | 0.39 | nd | nd | 0.79 | nd | 0.48 | 0.43 | 0.40 | 0.60 |
| nCohort 1 | 369 | nd | nd | 369 | nd | 339 | 369 | 376 | 339 |
| nCohort 2 | 3 | nd | nd | 6 | nd | 5 | 4 | 2 | 2 |
| Cutoff 1 | 95600 | nd | nd | 131000 | nd | 130000 | 147000 | 140000 | 147000 |
| Sens 1 | 100% | nd | nd | 83% | nd | 80% | 75% | 100% | 100% |
| Spec 1 | 7% | nd | nd | 20% | nd | 22% | 28% | 24% | 30% |
| Cutoff 2 | 95600 | nd | nd | 131000 | nd | 130000 | 140000 | 140000 | 147000 |
| Sens 2 | 100% | nd | nd | 83% | nd | 80% | 100% | 100% | 100% |
| Spec 2 | 7% | nd | nd | 20% | nd | 22% | 24% | 24% | 30% |
| Cutoff 3 | 95600 | nd | nd | 125000 | nd | 109000 | 140000 | 140000 | 147000 |
| Sens 3 | 100% | nd | nd | 100% | nd | 100% | 100% | 100% | 100% |
| Spec 3 | 7% | nd | nd | 16% | nd | 12% | 24% | 24% | 30% |
| Cutoff 4 | 208000 | nd | nd | 208000 | nd | 207000 | 208000 | 208000 | 207000 |
| Sens 4 | 33% | nd | nd | 33% | nd | 20% | 0% | 0% | 0% |
| Spec 4 | 70% | nd | nd | 70% | nd | 70% | 70% | 70% | 70% |
| Cutoff 5 | 229000 | nd | nd | 229000 | nd | 228000 | 229000 | 229000 | 228000 |
| Sens 5 | 33% | nd | nd | 33% | nd | 20% | 0% | 0% | 0% |
| Spec 5 | 80% | nd | nd | 80% | nd | 80% | 80% | 80% | 80% |
| Cutoff 6 | 268000 | nd | nd | 268000 | nd | 262000 | 268000 | 266000 | 262000 |
| Sens 6 | 0% | nd | nd | 0% | nd | 0% | 0% | 0% | 0% |
| Spec 6 | 90% | nd | nd | 90% | nd | 90% | 90% | 90% | 90% |
| OR Quart 2 | 0 | nd | nd | 0 | nd | 0 | >1.0 | >0 | >0 |
| p Value | na | nd | nd | na | nd | na | <0.99 | <na | <na |
| 95% CI of | na | nd | nd | na | nd | na | >0.063 | >na | >na |
| OR Quart 2 | na | nd | nd | na | nd | na | na | na | na |
| OR Quart 3 | 0 | nd | nd | 1.0 | nd | 2.0 | >2.1 | >1.0 | >2.1 |
| p Value | na | nd | nd | 1.0 | nd | 0.57 | <0.56 | <0.99 | <0.55 |
| 95% CI of | na | nd | nd | 0.14 | nd | 0.18 | >0.18 | >0.062 | >0.18 |
| OR Quart 3 | na | nd | nd | 7.3 | nd | 23 | na | na | na |
| OR Quart 4 | 2.0 | nd | nd | 1.0 | nd | 2.0 | >1.0 | >1.0 | >0 |
| p Value | 0.57 | nd | nd | 0.99 | nd | 0.57 | <0.99 | <0.99 | <na |
| 95% CI of | 0.18 | nd | nd | 0.14 | nd | 0.18 | >0.063 | >0.063 | >na |
| OR Quart 4 | 23 | nd | nd | 7.3 | nd | 23 | na | na | na |

Tumor necrosis factor ligand superfamily member 10

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| sCr or UO | | | | | | |
| Median | 0.0313 | 0.0313 | 0.0313 | 0.0271 | 0.0313 | 0.0313 |
| Average | 7.00 | 1.03 | 7.00 | 0.615 | 7.00 | 3.95 |
| Stdev | 29.0 | 2.23 | 29.0 | 1.44 | 29.0 | 7.84 |
| p (t-test) | | 0.65 | | 0.59 | | 0.83 |
| Min | 0.0162 | 0.0228 | 0.0162 | 0.0228 | 0.0162 | 0.0162 |
| Max | 292 | 5.02 | 292 | 3.56 | 292 | 15.7 |
| n (Samp) | 290 | 5 | 290 | 6 | 290 | 4 |
| n (Patient) | 174 | 5 | 174 | 6 | 174 | 4 |
| sCr only | | | | | | |
| Median | 0.0313 | 0.0271 | 0.0313 | 0.0271 | nd | nd |
| Average | 6.84 | 0.0271 | 6.84 | 0.0271 | nd | nd |

TABLE 10-continued

Comparison of marker levels in EDTA samples collected from Cohort 1
(patients that did not progress beyond RIFLE stage 0, R, or I) and in EDTA samples
collected from Cohort 2 (subjects who progress to RIFLE stage F) at 0, 24 hours,
and 48 hours prior to the subject reaching RIFLE stage I.

|   | | | | | | | |
|---|---|---|---|---|---|---|---|
| Stdev | 28.6 | 0.00598 | 28.6 | 0.00598 | nd | nd |
| p (t-test) |  | 0.74 |  | 0.74 | nd | nd |
| Min | 0.0162 | 0.0228 | 0.0162 | 0.0228 | nd | nd |
| Max | 292 | 0.0313 | 292 | 0.0313 | nd | nd |
| n (Samp) | 300 | 2 | 300 | 2 | nd | nd |
| n (Patient) | 180 | 2 | 180 | 2 | nd | nd |
| UO only |  |  |  |  |  |  |
| Median | nd | nd | 0.0313 | 0.0228 | 0.0313 | 0.0313 |
| Average | nd | nd | 6.81 | 0.0262 | 6.81 | 0.0313 |
| Stdev | nd | nd | 29.7 | 0.00463 | 29.7 | 0 |
| p (t-test) | nd | nd |  | 0.61 |  | 0.75 |
| Min | nd | nd | 0.0162 | 0.0228 | 0.0162 | 0.0313 |
| Max | nd | nd | 292 | 0.0313 | 292 | 0.0313 |
| n (Samp) | nd | nd | 271 | 5 | 271 | 2 |
| n (Patient) | nd | nd | 158 | 5 | 158 | 2 |

|  | 0 hr prior to AKI stage | | | 24 hr prior to AKI stage | | | 48 hr prior to AKI stage | | |
|---|---|---|---|---|---|---|---|---|---|
|  | sCr or UO | sCr only | UO only | sCr or UO | sCr only | UO only | sCr or UO | sCr only | UO only |
| AUC | 0.48 | 0.40 | nd | 0.45 | 0.40 | 0.37 | 0.48 | nd | 0.46 |
| SE | 0.13 | 0.21 | nd | 0.12 | 0.21 | 0.14 | 0.15 | nd | 0.21 |
| p | 0.89 | 0.62 | nd | 0.67 | 0.62 | 0.35 | 0.89 | nd | 0.86 |
| nCohort 1 | 290 | 300 | nd | 290 | 300 | 271 | 290 | nd | 271 |
| nCohort 2 | 5 | 2 | nd | 6 | 2 | 5 | 4 | nd | 2 |
| Cutoff 1 | 0.0205 | 0.0205 | nd | 0.0205 | 0.0205 | 0.0205 | 0.0269 | nd | 0.0269 |
| Sens 1 | 100% | 100% | nd | 100% | 100% | 100% | 75% | nd | 100% |
| Spec 1 | 23% | 23% | nd | 23% | 23% | 23% | 42% | nd | 41% |
| Cutoff 2 | 0.0205 | 0.0205 | nd | 0.0205 | 0.0205 | 0.0205 | 0 | nd | 0.0269 |
| Sens 2 | 100% | 100% | nd | 100% | 100% | 100% | 100% | nd | 100% |
| Spec 2 | 23% | 23% | nd | 23% | 23% | 23% | 0% | nd | 41% |
| Cutoff 3 | 0.0205 | 0.0205 | nd | 0.0205 | 0.0205 | 0.0205 | 0 | nd | 0.0269 |
| Sens 3 | 100% | 100% | nd | 100% | 100% | 100% | 100% | nd | 100% |
| Spec 3 | 23% | 23% | nd | 23% | 23% | 23% | 0% | nd | 41% |
| Cutoff 4 | 0.171 | 0.0943 | nd | 0.171 | 0.0943 | 0.0700 | 0.171 | nd | 0.0700 |
| Sens 4 | 20% | 0% | nd | 17% | 0% | 0% | 25% | nd | 0% |
| Spec 4 | 70% | 70% | nd | 70% | 70% | 70% | 70% | nd | 70% |
| Cutoff 5 | 3.61 | 3.61 | nd | 3.61 | 3.61 | 3.32 | 3.61 | nd | 3.32 |
| Sens 5 | 20% | 0% | nd | 0% | 0% | 0% | 25% | nd | 0% |
| Spec 5 | 81% | 80% | nd | 81% | 80% | 80% | 81% | nd | 80% |
| Cutoff 6 | 14.0 | 14.0 | nd | 14.0 | 14.0 | 13.4 | 14.0 | nd | 13.4 |
| Sens 6 | 0% | 0% | nd | 0% | 0% | 0% | 25% | nd | 0% |
| Spec 6 | 90% | 90% | nd | 90% | 90% | 90% | 90% | nd | 90% |
| OR Quart 2 | 0 | >0 | nd | 0 | >0 | >0 | 0 | nd | >0 |
| p Value | na | <na | nd | na | <na | <na | na | nd | <na |
| 95% CI of | na | >na | nd | na | >na | >na | na | nd | >na |
| OR Quart 2 | na | na | nd | na | na | na | na | nd | na |
| OR Quart 3 | 4.2 | >2.1 | nd | 5.3 | >2.1 | >5.4 | 2.0 | nd | >2.1 |
| p Value | 0.21 | <0.56 | nd | 0.13 | <0.56 | <0.13 | 0.57 | nd | <0.55 |
| 95% CI of | 0.45 | >0.18 | nd | 0.60 | >0.18 | >0.61 | 0.18 | nd | >0.19 |
| OR Quart 3 | 38 | na | nd | 46 | na | na | 23 | nd | na |
| OR Quart 4 | 0 | >0 | nd | 0 | >0 | >0 | 1.0 | nd | >0 |
| p Value | na | <na | nd | na | <na | <na | 0.99 | nd | <na |
| 95% CI of | na | >na | nd | na | >na | >na | 0.062 | nd | >na |
| OR Quart 4 | na | na | nd | na | na | na | 17 | nd | na |

Myeloid differentiation primary response protein MyD88

|  | 24 hr prior to AKI stage | |
|---|---|---|
|  | Cohort 1 | Cohort 2 |
| sCr or UO |  |  |
| Median | 0.000368 | 0.000368 |
| Average | 0.00229 | 0.000350 |
| Stdev | 0.0167 | 0.000118 |
| p (t-test) |  | 0.84 |
| Min | 0.000126 | 0.000224 |
| Max | 0.194 | 0.000457 |
| n (Samp) | 253 | 3 |
| n (Patient) | 144 | 3 |

TABLE 10-continued

Comparison of marker levels in EDTA samples collected from Cohort 1
(patients that did not progress beyond RIFLE stage 0, R, or I) and in EDTA samples
collected from Cohort 2 (subjects who progress to RIFLE stage F) at 0, 24 hours,
and 48 hours prior to the subject reaching RIFLE stage I.

| UO only | | |
|---|---|---|
| Median | 0.000245 | 0.000413 |
| Average | 0.00239 | 0.000413 |
| Stdev | 0.0171 | 6.30E−5 |
| p (t-test) | | 0.87 |
| Min | 0.000126 | 0.000368 |
| Max | 0.194 | 0.000457 |
| n (Samp) | 240 | 2 |
| n (Patient) | 129 | 2 |

| | 24 hr prior to AKI stage | | |
|---|---|---|---|
| | sCr or UO | sCr only | UO only |
| AUC | 0.53 | nd | 0.74 |
| SE | 0.17 | nd | 0.20 |
| p | 0.87 | nd | 0.23 |
| nCohort 1 | 253 | nd | 240 |
| nCohort 2 | 3 | nd | 2 |
| Cutoff 1 | 0.000126 | nd | 0.000296 |
| Sens 1 | 100% | nd | 100% |
| Spec 1 | 0% | nd | 53% |
| Cutoff 2 | 0.000126 | nd | 0.000296 |
| Sens 2 | 100% | nd | 100% |
| Spec 2 | 0% | nd | 53% |
| Cutoff 3 | 0.000126 | nd | 0.000296 |
| Sens 3 | 100% | nd | 100% |
| Spec 3 | 0% | nd | 53% |
| Cutoff 4 | 0.000368 | nd | 0.000368 |
| Sens 4 | 33% | nd | 50% |
| Spec 4 | 73% | nd | 74% |
| Cutoff 5 | 0.000457 | nd | 0.000457 |
| Sens 5 | 0% | nd | 0% |
| Spec 5 | 96% | nd | 96% |
| Cutoff 6 | 0.000457 | nd | 0.000457 |
| Sens 6 | 0% | nd | 0% |
| Spec 6 | 96% | nd | 96% |
| OR Quart 2 | 1.0 | nd | >0 |
| p Value | 1.0 | nd | <na |
| 95% CI of | 0.061 | nd | >na |
| OR Quart 2 | 16 | nd | na |
| OR Quart 3 | 0 | nd | >2.1 |
| p Value | na | nd | <0.56 |
| 95% CI of | na | nd | >0.18 |
| OR Quart 3 | na | nd | na |
| OR Quart 4 | 1.0 | nd | >0 |
| p Value | 1.0 | nd | <na |
| 95% CI of | 0.061 | nd | >na |
| OR Quart 4 | 16 | nd | na |

TABLE 11

Comparison of marker levels in enroll urine samples collected from
Cohort 1 (patients that did not progress beyond RIFLE stage 0 or R within 48 hrs) and in
enroll urine samples collected from Cohort 2 (subjects reaching RIFLE stage I or F
within 48 hrs). Enroll samples from patients already at RIFLE stage I or F were
included in Cohort 2.

| Stromelysin-1:Metalloproteinase inhibitor 2 complex | | | | | | |
|---|---|---|---|---|---|---|
| | sCr or UO | | sCr only | | UO only | |
| | Cohort 1 | Cohort 2 | Cohort 1 | Cohort 2 | Cohort 1 | Cohort 2 |
| Median | 0.487 | 10.9 | 0.487 | 343 | 0.237 | 31.8 |
| Average | 85.9 | 135 | 82.5 | 295 | 63.8 | 151 |
| Stdev | 314 | 197 | 298 | 263 | 303 | 204 |
| p (t-test) | | 0.65 | | 0.23 | | 0.44 |
| Min | 0.237 | 0.487 | 0.237 | 10.9 | 0.237 | 0.487 |

TABLE 11-continued

Comparison of marker levels in enroll urine samples collected from Cohort 1 (patients that did not progress beyond RIFLE stage 0 or R within 48 hrs) and in enroll urine samples collected from Cohort 2 (subjects reaching RIFLE stage I or F within 48 hrs). Enroll samples from patients already at RIFLE stage I or F were included in Cohort 2.

| | | | | | | |
|---|---|---|---|---|---|---|
| Max | 1930 | 530 | 1930 | 530 | 1930 | 530 |
| n (Samp) | 49 | 9 | 55 | 3 | 41 | 8 |
| n (Patient) | 49 | 9 | 55 | 3 | 41 | 8 |

| | At Enrollment | | |
|---|---|---|---|
| | sCr or UO | sCr only | UO only |
| AUC | 0.79 | 0.90 | 0.82 |
| SE | 0.094 | 0.12 | 0.094 |
| p | 0.0019 | 7.3E−4 | 6.2E−4 |
| nCohort 1 | 49 | 55 | 41 |
| nCohort 2 | 9 | 3 | 8 |
| Cutoff 1 | 0.237 | 3.84 | 0.237 |
| Sens 1 | 100% | 100% | 100% |
| Spec 1 | 49% | 82% | 56% |
| Cutoff 2 | 0.237 | 3.84 | 0.237 |
| Sens 2 | 100% | 100% | 100% |
| Spec 2 | 49% | 82% | 56% |
| Cutoff 3 | 0.237 | 3.84 | 0.237 |
| Sens 3 | 100% | 100% | 100% |
| Spec 3 | 49% | 82% | 56% |
| Cutoff 4 | 0.487 | 0.487 | 0.487 |
| Sens 4 | 56% | 100% | 50% |
| Spec 4 | 82% | 80% | 83% |
| Cutoff 5 | 0.487 | 0.487 | 0.487 |
| Sens 5 | 56% | 100% | 50% |
| Spec 5 | 82% | 80% | 83% |
| Cutoff 6 | 201 | 201 | 85.2 |
| Sens 6 | 33% | 67% | 38% |
| Spec 6 | 92% | 91% | 90% |
| OR Quart 2 | >2.2 | >0 | >1.1 |
| p Value | <0.55 | <na | <0.95 |
| 95% CI of | >0.17 | >na | >0.061 |
| OR Quart 2 | na | na | na |
| OR Quart 3 | >2.3 | >0 | >4.0 |
| p Value | <0.51 | <na | <0.26 |
| 95% CI of | >0.19 | >na | >0.35 |
| OR Quart 3 | na | na | na |
| OR Quart 4 | >7.0 | >3.5 | >5.3 |
| p Value | <0.097 | <0.30 | <0.16 |
| 95% CI of | >0.71 | >0.32 | >0.51 |
| OR Quart 4 | na | na | na |

Heat shock 70 kDa protein 1

| | sCr or UO | | sCr only | | UO only | |
|---|---|---|---|---|---|---|
| | Cohort 1 | Cohort 2 | Cohort 1 | Cohort 2 | Cohort 1 | Cohort 2 |
| Median | 257 | 1300 | 342 | 1510 | 225 | 1090 |
| Average | 437 | 3130 | 690 | 3320 | 449 | 3360 |
| Stdev | 457 | 4180 | 1660 | 3510 | 484 | 4460 |
| p (t-test) | | 5.2E−5 | | 0.015 | | 1.0E−4 |
| Min | 0.297 | 250 | 0.297 | 1090 | 0.297 | 250 |
| Max | 1870 | 11800 | 11800 | 7360 | 1870 | 11800 |
| n (Samp) | 46 | 8 | 51 | 3 | 41 | 7 |
| n (Patient) | 46 | 8 | 51 | 3 | 41 | 7 |

| | At Enrollment | | |
|---|---|---|---|
| | sCr or UO | sCr only | UO only |
| AUC | 0.85 | 0.93 | 0.83 |
| SE | 0.090 | 0.10 | 0.099 |
| p | 1.2E−4 | 4.4E−5 | 9.2E−4 |
| nCohort 1 | 46 | 51 | 41 |
| nCohort 2 | 8 | 3 | 7 |
| Cutoff 1 | 755 | 1020 | 755 |
| Sens 1 | 75% | 100% | 71% |
| Spec 1 | 80% | 88% | 80% |
| Cutoff 2 | 408 | 1020 | 408 |
| Sens 2 | 88% | 100% | 86% |
| Spec 2 | 61% | 88% | 61% |

TABLE 11-continued

Comparison of marker levels in enroll urine samples collected from Cohort 1 (patients that did not progress beyond RIFLE stage 0 or R within 48 hrs) and in enroll urine samples collected from Cohort 2 (subjects reaching RIFLE stage I or F within 48 hrs). Enroll samples from patients already at RIFLE stage I or F were included in Cohort 2.

| | | | |
|---|---|---|---|
| Cutoff 3 | 225 | 1020 | 225 |
| Sens 3 | 100% | 100% | 100% |
| Spec 3 | 50% | 88% | 51% |
| Cutoff 4 | 634 | 660 | 627 |
| Sens 4 | 75% | 100% | 71% |
| Spec 4 | 72% | 71% | 71% |
| Cutoff 5 | 755 | 782 | 755 |
| Sens 5 | 75% | 100% | 71% |
| Spec 5 | 80% | 80% | 80% |
| Cutoff 6 | 1020 | 1150 | 1020 |
| Sens 6 | 62% | 67% | 57% |
| Spec 6 | 91% | 90% | 90% |
| OR Quart 2 | >1.0 | >0 | >1.1 |
| p Value | <1.0 | <na | <0.95 |
| 95% CI of | >0.056 | >na | >0.061 |
| OR Quart 2 | na | na | na |
| OR Quart 3 | >2.4 | >0 | >2.4 |
| p Value | <0.51 | <na | <0.50 |
| 95% CI of | >0.19 | >na | >0.19 |
| OR Quart 3 | na | na | na |
| OR Quart 4 | >7.2 | >3.5 | >6.0 |
| p Value | <0.093 | <0.30 | <0.14 |
| 95% CI of | >0.72 | >0.32 | >0.56 |
| OR Quart 4 | na | na | na |

Insulin-like growth factor 1 receptor

| | sCr or UO | | sCr only | | UO only | |
|---|---|---|---|---|---|---|
| | Cohort 1 | Cohort 2 | Cohort 1 | Cohort 2 | Cohort 1 | Cohort 2 |
| Median | 0.0103 | 0.0197 | 0.0103 | 0.0197 | 0.0103 | 0.0292 |
| Average | 0.0179 | 0.0599 | 0.0245 | 0.0223 | 0.0174 | 0.0664 |
| Stdev | 0.0223 | 0.115 | 0.0515 | 0.0152 | 0.0233 | 0.122 |
| p (t-test) | | 0.020 | | 0.94 | | 0.018 |
| Min | 0.000123 | 0.00132 | 0.000123 | 0.00862 | 0.000123 | 0.00132 |
| Max | 0.0976 | 0.365 | 0.365 | 0.0388 | 0.0976 | 0.365 |
| n (Samp) | 49 | 9 | 55 | 3 | 41 | 8 |
| n (Patient) | 49 | 9 | 55 | 3 | 41 | 8 |

| | At Enrollment | | |
|---|---|---|---|
| | sCr or UO | sCr only | UO only |
| AUC | 0.67 | 0.62 | 0.72 |
| SE | 0.11 | 0.18 | 0.11 |
| p | 0.11 | 0.49 | 0.039 |
| nCohort 1 | 49 | 55 | 41 |
| nCohort 2 | 9 | 3 | 8 |
| Cutoff 1 | 0.00862 | 0.00454 | 0.00862 |
| Sens 1 | 78% | 100% | 88% |
| Spec 1 | 41% | 33% | 46% |
| Cutoff 2 | 0.00454 | 0.00454 | 0.00862 |
| Sens 2 | 89% | 100% | 88% |
| Spec 2 | 35% | 33% | 46% |
| Cutoff 3 | 0.000519 | 0.00454 | 0.000519 |
| Sens 3 | 100% | 100% | 100% |
| Spec 3 | 24% | 33% | 29% |
| Cutoff 4 | 0.0197 | 0.0211 | 0.0169 |
| Sens 4 | 44% | 33% | 62% |
| Spec 4 | 71% | 71% | 71% |
| Cutoff 5 | 0.0296 | 0.0339 | 0.0292 |
| Sens 5 | 44% | 33% | 50% |
| Spec 5 | 82% | 80% | 80% |
| Cutoff 6 | 0.0423 | 0.0436 | 0.0388 |
| Sens 6 | 22% | 0% | 38% |
| Spec 6 | 92% | 91% | 90% |
| OR Quart 2 | 3.2 | >1.0 | >1.1 |
| p Value | 0.33 | <1.0 | <0.95 |
| 95% CI of | 0.30 | >0.057 | >0.061 |
| OR Quart 2 | 36 | na | na |
| OR Quart 3 | 1.0 | >1.1 | >4.0 |
| p Value | 1.0 | <0.96 | <0.26 |
| 95% CI of | 0.056 | >0.061 | >0.35 |

TABLE 11-continued

Comparison of marker levels in enroll urine samples collected from Cohort 1 (patients that did not progress beyond RIFLE stage 0 or R within 48 hrs) and in enroll urine samples collected from Cohort 2 (subjects reaching RIFLE stage I or F within 48 hrs). Enroll samples from patients already at RIFLE stage I or F were included in Cohort 2.

| | | | |
|---|---|---|---|
| OR Quart 3 | 18 | na | na |
| OR Quart 4 | 4.7 | >1.0 | >5.3 |
| p Value | 0.19 | <1.0 | <0.16 |
| 95% CI of | 0.46 | >0.057 | >0.51 |
| OR Quart 4 | 49 | na | na |

72 kDa type IV collagenase:Metalloproteinase inhibitor 2 complex

| | sCr or UO | | sCr only | | UO only | |
|---|---|---|---|---|---|---|
| | Cohort 1 | Cohort 2 | Cohort 1 | Cohort 2 | Cohort 1 | Cohort 2 |
| Median | 36.4 | 527 | 57.4 | 527 | 46.9 | 561 |
| Average | 345 | 4960 | 853 | 5570 | 320 | 5560 |
| Stdev | 585 | 7200 | 2700 | 9040 | 551 | 7450 |
| p (t-test) | | 5.4E−5 | | 0.016 | | 3.4E−5 |
| Min | 1.15 | 1.15 | 1.15 | 171 | 1.15 | 1.15 |
| Max | 2270 | 16000 | 16000 | 16000 | 2270 | 16000 |
| n (Samp) | 45 | 9 | 51 | 3 | 40 | 8 |
| n (Patient) | 45 | 9 | 51 | 3 | 40 | 8 |

| | At Enrollment | | |
|---|---|---|---|
| | sCr or UO | sCr only | UO only |
| AUC | 0.67 | 0.78 | 0.68 |
| SE | 0.11 | 0.16 | 0.11 |
| p | 0.10 | 0.081 | 0.11 |
| nCohort 1 | 45 | 51 | 40 |
| nCohort 2 | 9 | 3 | 8 |
| Cutoff 1 | 158 | 158 | 234 |
| Sens 1 | 78% | 100% | 75% |
| Spec 1 | 64% | 61% | 72% |
| Cutoff 2 | 0 | 158 | 0 |
| Sens 2 | 100% | 100% | 100% |
| Spec 2 | 0% | 61% | 0% |
| Cutoff 3 | 0 | 158 | 0 |
| Sens 3 | 100% | 100% | 100% |
| Spec 3 | 0% | 61% | 0% |
| Cutoff 4 | 234 | 378 | 189 |
| Sens 4 | 67% | 67% | 75% |
| Spec 4 | 71% | 71% | 70% |
| Cutoff 5 | 656 | 660 | 419 |
| Sens 5 | 33% | 33% | 62% |
| Spec 5 | 80% | 80% | 80% |
| Cutoff 6 | 1380 | 1450 | 1120 |
| Sens 6 | 33% | 33% | 38% |
| Spec 6 | 91% | 90% | 90% |
| OR Quart 2 | 0 | >0 | 0 |
| p Value | na | <na | na |
| 95% CI of | na | >na | na |
| OR Quart 2 | na | na | na |
| OR Quart 3 | 1.6 | >2.4 | 1.0 |
| p Value | 0.62 | <0.51 | 1.0 |
| 95% CI of | 0.23 | >0.19 | 0.12 |
| OR Quart3 | 12 | na | 8.6 |
| OR Quart 4 | 2.2 | >1.0 | 2.5 |
| p Value | 0.42 | <1.0 | 0.35 |
| 95% CI of | 0.33 | >0.056 | 0.36 |
| OR Quart 4 | 15 | na | 17 |

Neural cell adhesion molecule 1

| | sCr or UO | | sCr only | | UO only | |
|---|---|---|---|---|---|---|
| | Cohort 1 | Cohort 2 | Cohort 1 | Cohort 2 | Cohort 1 | Cohort 2 |
| Median | 2440 | 3710 | 2670 | 4860 | 2490 | 3900 |
| Average | 3050 | 5520 | 3340 | 7980 | 3120 | 5680 |
| Stdev | 2340 | 7260 | 3480 | 8950 | 2140 | 7560 |
| p (t-test) | | 5.1E−8 | | 3.7E−7 | | 4.7E−7 |
| Min | 6.83 | 138 | 6.83 | 171 | 173 | 138 |

TABLE 11-continued

Comparison of marker levels in enroll urine samples collected from Cohort 1 (patients that did not progress beyond RIFLE stage 0 or R within 48 hrs) and in enroll urine samples collected from Cohort 2 (subjects reaching RIFLE stage I or F within 48 hrs). Enroll samples from patients already at RIFLE stage I or F were included in Cohort 2.

|            |       |       |       |       |       |       |
|------------|-------|-------|-------|-------|-------|-------|
| Max        | 22000 | 55700 | 55700 | 31700 | 15500 | 55700 |
| n (Samp)   | 380   | 91    | 448   | 19    | 297   | 79    |
| n (Patient)| 380   | 91    | 448   | 19    | 297   | 79    |

|              | At Enrollment | | |
|--------------|---------------|---------|---------|
|              | sCr or UO | sCr only | UO only |
| AUC          | 0.65   | 0.68   | 0.64   |
| SE           | 0.034  | 0.069  | 0.037  |
| p            | 1.8E−5 | 0.011  | 1.2E−4 |
| nCohort 1    | 380    | 448    | 297    |
| nCohort 2    | 91     | 19     | 79     |
| Cutoff 1     | 2670   | 2850   | 2670   |
| Sens 1       | 70%    | 74%    | 71%    |
| Spec 1       | 54%    | 55%    | 53%    |
| Cutoff 2     | 2130   | 2200   | 2080   |
| Sens 2       | 80%    | 84%    | 81%    |
| Spec 2       | 42%    | 42%    | 39%    |
| Cutoff 3     | 1210   | 1230   | 1110   |
| Sens 3       | 90%    | 95%    | 91%    |
| Spec 3       | 19%    | 19%    | 14%    |
| Cutoff 4     | 3740   | 3910   | 3910   |
| Sens 4       | 49%    | 53%    | 49%    |
| Spec 4       | 70%    | 70%    | 70%    |
| Cutoff 5     | 4550   | 4730   | 4750   |
| Sens 5       | 34%    | 53%    | 34%    |
| Spec 5       | 80%    | 80%    | 80%    |
| Cutoff 6     | 5740   | 6280   | 6040   |
| Sens 6       | 23%    | 32%    | 24%    |
| Spec 6       | 90%    | 90%    | 90%    |
| OR Quart 2   | 1.3    | 0.66   | 1.5    |
| p Value      | 0.57   | 0.65   | 0.30   |
| 95% CI of    | 0.57   | 0.11   | 0.68   |
| OR Quart2    | 2.7    | 4.0    | 3.5    |
| OR Quart 3   | 2.5    | 1.3    | 2.6    |
| p Value      | 0.013  | 0.71   | 0.017  |
| 95% CI of    | 1.2    | 0.29   | 1.2    |
| OR Quart 3   | 5.1    | 6.1    | 5.7    |
| OR Quart 4   | 3.2    | 3.5    | 3.2    |
| p Value      | 0.0010 | 0.061  | 0.0030 |
| 95% CI of    | 1.6    | 0.94   | 1.5    |
| OR Quart 4   | 6.5    | 13     | 6.9    |

Tumor necrosis factor ligand superfamily member 10

|           | sCr or UO | | sCr only | | UO only | |
|-----------|-----------|-----------|-----------|-----------|-----------|-----------|
|           | Cohort 1 | Cohort 2 | Cohort 1 | Cohort 2 | Cohort 1 | Cohort 2 |
| Median    | 0.0257 | 0.0269 | 0.0257 | 0.0271 | 0.0257 | 0.0285 |
| Average   | 2.34   | 4.96   | 2.69   | 6.59   | 2.28   | 5.68   |
| Stdev     | 9.11   | 19.8   | 11.1   | 25.2   | 9.37   | 21.4   |
| p (t-test)|        | 0.064  |        | 0.16   |        | 0.040  |
| Min       | 0.0110 | 0.0110 | 0.0110 | 0.0110 | 0.0110 | 0.0139 |
| Max       | 83.5   | 134    | 134    | 113    | 83.5   | 134    |
| n (Samp)  | 370    | 89     | 435    | 20     | 291    | 76     |
| n (Patient)| 370   | 89     | 435    | 20     | 291    | 76     |

|              | At Enrollment | | |
|--------------|---------------|---------|---------|
|              | sCr or UO | sCr only | UO only |
| AUC          | 0.58   | 0.56   | 0.58   |
| SE           | 0.035  | 0.068  | 0.038  |
| p            | 0.015  | 0.37   | 0.024  |
| nCohort 1    | 370    | 435    | 291    |
| nCohort 2    | 89     | 20     | 76     |
| Cutoff 1     | 0.0239 | 0.0239 | 0.0239 |
| Sens 1       | 80%    | 70%    | 79%    |
| Spec 1       | 46%    | 44%    | 42%    |
| Cutoff 2     | 0.0237 | 0.0239 | 0.0237 |
| Sens 2       | 85%    | 85%    | 86%    |
| Spec 2       | 43%    | 42%    | 40%    |

TABLE 11-continued

Comparison of marker levels in enroll urine samples collected from Cohort 1 (patients that did not progress beyond RIFLE stage 0 or R within 48 hrs) and in enroll urine samples collected from Cohort 2 (subjects reaching RIFLE stage I or F within 48 hrs). Enroll samples from patients already at RIFLE stage I or F were included in Cohort 2.

| | | | |
|---|---|---|---|
| Cutoff 3 | 0.0217 | 0.0217 | 0.0227 |
| Sens 3 | 93% | 90% | 91% |
| Spec 3 | 34% | 29% | 35% |
| Cutoff 4 | 0.0439 | 0.0410 | 0.0439 |
| Sens 4 | 21% | 30% | 22% |
| Spec 4 | 74% | 70% | 75% |
| Cutoff 5 | 0.0597 | 0.0597 | 0.0526 |
| Sens 5 | 20% | 30% | 22% |
| Spec 5 | 82% | 82% | 81% |
| Cutoff 6 | 4.27 | 4.75 | 3.36 |
| Sens 6 | 13% | 10% | 17% |
| Spec 6 | 90% | 90% | 90% |
| OR Quart 2 | 7.6 | 4.2 | 12 |
| p Value | 1.5E−5 | 0.074 | 1.1E−5 |
| 95% CI of | 3.0 | 0.87 | 3.9 |
| OR Quart 2 | 19 | 20 | 35 |
| OR Quart 3 | 6.4 | 2.0 | 7.2 |
| p Value | 8.4E−5 | 0.42 | 4.6E−4 |
| 95% CI of | 2.5 | 0.36 | 2.4 |
| OR Quart 3 | 16 | 11 | 22 |
| OR Quart 4 | 3.6 | 3.1 | 4.9 |
| p Value | 0.0094 | 0.17 | 0.0057 |
| 95% CI of | 1.4 | 0.61 | 1.6 |
| OR Quart 4 | 9.3 | 16 | 15 |

TABLE 12

Comparison of marker levels in enroll EDTA samples collected from Cohort 1 (patients that did not progress beyond RIFLE stage 0 or R within 48 hrs) and in enroll EDTA samples collected from Cohort 2 (subjects reaching RIFLE stage I or F within 48 hrs). Enroll samples from patients already at stage I or F were included in Cohort 2.

| Heat shock 70 kDa protein 1 | | | | | | |
|---|---|---|---|---|---|---|
| | sCr or UO | | sCr only | | UO only | |
| | Cohort 1 | Cohort 2 | Cohort 1 | Cohort 2 | Cohort 1 | Cohort 2 |
| Median | 905 | 1080 | nd | nd | 949 | 1080 |
| Average | 1300 | 1080 | nd | nd | 1200 | 1080 |
| Stdev | 1610 | 642 | nd | nd | 1150 | 642 |
| p (t-test) | | 0.70 | nd | nd | | 0.77 |
| Min | 4.58 | 261 | nd | nd | 4.58 | 261 |
| Max | 9150 | 2280 | nd | nd | 4430 | 2280 |
| n (Samp) | 46 | 9 | nd | nd | 40 | 9 |
| n (Patient) | 46 | 9 | nd | nd | 40 | 9 |

| | At Enrollment | | |
|---|---|---|---|
| | sCr or UO | sCr only | UO only |
| AUC | 0.56 | nd | 0.54 |
| SE | 0.11 | nd | 0.11 |
| p | 0.60 | nd | 0.73 |
| nCohort 1 | 46 | nd | 40 |
| nCohort 2 | 9 | nd | 9 |
| Cutoff 1 | 705 | nd | 618 |
| Sens 1 | 78% | nd | 78% |
| Spec 1 | 48% | nd | 45% |
| Cutoff 2 | 297 | nd | 297 |
| Sens 2 | 89% | nd | 89% |
| Spec 2 | 28% | nd | 28% |
| Cutoff 3 | 252 | nd | 252 |
| Sens 3 | 100% | nd | 100% |
| Spec 3 | 24% | nd | 22% |
| Cutoff 4 | 1370 | nd | 1370 |
| Sens 4 | 33% | nd | 33% |
| Spec 4 | 72% | nd | 70% |
| Cutoff 5 | 1970 | nd | 1970 |
| Sens 5 | 11% | nd | 11% |

TABLE 12-continued

Comparison of marker levels in enroll EDTA samples collected from Cohort 1 (patients that did not progress beyond RIFLE stage 0 or R within 48 hrs) and in enroll EDTA samples collected from Cohort 2 (subjects reaching RIFLE stage I or F within 48 hrs). Enroll samples from patients already at stage I or F were included in Cohort 2.

| | | | |
|---|---|---|---|
| Spec 5 | 80% | nd | 80% |
| Cutoff 6 | 3400 | nd | 3300 |
| Sens 6 | 0% | nd | 0% |
| Spec 6 | 91% | nd | 90% |
| OR Quart 2 | 3.3 | nd | 3.7 |
| p Value | 0.33 | nd | 0.29 |
| 95% CI of | 0.29 | nd | 0.32 |
| OR Quart 2 | 36 | nd | 42 |
| OR Quart 3 | 3.3 | nd | 3.7 |
| p Value | 0.33 | nd | 0.29 |
| 95% CI of | 0.29 | nd | 0.32 |
| OR Quart 3 | 36 | nd | 42 |
| OR Quart 4 | 2.0 | nd | 2.0 |
| p Value | 0.59 | nd | 0.59 |
| 95% CI of | 0.16 | nd | 0.16 |
| OR Quart 4 | 25 | nd | 25 |

Insulin-like growth factor 1 receptor

| | sCr or UO | | sCr only | | UO only | |
|---|---|---|---|---|---|---|
| | Cohort 1 | Cohort 2 | Cohort 1 | Cohort 2 | Cohort 1 | Cohort 2 |
| Median | 0.0458 | 0.0656 | 0.0498 | 0.0283 | 0.0514 | 0.0619 |
| Average | 0.465 | 1.16 | 0.412 | 3.91 | 0.540 | 0.0941 |
| Stdev | 2.58 | 4.56 | 2.38 | 8.68 | 2.79 | 0.133 |
| p (t-test) | | 0.40 | | 0.013 | | 0.54 |
| Min | 0.000208 | 0.000172 | 0.000172 | 0.00927 | 0.000208 | 0.000172 |
| Max | 20.5 | 19.4 | 20.5 | 19.4 | 20.5 | 0.543 |
| n (Samp) | 68 | 18 | 80 | 5 | 58 | 15 |
| n (Patient) | 68 | 18 | 80 | 5 | 58 | 15 |

At Enrollment

| | sCr or UO | sCr only | UO only |
|---|---|---|---|
| AUC | 0.57 | 0.43 | 0.53 |
| SE | 0.078 | 0.14 | 0.085 |
| p | 0.39 | 0.62 | 0.70 |
| nCohort 1 | 68 | 80 | 58 |
| nCohort 2 | 18 | 5 | 15 |
| Cutoff 1 | 0.0373 | 0.0134 | 0.0373 |
| Sens 1 | 72% | 80% | 73% |
| Spec 1 | 41% | 12% | 36% |
| Cutoff 2 | 0.0134 | 0.0134 | 0.0258 |
| Sens 2 | 83% | 80% | 80% |
| Spec 2 | 12% | 12% | 26% |
| Cutoff 3 | 0.000208 | 0.00497 | 0.000208 |
| Sens 3 | 94% | 100% | 93% |
| Spec 3 | 3% | 9% | 2% |
| Cutoff 4 | 0.0668 | 0.0766 | 0.0766 |
| Sens 4 | 50% | 20% | 40% |
| Spec 4 | 71% | 70% | 71% |
| Cutoff 5 | 0.0839 | 0.0839 | 0.0839 |
| Sens 5 | 33% | 20% | 33% |
| Spec 5 | 84% | 80% | 83% |
| Cutoff 6 | 0.139 | 0.139 | 0.167 |
| Sens 6 | 17% | 20% | 7% |
| Spec 6 | 91% | 90% | 91% |
| OR Quart 2 | 0.94 | 1.0 | 1.4 |
| p Value | 0.94 | 0.97 | 0.67 |
| 95% CI of | 0.20 | 0.061 | 0.27 |
| OR Quart 2 | 4.4 | 18 | 7.5 |
| OR Quart 3 | 1.0 | 1.0 | 1.0 |
| p Value | 1.0 | 0.97 | 1.0 |
| 95% CI of | 0.21 | 0.061 | 0.17 |
| OR Quart 3 | 4.7 | 18 | 5.8 |
| OR Quart 4 | 1.6 | 2.2 | 1.8 |
| p Value | 0.53 | 0.53 | 0.48 |
| 95% CI of | 0.38 | 0.19 | 0.36 |
| OR Quart 4 | 6.7 | 26 | 8.9 |

TABLE 12-continued

Comparison of marker levels in enroll EDTA samples collected from Cohort 1 (patients that did not progress beyond RIFLE stage 0 or R within 48 hrs) and in enroll EDTA samples collected from Cohort 2 (subjects reaching RIFLE stage I or F within 48 hrs). Enroll samples from patients already at stage I or F were included in Cohort 2.

Neural cell adhesion molecule 1

|  | sCr or UO | | sCr only | | UO only | |
| --- | --- | --- | --- | --- | --- | --- |
|  | Cohort 1 | Cohort 2 | Cohort 1 | Cohort 2 | Cohort 1 | Cohort 2 |
| Median | 183000 | 162000 | 179000 | 147000 | 181000 | 162000 |
| Average | 186000 | 154000 | 180000 | 158000 | 184000 | 152000 |
| Stdev | 73200 | 64800 | 73400 | 55400 | 68800 | 65200 |
| p (t-test) |  | 0.034 |  | 0.56 |  | 0.036 |
| Min | 791 | 190 | 190 | 111000 | 791 | 190 |
| Max | 494000 | 331000 | 494000 | 230000 | 461000 | 331000 |
| n (Samp) | 111 | 28 | 134 | 4 | 100 | 26 |
| n (Patient) | 111 | 28 | 134 | 4 | 100 | 26 |

At Enrollment

|  | sCr or UO | sCr only | UO only |
| --- | --- | --- | --- |
| AUC | 0.35 | 0.40 | 0.35 |
| SE | 0.061 | 0.15 | 0.064 |
| p | 0.018 | 0.52 | 0.018 |
| nCohort 1 | 111 | 134 | 100 |
| nCohort 2 | 28 | 4 | 26 |
| Cutoff 1 | 111000 | 114000 | 109000 |
| Sens 1 | 71% | 75% | 73% |
| Spec 1 | 13% | 18% | 12% |
| Cutoff 2 | 93300 | 109000 | 93300 |
| Sens 2 | 82% | 100% | 81% |
| Spec 2 | 8% | 15% | 8% |
| Cutoff 3 | 79400 | 109000 | 79400 |
| Sens 3 | 93% | 100% | 92% |
| Spec 3 | 5% | 15% | 5% |
| Cutoff 4 | 214000 | 208000 | 214000 |
| Sens 4 | 14% | 25% | 12% |
| Spec 4 | 70% | 70% | 70% |
| Cutoff 5 | 229000 | 228000 | 229000 |
| Sens 5 | 11% | 25% | 8% |
| Spec 5 | 80% | 81% | 80% |
| Cutoff 6 | 268000 | 265000 | 265000 |
| Sens 6 | 4% | 0% | 4% |
| Spec 6 | 90% | 90% | 90% |
| OR Quart 2 | 1.3 | 0 | 1.9 |
| p Value | 0.72 | na | 0.43 |
| 95% CI of | 0.32 | na | 0.40 |
| OR Quart 2 | 5.3 | na | 8.6 |
| OR Quart 3 | 2.3 | 1.0 | 3.2 |
| p Value | 0.21 | 1.0 | 0.11 |
| 95% CI of | 0.62 | 0.060 | 0.77 |
| OR Quart 3 | 8.5 | 17 | 14 |
| OR Quart 4 | 3.7 | 2.1 | 4.6 |
| p Value | 0.042 | 0.55 | 0.033 |
| 95% CI of | 1.0 | 0.18 | 1.1 |
| OR Quart 4 | 13 | 25 | 19 |

Tumor necrosis factor ligand superfamily member 10

|  | sCr or UO | | sCr only | | UO only | |
| --- | --- | --- | --- | --- | --- | --- |
|  | Cohort 1 | Cohort 2 | Cohort 1 | Cohort 2 | Cohort 1 | Cohort 2 |
| Median | 0.0247 | 0.0276 | 0.0247 | 0.0313 | 0.0313 | 0.0276 |
| Average | 10.2 | 2.74 | 8.59 | 7.70 | 11.1 | 1.20 |
| Stdev | 28.2 | 9.26 | 25.9 | 16.7 | 29.3 | 3.76 |
| p (t-test) |  | 0.19 |  | 0.93 |  | 0.12 |
| Min | 0.0162 | 0.0162 | 0.0162 | 0.0162 | 0.0162 | 0.0162 |
| Max | 172 | 44.8 | 172 | 44.8 | 172 | 15.7 |
| n (Samp) | 85 | 26 | 103 | 7 | 78 | 22 |
| n (Patient) | 85 | 26 | 103 | 7 | 78 | 22 |

TABLE 12-continued

Comparison of marker levels in enroll EDTA samples collected
from Cohort 1 (patients that did not progress beyond RIFLE stage 0 or
R within 48 hrs) and in enroll EDTA samples collected from Cohort 2
(subjects reaching RIFLE stage I or F within 48 hrs). Enroll samples
from patients already at stage I or F were included in Cohort 2.

|  | At Enrollment | | |
| --- | --- | --- | --- |
|  | sCr or UO | sCr only | UO only |
| AUC | 0.47 | 0.53 | 0.46 |
| SE | 0.065 | 0.11 | 0.071 |
| p | 0.70 | 0.82 | 0.60 |
| nCohort 1 | 85 | 103 | 78 |
| nCohort 2 | 26 | 7 | 22 |
| Cutoff 1 | 0.0197 | 0.0197 | 0.0197 |
| Sens 1 | 81% | 86% | 82% |
| Spec 1 | 21% | 21% | 21% |
| Cutoff 2 | 0.0197 | 0.0197 | 0.0197 |
| Sens 2 | 81% | 86% | 82% |
| Spec 2 | 21% | 21% | 21% |
| Cutoff 3 | 0 | 0 | 0.0162 |
| Sens 3 | 100% | 100% | 91% |
| Spec 3 | 0% | 0% | 9% |
| Cutoff 4 | 0.0317 | 0.0317 | 0.0700 |
| Sens 4 | 19% | 29% | 18% |
| Spec 4 | 71% | 73% | 71% |
| Cutoff 5 | 2.48 | 1.46 | 4.64 |
| Sens 5 | 12% | 29% | 9% |
| Spec 5 | 80% | 81% | 81% |
| Cutoff 6 | 33.1 | 25.8 | 43.5 |
| Sens 6 | 4% | 14% | 0% |
| Spec 6 | 91% | 90% | 91% |
| OR Quart 2 | 2.8 | 2.0 | 2.9 |
| p Value | 0.12 | 0.58 | 0.17 |
| 95% CI of | 0.76 | 0.17 | 0.64 |
| OR Quart 2 | 11 | 23 | 13 |
| OR Quart 3 | 2.4 | 2.1 | 1.8 |
| p Value | 0.20 | 0.56 | 0.44 |
| 95% CI of | 0.63 | 0.18 | 0.39 |
| OR Quart 3 | 9.2 | 24 | 8.7 |
| OR Quart 4 | 1.4 | 2.0 | 2.9 |
| p Value | 0.67 | 0.58 | 0.17 |
| 95% CI of | 0.32 | 0.17 | 0.64 |
| OR Quart 4 | 5.7 | 23 | 13 |

While the invention has been described and exemplified in sufficient detail for those skilled in this art to make and use it, various alternatives, modifications, and improvements should be apparent without departing from the spirit and scope of the invention. The examples provided herein are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Other embodiments are set forth within the following claims.

We claim:

1. A method for evaluating renal status in a subject, comprising:
performing one or more assays configured to detect Stromelysin-1:Metalloproteinase inhibitor 2 complex, on a body fluid sample obtained from the subject to provide an assay result;
correlating the assay result(s) to the renal status of the subject by introducing the body fluid sample obtained from the subject into an assay instrument which contacts all or a portion of the body fluid sample with a binding reagent which specifically binds for detection Stromelysin-1:Metalloproteinase inhibitor 2 complex, and (ii) generates an assay result indicative of binding of Stromelysin-1:Metalloproteinase inhibitor 2 complex to the binding reagent; and
correlating the assay result generated by the assay instrument to the renal status of the subject by using the assay result to assign the subject to a predetermined subpopulation of individuals having a known predisposition of a future acute renal injury within 72 hours of the time at which the body fluid sample is obtained; and
treating the patient based on the predetermined subpopulation of individuals to which the patient is assigned, wherein the treatment comprises one or more of initiating renal replacement therapy, withdrawing delivery of compounds that are known to be damaging to the kidney, delaying or avoiding procedures that are known to be damaging to the kidney, and modifying diuretic administration.

2. A method according to claim 1, wherein said assay result comprises a measured concentration of Stromelysin-1:Metalloproteinase inhibitor 2 complex.

3. A method according to claim 1, wherein a plurality of assay results are combined using a function that converts the plurality of assay results into a single composite result.

4. A method according to claim 1, wherein the subject is selected for evaluation of renal status based on the pre-existence in the subject of one or more known risk factors for prerenal, intrinsic renal, or postrenal ARF.

5. A method according to claim 1, wherein the subject is selected for evaluation of renal status based on an existing diagnosis of one or more of congestive heart failure, preeclampsia, eclampsia, diabetes mellitus, hypertension, coronary artery disease, proteinuria, renal insufficiency, glomerular filtration below the normal range, cirrhosis, serum creatinine above the normal range, sepsis, injury to renal function, reduced renal function, or ARF, or based on undergoing or having undergone major vascular surgery, coronary artery bypass, or other cardiac surgery, or based on exposure to NSAIDs, cyclosporines, tacrolimus, aminoglycosides, foscarnet, ethylene glycol, hemoglobin, myoglobin, ifosfamide, heavy metals, methotrexate, radiopaque contrast agents, or streptozotocin.

6. A method according to claim 1, wherein said one or more future changes in renal status comprise one or more of a future injury to renal function, future reduced renal function, future improvement in renal function, and future acute renal failure (ARF) within 48 hours of the time at which the body fluid sample is obtained.

7. A method according to claim 1, wherein said one or more future changes in renal status comprise one or more of a future injury to renal function, future reduced renal function, future improvement in renal function, and future acute renal failure (ARF) within 24 hours of the time at which the body fluid sample is obtained.

8. A method according to claim 1, wherein the subject is in RIFLE stage 0 or R.

9. A method according to claim 8, wherein the subject is in RIFLE stage 0 or R, and said correlating step comprises assigning a likelihood that the subject will reach RIFLE stage I or F within 72 hours.

10. A method according to claim 1, wherein the subject is not in acute renal failure.

* * * * *